US007211711B2

(12) United States Patent
Perera et al.

(10) Patent No.: US 7,211,711 B2
(45) Date of Patent: May 1, 2007

(54) COMPOSITIONS AND METHODS FOR THE MODIFICATION OF GENE EXPRESSION

(75) Inventors: Ranjan Perera, Carlsbad, CA (US); Stephen Rice, Oxford (GB); Marion Wood, Auckland (NZ); Clare Eagleton, Auckland (NZ); Elizabeth Visser, Auckland (NZ)

(73) Assignees: ArborGen, LLC, Summerville, SC (US); Rubicon Forests Holdings Limited, Auckland (NZ)

( * ) Notice: Subject to any disclaimer, the term of this patent is extended or adjusted under 35 U.S.C. 154(b) by 544 days.

(21) Appl. No.: 10/137,036

(22) Filed: Apr. 30, 2002

(65) Prior Publication Data

US 2003/0101478 A1 May 29, 2003

Related U.S. Application Data

(63) Continuation-in-part of application No. 09/724,624, filed on Nov. 28, 2000, now abandoned, which is a continuation-in-part of application No. 09/598,401, filed on Jun. 20, 2000, now Pat. No. 6,596,925, which is a continuation-in-part of application No. 09/276,599, filed on Mar. 25, 1999, now Pat. No. 6,380,459.

(60) Provisional application No. 60/146,591, filed on Jul. 30, 1999.

(30) Foreign Application Priority Data

Feb. 24, 2000 (WO) ............... PCT/NZ00/00018
Jun. 20, 2001 (WO) ............... PCT/NZ01/00115

(51) Int. Cl.
*C12N 15/09* (2006.01)
*C12N 15/63* (2006.01)
*C12N 15/82* (2006.01)
*A01H 5/00* (2006.01)
*A01H 5/10* (2006.01)

(52) U.S. Cl. ............... 800/287; 800/298; 435/320.1; 435/419; 536/23.1; 536/24.1

(58) Field of Classification Search ............... 536/23.1, 536/24.1; 435/419, 465, 320.1; 800/278, 800/282, 283, 284, 285, 286, 287, 288, 289, 800/290, 298

See application file for complete search history.

(56) References Cited

U.S. PATENT DOCUMENTS

| 5,510,474 A | 4/1996 | Quail et al. |
| 5,639,952 A | 6/1997 | Quail et al. ............... 800/205 |
| 5,656,496 A | 8/1997 | Quail et al. ............... 435/320 |
| 5,750,385 A | 5/1998 | Shewmaker et al. |
| 6,054,574 A | 4/2000 | Quail et al. ............... 536/24.1 |
| 6,225,529 B1 | 5/2001 | Lappegard et al. ............... 800/287 |

FOREIGN PATENT DOCUMENTS

| WO | 9747756 | 12/1997 |
| WO | 0058474 | 10/2000 |
| WO | WO 01/98485 A1 * | 12/2001 |

OTHER PUBLICATIONS

Benfey et al., Science 250:959-966, 1990.*
GenBank GI:1838898 Feb. 10, 1997.*
Ellis J. et al., EMBO Journal, 1987, vol. 6, No. 1, pp. 11-16.*
Szczglowski K. et al. The Plant Cell, 1994, vol. 6, pp. 317-332.*
Kim Y. et al. Plant Molecular Biology, 1994, vol. 24, pp. 105-117.*
GenBank Accession No. AJ012552 (VFA012552), submitted Nov. 13, 1998.
GenBank Accession No. L41658 (SCFPOLY), submitted Nov. 28, 1995.
GenPept Accession No. AAB21993, submitted May 7, 1993.
Christensen, Allen H. et al., "Maize polyubiquitin genes: structure, thermal perturbation of expression and transcript splicing, and promoter activity following transfer to protoplasts by electroporation", *Plant Molecular Biology*, vol. 18, pp. 675-689 (1992).
GenPept Accession No. AA68878, submitted Jun. 23, 1995.
Callis, Judy et al., "Structure and Evolution of Genes Encoding Polyubiquitin and Ubiquitin-Like Proteins in *Arabidosis thaliana* Ecotype Columbia", *Genetics*, vol. 139, pp. 921-939 (1995).
EMBL Accession No. D10851 (ATHCDC2BG), submitted Apr. 14, 2000.
Imajuku, Yoshiro et al., "Exon-intron organization of the *Arabidopsis thaliana* protein kinase genes CDC2a and CDC2b", *FEBS Letters*, vol. 304, No. 1, pp. 73-77 (1992).
EMBL Accession No. U12012 (PTU12012), submitted Mar. 23, 1996.
Voo, Kui Shin et al., "4-Coumarate:Coenzyme A Ligase from Loblolly Pine Xylem. Isolation, Characterization, and Complementary DNA Cloning", *Plant Physiology*, vol. 108, pp. 85-97 (1995).
GenBank Accession No. AF139445, submitted Jun. 1, 1999.
Asamizu, Erika et al., "Structural Analysis of *Arabidopsis thaliana* Chromosome 5.VIII. Sequence Features of the Regions of 1,081,958 bp Covered by Seventeen Physically assigned P1 and TAC Clones", *DNA Research*, vol. 5, pp. 379-391 (1998).
GenBank Accession No. AB016885, submitted Dec. 27, 2000.
SWISS-PROT Accession No. O24493 (MCI PINRA), submitted Jul. 15, 1999.
GenBank Accession No. AF075270, submitted Sep. 24, 1998.
GenBank Accession No. U53418 (GMU53418), submitted May 28, 1997.

(Continued)

Primary Examiner—Russell P. Kallis
(74) Attorney, Agent, or Firm—Cooley Codward Kronish LLP

(57) ABSTRACT

Novel isolated plant polynucleotide promoter sequences are provided, together with genetic constructs comprising such polynucleotides. Methods for using such constructs in modulating the transcription of DNA sequences of interest are also disclosed, together with transgenic plants comprising such constructs.

9 Claims, 19 Drawing Sheets

OTHER PUBLICATIONS

Tenhaken, Raimund at al., "Cloning of an Enzyme That Synthesizes a Key Nucleotide-Sugar Precursor of Hemicellulose Biosynthesis from Soybean: UDP-Glucose Dehydrogenase", *Plant Physiology*, vol. 112, pp. 1127-1134 (1996).

GenBank Accession No. Z14990 (ATUBC9), submitted May 18, 1993.

Girod, Pierre-Alain et al., "Homologs of the essential ubiquitin conjugating enzymes UBC1, 4 and 5 in yeast are encoded by a multigene family in *Arabidopsis thaliana*", *Plant Journal*, vol. 3, No. 4, pp. 545-552 (1993).

Walden, Adrian R. et al., "Gene Expressed in *Pinus radiata* Male Cones Include Homologs to Anther-Specific and Pathogenesis Response Genes", *Plant Physiology*, vol. 121, pp. 1103-1116 (1999).

GenBank Accession No. U90350 (PRU90350), submitted Oct. 10, 1997.

EMBL Accession No. D63396 (NTBY2A, TOBBY2A), submitted Feb. 13, 1999.

Kumagai, F. et al., "The Involvement of Protein Synthesis Elongation Factor 1α in the Organization of Microtubules on the Perinuclear Region during the Cell Cycle Transition from M Phase to $G_1$ Phase in Tobacco BY-2 Cells", *Bot. Acta.*, vol. 108, pp. 467-473 (1995).

GenPept Accession No. AAD56019 (AF18149_1), submitted Sep. 22, 1999.

GenBank Accession No. X74814 (EGOMTRN), submitted Sep. 22, 1994.

Poeydomenge, Odile et al., "A cDNA Encoding S-Adenosyl-L-Methionine:Caffeic Acid 3-O-Methyltransferase from *Eucalyptus*", *Plant Physiology*, vol. 105, pp. 749-750 (1994).

GenBank Accession No. X53043 (LEEFIA), submitted May 9, 1995.

Curie, Catherine et al., "The activation process of *Arabidopsis thaliana* A1 gene encoding the translation elongation factor EF-1α is conserved among angiosperms", *Plant Molecular Biology*, vol. 18, pp. 1083-1089 (1992).

Belknap, William R. and Garbarino, Joan E. "The Role of ubiquitin in plant senescence and stress responses." *Trends in Plant Science* vol. 1, No. 10:331-335, Oct. 1996.

Scharf, Klaus-Dieter, Materna, Tilo, Trueter, Eckardt, and Nover, Lutz. "Heat Stress Promoters and Transcription Factors." *Results Probl Cell Differ* 20:125-62, 1994.

Callis, Judy et al., "Ubiquitin Extension Proteins of *Arabidopsis thaliana*", *JBC*, vol. 265, pp. 12486-12493 (1990).

GenPept Assession No. CAA63531; submitted Nov. 9, 1995 by Ruiter, R.K.

GenPept Assession No. CAA10056; submitted Nov. 12, 1998 by Fruehling, M.

GenBank Assession No. M55147 X51434: Liaud, M. and Cerff, R., *Proc. Nat'l Acad. Sci.*, vol. 87, No. 22, pp. 8918-8922 (1990).

GenBank Assession No. X74814; submitted Aug. 27, 1993 by Poeyudomenge. O., et al.

GenBank Assession No. AF077743; submitted Jul. 13, 1998 by Rehli, M., et al.

GenBank Assession No. U73588; submitted Oct. 7, 1996 by Pere-Grau, L., et al.

GenBank Assession No. U90350; submitted Feb. 24, 1997 by Walden, A.R., et al.

GenBank Assession No. AF041463; submitted Jan. 6, 1998 by Suhandono, et al.

\* cited by examiner

*In vitro* analysis of the superubiquitin promoter using deletion constructs

```
AAAACCCCTCACAAATACATAAAAAAAATTCTTTATTTAATTATCAAACTCTCCACTACC        60
    13           36            3           7      6
TTTCCCACCAACCGTTACAATCCTGAATGTTGGAAAAAACTAACTACATTGATATAAAAA       120
     25      20                                 11
AACTACATTACTTCCTAAATCATATCAAAATTGTATAAATATATCCACTCAAAGGAGTCT       180
                                            35
AGAAGATCCACTTGGACAAATTGCCCATAGTTGGAAAGATGTTCACCAAGTCAACAAGAT       240
                                                     31
TTATCAATGGAAAAATCCATCTACCAAACTTACTTTCAAGAAAATCCAAGGATTATAGAG       300
    20                                  29    32
TAAAAAATCTATGTATTATTAAGTCAAAAAGAAAACCAAAGTGAACAAATATTGATGTAC       360
                              29   33
AAGTTTGAGAGGATAAGACATTGGAATCGTCTAACCAGGAGGCGGAGGAATTCCCTAGAC       420
           11,16,8             23
AGTTAAAAGTGGCCGGAATCCCGGTAAAAAAGATTAAAATTTTTTTGTAGAGGGAGTGCT       480
        12
TGAATCATGTTTTTTATGATGGAAATAGATTCAGCACCATCAAAAACATTCAGGACACCT       540

AAAATTTTGAAGTTTAACAAAAATAACTTGGATCTACAAAAATCCGTATCGGATTTTCTC       600
               24
TAAATATAACTAGAATTTTCATAACTTTCAAAGCAACTCCTCCCCTAACCGTAAAACTTT       660
                                       13
TCCTACTTCACCGTTAATTACATTCCTTAAGAGTAGATAAAGAAATAAAGTAAATAAAAG       720
                                  11   29
TATTCACAAACCAACAATTTATTTCTTTTATTTACTTAAAAAAACAAAAAGTTTATTTAT       780
        33  31
TTTACTTAAATGGCATAATGACATATCGGAGATCCCTCGAACGAGAATCTTTTATCTCCC       840

TGGTTTTGTATTAAAAAGTAATTTATTGTGGGGTCCACGCGGAGTTGGAATCCTACAGAC       900
                            12       14
GCGCTTTACATACGTCTCGAGAAGCGTGACGGATGTGCGACCGGATGACCCTGTATAACC       960
             4       15     10                            9
CACCGACACAGCCAGCGCACAGTATACACGTGTCATTTCTCTATTGGAAAATGTCGTTGT      1020
  22                      4
TATCCCCGCTGGTACGCAACCACCGATGGTGACAGGTCGTCTGTTGTCGTGTCGCGTAGC      1080
   13                                                     19
GGGAGAAGGGTCTCATCCAACGCTATTAAATACTCGCCTTCACCGCGTTACTTCTCATCT      1140
   15         27         2                                5
TTTCTCTTGCGTTGTATAATCAGTGCGATATTCTCAGAGCTTTTCATTCAAAGGTATG       1200
 1              1             11
GAGTTTTGAAGGGCTTTACTCTTAACATTTGTTTTTCTTTGTAAATTGTTAATGGTGGTT      1260
                                                       12
TCTGTGGGGGAAGAATCTTTTGCCAGGTCCTTTTGGGTTTCGCATGTTTATTTGGGTTAT      1320
   12                    30
TTTTCTCGACTATGGCTGACATTACTAGGGCTTTCGTGCTTTCATCTGTGTTTTCTTCCC      1380

TTAATAGGTCTGTCTCTCTGGAATATTTAATTTTCGTATGTAAGTTATGAGTAGTCGCTG      1440
         18
TTTGTAATAGGCTCTTGTCTGTAAAGGTTTCAGCAGGTGTTTGCGTTTTATTGCGTCATG      1500
              17
TGTTTCAGAAGGCCTTTGCAGATTATTGCGTTGTACTTTAATATTTTGTCTCCAACCTTG      1560
                                    28       18    25
```
Fig. 6A

```
TTATAGTTTCCCTCCTTTGATCTCACAGGAACCCTTTCTTCTTTGAGCATTTTCTTGTGG        1620
                                                         12
CGTTCTGTAGTAATATTTTAATTTTGGGCCCGGGTTCTGAGGGTAGGTGATTATTCACAG        1680
TGATGTGCTTTCCCTATAAGGTCCTCTATGTGTAAGCTGTTAGGGTTTGTGCGTTACTAT        1740
                                                         34
TGACATGTCACATGTCACATATTTTCTTCCTCTTATCCTTCGAACTGATGGTTCTTTTTC        1800
        26
TAATTCGTGGATTGCTGGTGCCATATTTTATTTCTATTGCAACTGTATTTTAGGGTGTCT        1860
      12                                                 18
CTTTCTTTTTGATTTCTTGTTAATATTTGTGTTCAGGTTGTAACTATGGGTTGCTAGGGT        1920
GTCTGCCCTCTTCTTTTGTGCTTCTTTCGCAGAATCTGTCCGTTGGTCTGTATTTGGGTG        1980
ATGAATTATTTATTCCTTGAAGTATCTGTCTAATTAGCTTGTGATGATGTGCAGGTATAT        2040
                                                    21
TCGTTAGTCATATTTCAATTTCAAGATGCAGATCTTTGTCAAGACTCTCACCGGTAAGAC        2100
              20
```

CATCACTCTCGAGGTCGAGAGCTCTGACACCATTGACAATGTTAAAGCTAAGATCCAGGA        2160

CAAGGAAGGGATTCCCCCCGACCAGCAGCGTCTGATCTTCGCAGGAAAGCAGCTTGAGGA        2220

CGGCCGAACCCTTGCCGATTACAACATCCAGAAAGAATCTACCCTCCACCTTGTTCTCCG        2280

TTTGAGGGGTGGCATGCAAATCTTTGTAAAAACACTAACTGGAAAGACAATTACATTGGA        2340

AGTTGAGAGCTCGGACACCATTGACAACGTCAAGGCCAAGATCCAGGACAAGGAAGGAAT        2400

TCCCCCTGACCAGCAGAGGCTTATCTTCGCTGGTAAGCAGCTGGAGGATGGCAGGACCTT        2460

GGCTGATTACAATATTCAAAAGGAATCGACCCTGCATTTGGTGCTTCGTCTAAGAGGAGG        2520

CATGCAAATCTTTGTGAAAACCCTTACAGGTAAAACCATTACTCTGGAAGTGGAAAGCTC        2580

GGACACCATTGACAATGTGAAGGCTAAGATCCAGGACAAGGAGGGAATTCCACCTGACCA        2640

GCAGAGGTTGATCTTTGCCGGTAAGCAGCTGGAAGATGGTCGTACTCTCGCCGATTACAA        2700

TATTCAGAAGGAATCGACCCTTCACCTGGTGCTCCGTCTCCGCGGTGGCTTTTAGGTTTG        2760

GGTGTTATTTGTGGATAATAAATTCGGGTGATGTTCAGTGTTTGTCGTATTTCTCACGAA        2820

TAAATTGTGTTTATGTATGTGTTAGTGTTGTTTGTCTGTTTCAGACCCTCTTATGTTATA        2880

TTTTTCTTTTCGTCGGTCAGTTGAAGCCAATACTGGTGTCCTGGCCGGCACTGCAATACC        2940

ATTTCGTTTAATATAAAGACTCTGTTATCCGTTATGTAATTCCATGTTATGTGGTGAAAT        3000

GTGGATGAAATTCTTAGAAATTATTATTGTAATTTGAAACTTCCTTCGTCAATAATCTGC        3060

ACAACACATTTACCAAAAAAAAAA        3084

Fig. 6B

```
CAT ACGT CTC GAGAAG CG TGACG GATGTGCGACCGGATGACCCTGTAT AACCCA CCGACA      60
    4       15      10                                  9      22
CAGCCAGCGCACAGTATA CACGTG TCATTTCTCTATTGGAAAATGTCGTTGTTAT CCCC G         120
                     4                                         13
CTGGTACGCAACCACCGATGGTGACAGGTCGTCTGTTGTCGTGTCGCGTAGCGG  GAGAAG          180
                                                   19      15
GGTCT CATCCAACG C TATTAAA TACTCGCCTTCACCGCGTTACTTCTCA TCTTTTC TCTT       240
        27        2                                   5
GCGTTG TATAAT CAGTGC GATA TTCTCAGAGAGCTTTTCATTCAA                        300
         1           11
```

Fig. 7 - Superubiquitin construct without intron
SR52  195bp deletion (195 bp upstream of TATA box)

```
AATTTATTTCTTTTATTTACTTAAAAAAACAAAAAGTTTATTTATTTTACTTAAATGGCA                    60

TAATGACATATCGGAGATCCCTCGAACGAGAATCTTTTATCTCCCTGGTTTTGTATTAAA                   120

AAGTAATTTATT GTGG GGT CCACGCGG AGTTGGAATCCTACAGACGCGCTTTACAT ACGT              180
             12      14                                       4
CTC GAGAAG CG TGACG GATGTGCGACCGGATGACCCTGTAT AACCCA CCGACA CAGCCAG            240
    15        10                               9      22
CGCACAGTATA CACGTG TCATTTCTCTATTGGAAAATGTCGTTGTTAT CCCC GCTGGTAC               300
            4                                      13
GCAACCACCGATGGTGACAGGTCGTCTGTTGTCGTGTCGCGTAGCGG GAGAAG GGTCT CA                360
                                                19      15
TCCAACG C TATTAAA TACTCGCCTTCACCGCGTTACTTCTCA TCTTTTC TCTTGCGTTG T             420
27        2                                   5
ATAAT CAGTGC GATA TTCTCAGAGAGCTTTTCATTCAA                                      480
1            11
```

Fig. 8 - Superubiquitin construct without intron
SR54  368bp deletion (368 bp upstream of TATA box)

```
TTTTCCTACTTCACCGTTAATTACATTCCTTAAGAGTA GATA AAGAAA TAAAGTAAATAA         60
                                         11   29
AAGTATTCACA AAC CAA CA ATTTATTTCTTTTATTTACTTAAAAAAACAAAAAGTTTATT       120
            33  31
TATTTTACTTAAATGGCATAATGACATATCGGAGATCCCTCGAACGAGAATCTTTTATCT          180

CCCTGGTTTTGTATTAAAAAGTAATTTATT GTGG GGT CCACGCGG AGTTGGAATCCTACA       240
                                12      14
GACGCGCTTTACAT ACGT CTC GAGAAG CG TGACG GATGTGCGACCGGATGACCCTGTAT A    300
                4       15        10
ACCCA CCGACA CAGCCAGCGCACAGTATA CACGTG TCATTTCTCTATTGGAAAATGTCGT       360
 9    22                         4
TGTTAT CCCC GCTGGTACGCAACCACCGATGGTGACAGGTCGTCTGTTGTCGTGTCGCGT         420
       13
AGCGG GAGAAG GGTCT CATCCAACG C TATTAAA TACTCGCCTTCACCGCGTTACTTCTCA     480
 19    15      27              2
TCTTTTC TCTTGCGTTG TATAAT CAGTGC GATA TTCTCAGAGAGCTTTTCATTCAA          540
 5                  1            11
```

Fig. 9 - Superubiquitin construct without intron
SR53    446bp deletion (446 bp upstream of TATA box)

```
CAGGACACCTAAAATTTTGAAGTT TAACAAA AATAACTTGGATCTACAAAAATCCGTATC          60
                             24
GGATTTTCTCTAAATATAACTAGAATTTTCATAACTTTCAAAGCAACTCCT CCCC TAACC         120
                                                      13
GTAAAACTTTTCCTACTTCACCGTTAATTACATTCCTTAAGAGTA GATA AAGAAA TAAAG        180
                                                11    29
TAAATAAAAGTATTCACA AACCAACA ATTTATTTCTTTTATTTACTTAAAAAAACAAAAA        240
                    33  31
GTTTATTTATTTTACTTAAATGGCATAATGACATATCGGAGATCCCTCGAACGAGAATCT          300

TTTATCTCCCTGGTTTTGTATTAAAAAGTAATTTATT GTGG GGT CCACGCGG AGTTGGAA       360
                                        12      14
TCCTACAGACGCGCTTTACAT ACGT CTC GAGAAG CG TGACG GATGTGCGACCGGATGACC     420
                        4      15     10
CTGTAT AACCCA CCGACA CAGCCAGCGCACAGTATA CACGTG TCATTTCTCTATTGGAAA      480
         9    22                           4
ATGTCGTTGTTAT CCCC GCTGGTACGCAACCACCGATGGTGACAGGTCGTCTGTTGTCGT         540
                13
GTCGCGT AGCGG GAGAAG GGTCT CATCCAACG C TATTAAA TACTCGCCTTCACCGCGTTA    600
          19   15          27            2
CTTCTCA TCTTTTC TCTTGCGTTG TATAAT CAGTGC GATA TTCTCAGAGAGCTTTTCATT     660
           5                 1          11
CAA                                                                   703
```

Fig. 10 - Superubiquitin construct without intron
SR55   573bp deletion (573 bp upstream of TATA box)

```
ATTGATGTACAAGTTTGAGAG GATAAG ACATTGGAATCGT CTAACCA GGAGGCGGAGGAA      60
                       11,16,8              23
TTCCCTAGACAGTTAAAA GTGG CCGGAATCCCGGTAAAAAGATTAAAATTTTTTTGTAG         120
                   12
AGGGAGTGCTTGAATCATGTTTTTTATGATGGAAATAGATTCAGCACCATCAAAAACATT         180
CAGGACACCTAAAATTTTGAAGTT TAACAAA AATAACTTGGATCTACAAAAATCCGTATC        240
                         24
GGATTTTCTCTAAATATAACTAGAATTTTCATAACTTTCAAAGCAACTCCT CCCC TAACC       300
                                                    13
GTAAAACTTTTCCTACTTCACCGTTAATTACATTCCTTAAGAGTA GATA AAGAAA TAAAG      360
                                              11   29
TAAATAAAAGTATTCACA AACCAA CA ATTTATTTCTTTTATTTACTTAAAAAAACAAAAA      420
                   33    31
GTTTATTTATTTTACTTAAATGGCATAATGACATATCGGAGATCCCTCGAACGAGAATCT         480
TTTATCTCCCTGGTTTTGTATTAAAAAGTAATTTATT GTGG GGT CCACGCGG AGTTGGAA     540
                                      12      14
TCCTACAGACGCGCTTTACAT ACGT CTC GAGAAG CG TGACG GATGTGCGACCGGATGACC   600
                      4       15      10
CTGTAT AACCCA CCGACA CAGCCAGCGCACAGTATA CACGTG TCATTTCTCTATTGGAAA    660
       9     22                         4
ATGTCGTTGTTAT CCCC GCTGGTACGCAACCACCGATGGTGACAGGTCGTCTGTTGTCGT       720
              13
GTCGCGT AGCGG GAGAAG GGTCT CATCCAACG C TATTAAA TACTCGCCTTCACCGCGTTA  780
        19    15          27             2
CTTCTCA TCTTTTC TCTTGCGTTG TATAAT CAGTGC GATA TTCTCAGAGCTTTTCATT     840
        5                 1             11
CAA                                                                  883
```

Fig. 11 - Superubiquitin construct without intron
SR56  753bp deletion (753 bp upstream of TATA box)

```
CAT ACGT CTC GAGAAG CG TGACG GATGTGCGACCGGATGACCCTGTAT AACCCA CCGACA        60
    4       15      10                                    9      22
CAGCCAGCGCACAGTATA CACGTG TCATTTCTCTATTGGAAAATGTCGTTGTTAT CCCC G           120
                    4                                            13
CTGGTACGCAACCACCGATGGTGACAGGTCGTCTGTTGTCGTGTCGCGT AGCGG  GAGAAG           180
                                                            19     15
GGTCT CATCCAACG C TATTAAA TACTCGCCTTCACCGCGTTACTTCTCA TCTTTTC TCTT         240
       27           2                                    5
GCGTTG TATAAT CAGTGC GATA TTCTCAGAGAGCTTTTCATTCAAACGTATCGAGTTTTG           300
        1            11
AAGGGCTTTACTCTTAACATTTGTTTTTCTTTGTAAATTGTTAATG GTGG TTTCT GTGG G           360
                                                 12        12
GGAAGAATCTTTTGCCAGGT CCTTTT GGGTTTCGCATGTTTATTTGGGTTATTTTCTCG             420
                       30
ACTATGGCTGACATTACTAGGGCTTTCGTGCTTTCATCTGTGTTTTCTTCCCTTAATAGG              480

TC TGTCTC TCTGGAATATTTAATTTTCGTATGTAAGTTATGAGTAGTCGCTGTTTGTAAT            540
    18
AGGCTCTTGTC TGTAAAG GTTTCAGCAGGTGTTTGCGTTTTATTGCGTCATGTGTTTCAG            600
             17
AAGGCCTTTGCAGATTATTGCGTTGT ACTTTA ATATTT TGTCTC CAACC TTGTTATAGTT         660
                            28       18      25
TCCCTCCTTTGATCTCACAGGAACCCTTTCTTCTTTGAGCATTTTCTT GTGG CGTTCTGT            720
                                                  12
AGTAATATTTTAATTTTGGGCCCGGGTTCTGAGGGTAGGTGATTATTCACAGTGATGTGC              780

TTTCCCTATAAGGTCCTCTATGTGTAAGCTGTTAGGGTTTGTGCGT TACTATT GACATGT            840
                                                34
CACATG TCACATATTTTCTTCCTCTTATCCTTCGAACTGATGGTTCTTTTTCTAATTC  GT           900
 26                                                          12
GG ATTGCTGGTGCCATATTTTATTTCTATTGCAACTGTATTTTAGGG TGTCTC TTTCTTT           960
                                                  18
TTGATTTCTTGTTAATATTTGTGTTCAGGTTGTAACTATGGGTTGCTAGGGTGTCTGCCC             1020

TCTTCTTTTGTGCTTCTTTCGCAGAATCTGTCCGTTGGTCTGTATTTGGGTGATGAATTA             1080

TTTATTCCTTGAAGTATCTGTCTAATTAGCTTGTGATGATG TGCAGG TATATTCGTTAGT           1140
                                           21
CATATTT CAAT TTCAAGATGCAGA                                               1164
         20
```

Fig. 12 Superubiquitin construct with the intron
SR52 195bp deletion (195 bp upstream of TATA box)

```
AATTTATTTCTTTTATTTACTTAAAAAAACAAAAAGTTTATTTATTTTACTTAAATGGCA                    60

TAATGACATATCGGAGATCCCTCGAACGAGAATCTTTTATCTCCCTGGTTTTGTATTAAA                    120

AAGTAATTTATT GTGG GGT CCACGCGG AGTTGGAATCCTACAGACGCGCTTTACAT ACGT               180
             12      14                                        4
CTC GAGAAG CG TGACG GATGTGCGACCGGATGACCCTGTAT AACCCA CCGACA CAGCCAG              240
    15        10                              9      22
CGCACAGTATA CACGTG TCATTTCTCTATTGGAAAATGTCGTTGTTAT CCCC GCTGGTAC                 300
            4                                      13
GCAACCACCGATGGTGACAGGTCGTCTGTTGTCGTGTCGCGTAGCGG GAGAAG GGTCT CA                  360
                                                 19      15
TCCAACG C TATTAAA TACTCGCCTTCACCGCGTTACTTCTCA TCTTTTC TCTTGCGTTG T               420
27        2                                    5
ATAAT CAGTGC GATA TTCTCAGAGAGCTTTTCATTCAAAGGTATGGAGTTTTGAAGGGCT                  480
1            11
TTACTCTTAACATTTGTTTTTCTTTGTAAATTGTTAATG GTGG TTTCT GTGG GGGAAGAA                 540
                                        12         12
TCTTTTGCCAGGT CCTTTT GGGTTTCGCATGTTTATTTGGGTTATTTTCTCGACTATGG                    600
              30
CTGACATTACTAGGGCTTTCGTGCTTTCATCTGTGTTTTCTTCCCTTAATAGGTC TGTCT                   660
                                                         18
C TCTGGAATATTTAATTTTCGTATGTAAGTTATGAGTAGTCGCTGTTTGTAATAGGCTCT                   720

TGTC TGTAAAG GTTTCAGCAGGTGTTTGCGTTTTATTGCGTCATGTGTTTCAGAAGGCCT                   780
     17
TTGCAGATTATTGCGTTGT ACTTTA ATATTT TGTCTC CAACCTTGTTATAGTTTCCCTCC                 840
                    28            18     25
TTTGATCTCACAGGAACCCTTTCTTCTTTGAGCATTTTCTT GTGG CGTTCTGTAGTAATA                   900
                                           12
TTTTAATTTTGGGCCCGGGTTCTGAGGGTAGGTGATTATTCACAGTGATGTGCTTTCCCT                    960

ATAAGGTCCTCTATGTGTAAGCTGTTAGGGTTTGTGCGT TACTATT GACATGT CACATG T                 1020
                                        34              26
CACATATTTTCTTCCTCTTATCCTTCGAACTGATGGTTCTTTTTCTAATTC GTGG ATTGC                   1080
                                                    12
TGGTGCCATATTTTATTTCTATTGCAACTGTATTTTAGGG TGTCTC TTTCTTTTTGATTT                   1140
                                         18
CTTGTTAATATTTGTGTTCAGGTTGTAACTATGGGTTGCTAGGGTGTCTGCCCTCTTCTT                    1200

TTGTGCTTCTTTCGCAGAATCTGTCCGTTGGTCTGTATTTGGGTGATGAATTATTTATTC                    1260

CTTGAAGTATCTGTCTAATTAGCTTGTGATGATG TGCAGG TATATTCGTTAGTCATATTT                   1320
                                   21
CAAT TTCAAGATGCAGA                                                              1337
20
```

Fig. 13 Superubiquitin construct with the intron
SR54 368bp deletion (368 bp upstream of TATA box)

```
TTTTCCTACTTCACCGTTAATTACATTCCTTAAGAGTA GATA AAGAAA TAAAGTAAATAA      60
                                           11   29
AAGTATTCACA AAC CAA CAATTTATTTCTTTTATTTACTTAAAAAAACAAAAAGTTTATT       120
            33  31
TATTTTACTTAAATGGCATAATGACATATCGGAGATCCCTCGAACGAGAATCTTTTATCT         180
CCCTGGTTTTGTATTAAAAAGTAATTTATT GTGG GGT CCACGCGG AGTTGGAATCCTACA      240
                                12       14
GACGCGCTTTACAT ACGT CTC GAGAAG CG TGACG GATGTGCGACCGGATGACCCTGTAT A   300
               4       15      10
ACCCA CCGACA CAGCCAGCGCACAGTATA CACGTG TCATTTCTCTATTGGAAAATGTCGT     360
 9    22                        4
TGTTAT CCCC GCTGGTACGCAACCACCGATGGTGACAGGTCGTCTGTTGTCGTGTCGCGT       420
       13
AGCGG GAGAAG GGTCT CATCCAACG C TATTAAA TACTCGCCTTCACCGCGTTACTTCTCA   480
19    15     27              2
TCTTTTC TCTTGCGTTG TATAAT CAGTGC GATA TTCTCAGAGAGCTTTTCATTCAAAGGT    540
5                  1            11
ATGGAGTTTTGAAGGGCTTTACTCTTAACATTTGTTTTTCTTTGTAAATTGTTAATG GTG        600
                                                           12
G TTTCT GTGG GGGAAGAATCTTTTGCCAGGT CCTTTT GGGTTTCGCATGTTTATTTGGGT    660
        12                         30
TATTTTTCTCGACTATGGCTGACATTACTAGGGCTTTCGTGCTTTCATCTGTGTTTCTT         720
CCCTTAATAGGTC TGTCTC TCTGGAATATTTAATTTTCGTATGTAAGTTATGAGTAGTCG       780
              18
CTGTTTGTAATAGGCTCTTGTC TGTAAAG GTTTCAGCAGGTGTTTGCGTTTTATTGCGTC       840
                       17
ATGTGTTTCAGAAGGCCTTTGCAGATTATTGCGTTGT ACTTTA ATATTT TGTCTC CAACC     900
                                      28     18     25
TTGTTATAGTTTCCCTCCTTTGATCTCACAGGAACCCTTTCTTCTTTGAGCATTTTCTT G        960
TGG CGTTCTGTAGTAATATTTTAATTTTGGGCCCGGGTTCTGAGGGTAGGTGATTATTCA       1020
12
CAGTGATGTGCTTTCCCTATAAGGTCCTCTATGTGTAAGCTGTTAGGGTTTGTGCGT TAC       1080
TATT GACATGT CACATG TCACATATTTTCTTCCTCTTATCCTTCGAACTGATGGTTCTTT    1140
34           26
TTCTAATTC GTGG ATTGCTGGTGCCATATTTTATTTCTATTGCAACTGTATTTTAGGG TG     1200
          12
TCTC TTTCTTTTTGATTTCTTGTTAATATTTGTGTTCAGGTTGTAACTATGGGTTGCTAG      1260
18
GGTGTCTGCCCTCTTCTTTTGTGCTTCTTTCGCAGAATCTGTCCGTTGGTCTGTATTTGG       1320
GTGATGAATTATTTATTCCTTGAAGTATCTGTCTAATTAGCTTGTGATGATG TGCAGG TA     1380
                                                            21
TATTCGTTAGTCATATTT CAAT TTCAAGATGCAGA                              1415
                   20
```

Fig. 14 Superubiquitin construct with the intron
SR53    446bp deletion (446 bp upstream of TATA box)

```
CAGGACACCTAAAATTTTGAAGTT TAACAAA AATAACTTGGATCTACAAAAATCCGTATC        60
                              24
GGATTTTCTCTAAATATAACTAGAATTTTCATAACTTTCAAAGCAACTCCT CCCC TAACC       120
                                                     13
GTAAAACTTTTCCTACTTCACCGTTAATTACATTCCTTAAGAGTA GATA AAGAAA TAAAG      180
                                               11    29
TAAATAAAAGTATTCACA AACCAACAA TTTATTTCTTTTATTTACTTAAAAAACAAAAA        240
                   33  31
GTTTATTTATTTTACTTAAATGGCATAATGACATATCGGAGATCCCTCGAACGAGAATCT        300
TTTATCTCCCTGGTTTTGTATTAAAAAGTAATTTATT GTGG GGT CCACGCGG AGTTGGAA    360
                                       12      14
TCCTACAGACGCGCTTTACAT ACGT CTC GAGAAG CG TGACG GATGTGCGACCGGATGACC  420
                       4      15      10
CTGTAT AACCCA CCGACA CAGCCAGCGCACAGTATA CACGTG TCATTTCTCTATTGGAAA   480
        9      22                        4
ATGTCGTTGTTAT CCCC GCTGGTACGCAACCACCGATGGTGACAGGTCGTCTGTTGTCGT      540
               13
GTCGCGT AGCGG GAGAAG GGTCT CATCCAACG C TATTAAA TACTCGCCTTCACCGCGTTA 600
         19    15      27              2
CTTCTCA TCTTTTC TCTTGCGTTG TATAAT CAGTGC GATA TTCTCAGAGAGCTTTTCATT  660
         5                  1       11
CAAAGGTATGGAGTTTTGAAGGGCTTTACTCTTAACATTTGTTTTTCTTTGTAAATTGTT        720

AATG GTGG TTTCT GTGG GGGAAGAATCTTTTGCCAGGT CCTTTT GGGTTTCGCATGTTTA 780
      12      12                            30
TTTGGGTTATTTTTCTCGACTATGGCTGACATTACTAGGGCTTTCGTGCTTTCATCTGTG        840

TTTTCTTCCCTTAATAGGTC TGTCTC TCTGGAATATTTAATTTTCGTATGTAAGTTATGA      900
                      18
GTAGTCGCTGTTTGTAATAGGCTCTTGTC TGTAAAG GTTTCAGCAGGTGTTTGCGTTTTA     960
                               17
TTGCGTCATGTGTTTCAGAAGGCCTTTGCAGATTATTGCGTTGT ACTTTA ATATTT TGTC    1020
                                              28          18
TC CAACCTTGTTATAGTTTCCCTCCTTTGATCTCACAGGAACCCTTTCTTCTTTGAGCAT     1080
25
TTTCTT GTGG CGTTCTGTAGTAATATTTTAATTTTGGGCCCGGGTTCTGAGGGTAGGTGA    1140
        12
TTATTCACAGTGATGTGCTTTCCCTATAAGGTCCTCTATGTGTAAGCTGTTAGGGTTTGT        1200

GCGT TACTATT GACATGT CACATG TCACATATTTTCTTCCTCTTATCCTTCGAACTGATG  1260
      34              26
```

Fig. 15A Superubiquitin construct with the intron
SR55    573bp deletion (573 bp upstream of TATA box)

```
GTTCTTTTTCTAATTC GTGG ATTGCTGGTGCCATATTTTATTTCTATTGCAACTGTATTT        1320
                 12
TAGGG TGTCTC TTTCTTTTTGATTTCTTGTTAATATTTGTGTTCAGGTTGTAACTATGGG        1380
      18
TTGCTAGGGTGTCTGCCCTCTTCTTTTGTGCTTCTTTCGCAGAATCTGTCCGTTGGTCTG          1440

TATTTGGGTGATGAATTATTTATTCCTTGAAGTATCTGTCTAATTAGCTTGTGATGATG T         1500

GCAGG TATATTCGTTAGTCATATTT CAAT TTCAAGATGCAGA                         1542
21                          20
```

Fig. 15B Superubiquitin construct with the intron
SR55    573bp deletion (573 bp upstream of TATA box)

```
ATTGATGTACAAGTTTGAGAG GATAAG ACATTGGAATCGT CTAACCA GGAGGCGGAGGAA      60
                      11,16,8                23
TTCCCTAGACAGTTAAAA GTGG CCGGAATCCCGGTAAAAAGATTAAAATTTTTTGTAG         120
                   12
AGGGAGTGCTTGAATCATGTTTTTTATGATGGAAATAGATTCAGCACCATCAAAAACATT        180

CAGGACACCTAAAATTTTGAAGTT TAACAAA AATAACTTGGATCTACAAAAATCCGTATC       240
                         24
GGATTTTCTCTAAATATAACTAGAATTTTCATAACTTTCAAAGCAACTCCT CCCC TAACC       300
                                                    13
GTAAAACTTTTCCTACTTCACCGTTAATTACATTCCTTAAGAGTA GATA AAGAAA TAAAG      360
                                              11   29
TAAATAAAAGTATTCACA AACCAA CAATTTATTTCTTTTATTTACTTAAAAAAACAAAAA       420
                   33    31
GTTTATTTATTTTACTTAAATGGCATAATGACATATCGGAGATCCCTCGAACGAGAATCT        480

TTTATCTCCCTGGTTTTGTATTAAAAAGTAATTTATT GTGG GGT CCACGCGG AGTTGGAA     540
                                      12      14
TCCTACAGACGCGCTTTACAT ACGT CTC GAGAAG CG TGACG GATGTGCGACCGGATGACC   600
                      4       15      10
CTGTAT AACCCA CCGACA CAGCCAGCGCACAGTATA CACGTG TCATTTCTCTATTGGAAA    660
       9      22                       4
ATGTCGTTGTTAT CCCC GCTGGTACGCAACCACCGATGGTGACAGGTCGTCTGTTGTCGT       720
              13
GTCGCGT AGCGG GAGAAG GGTCT CATCCAACG C TATTAAA TACTCGCCTTCACCGCGTTA  780
        19    15          27           2
CTTCTCA TCTTTTC TCTTGCGTTG TATAAT CAGTGC GATA TTCTCAGAGAGCTTTTCATT   840
        5                 1              11
CAAAGGTATGGAGTTTTGAAGGGCTTTACTCTTAACATTTGTTTTTCTTTGTAAATTGTT        900

AATG GTGG TTTCT GTGG GGGAAGAATCTTTTGCCAGGT CCTTTT GGGTTTCGCATGTTTA   960
     12         12                        30
TTTGGGTTATTTTTCTCGACTATGGCTGACATTACTAGGGCTTTCGTGCTTTCATCTGTG       1020

TTTTCTTCCCTTAATAGGTC TGTCTC TCTGGAATATTTAATTTTCGTATGTAAGTTATGA     1080
                     18
GTAGTCGCTGTTTGTAATAGGCTCTTGTC TGTAAAG GTTTCAGCAGGTGTTTGCGTTTTA     1140
                              17
TTGCGTCATGTGTTTCAGAAGGCCTTTGCAGATTATTGCGTTGT ACTTTA ATATTT TGTC    1200
                                             28            18
TC CAACCTTGTTATAGTTTCCCTCCTTTGATCTCACAGGAACCCTTTCTTCTTTGAGCAT     1260

TTTCTT GTGG CGTTCTGTAGTAATATTTTAATTTTGGGCCCGGGTTCTGAGGGTAGGTGA    1320
       12
TTATTCACAGTGATGTGCTTTCCCTATAAGGTCCTCTATGTGTAAGCTGTTAGGGTTTGT     1380
```

Fig. 16A Superubiquitin construct with the intron
SR56 753bp deletion (753 bp upstream of TATA box)

```
GCGT TACTATT GACATGT CACATG TCACATATTTTCTTCCTCTTATCCTTCGAACTGATG        1440
     34              26
GTTCTTTTTCTAATTC GTGG ATTGCTGGTGCCATATTTTATTTCTATTGCAACTGTATTT         1500
                 12
TAGGG TGTCTC TTTCTTTTTGATTTCTTGTTAATATTTGTGTTCAGGTTGTAACTATGGG         1560
      18
TTGCTAGGGTGTCTGCCCTCTTCTTTTGTGCTTCTTTCGCAGAATCTGTCCGTTGGTCTG          1620

TATTTGGGTGATGAATTATTTATTCCTTGAAGTATCTGTCTAATTAGCTTGTGATGATG T         1680

GCAGG TATATTCGTTAGTCATATTT CAAT TTCAAGATGCAGA                         1722
21                         20
```

Fig. 16B Superubiquitin construct with the intron
SR56 753bp deletion (753 bp upstream of TATA box)

ical field of the invention and the background of the invention...

SEQUENCE LISTING

<160> NUMBER OF SEQ ID NOS: 143

<210> SEQ ID NO 1
<211> LENGTH: 3083
<212> TYPE: DNA
<213> ORGANISM: Pinus radiata
<220> FEATURE:
<221> NAME/KEY: 5'UTR
<222> LOCATION: (1)...(2064)
<220> FEATURE:
<221> NAME/KEY: intron
<222> LOCATION: (1196)...(2033)
<220> FEATURE:
<221> NAME/KEY: CDS
<222> LOCATION: (2065)...(2751)
<220> FEATURE:
<221> NAME/KEY: 3'UTR
<222> LOCATION: (2755)...(3083)

<400> SEQUENCE: 1

```
aaaaccccctc acaaatacat aaaaaaaatt ctttatttaa ttatcaaact ctccactacc      60
tttcccacca accgttacaa tcctgaatgt tggaaaaaac taactacatt gatataaaaa     120
aactacatta cttcctaaat catatcaaaa ttgtataaat atatccactc aaaggagtct     180
agaagatcca cttggacaaa ttgcccatag ttggaaagat gttcaccaag tcaacaagat     240
ttatcaatgg aaaaatccat ctaccaaact tactttcaag aaaatccaag gattatagag     300
taaaaaatct atgtattatt aagtcaaaaa gaaaaccaaa gtgaacaaat attgatgtac     360
aagtttgaga ggataagaca ttggaatcgt ctaaccagga ggcggaggaa ttccctagac     420
agttaaaagt ggccggaatc ccggtaaaaa agattaaaat tttttttgtag agggagtgct     480
tgaatcatgt tttttatgat ggaaatagat tcagcaccat caaaaacatt caggacacct     540
aaaattttga gtttaacaa aaataacttg gatctacaaa aatccgtatc ggattttctc     600
taaatataac tagaattttc ataactttca aagcaactcc tccctaacc gtaaaacttt     660
tcctacttca ccgttaatta cattccttaa gagtagataa agaaataaag taaataaaag     720
tattcacaaa ccaacaattt atttctttta tttacttaaa aaaacaaaaa gtttatttat     780
tttacttaaa tggcataatg acatatcgga gatccctcga acgagaatct tttatctccc     840
tggttttgta ttaaaaagta atttattgtg gggtccacgc ggagttggaa tcctacagac     900
gcgctttaca tacgtctcga gaagcgtgac ggatgtgcga ccggatgacc ctgtataacc     960
caccgacaca gccagcgcac agtatacacg tgtcatttct ctattggaaa atgtcgttgt    1020
tatccccgct ggtacgcaac caccgatggt gacaggtcgt ctgttgtcgt gtcgcgtagc    1080
gggagaaggg tctcatccaa cgctattaaa tactcgcctt caccgcgtta cttctcatct    1140
tttctcttgc gttgtataat cagtgcgata ttctcagaga gcttttcatt caaaggtatg    1200
gagttttgaa gggcttttact cttaacattt gtttttcttt gtaaattgtt aatggtggtt    1260
tctgtggggg aagaatcttt tgccaggtcc ttttgggttt cgcatgttta tttgggttat    1320
ttttctcgac tatggctgac attactaggg ctttcgtgct ttcatctgtg ttttcttccc    1380
ttaataggtc tgtctctctg gaatatttaa ttttcgtatg taagttatga gtagtcgctg    1440
tttgtaatag gctcttgtct gtaaaggttt cagcaggtgt ttgcgtttta ttgcgtcatg    1500
tgtttcagaa ggccttttgca gattattgcg ttgtacttta atattttgtc tccaaccttg    1560
ttatagtttc cctcctttga tctcacagga acccttctt ctttgagcat tttcttgtgg    1620
cgttctgtag taatatttta atttgggcc cgggttctga gggtaggtga ttattccagt    1680
```

-continued

```
gatgtgcttt ccctataagg tcctctatgt gtaagctgtt agggtttgtg cgttactatt    1740
gacatgtcac atgtcacata ttttcttcct cttatccttc gaactgatgg ttcttttttct   1800 aattcgtgga ttgctggtgc catattttat ttctattgca actgtatttt agggtgtctc    1860 tttcttttg atttcttgtt aatatttgtg ttcaggttgt aactatgggt tgctagggtg     1920
tctgccctct tcttttgtgc ttctttcgca gaatctgtcc gttggtctgt atttgggtga    1980
tgaattattt attccttgaa gtatctgtct aattagcttg tgatgatgtg caggtatatt    2040
cgttagtcat atttcaattt caag atg cag atc ttt gtc aag act ctc acc       2091
                          Met Gln Ile Phe Val Lys Thr Leu Thr
                           1               5
```

| | |
|---|---|
| ggt aag acc atc act ctc gag gtc gag agc tct gac acc att gac aat<br>Gly Lys Thr Ile Thr Leu Glu Val Glu Ser Ser Asp Thr Ile Asp Asn<br> 10            15                  20                  25 | 2139 |
| gtt aaa gct aag atc cag gac aag gaa ggg att ccc ccc gac cag cag<br>Val Lys Ala Lys Ile Gln Asp Lys Glu Gly Ile Pro Pro Asp Gln Gln<br>                30                      35                      40 | 2187 |
| cgt ctg atc ttc gca gga aag cag ctt gag gac ggc cga acc ctt gcc<br>Arg Leu Ile Phe Ala Gly Lys Gln Leu Glu Asp Gly Arg Thr Leu Ala<br>                   45                      50                    55 | 2235 |
| gat tac aac atc cag aaa gaa tct acc ctc cac ctt gtt ctc cgt ttg<br>Asp Tyr Asn Ile Gln Lys Glu Ser Thr Leu His Leu Val Leu Arg Leu<br>     60                      65                      70 | 2283 |
| agg ggt ggc atg caa atc ttt gta aaa aca cta act gga aag aca att<br>Arg Gly Gly Met Gln Ile Phe Val Lys Thr Leu Thr Gly Lys Thr Ile<br> 75                  80                  85 | 2331 |
| aca ttg gaa gtt gag agc tcg gac acc att gac aac gtc aag gcc aag<br>Thr Leu Glu Val Glu Ser Ser Asp Thr Ile Asp Asn Val Lys Ala Lys<br> 90                  95                100             105 | 2379 |
| atc cag gac aag gaa gga att ccc cct gac cag cag agg ctt atc ttc<br>Ile Gln Asp Lys Glu Gly Ile Pro Pro Asp Gln Gln Arg Leu Ile Phe<br>                110                    115             120 | 2427 |
| gct ggt aag cag ctg gag gat ggc agg acc ttg gct gat tac aat att<br>Ala Gly Lys Gln Leu Glu Asp Gly Arg Thr Leu Ala Asp Tyr Asn Ile<br>                125                    130             135 | 2475 |
| caa aag gaa tcg acc ctg cat ttg gtg ctt cgt cta aga gga ggc atg<br>Gln Lys Glu Ser Thr Leu His Leu Val Leu Arg Leu Arg Gly Gly Met<br>                140                    145             150 | 2523 |
| caa atc ttt gtg aaa acc ctt aca ggt aaa acc att act ctg gaa gtg<br>Gln Ile Phe Val Lys Thr Leu Thr Gly Lys Thr Ile Thr Leu Glu Val<br>                155                    160             165 | 2571 |
| gaa agc tcg gac acc att gac aat gtg aag gct aag atc cag gac aag<br>Glu Ser Ser Asp Thr Ile Asp Asn Val Lys Ala Lys Ile Gln Asp Lys<br>170                  175                    180             185 | 2619 |
| gag gga att cca cct gac cag cag agg ttg atc ttt gcc ggt aag cag<br>Glu Gly Ile Pro Pro Asp Gln Gln Arg Leu Ile Phe Ala Gly Lys Gln<br>                  190                    195             200 | 2667 |
| ctg gaa gat ggt cgt act ctc gcc gat tac aat att cag aag gaa tcg<br>Leu Glu Asp Gly Arg Thr Leu Ala Asp Tyr Asn Ile Gln Lys Glu Ser<br>                205                    210             215 | 2715 |
| acc ctt cac ctg gtg ctc cgt ctc cgc ggt ggc ttt taggtttggg<br>Thr Leu His Leu Val Leu Arg Leu Arg Gly Gly Phe<br>            220                    225 | 2761 |

```
tgttatttgt ggataataaa ttcgggtgat gttcagtgtt tgtcgtattt ctcacgaata    2821
aattgtgttt atgtatgtgt tagtgttgtt tgtctgtttc agaccctctt atgttatatt    2881
tttcttttcg tcggtcagtt gaagccaata ctggtgtcct ggccggcact gcaataccat    2941
```

```
ttcgtttaat ataaagactc tgttatccgt tatgtaattc catgttatgt ggtgaaatgt       3001
ggatgaaatt cttagaaatt attattgtaa tttgaaactt ccttcgtcaa taatctgcac       3061
aacacattta ccaaaaaaaa aa                                                3083

<210> SEQ ID NO 2
<211> LENGTH: 2064
<212> TYPE: DNA
<213> ORGANISM: Pinus radiata
<220> FEATURE:
<221> NAME/KEY: 5'UTR
<222> LOCATION: (1)...(2064)
<220> FEATURE:
<221> NAME/KEY: intron
<222> LOCATION: (1196)...(2033)

<400> SEQUENCE: 2 aaaaccccctc acaaatacat aaaaaaaatt ctttatttaa ttatcaaact ctccactacc       60
tttcccacca accgttacaa tcctgaatgt tggaaaaaac taactacatt gatataaaaa       120
aactacatta cttcctaaat catatcaaaa ttgtataaat atatccactc aaaggagtct       180
agaagatcca cttggacaaa ttgcccatag ttggaaagat gttcaccaag tcaacaagat       240
ttatcaatgg aaaaatccat ctaccaaact tactttcaag aaaatccaag gattatagag       300
taaaaaatct atgtattatt aagtcaaaaa gaaaaccaaa gtgaacaaat attgatgtac       360
aagtttgaga ggataagaca ttggaatcgt ctaaccagga ggcggaggaa ttccctagac       420
agttaaaagt ggccggaatc ccggtaaaaa agattaaaat tttttttgtag agggagtgct       480 tgaatcatgt ttttatgat ggaaatagat tcagcaccat caaaaacatt caggacacct       540
aaaattttga agtttaacaa aaataacttg gatctacaaa aatccgtatc ggatttcctc       600
taaatataac tagaattttc ataactttca aagcaactcc tccctaacc gtaaaacttt       660 tcctacttca ccgttaatta cattcctaa gagtagataa agaaataaag taaataaaag       720
tattcacaaa ccaacaattt atttcttta tttacttaaa aaaacaaaaa gtttatttat       780
tttacttaaa tggcataatg acatatcgga gatccctcga acgagaatct tttatctccc       840
tggttttgta ttaaaaagta atttattgtg gggtccacgc ggagttggaa tcctacagac       900
gcgctttaca tacgtctcga aagcgtgac ggatgtgcga ccggatgacc ctgtataacc       960
caccgacaca gccagcgcac agtatacacg tgtcatttct ctattggaaa atgtcgttgt      1020
tatccccgct ggtacgcaac caccgatggt gacaggtcgt ctgttgtcgt gtcgcgtagc      1080
gggagaaggg tctcatccaa cgctattaaa tactcgcctt caccgcgtta cttctcatct      1140
tttctcttgc gttgtataat cagtgcgata ttctcagaga cttttcatt caaaggtatg      1200 gagttttgaa gggctttact cttaacattt gtttttcttt gtaaattgtt aatggtggtt      1260
tctgtggggg aagaatcttt tgccaggtcc ttttgggttt cgcatgttta tttgggttat      1320
ttttctcgac tatggctgac attactaggg ctttcgtgct ttcatctgtg ttttcttccc      1380
ttaataggtc tgtctctctg gaatatttaa ttttcgtatg taagttatga gtagtcgctg      1440
tttgtaatag gctcttgtct gtaaaggttt cagcaggtgt ttgcgttta ttgcgtcatg       1500 tgtttcagaa ggcctttgca gattattgcg ttgtacttta atatttgtc tccaaccttg      1560 ttatagtttc cctcctttga tctcacagga acccttcctt ctttgagcat ttcttgtgg      1620 cgttctgtag taatattta attttgggcc cgggttctga gggtaggtga ttattccagt      1680
gatgtgcttt ccctataagg tcctctatgt gtaagctgtt agggtttgtg cgttactatt      1740
gacatgtcac atgtcacata ttttcttcct cttatccttc gaactgatgg ttctttttct      1800
```

-continued

```
aattcgtgga ttgctggtgc catattttat ttctattgca actgtatttt agggtgtctc   1860 tttcttttg  atttcttgtt aatatttgtg ttcaggttgt aactatgggt tgctagggtg   1920
tctgccctct tctttgtgc  ttctttcgca gaatctgtcc gttggtctgt atttgggtga   1980
tgaattattt attccttgaa gtatctgtct aattagcttg tgatgatgtg caggtatatt   2040
cgttagtcat atttcaattt caag                                          2064
```

<210> SEQ ID NO 3
<211> LENGTH: 1226
<212> TYPE: DNA
<213> ORGANISM: Pinus radiata
<220> FEATURE:
<221> NAME/KEY: 5'UTR
<222> LOCATION: (1)...(1266)

<400> SEQUENCE: 3

```
aaacccctc  acaaatacat aaaaaaaatt ctttatttaa ttatcaaact ctccactacc    60
tttcccacca accgttacaa tcctgaatgt tggaaaaaac taactacatt gatataaaaa   120
aactacatta cttcctaaat catatcaaaa ttgtataaat atatccactc aaaggagtct   180
agaagatcca cttggacaaa ttgcccatag ttggaaagat gttcaccaag tcaacaagat   240
ttatcaatgg aaaaatccat ctaccaaact tactttcaag aaaatccaag gattatagag   300
taaaaaatct atgtattatt aagtcaaaaa gaaaaccaaa gtgaacaaat attgatgtac   360
aagtttgaga ggataagaca ttggaatcgt ctaaccagga ggcggaggaa ttccctagac   420
agttaaaagt ggccggaatc ccggtaaaaa agattaaaat ttttttgtag agggagtgct   480
tgaatcatgt ttttatgat  ggaaatagat tcagcaccat caaaaacatt caggacacct   540 aaaatttga  agtttaacaa aaataacttg gatctacaaa aatccgtatc ggattttctc   600
taaatataac tagaatttc  ataactttca aagcaactcc tccctaacc  gtaaaacttt   660 tcctacttca ccgttaatta cattccttaa gagtagataa agaaataaag taaataaaag   720
tattcacaaa ccaacaattt atttcttta  tttacttaaa aaaacaaaaa gtttatttat   780
tttacttaaa tggcataatg acatatcgga gatccctcga acgagaatct tttatctccc   840
tggttttgta ttaaaaagta atttattgtg gggtccacgc ggagttggaa tcctacagac   900
gcgctttaca tacgtctcga gaagcgtgac ggatgtgcga ccggatgacc ctgtataacc   960
caccgacaca gccagcgcac agtatacacg tgtcatttct ctattggaaa atgtcgttgt  1020
tatccccgct ggtacgcaac caccgatggt gacaggtcgt ctgttgtcgt gtcgcgtagc  1080
gggagaaggg tctcatccaa cgctattaaa tactcgcctt caccgcgtta cttctcatct  1140
tttctcttgc gttgtataat cagtgcgata ttctcagaga gcttttcatt caaggtata   1200 ttcgttagtc atatttcaat ttcaag                                       1226
```

<210> SEQ ID NO 4
<211> LENGTH: 485
<212> TYPE: DNA
<213> ORGANISM: Pinus radiata
<220> FEATURE:
<221> NAME/KEY: 5'UTR
<222> LOCATION: (1)...(431)
<220> FEATURE:
<221> NAME/KEY: TATA_signal
<222> LOCATION: (350)...(356)
<220> FEATURE:
<221> NAME/KEY: CAAT_signal
<222> LOCATION: (326)...(333)

```
<400> SEQUENCE: 4
agtaaaattg gcccatgtag gactaagtca aaatcaaaat tccatctcta aaagcggaac      60
tttgtcccct gaaaattttg actaatttcc aaccaaaaaa aagtgggggga aaatataaaa     120 ctctaactaa taaaacaata atcaccaaaa atctatcacc aaaaatgaaa aaagattttg     180
aatactaggc catatgagct acacaaattt caaaagtatc ttacacttat tacgcacccg     240
gatgtcccca ctttcgaaaa acccgtttca agcctttcac gaaagtccaa cggtcagaaa     300
attcaaaatg actgtttgag gcagagccaa tctaggacca cgctccattt atatatggcc     360
tctgcttctc tcgacccttta gagtcctctg ctctgcgaat cttgttgtta gttactgtgt     420
acgctgtaac aatggatgcc tatgagaagt tggagaaggt gggagaagga acctatggga    480
aggtg                                                                485

<210> SEQ ID NO 5
<211> LENGTH: 246
<212> TYPE: DNA
<213> ORGANISM: Pinus radiata
<220> FEATURE:
<221> NAME/KEY: 5'UTR
<222> LOCATION: (1)...(167)
<220> FEATURE:
<221> NAME/KEY: TATA_signal
<222> LOCATION: (185)...(191)

<400> SEQUENCE: 5
tgagaacatg ataagctgtg taaattcatg ctagtcacca taacttttct cattgctttt      60
catccacact gttgattcat tcattatata agatcagatt cgtatgatat acaggcaacc    120
atagaaacaa ccagcaaagt tactagcagg aaatccaact aggtatcatg aagactacca    180
acgcaggctc gataatgttg gtgctcatta ttttttgggtg ctgtttcatt ggggtcatag   240
ctacat                                                              246

<210> SEQ ID NO 6
<211> LENGTH: 600
<212> TYPE: DNA
<213> ORGANISM: Pinus radiata
<220> FEATURE:
<221> NAME/KEY: 5'UTR
<222> LOCATION: (1)...(167)
<220> FEATURE:
<221> NAME/KEY: TATA_signal
<222> LOCATION: (471)...(477)
<220> FEATURE:
<221> NAME/KEY: CAAT_signal
<222> LOCATION: (444)...(451)

<400> SEQUENCE: 6
caccaattta atgggatttc agatttgtat cccatgctat tggctaagcc attttttctta     60 ttgtaatcta accaattcca atttccaccc tggtgtgaac tgactgacaa atgcggcccg    120
aaaacagcga atgaaatgtc tgggtgatcg gtcaaacaag cggtgggcga gagaacgcgg    180
gtgttggcct agccgggatg ggggtaggta gacggcgtat taccggcgag ttgtccgaat    240
ggagttttcg gggtaggtag taacgtagac gtcaatggaa aaagtcataa tctccgtcaa    300
aaatccaacc gctccttcac accgcagagt tggtggccac gggaccctcc acccactcac    360
tcaatcgatc gcctgccgtg gttgcccatt attcaaccat acgccacttg actcttcacc    420
aacaattcca ggccggcttt cgagacaatg tactgcacag gaaaatccaa tataaaaggc    480
cggcctccgc ttccttctca gtagccccca gctcattcaa ttcttcccac tgcaggctac    540
```

```
atttgtcaga cacgttttcc gccattttc gcctgtttct gcggagaatt tgatcaggtt    600
```

<210> SEQ ID NO 7
<211> LENGTH: 591
<212> TYPE: DNA
<213> ORGANISM: Eucalyptus grandis
<220> FEATURE:
<221> NAME/KEY: 5'UTR
<222> LOCATION: (1)...(591)
<220> FEATURE:
<221> NAME/KEY: TATA_signal
<222> LOCATION: (432)...(437)

<400> SEQUENCE: 7

```
agtttggaat gtgttgtgtg tgatgtgatg gagagtatca gcattccaaa catgacatgg    60
ttttaactta tctgcaatgg tttcttttt attcagcgaa ctcgatggct gatgctgaga    120
gaaatgaatt gggaagtcga tcgacaatgg cagctcaact caatgatcct caggtataag    180
cattttttg gcagctctgg tcattgtgtc ttcaactttt agatgagagc aaatcaaatt    240
gactctaata ccggttatgt gatgagtgaa tcatttgctt ttagtagctt taatttatgc    300
ccccatctta gttgggtata aaggttcaga gtgcgaagat tacatctatt ttggttcttg    360
caggacacag ggattcatgc tagacacatc agcagtgttt ctacgttgga tagtggtatg    420
tacttagcta ctataaagga aattttgata gatatgtttg atatggtgct tgtacagatc    480
tatttaatgt caatgtattt gaaactatct tgtctcataa ctttcttgaa gaatacaatg    540
atgagactgg gaaccctatc tggaagaata gagtggagag ctggaaggac a            591
```

<210> SEQ ID NO 8
<211> LENGTH: 480
<212> TYPE: DNA
<213> ORGANISM: Eucalyptus grandis
<220> FEATURE:
<221> NAME/KEY: 5'UTR
<222> LOCATION: (1)...(480)

<400> SEQUENCE: 8

```
atgctgagag aaatgaattg ggaagtcgat cgacaatggc agctcaactc aatgatcctc    60
aggtataagc attttttgg cagctctggt cattgtgtct tcaactttta gatgagagca    120
aatcaaattg actctaatac cagttatgtg atgagtgaat catttgcttt tagtagcttt    180
aatttatgcc cccatcttag ttgggtataa aggttcagag tgcgaagatt acatctattt    240
tggttcttgc aggacacagg gattcatgct agacacatca gcagtgttc tacgttggat    300
agtggtatgt acttagctac tataaaggaa attttgatag atatgtttga tatggtgctt    360
gtacagatct atttaatgcc aatgtatttg aaactatctt gtctcataac tttcttgaag    420
aatacaatga tgagactggg aaccctatct ggaagaatag agtggagagc tggaaggaca    480
```

<210> SEQ ID NO 9
<211> LENGTH: 308
<212> TYPE: DNA
<213> ORGANISM: Eucalyptus grandis
<220> FEATURE:
<221> NAME/KEY: 5'UTR
<222> LOCATION: (1)...(259)

<400> SEQUENCE: 9

```
gcccatctca ggtgcaacgg tttaactgat gtttactaca cgcaaggggg aggtatccgg    60
aaagcttgca atcgggtaa aaacgaaaat gggcgacgtg gactcagcct gcccatgttt    120
tcggtctctc tcctggactt ccatgcccga taagggccgc caactctctc tctctctctc    180
```

```
tttttctctc acatctctct gcctgttcat gtcgcctgca agtgaagatt cgtcggagca      240
agaaggacga accgggcaca tggcggggtc ggcggtcgcg acggttctaa agggtctctt      300
cctggtgt                                                              308
```

```
<210> SEQ ID NO 10
<211> LENGTH: 300
<212> TYPE: DNA
<213> ORGANISM: Eucalyptus grandis
<220> FEATURE:
<221> NAME/KEY: 5'UTR
<222> LOCATION: (1)...(251)

<400> SEQUENCE: 10
```

```
gcccatctca ggtgcaacgg tttaactgat gtttactaca cgcaaggggg aggtatccgg       60
aaagcttgca atcgggtaa aaacgaaaat gggcgacgtg gactcagcct gcccatgttt      120
tcggtccctc tcctggactt ccatgcccga taaaggccgc caactctctc tcttttctc      180 tcacatctct ctgcctgttc atgtcgcctg caagtgaaga ttcgtcggag caagaaggac      240
gaactgggca tatggcgggg tcggcggtcg cgacggttct aaagggtctc ttcctggtgt      300
```

```
<210> SEQ ID NO 11
<211> LENGTH: 297
<212> TYPE: DNA
<213> ORGANISM: Eucalyptus grandis

<400> SEQUENCE: 11
```

```
gtgcaacggt taactgatg tttactacac gcaaggggga ggtatccgga aagcttgcaa       60
atcgggtaaa aacgaaaatg ggcgacgtgg actcagcctg cccatgtttt cggtctctct      120
cctggacttc catgcccgat aagggccgcc aactctctct ctctctctct tttctctca      180 catctctctg cctgttcatg tcgcctgcaa gtgaagattc gtcggagcaa gaaggacgaa      240
ctgggcatat ggcggggtcg gcggtcgcga cggttctaaa gggtctcttc ctggtgt        297
```

```
<210> SEQ ID NO 12
<211> LENGTH: 661
<212> TYPE: DNA
<213> ORGANISM: Eucalyptus grandis

<400> SEQUENCE: 12
```

```
ctgagccatt taattcgaga gcacatcgcc caaaattatt cttcttgctg ccataactgt       60
cgaattttct cttttaggta agtaaccaat gatgcatcat gttgacaaaa aggctgatta      120
gtatgatctt ggagttgttg gtgcaaattt gcaagctgac gatggcccct cagggaaatt      180
aaggcgccaa cccagattgc aaagagcaca agagcacga tccaaccttt ccttaacaag      240
atcatcacca gatcggccag taagggtaat attaatttaa caaatagctc ttgtaccggg      300
aactccgtat ttctctcact tccataaacc cctgattaat ttggtgggaa agcgacagcc      360
aacccacaaa aggtcagatg tcatcccacg agagagagag agagagagag agagagagag      420
agagttttct ctctatattc tggttcaccg gttggagtca atggcatgcg tgacgaatgt      480
acatattggt gtagggtcca atattttgcg ggagggttgg tgaaccgcaa agttcctata      540
tatcgaacct ccaccaccat acctcacttc aatccccacc atttatccgt tttatttcct      600
ctgctttcct ttgctcgagt ctcgcggaag agagagaaga gaggagaggga gagaatgggt      660 t                                                                    661
```

<210> SEQ ID NO 13
<211> LENGTH: 336
<212> TYPE: DNA
<213> ORGANISM: Pinus radiata

<400> SEQUENCE: 13

| | | | | | |
|---|---|---|---|---|---|
| actagtgatt | tgttgagaat | gagtaggcat | tgctacaccc | atcatcacaa | gcatcatcat | 60 |
| gaggagaaga | agatccattt | ctcactctat | tactcgaact | tccttcagat | taggctgtgt | 120 |
| atttctcact | ctaccactcc | aacttccttc | aaatgctgtg | agttttttgtt | gtaattgccc | 180 |
| cgtctattta | aatcgcagc | agcactcgtc | atataaagac | ccgtgtgtgt | gaacaacaac | 240 |
| caagtgattt | gaattggaaa | tgaagagcga | gaatggcggt | gtcatgaccg | ggagcaacca | 300 |
| gcccgggccg | tcgaccacgc | gtgccctata | gtaatc | | | 336 |

<210> SEQ ID NO 14
<211> LENGTH: 763
<212> TYPE: DNA
<213> ORGANISM: Pinus radiata

<400> SEQUENCE: 14

| | | | | | |
|---|---|---|---|---|---|
| actagtgatt | tgttgagaat | gagtaggcat | tgctacaccc | atcatcacaa | gcatcaacat | 60 |
| gaagagaaga | agacgatcca | tttctcactc | tatcactcca | acttccttca | gattaggctg | 120 |
| tgtatttctc | actctaccac | tccaactacc | actccaactt | attgccgcaa | aagagagagg | 180 |
| ttcccaaact | ctgtcggaat | tctcccactc | aaagcattaa | aggaaagatc | taattgctgc | 240 |
| aaaaagaga | gattcccaat | atatttctca | actcccttca | aatgatttct | cactctacca | 300 |
| ctccaactcc | cttcaaatga | tttctcactc | taccactcca | acttccttca | aatgctgtga | 360 |
| gttttttgttg | taattgcccc | gtctatttat | aatcgcagca | gcactcgtca | tataaagacc | 420 |
| cgtgcgtgtg | aacaacaatg | gcggtgtctt | gactgggagc | aaccgcataa | agaaagtggg | 480 |
| cttcatacat | taaaaaaatc | tgtaaatttt | acggatttgg | aaaaaggaag | agcaggaggg | 540 |
| acctcccgac | ttgacccgag | aatggcggtg | tcttgaccgc | gtaaagaaag | tggtcttctg | 600 |
| tacccgactt | gacccgaaaa | aagaggaaac | gttgaacgag | acaatctctg | ggaacttcat | 660 |
| cgaaatgaac | ctcacgactt | gactctttcg | attgtactgt | tttcattgtt | cccgcgtaaa | 720 |
| acgaccagcc | cggccgtcg | accacgcgtg | ccctatagta | atc | | 763 |

<210> SEQ ID NO 15
<211> LENGTH: 40
<212> TYPE: DNA
<213> ORGANISM: Artificial Sequence
<220> FEATURE:
<223> OTHER INFORMATION: Made in a lab

<400> SEQUENCE: 15

| | | |
|---|---|---|
| acggataaca | gagtctttat | attaaacgaa atggtattgc | 40 |

<210> SEQ ID NO 16
<211> LENGTH: 51
<212> TYPE: DNA
<213> ORGANISM: Artificial Sequence
<220> FEATURE:
<223> OTHER INFORMATION: Made in a lab

<400> SEQUENCE: 16

| | | | |
|---|---|---|---|
| tgacgcggcc | gcgaccgacg | aaaagaaaaa | tataacataa gagagtctga a | 51 |

<210> SEQ ID NO 17

```
<211> LENGTH: 27
<212> TYPE: DNA
<213> ORGANISM: Artificial Sequence
<220> FEATURE:
<223> OTHER INFORMATION: Made in a lab

<400> SEQUENCE: 17
tatagcggcc gcggggggggg ggggggg                                         27

<210> SEQ ID NO 18
<211> LENGTH: 30
<212> TYPE: DNA
<213> ORGANISM: Artificial Sequence
<220> FEATURE:
<223> OTHER INFORMATION: Made in a lab

<400> SEQUENCE: 18
cggagaacaa ggtggagggt agattctttc                                      30

<210> SEQ ID NO 19
<211> LENGTH: 31
<212> TYPE: DNA
<213> ORGANISM: Artificial Sequence
<220> FEATURE:
<223> OTHER INFORMATION: Made in a lab

<400> SEQUENCE: 19
tctgcatctt gaaattgaaa tatgactaac g                                    31

<210> SEQ ID NO 20
<211> LENGTH: 363
<212> TYPE: DNA
<213> ORGANISM: Eucalyptus grandis

<400> SEQUENCE: 20
aatcgggtga aaatagggcc gccctaaatt agaattgaca acatttcttg ggcaaagtta      60
atgtaagtta catgaaaaaa aaaaaaaagg atagtttgtt ggaagtaatg gagcatttgt     120
attgtgaaat tcacgataga gctaacaaaa ataaaggtag ttggtgggtt aacccagtta     180
aaaaagaaca ataatttgaa gagaggagag agagagagag gaggggagga gcatttcgat     240
aaattcacta gaaaaaatgc gtgttttagt ataaatgaga gtggaaatag ggccatctag     300
ggaacgatcg atcgcccctg cacccggcca tctggagagt ctgtttatac ttctctccgg     360
ctt                                                                  363

<210> SEQ ID NO 21
<211> LENGTH: 839
<212> TYPE: DNA
<213> ORGANISM: Pinus radiata
<220> FEATURE:
<221> NAME/KEY: misc_feature
<222> LOCATION: (1)...(839)
<223> OTHER INFORMATION: n = A,T,C or G

<400> SEQUENCE: 21
gtatggagtt tgaagggct ttactcttaa catttgtttt tctttgtaaa ttgttaatgg       60
tggtttctgt gggggaagaa tcttttgcca ggtccttttg ggtttcgcat gtttatttgg    120 gttattttc tcgactatgg ctgacattac tagggctttc gtgctttcat ctgtgttttc     180
ttcccttaat aggtctgtct ctctggaata tttaattttc gtatgtaagt tatgagtagt    240
cgctgtttgt aataggctct tgtctgtaaa ggtttcagca ggtgtttgcg ttttattgcg    300
tcatgtgttt cagaaggcct ttgcagatta ttgcgttgta ctttaatatt ttgtctccaa    360
```

```
ccttgttata gtttccctcc tttgatctca caggaaccct ttcttctttg agcattttct    420
tgtggcgttc tgtagtaata ttttaatttt gggcccgggt tctgagggta ggtgattatt    480
cncagtgatg tgctttccct ataaggtcct ctatgtgtaa gctgttaggg tttgtgcgtt    540
actattgaca tgtcacatgt cacatatttt cttcctctta tccttcgaac tgatggttct    600
ttttctaatt cgtggattgc tggtgccata ttttatttct attgcaactg tattttaggg    660
tgtctctttc tttttgattt cttgttaata tttgtgttca ggttgtaact atgggttgct    720
agggtgtctg ccctcttctt ttgtgcttct ttcgcagaat ctgtccgttg gtctgtattt    780
gggtgatgaa ttatttattc cttgaagtat ctgtctaatt agcttgtgat gatgtgcag    839
```

<210> SEQ ID NO 22
<211> LENGTH: 881
<212> TYPE: DNA
<213> ORGANISM: Eucalyptus grandis

<400> SEQUENCE: 22

```
acgtgacgat gctcgagtct cgcgttctcc tctctcttgt tctgcaaaac agaaaagaga     60
gaatggaggt tggcctctct caattacgtg gacgccaatg agataactca ggtgggcgac    120
aaaacaaacg cctcttgatt tcctcaaacc ccaaaccgaa tccctcgtca aggggcaagg    180
cttttggtcc cgcggcccca cggatcgctc gttcccgtct cgccacgtcg cgtcgcagcg    240
tgtcgagcaa acagaggggt ccgagcgact ataaaatccc gacgccatcg acaccacagt    300
ccatcgaaaa ccttgttcaa ttcccaagtg aaagtgagta actgtgaacg aagagttgaa    360
ctttgcatct cggcgtgtgg attcaagagg aagcagcaaa gtggaaatgg acaactccaa    420
gatgggcttc aatgcaggc aggccaaggg ccagactcag gagaagagca accagatgat    480
ggataaggca tccaacactg ctcaatctgc aagggattcc atgcaagaga ctggtcagca    540
gatgaaggcc aaagcccagg gtgctgctga tgcagtgaag aatgccaccg ggatgaacaa    600
atgaagagct caagacatga atgaataaat aattaagctc tggttatcat ttgcttttcc    660
ggtcgtttgt tgtcctgttt ttccttgtca agagcttatt atgagggtcc ttttgctctt    720
tccttagttc tttttgtttc ttggttgttc catgaagaga gcaactctct gtgtttgaga    780
gtactcatct cgcttcataa ggtctcagta tgtagttgcc tttcgagaat gttatgttct    840
ctctcataat gctattctga ttttataaaa aaaaaaaaa a                          881
```

<210> SEQ ID NO 23
<211> LENGTH: 350
<212> TYPE: DNA
<213> ORGANISM: Eucalyptus grandis

<400> SEQUENCE: 23

```
ctatagggca cgcgtggtcg acggcccggg ctggtccttt cttacaaaaa gcaaaattct     60
tataattttt tttgatataa taaaaatgat ccataaactt ttgcttaatg tgcaacgtaa    120
accataatat attcaacgtg atgcttaaac tttaatcgag tatgcaatgt agtccataat    180
atattcaata tgatccttca atccaattga agtgtgcaat gtggtcgcta gattttttta    240
tgtattcaac ttagtcttta agctaccaac cttccaataa tttatgtttt agaaataata    300
tcgaacatct tttatattat tcaaggaata aaacgaacat gcatcaaaag                350
```

<210> SEQ ID NO 24
<211> LENGTH: 49
<212> TYPE: DNA

<213> ORGANISM: Eucalyptus grandis

<400> SEQUENCE: 24

```
actatagggc acgcgtggtc gacggcccgg gctggtactt ttttttttct        49
```

<210> SEQ ID NO 25
<211> LENGTH: 909
<212> TYPE: DNA
<213> ORGANISM: Eucalyptus grandis

<400> SEQUENCE: 25

```
cagggtaaag aaaatggaat atttgcttgg ccccccagct ttgaaagttg ctgtaagaac    60
acactcacct tgcatttata cgatggttgt gagcagtgca ggctggtggt gctgcaaatt   120
tatgatgctg atgtgatagg cagatgaatg cagttgagc taagttaaag ccctcataca    180
tagatcagag caggaggagt agtatatata ggcatcttgg caagtcccta aaagagcggc   240
ttcgtgtatt cccacatatt cctctctcgt tagaacgttc agaaatgggt ggcccttga    300
ctcttgatgc agaggttgag gttaagtctc ctgcagacaa gttctgggtg agcgtgagag   360
actccaccaa actgttccca agatcttcc cggaccagta caagaatatt gaagtccttg    420
agggagatgg gaaggctcct ggctcagttc gcctcttcac gtatggtgaa ggttctccac   480
ttgttaaagt atcaaaggag aagattgatg gtgtggacga agcagacaag gtcgtgacct    540
acagcgttat agacggtgat ctcctgaagt actacaagaa tttcaatggc agcatcaagg    600
taattcctaa aggagacgga agcttggtga atggtcgtg tgggtttgag aaggcaagcg    660
atgaaattcc tgatccccac gtaatcaagg acttcgcaat ccagaatttc aaagagcttg    720
atgagttcat cctcaaggca tagatgccgc caatcgtcta tccggatttg cactaaatat   780
caataaaata atgcggagct ggactccgca cttctatatg catctagtat gagagtcccc    840
tgctgtctct gtttgtattc acttgaaggg ttttctatta agctctcttt actgcctccg    900
aaaaaaaaa                                                          909
```

<210> SEQ ID NO 26
<211> LENGTH: 430
<212> TYPE: DNA
<213> ORGANISM: Eucalyptus grandis

<400> SEQUENCE: 26

```
tggagcttga gatagatcga ccgagagatc ccagcggaaa tagaagattt cctgatacca    60
tcgatccttc ttctccaatg gctgcgaatt tcgtcattcc gaccaaaatg aaggcttggg   120
tgtaccgtga gcacggaaac gtcgccgacg tattgggatt ggacccggaa ctcaaggtcc   180
ctgaattgca agaaggccaa gtgctggtta agttcttgc cgcagcgctc aatccagtcg    240
acgccgcgag aatgaagggg gttatcaagc tcccgggctt ttctctaccg gccgtgccag   300
gttacgatct cgccggcgtt gtggtaaagg tgggccgcga agtgaaggag ctcaagatcg    360
gggacgaggt atatggattt atgtttcacg ccaagaaaga cgggacgctg gctgagtacg    420
cagccgtgga                                                         430
```

<210> SEQ ID NO 27
<211> LENGTH: 1253
<212> TYPE: DNA
<213> ORGANISM: Eucalyptus grandis

<400> SEQUENCE: 27

```
gcttgagata gatcgactga gagatcctag tggaaataga agatttcctg ataccatcga    60
```

-continued

```
tccattcttc tccaatggct gcgaatttcg tcattccaac caaaatgaag gcttgggtgt         120
accgtgagca cggagacgtc gccaacgtat tgggattgga cccggaactc aaggtccctg         180
aattgcaaga aggccaagtg ctggttaaag ttcttgccgc ggcgctcaat ccaatcgaca         240
ccgcgagagt gaagggggtt atcaagctcc cgggcttttc tctaccggcc gtgccaggtt         300
acgatctcgc cggcgttgtg gtgaaggtgg gccgcgaagt gaaggagctc aaggtcgggg         360
acgaggtata tggatttatg tttcacgcca agaaagacgg gacgctggct gagtacgcag         420
ccgtggaaga gtcgttcttg ctttgaagc caagaagct gcgtttcggg gaggctgctt          480
ctctgccggt ggtcattcag accgcctatg gaggccttga aagagctggc ctctctcatg        540
gcaagtccct cctcgtctta ggtggtgctg gtggcgtcgg cacactcata atacagctag        600
ctaaggaagt ttttggtgca tcaagagtag cagctacatc cagcactggg aagctagagt        660
tgttgaagag cttgggtgct gatctggcca ttgactacac caaagtcaac tttgaagacc        720
tcccagaaaa gtttgatgtt gtctacgata cagttgggga aattgagcgg gcagcgaagg        780
ctgtgaagcc aggagggagc atcgtgacga tcgtaaaaca aaacaagaca ttaccccgc         840 ctgctttctt ttttgcagta acttcgaacc gttcgacctt ggagaagttg aagcccttct        900
tggagagcgg gaaggtgaag ccggtgatcg accccaagag cccgttccca ttttcgcaag        960
ccattgaggc cttctcgtat cttcaaaccc gccgggcaac tggaaaactc gtgattcacc       1020
ccgtcccatg atacacaaac gagaaagaaa taaagcgtcc acatggatct gccttaatca       1080
cgagtcctta attagtagtc gatggtgctt gctgtttgtc tccgtacatt cagcttctct       1140
ttgcatagta gtttctacat agtgcgtgta gagaagcaag tggatgtaca agtaaaataa       1200 ttacttttc tataaacaat attacaaact caaaaaaaaa aaaaaaaaaa aaa              1253
```

<210> SEQ ID NO 28
<211> LENGTH: 99
<212> TYPE: DNA
<213> ORGANISM: Eucalyptus grandis

<400> SEQUENCE: 28

```
gatagatcga ccgagagatc ccagcggaaa tagaagattt cctgatacca tcgatccatt          60
cttctccaat ggctgcgaat ttcgtcattc cgaccaaaa                                 99
```

<210> SEQ ID NO 29
<211> LENGTH: 927
<212> TYPE: DNA
<213> ORGANISM: Eucalyptus grandis

<400> SEQUENCE: 29

```
cgacgtcgca tgctcccggc cgccatgcgg ccgcgggaat tcgattacta tagggcacgc          60
gtggtcgacg gcccgggctg gtactctcac taattcttta gttttccaat ttagcccctt         120
ctgtaattgc tcatcttctt taccaaattc tctaatttgg ccggcgaagg gctgacaagg         180
gattggtcat gtcaccctca ccaaaggttg ccgaaggtcc ggtgacctca gctgacggcc         240
acctacacca atctagctc actagcagcc taagcccttc atcaactcta gtgaaaggtt         300
ttgagtattt tttaataaaa aatatttaaa aatatatag cgagagctca ttacaaaaaa         360 atttaaaaa aaaatctaaa cattacttga actcaaagtg actttataaa gagttttttac        420 caaaggatct tggtttcatc atttgcacta caccccaaaac ccaatttcta agttaaatca       480
aacccactgt ctaatagaga taaggtaaat gttataaacc aaattccaaa attccgaagc       540
```

```
actaaatata tttgctgatc ttataatcgc caattgagag ggtctcattc tccaagggat    600
tgtgacatat tagtaattga tagggtctca tccgtaggac tccgactcag ccgcgccacg    660
tgactggatc gctgaacggc gcggaaccag aggagcgtga ttacctaata ttttctccta    720
ccttggcctt gagattgaat ttcagaaaaa gaaaagaaaa aggaacaac ttcgccgact     780 gttctataaa atgcatgcgc caccccgacc cccacccacg catcacatcc atccagcctc    840
cacgacagac gcataaacac aacacacgtc ggttagagag agagagagag agagagagag    900
agagagagag atgcttggac agttgtc                                       927

<210> SEQ ID NO 30
<211> LENGTH: 411
<212> TYPE: DNA
<213> ORGANISM: Eucalyptus grandis

<400> SEQUENCE: 30
actatagggc acgcgtggtc gacggcccgg gctggtctga aactgtcgct cggcgatgca     60
taccaaaggc tgaaggtatc agaatctaat gcagcttatg taaaagcgcg atcaatttat    120
tgaccccgac gaccttgact ccatacttca cgcctcagct ttgtgttgga tggtcttgac    180
ctctctcacc ctaaaaggta gctcaaaaga atgagacttt ccgtcatact tataaaccga    240
ccaccagcct ctttcacaac cgacatggga caacctcaaa tagaattttt aacaacaccc    300
ttgcacgctc tttctatcca ctttattatg ccatcacatg agcgttttcc acgcgtaaat    360
cggctaccac ccactttcac acggcggcga aacgagaaaa aggtcctacc t            411

<210> SEQ ID NO 31
<211> LENGTH: 178
<212> TYPE: DNA
<213> ORGANISM: Eucalyptus grandis

<400> SEQUENCE: 31
cgagtcagca gaaacccagt tacactccgc ccaaacggaa gctaaacctg atgggccata     60
cgatttcttt cactgagcct cttgcttttc ctccggaatc tcacggcacc ggaatgccgg    120
aggaacttgg gaagaaccaa tgatgcctgg tcactgagtg atcgatgaat gcaatagt     178

<210> SEQ ID NO 32
<211> LENGTH: 178
<212> TYPE: DNA
<213> ORGANISM: Eucalyptus grandis

<400> SEQUENCE: 32
gtccaatgtc ctgtcaaagg aggaaagatg actatggccc cggcgccggc ggggactgca     60
tgggatttag tatgttgatt gagtacccgt cgccaccacc ttcaagtaaa tcaggagtca    120
gcagaaaccc agtacactcg ccaaacggag ctaaacctga tggccatacg atttcttt     178

<210> SEQ ID NO 33
<211> LENGTH: 178
<212> TYPE: DNA
<213> ORGANISM: Eucalyptus grandis

<400> SEQUENCE: 33
gcatgggatt tagtatgttg attgagtacc cgtcgccacc accttcaagt aaatcaggag     60
tcagcagaaa cccagtacac tcgccaaacg gagctaaacc tgatggccat acgatttctt    120
tcactgagcc tcttgctttt cctccggaat ctcacggcac cggaatgccg gaggcaac     178
```

<210> SEQ ID NO 34
<211> LENGTH: 1274
<212> TYPE: DNA
<213> ORGANISM: Eucalyptus grandis

<400> SEQUENCE: 34

| | | | | | |
|---|---|---|---|---|---|
| ctatagggca | cgcgtggtcg | acggcccggg | ctggtccttt | cttacaaaaa | gcaaaattct | 60 |
| tataatttt | tttgatataa | taaaaatgat | ccataaactt | ttgcttaatg | tgcaacgtaa | 120 |
| accataatat | attcaacgtg | atgcttaaac | tttaatcgag | tatgcaatgt | agtccataat | 180 |
| atattcaata | tgatccttca | attttaattg | aatgtgcaat | gtggtcgcta | gatttttta | 240 |
| tgtattcaac | ttagtctta | agctaccaac | cttccaataa | tttatgttta | gaaataatat | 300 |
| cgaacatctt | ttatattatt | caaggaataa | acgaacatg | catcaaaagt | ttaaatatat | 360 |
| caaataaaat | aaaattttaa | gaattatatt | acatattaaa | attaaagttc | atgattaaat | 420 |
| tgaaataaaa | taaaaattta | aaaatcacgt | tgtatgttgt | gccgaaacaa | aattcagtga | 480 |
| cttgtggtgt | caattttctt | aggtggagct | ccacaagcat | tgagatggag | tgttccttcc | 540 |
| gccgaggttt | tcattgcgtg | gctcaaaacg | gtggcgcgtt | ttgcacgaca | cgagatgcct | 600 |
| cgattgccgc | atcgtgtagg | cgacgcaacg | gaaaaacgcg | ttgccgtggc | gtctatccgg | 660 |
| ggtttcgtct | ccgatgcggc | acgtagccta | taaatgcgca | cgatctcccg | gtctgccaat | 720 |
| tcgctatcga | ttgcagaaga | aaactcaaac | cctaggcgct | ctctctccgt | tcgacctctc | 780 |
| gaagttctcc | tctcttcgcg | tcaagatgca | aatctttgtg | aaaaccctta | ctggcaagac | 840 |
| aatcaccctc | gaggtggaaa | gctcggacac | agtcgataat | gtgaaagcaa | aaatccagga | 900 |
| caaggaaggg | atccctccgg | accagcagag | gcttatcttt | gctggcaagc | agctggaaga | 960 |
| tggccgaacc | ttggccgatt | ataacattca | gaaggagtcc | accctccact | tggtgctccg | 1020 |
| tctcagggga | ggcatgcaaa | ttttttgtgaa | gactcttact | ggcaagacaa | tcaccctcga | 1080 |
| ggtggaaagc | tccgacacag | ttgataatgt | gaaagcaaaa | atccaggaca | aggaagggat | 1140 |
| ccctccggac | cagcagaggc | ttatctttgc | tggcaagcag | ctggaagatg | ccgaaccttt | 1200 |
| ggccgattat | aacattcaga | aggagtccac | cctccacttg | gtgctccgtc | tcaagggagg | 1260 |
| catgcaaatc | tttg | | | | | 1274 |

<210> SEQ ID NO 35
<211> LENGTH: 795
<212> TYPE: DNA
<213> ORGANISM: Eucalyptus grandis

<400> SEQUENCE: 35

| | | | | | |
|---|---|---|---|---|---|
| aaaaatacag | gctttcgaaa | gctagtgcgg | tataaataac | ctgggaaaag | caagccgctt | 60 |
| gagctttagt | ttcagtcagc | catggccact | cacgcagctc | ttgctccctc | aaccctcccc | 120 |
| gccaatgcca | agttctctag | caagagctcc | tctcactcct | tccccactca | atgcttctct | 180 |
| aagaggctcg | aggtggcgga | attctcaggc | cttcgtgctg | atcgtgtgt | gacttatgcg | 240 |
| aagaatgccg | gggagggatc | cttcttcgat | gctgtggctg | ctcagctcac | tcccaagact | 300 |
| tcagcaccag | ctccagctaa | gggagagact | gtcgctaaac | tgaaggtggc | aatcaatggt | 360 |
| ttcggtcgca | ttggtcggaa | cttccttaga | tgctggcacg | ggagaaagaa | ctcgcccctt | 420 |
| gatgtcattg | ttgtcaatga | cagcggtggt | gtcaaaaatg | cttcacattt | gctgaagtat | 480 |
| gattccatgc | tgggactt | caaagctgat | gtgaaaattg | tggacaatga | gaccatcagc | 540 |
| gtcgatggga | agcccgttaa | ggtcgtctct | aaccgggacc | ctctcaagct | ccctggggct | 600 |

```
gagctcggca tcgacattgt cattgaggga actggagtct tcgtggatgg ccctggtgct      660
ggaaaacata ttcaagctgg tgccaagaaa gttatcatca ctgcaccagc aaaaggcgct      720 gatatacccca cctacgtcta tggtgtgaat gagacagatt attcgcatga agttgctaac    780
ataatcagca atgct                                                       795

<210> SEQ ID NO 36
<211> LENGTH: 1200
<212> TYPE: DNA
<213> ORGANISM: Eucalyptus grandis

<400> SEQUENCE: 36
aaaatatcca tcgacagcat caccccgctt agagaacggt gtctcggctt ctcacaatgt      60
ctatagccga atgtacaaaa tcggcataat gttctataat atagcggact ttacagatga      120
gcattcaaat acgtacgccg tactcgattc ccattcgatt gttcattcat ccgcatgcaa      180
atttcataga gataatatct gtgcacgtcc ttagattaag acaaccaaa gagtatctgg       240 tggaagtttg aagcatgacc accgaagtca gatggaacaa acaaggtggg tggtggggat     300
atagtggaca aaggaacgag aggtgaatag gaaaaggaga aggcaagatg cgggagatag    360
gatttacgtg gcgagcggcg attgcacgca tggtccaccc caccctcaac ctcaaacttt     420
cgaaaatgca acgggcatca gggtggcgat gaaggagacg atggagatat tgttgctttc    480
tccccccaaa aaacatcatc caatccatcc ccattcctca tcttcaccac aaggagtctg     540
aagctctcct tcaccggtcc gtcgcttttct ctcttatctt cttcttctcc ctcctcttct   600
cgttcttcct tcgaccgttc tctcggtatc gtgaatttat tgcggggtgg ttcgcatgct     660
ataaattcca cagcaacgag ggcccctttgc cacaatgtcg acgtctccgg ttagcagctg    720
gtgcgccacc tccttctccc ctgcccattc ctcgctcaag agagccgccg gcctacggcc     780
ctctctctcc gcccgcctcg gcccttcctc tcctcctcc tccgtctctc ctccgaccct    840
catccgtaac gagcccgttt tcgccgcccc cgcccctgtc atcaacccca cttggacaga     900
agagatgggc aaggactatg acgaggccat tgaggctctc aagaaactcc tcagtgagaa     960
gggggacctg aaagccacag cagccgcaaa agtggagcaa ataactgcgg agttgcaaac    1020
tgcttcccca gacatcaagc catccagctc cgttgacaga atcaaaactg gcttcacctt    1080
cttcaagaag gagaaatacg acaagaaccc tgctttatat ggtgaactgg caaagcagag    1140
tccaaagttc atggtgtttg cttgctcgga ctcgagagtg tgcccatctc atgtgctgga    1200

<210> SEQ ID NO 37
<211> LENGTH: 648
<212> TYPE: DNA
<213> ORGANISM: Eucalyptus grandis

<400> SEQUENCE: 37
cgacggactc ctttcacgat atcgaaacga ggaaacggag gagaagcaga agaaagaaga      60
tgaagaaagg cagatggttg gtgatggatg aaactgtcgg gaagctggga gcttcaggga     120
gttctattta tggggcgaaa caggggaggg gaaaccgaat ttaccaagat gcccttcttg     180
gtgggattgg acatggagct gcacgaccgt cgtcccatca cgaagagtct tgctcttcgg     240
tacacatgca atcgtcggcg aaccgacctt atccgaccgg ttccaagctt gtcctggtaa     300
aaggtttcga accttggaaa aggcttaaga gatgtatcgg tgccttaacc attattccat     360
gttcacataa tatttggccc ggttttcagg tcaattttgg agtagccggg ttcggttcta     420
gtcccgctcc cgattcaaaa attcattggg aacaaatttt gacactgtct ggtatttttg     480
```

```
gtctaagacc ctacccaatt ttagaactgt acacccttgc tttatcccaa aataaaattg      540
tcaattagtc aacttttcac acttgatgat cgattaagta gatggatgac atggtctttt      600
accagcccgg gccgtcgacc acgcgtgccc tatagtgagt cgtattac                  648
```

<210> SEQ ID NO 38
<211> LENGTH: 288
<212> TYPE: DNA
<213> ORGANISM: Eucalyptus grandis

<400> SEQUENCE: 38

```
gattgtaata cgactcacta tagggcacgc gtggtcgacg gcccgggctg gtatcgtgaa       60
agaagtccgt cgacgacaat ggccgagaag agcaaggtcc tgatcatcgg agagaagagc      120
aaggtcctga tcatcggaga agagcaaggt cctgatcatc ggagagaaga gcagggtc       180 cttatcatcg gagaatcgaa ttcccgcggc cgccatggcg gccggagca tgcgacgtcg      240 ggcccaattc gccctatagt gagtcgtatt acaattcact ggccgtcg                 288
```

<210> SEQ ID NO 39
<211> LENGTH: 382
<212> TYPE: DNA
<213> ORGANISM: Eucalyptus grandis

<400> SEQUENCE: 39

```
acagcaatct catctgatga ttcttcagtt cggagctcag aggatacatc atctatagct       60
gaattgagct gtgcaatctt ctcggcaagc accttcctcg ttttctgaaa atcatcagat      120
tttaaggtga atccatattt cgcagatggc catgttactg ctacactctc ttcacagcat      180
acatgaagga ggtcacatag caagcataca taggacctca tatacaaata tgacagcaga      240
ccagcccggg ccgtcgacca cgcgtgccct atagtagtag tggggaagga gtgagaggag      300
ctcttgatga ggaatgtcgg cttttcttcc atcagttgat gttccgggtt cctagtcatt      360
atgccgatgg tggccactcc ag                                              382
```

<210> SEQ ID NO 40
<211> LENGTH: 986
<212> TYPE: DNA
<213> ORGANISM: Eucalyptus grandis

<400> SEQUENCE: 40

```
aaatacaaac tggtttaata ttcaactcag ataattacat gacaccacct aaataatgga       60
aagtcaagca aatagacata ttatccccac acataatcaa ctatattcat gactggagag      120
gtgctagatg gtatagagtc cctagttatt atttattttt ttgggcccga aaagatcctg      180
atggatctat gctgtttgat actttcagat ttgttttgtc tacagctcaa ataaattagt      240
gcttgggttt tgatatatta tctaatctga tacaagtctt tgtcctggcc aatttttgca      300
gagtttcctg caaaacagtg cactaaagct tccagaggac ctcatgccat gcccaagggc      360
accacctatg atggaacgga gaatcaaacc acagactgaa caggcgttga aatgccccag      420
atgtgattct acaaacacaa aattctgtta ctataacaac tacaatcttt cacaacctcg      480
ccatttctgc aagacctgca ggcgatactg gaccaaagga ggtgccttac gtaacgttcc      540
tgttggtggg ggttgcagaa agaataaacg agccaagcga gcagtagacc atcctgtctc      600
tgctcagaat gaagcatcca cctctgcagc cccaggcaac gaagtacctg accggtctcc      660
ctttgagcca ccatcttcaa aatccattta ctatggggga gaaaacatga acttaaccgg      720
```

-continued

```
tctcccttt agcagaattc agcaggaccg agctgcattg gcccactgca actcttcttc      780 cttttctagga atgtcatgtg gcacccaatc ggcctctctg gaaccacatc tttcggcttt      840
aaatacattt aattcattca gtctaacaa tcctggtctg gattttccta gcttaagcac       900
agaccagaat tcactgtttg agaccagcca gccacaactg tcaagagcaa tggcatctgc      960
ccttttttct atgccaatgg ctcctg                                            986
```

<210> SEQ ID NO 41
<211> LENGTH: 313
<212> TYPE: DNA
<213> ORGANISM: Pinus radiata

<400> SEQUENCE: 41

```
aaaggaaaat tcaaagatct ttagccaatt tttgttgttg tgaccttgaa tttctaaaaa       60
atttaatgga ttcgttttct aaattcctga ttcgtcaaag gctgaagggc acgatagtaa      120
tagaaaatgg acggcagttt atcctttcat ggctggacac acagaatttg tggagggact      180
ctccattctg gtttatccgc cgttagttct ctctgtactc caccttagt tctctttgta      240 ctcgagacct ttaatgatta gccctgctta tgctgtcatt actgaactca cttccagagc      300
cccaaaaatc tct                                                          313
```

<210> SEQ ID NO 42
<211> LENGTH: 713
<212> TYPE: DNA
<213> ORGANISM: Pinus radiata

<400> SEQUENCE: 42

```
taattcacaa gtagaaaatg agattttgc aattttgtaa ctaacatttc ccggtctcct        60
ctgtatgttt tcaccccta atgtaattga aatttgcacc cgggttagat tcaaagcgga      120
gaataacatc ggggccttgt tctagacaga gatttttcac aaataacagg ttcgaaggta      180
tgtgtagaca tctgggtagt tgtagaataa agacggagcc cattaggtga tccaatcgaa      240
gagctcagat gggaaaacag ataaaaatta tcgggtggac cttccttcac atgttaatta      300
tatatcaagt gtcgccaatc cttatgtgaa acatttagta aagcttcgcc agagcacttc      360
ttataggcat tctgtgggct ctgttgttgt ggttggaagt actcctttaa gggaggtatc      420
tgaatatttg caacagaagt cagttaaaca agtggttgac tgtctgtttg tacaagatgt      480
tactggcata cctgtgggct tgatagagac ttccaggcgc attgtgcatg taaatcattt      540
ggtgatgcag aagctagccg gagtagagtc tatagagccc actgaagcaa ttggtgtaat      600
caagcttcct agcagcttct acaacttgga atctcttgaa attcactcta gttcccagat      660
atggtgctcg tcgccacatc gtctgcttgt acttgatggc attcaggatc ctg            713
```

<210> SEQ ID NO 43
<211> LENGTH: 28
<212> TYPE: DNA
<213> ORGANISM: Pinus radiata

<400> SEQUENCE: 43

```
ccacctcaca tcaataaatt ttatacga                                          28
```

<210> SEQ ID NO 44
<211> LENGTH: 35
<212> TYPE: DNA
<213> ORGANISM: Pinus radiata

<400> SEQUENCE: 44

```
gctgtttcat tggggtcata gctacgtggt gctga                              35

<210> SEQ ID NO 45
<211> LENGTH: 1729
<212> TYPE: DNA
<213> ORGANISM: Pinus radiata

<400> SEQUENCE: 45
cttattgaca tataaaagca aagttggatc catctgttat tttgggtccc ctccagaagc    60
cttactaaat gcggacaaaa aatccacgta aagaacttct gaatttaccg tcatctgggc   120
tctgtaatta cgaatttagg gtttcctctg tcaatatctg gtagtgacaa acaaggttta   180
atggcagcct tagcaacaac tgaagtttgt gatacatatc cacgccttgt ggagaatggt   240
gagcttcgtg tcttgcaacc aatttttcag atatatggtc gacgtcgagc tttctctgga   300
cctatagtta cactgaaggt ctttgaggac aatgtccttt tgcgggaatt ccttgaggag   360
agaggtaatg gaagagtttt ggtagttgat ggaggaggaa gccttagatg tgccatactg   420
gggggcaatg tagttgtatc tgcccaaaac aatggttggt ctggaataat tgtcactggc   480
tgcataaggg acgttgatga aataaacaga tgtgacattg gtataagagc actgacatct   540
aacccactga aggccaacaa gaagggtgtg ggtgaaaaac atgcgcctat ttacattgct   600
ggtacccgca ttcttccggg ggaatggtgt tatgctgaca gtgatggtat tcttgtttca   660
cagcaagagt tatcactgtg agataataaa attcataagt ttcagattgt gactttcatg   720
tcctgtggaa catatatttg actcgagtta gattctaata ggattaattg atagattctg   780
aaaattgagg aatatctctg gtcatgaaaa tcttcttctc atgtgatctt ttatgctcag   840
ctttgagtac aggatgataa gaagtttgtg catgtttgtc taaaggttta gcaagtatta   900
tcggaccatc ataagagata gattatggaa ctcagggact tgctattttt aatccaaaat   960
aacatttatt ctttgtgttt ttgccaaatt aactttatt tcccttggca ccactagtga   1020
tttgcaatat ccagttgctg agaacataga agtgggcaac ggtgagagtt gcaacagtat   1080
ctagcataga tttaacaagt attgttggat cattataaga aaataaacta cagaaccaag   1140
ggaatctagt tgacaacata gttaaagtag gcatggtgct actgtatcga tacatcttca   1200
taaacagaaa aatatgaaca agctctaatg atgggagaaa ctccagcttg tgttttgat    1260 taagcatcca tattcacacc taaaaggtta caagttccaa aataaaaatt ccaatgaatt   1320
tagccaatct aatcagacct tataagaaat acactaggca tctggggatc aaaatccagt   1380
agtttagaaa gtagttgtaa ataacccaga gacaaaaatc tcaatgatag cttgcttggg   1440
tcataggttt gataataatt gaaaacatag ttgaaggag aatcctagca atggctagct    1500
tgaataatag atgtacagca aaattacagt agttgagaac aaagatggaa ggataatccc   1560
aacgatagct agcttggaca gtaggatgat tacatcaaaa tcatagcagt tgagaacata   1620
gttggaagga gaatccttat gatggctacg ttggataata ggcgtgatta tcgtaggtag   1680
attagagcac aagatcaaac taatagctgg cgcagctatc gactatttt                1729

<210> SEQ ID NO 46
<211> LENGTH: 1038
<212> TYPE: DNA
<213> ORGANISM: Pinus radiata

<400> SEQUENCE: 46
tgattactat agggcacgcg tggtcgacgg cccgggctgg taaatgagaa catgataagc    60
```

| | |
|---|---|
| tgtgtaaatt catgctagtc accataactt ttctcattgc ttttcatcca cactgttgat | 120 |
| tcattcatta tataagatca gattcgtatg atatacaggc aaccatagaa acaaccagca | 180 |
| aagttactag caggaaatcc aactaggtat catgaagact accaacgcag gctcgataat | 240 |
| gttggtgctc attattttg ggtgctgttt cattggggtc atagctacat cttttgattt | 300 |
| ctattacttc gttcaacagt ggcctggttc atactgcgat actcgtagag gatgctgtta | 360 |
| ccctcgcacg ggaaggcctg cttccgaatt ttccattcat ggcctctggc ccaactacaa | 420 |
| gaccggtaaa tggccacagt tctgtggttc ctccgaagaa ttcgactact caaagatctc | 480 |
| agatctggag gaggagctga acaggtattg gggttcgtta agctgtccaa gcagcgatgg | 540 |
| acaggaattt tggggacacg agtgggagaa acatggcact tgctctctca atcttgatga | 600 |
| gcattcatac tttgagaagg ctctctcctt gagacaaaat atagacattc ttggggctct | 660 |
| taaaactgca ggtattaaac ccgatggaag ccaatacagt ttgagcgata tcaaggaagc | 720 |
| cattaaacaa aacactgggc agctcccagg aatcgattgc aacacgagcg cagagggaga | 780 |
| gcatcaacta tatcaggtgt atgtgtgtgt tgataaatcc gatgcttcca ctgttattga | 840 |
| atgccccatt tatccacaca gcaattgccc atccatggtt gtgtttcctc cttttgggga | 900 |
| ggatcaggag gaccgagatg gttacacaga aggaatgtac gagctgtaga tctggacaaa | 960 |
| cagcatttct tctctccgca tttgatttt atcaatgaaa tttccgattc caacattttg | 1020 |
| taaaaaaaaa aaaaaaaa | 1038 |

<210> SEQ ID NO 47
<211> LENGTH: 91
<212> TYPE: DNA
<213> ORGANISM: Pinus radiata

<400> SEQUENCE: 47

| | |
|---|---|
| aattttccat tcatgcctct gcccaactac aagaccggta aatggccaca gttctgtggt | 60 |
| tcctccgaag aattcgatat caagcttatc g | 91 |

<210> SEQ ID NO 48
<211> LENGTH: 91
<212> TYPE: DNA
<213> ORGANISM: Pinus radiata

<400> SEQUENCE: 48

| | |
|---|---|
| gcttttcatc cacactggtg cctcattcat tatataagat cagattcgtg tgatatacag | 60 |
| gcaaccatag aaacaaccgg caaagttact a | 91 |

<210> SEQ ID NO 49
<211> LENGTH: 809
<212> TYPE: DNA
<213> ORGANISM: Pinus radiata

<400> SEQUENCE: 49

| | |
|---|---|
| tgatatatat aacttctagc agaatgacac gcgacttgta tatcttttca ttttttaacc | 60 |
| catgaaaacc gattagggta ttgcaaatta gggcattgcc attcaaataa ttctcagatg | 120 |
| aaagattctc tctaacaatt acaaatgatt attttttcc atgagtgttg catgttcgaa | 180 |
| cggtctgccc agtctgtgag agagcataga gaaccctccc tgcccaattt gttagagcat | 240 |
| agagaaccct actgcatgag tagtaagaaa atattcggt ctcaattcgg caaagaccac | 300 |
| ctcgaatgga tgacttcaac gacaatctca tgatagtgtt ctgatcagca ccagttcacc | 360 |
| tatatatttt atctagggtt tagtttgcat gtatcaatcc tctggtgcac taggtaattc | 420 |

```
tttcccagta tcatatatcc ttaatactgt tttgtctttt aatccatggc taccatcaga    480
acaagctcaa agcagaataa gggagcatca gccatcctct tgcttatcgc gattgcaggg    540
ttagtaaatg cgtgcaacgc tgtgggtatt gagccaatgt gcgacactgt ggtgtcgagt    600
cttctgaggc ttctgccatg caggacggct gttgatccct caattgccgc cattccactt    660
ccaagctgct gcaacgcggt tgagtcagct gggcttcaat gcctctgtct cgtcgttaac    720
ggccctcctt ttccaggggt cgaccgcggc ctcgcaatgc agctgcctgc caaatgccat    780
ctcacccttc ctccctgtaa cagttagtt                                     809

<210> SEQ ID NO 50
<211> LENGTH: 428
<212> TYPE: DNA
<213> ORGANISM: Eucalyptus grandis

<400> SEQUENCE: 50
tttcttgtga ctattcattt tcctcctgat tatccattca gcccccgaa ggttgcattt     60 aggactaaag ttttccaccc aaatataaat aacaatggaa gtatctgcct tgacatcttg    120
aaggaacagt ggagtcctgc tttgacaatc tccaaggttt tgctctcaat ttgctctttg    180
ttgacggatc caaacccaga tgatcctctt gtaccagaga ttgctcatat gtacaagact    240
gataggggca aatatgagtc cactgcacgg agttggactc agaaatatgc aatgggttaa    300
ctttaaaaac tatatatcag tgatggaact ttatccctaa gttggaatct cttcgaatca    360
atgacttgtt tgcttgtaag aaatgttttcc ttaagataag tggctttcct caaaacttga    420
ttgaagtg                                                            428

<210> SEQ ID NO 51
<211> LENGTH: 525
<212> TYPE: DNA
<213> ORGANISM: Pinus radiata

<400> SEQUENCE: 51
cccttctttg ccttcaacta atcctgctca tcctctcctg cccccattcc caaagatggc     60
tgcacccaga tcatccgcta aattgggtgc acttttggca atactgctca tagttgcggc    120
agcgcaggct caagattgct caaatgccat ggacaaattg gctccatgca cttcagcagt    180
gggactgtct agcaatggag tgaagccctc atctgagtgc tgtgatgccc tcaaaggaac    240
cagtactggc tgcgtctgca agtctgtgag agcagtgata tcacttcctg ctaagtgcaa    300
tctcccagcc ataacctgct ctggatctcg ctgaaggctc tctgttatgg cgattctcag    360
atcgtggatc tctttaagat tttcagcaag caagtgatag aataaattct cagatttga    420 gatatctata tagcgatttt cagtatcaga ttgtctatag tactcatata tttaagtgat    480
tgaatagcat tctccgattc cgagttggaa acacagacac aatga                   525

<210> SEQ ID NO 52
<211> LENGTH: 1126
<212> TYPE: DNA
<213> ORGANISM: Pinus radiata

<400> SEQUENCE: 52
actagtgatt actatagggc acgcgtggtc gacggcccgg gctggtaaat acccaactta     60
atttaattgt tattgagcca gagagatgcg tagtcgctca tgtcacttgt gtttaccaaa    120
aagacataca taaacacctg cacctaaaag ttataatgat aacatgcata caaccctaca    180
```

-continued

```
acgtacgtag tcacatgcgg ctagaactta aaccccctacc acaaacatag ccacctgcac      240
ccagaagtta taataataac atacatagaa cccttacaat aaaaaaagtt atctccaatg      300
attattaatc tactgcaggc cagccatact cagcttgaac gtgaaaattc gcattgtaag      360
catggcgcca cattaaaata acctcggcaa tattttcatg tccaagtggc cggccagcca      420
cgctcctcgc actctgagaa tactctattc atccacttgt ctctgccccg caactcatat      480
aaatgtggcc aacccaagca ccatatccat gttcattaat cccctctttg ccttcaacta      540
atcctgctca tccctcttg ccccaattcc caaagatggc tgcacccaga tcatccgcta      600
aatcggctgc acttttcgca atactgctca tagttgcggc agtacaggct gaagattgct      660
caaatgccat ggacaaattg gctccatgca cttcagcagt gggactgtct agcaatggag      720
tgaagccctc atctgagtgc tgtgatgccc tcaaaggaac cagtactggc tgcgtctgca      780
aatctgtgag agcagtgata tcacttcctg ctaagtgcaa tctcccagcc ttaacctgct      840
ctggatctcg ctgaaggctc tctgttatgg cgattctcag atcgtggatc tctttaagat      900
tttcaggaag caagtgatag aataaattct cagatgttga gatatctata tagcgatttt      960
cagtatcaga ttgtctacag taccaatata tttaagtgat tgaatggaat tctcggattc     1020
tgagatagaa atataggcac agaatgtggc cggaggaatg ttcgaattcg agaatgataa     1080
taaataataa atgattgatt tctctctgca aaaaaaaaaa aaaaaa                     1126

<210> SEQ ID NO 53
<211> LENGTH: 454
<212> TYPE: DNA
<213> ORGANISM: Pinus radiata

<400> SEQUENCE: 53
atcctgctca tcctctcctg cccccattcc caaagatggc tgcacccaga tcatccgcta       60
aattgggtgc acttttggca atactgctca tagttgcggc agcgcaggct caagattgct      120
caaatgccat ggacaaattg gctccatgca cttcagcagt gggactgtct agcaatggag      180
tgaagccctc atctgagtgc tgtgatgccc tcaaaggaac cagtactggc tgcgtctgca      240
agtctgtgag agcagtgata tcacttcctg ctaagtgcaa tctcccagcc ataacctgct      300
ctggatctcg ctgaaggctc tctgttatgg cgattctcag atcgtggata tctttaagat      360
tttcagcaag tgatagaata aattctcaga ttttgagata tctatatagc gattttcagt      420
atcagattgt ctatagtact catatattta agtg                                  454

<210> SEQ ID NO 54
<211> LENGTH: 335
<212> TYPE: DNA
<213> ORGANISM: Pinus radiata

<400> SEQUENCE: 54
agaagcacct gttaaaaagg aggcctgctc tttgttcatg agcttataga taagccctag       60
tctgcaagga ttattgccct gtagttattt ggaagtagat cattttcaca ggcccagatg      120
cattatattc taatgcagtt gtttgttaat tgaagtgcaa atagttccaa aatgtttaca      180
tgaatcaata gtgaacaaat ccctctgttt tatatcatat tgatggatta ttcgattttt      240
tggtgacgtg gcgcgaaact gcttttcgaa ctcatggaaa tagtaattgt tataatccat      300
aggcatgaga ttcttgttaa tcgtgcacaa ggttt                                 335

<210> SEQ ID NO 55
<211> LENGTH: 336
```

<212> TYPE: DNA
<213> ORGANISM: Pinus radiata

<400> SEQUENCE: 55

| | | | | | |
|---|---|---|---|---|---|
| aaaccttgtg | cacgattaac | aagaatctca | tgcctatgga | ttataacaat | tactatttcc | 60 |
| atgagttcga | aaagcagttt | cgcgccacgt | caccaaaaaa | tcgaataatc | catcaatatg | 120 |
| atataaaaca | gagggatttg | ttcactattg | attcatgtaa | acattttgga | actatttgca | 180 |
| cttcaattaa | caaacaactg | cattagaata | taatgcatct | ggtgcctgtg | aaaatgatct | 240 |
| acttccaaat | aactacaggg | caataatcct | gcagactag | gcttatcta | aagctcatg | 300 |
| aacaaagagc | aggcctcctt | tttaacaggt | gcttct | | | 336 |

<210> SEQ ID NO 56
<211> LENGTH: 532
<212> TYPE: DNA
<213> ORGANISM: Pinus radiata

<400> SEQUENCE: 56

| | | | | | |
|---|---|---|---|---|---|
| cgttcgttcc | cttcccttc | cattgttgcg | tttaagccct | ccaattttct | tttggcgtcc | 60 |
| cgttttggg | gctcccttga | agatctcctc | ttcatttcgg | gatttcctgc | cttcgccgcg | 120 |
| ccatttgaag | ttcttttttct | gagagaagaa | tttagacatg | gctgatcgca | tgttgactcg | 180 |
| aagccacagc | cttcgcgagc | gtttggacga | gaccctctct | gctcaccgca | acgatattgt | 240 |
| ggccttcctt | tcaagggttg | aagccaaggg | caaaggcatc | ttgcagcgcc | accagatttt | 300 |
| tgctgagttt | gaggccatct | ctgaggagag | cagagcaaag | cttcttgatg | ggccttttgg | 360 |
| tgaagtcctc | aaatccactc | aggaagcgat | tgtgtcgcct | ccatggggtg | ctcttgctgt | 420 |
| tcgtccaagg | ccgggcgtgt | gggagcacat | ccgtgtgaac | gtccatgcgc | ttgttcttga | 480 |
| gcaattggag | gttgctgagt | atctgcactt | caaagaagag | cttgctgatg | ga | 532 |

<210> SEQ ID NO 57
<211> LENGTH: 3103
<212> TYPE: DNA
<213> ORGANISM: Eucalyptus grandis

<400> SEQUENCE: 57

| | | | | | |
|---|---|---|---|---|---|
| gggtgaaaac | aattaatgag | atcatttgaa | ttaaggaaag | tggaaaggcg | gttttctgat | 60 |
| tggtacactg | aaacaacagg | aaggtggtgg | aggccgcaat | gatggaattt | atccacttta | 120 |
| atcattttat | gaaatcgata | cactaacctt | tgtttctcct | aaacccaaag | gcattaatcc | 180 |
| ctgtcctcct | cactcgatct | cgaaggccag | aaggggagg | ccgagcctct | tgcttttttt | 240 |
| cgtgtataaa | agggcctccc | ccattcctca | tttttcacca | tcctccgttc | gttcgttccc | 300 |
| ttcccttcc | attgttgcgt | ttaagccctc | caattttctt | ttggcgtccc | gttttttgggg | 360 |
| ctcccttgaa | gatctcctct | tcatttcggg | atttcctgcc | ttcgccgcgc | catttgaagt | 420 |
| tcttttttctg | agagaagaat | ttagacatgg | ctgatcgcat | gttgactcga | agccacagcc | 480 |
| ttcgcgagcg | tttggacgag | accctctctg | ctcaccgcaa | cgatattgtg | gccttccttt | 540 |
| caagggttga | agccaagggc | aaaggcatct | tgcagcgcca | ccagattttt | gctgagtttg | 600 |
| aggccatctc | tgaggagagc | agagcaaagc | ttcttgatgg | ggccttttggt | gaagtcctca | 660 |
| aatccactca | ggaagcgatt | gtgtcgcctc | catgggttgc | tcttgctgtt | cgtccaaggc | 720 |
| cgggcgtgtg | ggagcacatc | cgtgtgaacg | tccatgcgct | tgttcttgag | caattggagg | 780 |
| ttgctgagta | tctgcacttc | aaagaagagc | ttgctgatgg | aagcttgaat | ggtaacttttg | 840 |

```
tgcttgagct tgactttgag ccattcactg cctcttttcc gcgcccgact ctttccaagt    900
ctattggcaa tggcgtcgag tttctcaatc gccatctctc cgctaagctc ttccatgaca    960
aggaaagctt gcaccctctg cttgaattcc tccaagtcca ctgctacaag gggaagaaca   1020
tgatggtgaa tgccagaatc cagaatgtgt tctccctcca acatgtcctg aggaaggcgg   1080
aggagtatct gacctcgctc aaacccgaga ccccgtactc ccagttcgag cacaagttcc   1140
aggagatcgg gctcgagcgg gggtggggtg acacggctga gcgcgtcctc gagatgatcc   1200
agctcctgtt ggatctcctt gaggctcccg acccgtgcac tctcgagaag ttcttggata   1260
gggttcccat ggtcttcaac gtcgtgatca tgtctcccca cggatacttt gctcaggacg   1320
acgtccttgg ttatccggat accggtggcc aggttgttta catcctggat caagttcgtg   1380
ccctagagga agaaatgctt caccgcatta agcaacaagg actggatatt actcctcgga   1440
ttctcattat cactcggctt cttccagacg cggttggaac cacctgtggc cagcgccttg   1500
agaaagtttt tgggaccgag tactcccaca ttcttcgcgt ccccttcaga aatgagaagg   1560
gagtcgtccg caagtggatt tcccggttcg aggtgtggcc ctatttggaa agatacactg   1620
aggatgtcgc gagcgaactt gctggagagt tgcaggcaa gcctgatctg atcatcggaa    1680
actacagtga tggaaacatt gttgcttcct tgttagcaca taaattaggt gttacacagt   1740
gtacaatagc ccatgccctc gagaagacga agtacccaga gtcagacata tactggaaga   1800
aatttgagga aaagtaccac ttctcttgcc agttcactgc tgatctcatc gccatgaacc   1860
acaccgactt cattatcacc agcaccttcc aagaaattgc tggaagcaag gatacagtgg   1920
ggcagtatga gagtcacatg aacttcactc ttcctggact ctaccgagtt gtccacggga   1980
tcgacgtctt cgacccgaag ttcaacattg tttccaccagg tgctgacatg agcatctact   2040
ttgcttacac cgaacaggag cggcggttga atccttcca ccctgagatc gaggaactcc    2100
tcttcagcga tgttgagaac aaggaacact tgtgtgtgtt gaaagataag aagaagccta   2160
ttattttcac catggcaagg ctggaccgtg tcaagaactt gacagggctt gttgagtggt   2220
atggcaagaa ctccaagttg agggaactcg ccaacttggt cgtggttgga ggtgacagga   2280
ggaaggattc gaaggacttg gaagagcagt ctgagatgaa gaaaatgtac gacctcatcg   2340
aaaagtacaa gctgaatggc cagttcaggt ggatttcctc ccagatgaac cgggtgagga   2400
atggagagct ctaccgctac atctgtgaca cgaagggagt cttcgttcaa ccggctatct   2460
atgaagcttt cggggtgacc gtggttgagg ccatgacttg tggattgcca acctttgcca   2520
cttgcaatgg tggaccagct gagatcattg tgcatggcaa atcgggctac acattgatc    2580
cttaccatgg tgaccaggcg gccgagcttc ttgtagactt cttcaacaag tgcaagattg   2640
accagtccca ctgggacgag atctcaaagg gtgccatgca gagaattgaa gagaagtata   2700
catggaaaat atattctgag aggctgttga acctgactgc cgtgtatggc ttctggaagc   2760
atgtgactaa ccttgatcgg cgcgagagtc gccggtacct tgaaatgttc tatgccctca   2820
agtatcgccc actggcacag tctgttcctc cggctgtcga gtaaacaaag agacagattg   2880
ttaccagaag acgaagcat tggacttttg aagtttcaa ggataaaca ttggaaattg      2940
tttgaatttg ggattgccaa gagcgatctt tttcgtttcc ttttttttggt ccttttttctc  3000
ttctttgttt ccattccgcg aatgtttgca ttttgggggtt tgtacccatc aattcagtaa  3060
atggttcatt ttcttttcaa aaaaaaaaaa aaaaaaaaaa aaa                     3103
```

<210> SEQ ID NO 58
<211> LENGTH: 326

<212> TYPE: DNA
<213> ORGANISM: Eucalyptus grandis

<400> SEQUENCE: 58

```
ctcgaaaccg agacgctgac tgtgggttga gctctaacca atgggagtga tgtctctctt      60
acgtgcctgc cgtgggcccc agtgacgggc cccaaaagtg taaacgaagg aagctcccgg     120
ggatctgatt ggccgcgacg tccgcctctg acgtggcacc accgacgatt tttttttaat     180
atcttggtca agtcctaatt taactatggg gtccagatta gaagcttatc cactatggat     240
taaattaaat caaatgggaa ttaaattaaa ttaaaatcat cgtgcggagg tgcacgagat     300
gcacgagatc cgacggcgca gagcag                                          326
```

<210> SEQ ID NO 59
<211> LENGTH: 311
<212> TYPE: DNA
<213> ORGANISM: Eucalyptus grandis

<400> SEQUENCE: 59

```
attactatag ggcacgcgtg gtcgacggcc cgggctggta ctctcactaa ttctttagtt      60
ttccaattta gccccttctg taattgctca tcttctttac caaattctct aatttggccg     120
gcgaagggct gacaagggat tggtcatgtc accctcacca aaggttgccg aaggtccggt     180
gacctcagct gacggccacc tacaccaaat ctagctcact agcagcctaa gcccttcatc     240
aactctagtg aaaggttttg agtatttttt aataaaaaat atttaaaaaa tatatagcga     300
gagctcatta c                                                          311
```

<210> SEQ ID NO 60
<211> LENGTH: 2096
<212> TYPE: DNA
<213> ORGANISM: Eucalyptus grandis

<400> SEQUENCE: 60

```
gattactata gggcacgcgt ggtcgacggc ccgggctggt ctgagccatt taattcgaga      60
gcacatcgcc caaaattatt cttcttgctg ccataactgt cgaattttct cttttaggta     120
agtaaccaat gatgcatcat gttgacaaaa aggctgatta gtatgatctt ggagttgttg     180
gtgcaaattt gcaagctgac gatggcccct cagggaaatt aaggcgccaa cccagattgc     240
aaagagcaca aagagcacga tccaaccttt ccttaacaag atcatcacca gatcggccag     300
taagggtaat attaatttaa caaatagctc ttgtaccggg aactccgtat ttctctcact     360
tccataaacc cctgattaat ttggtgggaa agcgacagcc aacccacaaa aggtcagatg     420
tcatcccacg agagagagag agagagagag agagagagag agtttttct ctctatattc      480
tggttcaccg gttggagtca atggcatgcg tgacgaatgt acatattggt gtagggtcca     540
atattttgcg ggagggttgg tgaaccgcaa agttcctata tatcgaacct ccaccaccat     600
acctcacttc aatcccacac atttatccgt tttatttcct ctgctttcct ttgctcgagt     660
ctcgcggaag agagagaaga gaggagagga gagaatgggt tcgaccggat ccgagaccca     720
gatgacccg acccaagtct cggacgagga ggcgaacctc ttcgccatgc agctggcgag     780
cgcctccgtg ctccccatgg tcctcaaggc cgccatcgag ctcgacctcc tcgagatcat     840
ggccaaggcc gggccgggcg cgttcctctc ccgggggaa gtcgcggccc agctcccgac      900
ccagaacccc gaggcacccg tcatgctcga ccggatcttc cggctgctgg ccagctactc     960
cgtgctcacg tgcaccctcc gcgacctccc cgatggcaag gtcgagcggc tctacggctt    1020
```

```
agcgccggtg tgcaagttct tggtcaagaa cgaggacggg gtctccatcg ccgcactcaa    1080
cttgatgaac caggacaaaa tcctcatgga aagctggtat tacctgaaag atgcggtcct    1140
tgaaggcgga atcccattca acaaggcgta cgggatgacc gcgttcgagt atcatggcac    1200
cgacccgcga ttcaacaaga tctttaaccg gggaatgtct gatcactcca ccattactat    1260
gaagaagata ctggaaacat acaagggctt cgagggcctc gagaccgtgg tcgatgtcgg    1320
aggcggcact ggggccgtgc tcagcatgat cgttgccaaa tacccatcaa tgaaagggat    1380
caacttcgac cgccccaacg gattgaagac gccccacccc ttcctggtgt caagcacgtc    1440
ggaggcgaca tgttcgtcag cgttccaaag ggagatgcca ttttcatgaa gtggatatgc    1500
catgactgga gtgacgacca ttgcgcgaag ttcctcaaga actgctacga tgcgcttccc    1560
aacaatggaa aggtgatcgt tgcagagtgc gtactccctg tgtacccaga cacgagccta    1620
gcgaccaaga atgtgatcca catcgactgc atcatgttgg cccacaaccc aggcgggaaa    1680
gagaggacac agaaggagtt cgaggcattg gccaaagggg ccggatttca gggcttccaa    1740
gtcatgtgct gcgctttcgg cactcacgtc atggagttcc tgaagaccgc ttgatctgct    1800
cctctgtggt gatgttcatg gttcttggat ttgaaaggtc gtgaaggagc ccttttctca    1860
cagttggctt cggcatacca agttcttctc ataaaaggaa acaataagaa gcgactgtat    1920
gatggcgcaa gtggaagtta caagatttgt tgttttatgt ctataaagtt ttgagtcttc    1980
tgcatactga tttcacagaa tgtgtaacga acggcgtat atggatgtgc ctgaatgatg    2040
gaaattgtga tattctgtct tcttttttcag taaatcactt cgaacaaaaa aaaaaa      2096

<210> SEQ ID NO 61
<211> LENGTH: 522
<212> TYPE: DNA
<213> ORGANISM: Eucalyptus grandis

<400> SEQUENCE: 61
ctaaaacgct aatcctgccc tgcccttccc ttctgctgct gctgctcgtc acctctctct     60
ccctctcgcg gccagctgcg agatctgccg agtttaagcc tcgtacatca aaatgggtaa    120
ggagaagatt cacatcagca ttgtggtcat tggccatgtc gattctggga agtcaaccac    180
aactggccac ttgatataca agctcggagg aatcgacaag cgtgtgattg agagattcga    240
gaaggaagct gctgagatga acaagagatc gttcaagtat gcttgggtgc ttgacaagct    300
caaggccgag cgcgagcgcg gtattaccat tgatattgcc ttgtggaagt tcgagaccac    360
caagtactac tgcactgtca ttgatgctcc tggacatcgt gactttatta agaatatgat    420
tactggaacc tcccaggccg actgtgctgt ccttatcatt gattccacca ctggtggttt    480
cgaagctggt atttccaagg atggccagac ccgtgaacat gc                       522

<210> SEQ ID NO 62
<211> LENGTH: 420
<212> TYPE: DNA
<213> ORGANISM: Eucalyptus grandis

<400> SEQUENCE: 62
tttgatacgc taacaaacaa aacatgtgaa aagcttaatt atggcaatta tcataaatag     60
aaaaaaatta gaaaaaaaga gaggaaatgg gccattattt aaattgcaat cgaaagattg    120
agggcaattc tgtttctcta gtgtaaataa gggtgtattt ataattgag ggatggaaat    180 agcatggtca ctcggtaatt atcaaggaaa gcaagaataa aaatgaaaaa aaaaaaaaa    240 aaagcttgaa gaggccaatg tcgaaattat gagcgcgaga tgaggacact cctgggaaac    300
```

```
gaaaaatggc attcgcgggg ggtgctatat aaagcctcgt gtaagggtgc gttcctcact    360
ctcaaaccct aatcctgccc ttcccttctg ctgctgctgc tcgtcacctc tctcctccct    420
```

<210> SEQ ID NO 63
<211> LENGTH: 65
<212> TYPE: PRT
<213> ORGANISM: Eucalyptus grandis

<400> SEQUENCE: 63

```
Met Asp Asn Ser Lys Met Gly Phe Asn Ala Gly Gln Ala Lys Gly Gln
 1               5                  10                  15

Thr Gln Glu Lys Ser Asn Gln Met Met Asp Lys Ala Ser Asn Thr Ala
            20                  25                  30

Gln Ser Ala Arg Asp Ser Met Gln Glu Thr Gly Gln Gln Met Lys Ala
        35                  40                  45

Lys Ala Gln Gly Ala Ala Asp Ala Val Lys Asn Ala Thr Gly Met Asn
    50                  55                  60

Lys
65
```

<210> SEQ ID NO 64
<211> LENGTH: 152
<212> TYPE: PRT
<213> ORGANISM: Eucalyptus grandis

<400> SEQUENCE: 64

```
Met Gly Gly Pro Leu Thr Leu Asp Ala Glu Val Glu Val Lys Ser Pro
 1               5                  10                  15

Ala Asp Lys Phe Trp Val Ser Val Arg Asp Ser Thr Lys Leu Phe Pro
            20                  25                  30

Lys Ile Phe Pro Asp Gln Tyr Lys Asn Ile Glu Val Leu Glu Gly Asp
        35                  40                  45

Gly Lys Ala Pro Gly Ser Val Arg Leu Phe Thr Tyr Gly Glu Gly Ser
    50                  55                  60

Pro Leu Val Lys Val Ser Lys Glu Lys Ile Asp Gly Val Asp Glu Ala
65                  70                  75                  80

Asp Lys Val Val Thr Tyr Ser Val Ile Asp Gly Asp Leu Leu Lys Tyr
                85                  90                  95

Tyr Lys Asn Phe Asn Gly Ser Ile Lys Val Ile Pro Lys Gly Asp Gly
            100                 105                 110

Ser Leu Val Lys Trp Ser Cys Gly Phe Glu Lys Ala Ser Asp Glu Ile
        115                 120                 125

Pro Asp Pro His Val Ile Lys Asp Phe Ala Ile Gln Asn Phe Lys Glu
    130                 135                 140

Leu Asp Glu Phe Ile Leu Lys Ala
145                 150
```

<210> SEQ ID NO 65
<211> LENGTH: 117
<212> TYPE: PRT
<213> ORGANISM: Eucalyptus grandis

<400> SEQUENCE: 65

```
Met Ala Ala Asn Phe Val Ile Pro Thr Lys Met Lys Ala Trp Val Tyr
 1               5                  10                  15

Arg Glu His Gly Asn Val Ala Asp Val Leu Gly Leu Asp Pro Glu Leu
            20                  25                  30
```

```
Lys Val Pro Glu Leu Gln Glu Gly Gln Val Leu Val Lys Val Leu Ala
        35                  40                  45

Ala Ala Leu Asn Pro Val Asp Ala Ala Arg Met Lys Gly Val Ile Lys
        50                  55                  60

Leu Pro Gly Phe Ser Leu Pro Ala Val Pro Gly Tyr Asp Leu Ala Gly
 65                  70                  75                  80

Val Val Val Lys Val Gly Arg Glu Val Lys Glu Leu Lys Ile Gly Asp
                85                  90                  95

Glu Val Tyr Gly Phe Met Phe His Ala Lys Lys Asp Gly Thr Leu Ala
                100                 105                 110

Glu Tyr Ala Ala Val
        115

<210> SEQ ID NO 66
<211> LENGTH: 318
<212> TYPE: PRT
<213> ORGANISM: Eucalyptus grandis

<400> SEQUENCE: 66

Met Ala Ala Asn Phe Val Ile Pro Thr Lys Met Lys Ala Trp Val Tyr
 1               5                  10                  15

Arg Glu His Gly Asp Val Ala Asn Val Leu Gly Leu Asp Pro Glu Leu
                20                  25                  30

Lys Val Pro Glu Leu Gln Glu Gly Gln Val Leu Val Lys Val Leu Ala
        35                  40                  45

Ala Ala Leu Asn Pro Ile Asp Thr Ala Arg Val Lys Gly Val Ile Lys
        50                  55                  60

Leu Pro Gly Phe Ser Leu Pro Ala Val Pro Gly Tyr Asp Leu Ala Gly
 65                  70                  75                  80

Val Val Val Lys Val Gly Arg Glu Val Lys Glu Leu Lys Val Gly Asp
                85                  90                  95

Glu Val Tyr Gly Phe Met Phe His Ala Lys Lys Asp Gly Thr Leu Ala
                100                 105                 110

Glu Tyr Ala Ala Val Glu Glu Ser Phe Leu Ala Leu Lys Pro Lys Lys
        115                 120                 125

Leu Arg Phe Gly Glu Ala Ala Ser Leu Pro Val Val Ile Gln Thr Ala
        130                 135                 140

Tyr Gly Gly Leu Glu Arg Ala Gly Leu Ser His Gly Lys Ser Leu Leu
145                 150                 155                 160

Val Leu Gly Gly Ala Gly Gly Val Gly Thr Leu Ile Ile Gln Leu Ala
                165                 170                 175

Lys Glu Val Phe Gly Ala Ser Arg Val Ala Ala Thr Ser Ser Thr Gly
                180                 185                 190

Lys Leu Glu Leu Leu Lys Ser Leu Gly Ala Asp Leu Ala Ile Asp Tyr
        195                 200                 205

Thr Lys Val Asn Phe Glu Asp Leu Pro Glu Lys Phe Asp Val Val Tyr
        210                 215                 220

Asp Thr Val Gly Glu Ile Glu Arg Ala Ala Lys Ala Val Lys Pro Gly
225                 230                 235                 240

Gly Ser Ile Val Thr Ile Val Lys Gln Asn Lys Thr Leu Pro Pro Pro
                245                 250                 255

Ala Phe Phe Phe Ala Val Thr Ser Asn Arg Ser Thr Leu Glu Lys Leu
                260                 265                 270

Lys Pro Phe Leu Glu Ser Gly Lys Val Lys Pro Val Ile Asp Pro Lys
```

```
                   275                 280                 285
Ser Pro Phe Pro Phe Ser Gln Ala Ile Glu Ala Phe Ser Tyr Leu Gln
    290                 295                 300

Thr Arg Arg Ala Thr Gly Lys Leu Val Ile His Pro Val Pro
305                 310                 315

<210> SEQ ID NO 67
<211> LENGTH: 156
<212> TYPE: PRT
<213> ORGANISM: Eucalyptus grandis

<400> SEQUENCE: 67

Met Gln Ile Phe Val Lys Thr Leu Thr Gly Lys Thr Ile Thr Leu Glu
 1               5                  10                  15

Val Glu Ser Ser Asp Thr Val Asp Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ala Asp Tyr Asn Ile Gln Lys Glu
        50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Val Asp Asn Val Lys Ala Lys Ile Gln Asp Lys Glu Gly Ile
               100                 105                 110

Pro Pro Asp Gln Gln Arg Leu Ile Phe Ala Gly Lys Gln Leu Glu Asp
           115                 120                 125

Gly Arg Thr Leu Ala Asp Tyr Asn Ile Gln Lys Glu Ser Thr Leu His
       130                 135                 140

Leu Val Leu Arg Leu Lys Gly Gly Met Gln Ile Phe
145                 150                 155

<210> SEQ ID NO 68
<211> LENGTH: 238
<212> TYPE: PRT
<213> ORGANISM: Eucalyptus grandis

<400> SEQUENCE: 68

Met Ala Thr His Ala Ala Leu Ala Pro Ser Thr Leu Pro Ala Asn Ala
 1               5                  10                  15

Lys Phe Ser Ser Lys Ser Ser Ser His Ser Phe Pro Thr Gln Cys Phe
                20                  25                  30

Ser Lys Arg Leu Glu Val Ala Glu Phe Ser Gly Leu Arg Ala Gly Ser
            35                  40                  45

Cys Val Thr Tyr Ala Lys Asn Ala Gly Glu Gly Ser Phe Phe Asp Ala
        50                  55                  60

Val Ala Ala Gln Leu Thr Pro Lys Thr Ser Ala Pro Ala Pro Ala Lys
65                  70                  75                  80

Gly Glu Thr Val Ala Lys Leu Lys Val Ala Ile Asn Gly Phe Gly Arg
                85                  90                  95

Ile Gly Arg Asn Phe Leu Arg Cys Trp His Gly Arg Lys Asn Ser Pro
               100                 105                 110

Leu Asp Val Ile Val Val Asn Asp Ser Gly Gly Val Lys Asn Ala Ser
           115                 120                 125

His Leu Leu Lys Tyr Asp Ser Met Leu Gly Thr Phe Lys Ala Asp Val
```

```
                 130                 135                 140
Lys Ile Val Asp Asn Glu Thr Ile Ser Val Asp Gly Lys Pro Val Lys
145                 150                 155                 160

Val Val Ser Asn Arg Asp Pro Leu Lys Leu Pro Trp Ala Glu Leu Gly
                165                 170                 175

Ile Asp Ile Val Ile Glu Gly Thr Gly Val Phe Val Asp Gly Pro Gly
            180                 185                 190

Ala Gly Lys His Ile Gln Ala Gly Ala Lys Lys Val Ile Ile Thr Ala
        195                 200                 205

Pro Ala Lys Gly Ala Asp Ile Pro Thr Tyr Val Tyr Gly Val Asn Glu
    210                 215                 220

Thr Asp Tyr Ser His Glu Val Ala Asn Ile Ile Ser Asn Ala
225                 230                 235

<210> SEQ ID NO 69
<211> LENGTH: 168
<212> TYPE: PRT
<213> ORGANISM: Eucalyptus grandis

<400> SEQUENCE: 69

Met Ser Thr Ser Pro Val Ser Ser Trp Cys Ala Thr Ser Phe Ser Pro
1               5                   10                  15

Ala His Ser Ser Leu Lys Arg Ala Ala Gly Leu Arg Pro Ser Leu Ser
                20                  25                  30

Ala Arg Leu Gly Pro Ser Ser Ser Ser Val Ser Pro Pro Thr
            35                  40                  45

Leu Ile Arg Asn Glu Pro Val Phe Ala Pro Ala Pro Val Ile Asn
    50                  55                  60

Pro Thr Trp Thr Glu Glu Met Gly Lys Asp Tyr Asp Glu Ala Ile Glu
65                  70                  75                  80

Ala Leu Lys Lys Leu Leu Ser Glu Lys Gly Asp Leu Lys Ala Thr Ala
                85                  90                  95

Ala Ala Lys Val Glu Gln Ile Thr Ala Glu Leu Gln Thr Ala Ser Pro
            100                 105                 110

Asp Ile Lys Pro Ser Ser Ser Val Asp Arg Ile Lys Thr Gly Phe Thr
        115                 120                 125

Phe Phe Lys Lys Glu Lys Tyr Asp Lys Asn Pro Ala Leu Tyr Gly Glu
    130                 135                 140

Leu Ala Lys Gln Ser Pro Lys Phe Met Val Phe Ala Cys Ser Asp Ser
145                 150                 155                 160

Arg Val Cys Pro Ser His Val Leu
                165

<210> SEQ ID NO 70
<211> LENGTH: 214
<212> TYPE: PRT
<213> ORGANISM: Eucalyptus grandis

<400> SEQUENCE: 70

Met Pro Cys Pro Arg Ala Pro Pro Met Met Glu Arg Arg Ile Lys Pro
1               5                   10                  15

Gln Thr Glu Gln Ala Leu Lys Cys Pro Arg Cys Asp Ser Thr Asn Thr
                20                  25                  30

Lys Phe Cys Tyr Tyr Asn Asn Tyr Asn Leu Ser Gln Pro Arg His Phe
            35                  40                  45

Cys Lys Thr Cys Arg Arg Tyr Trp Thr Lys Gly Gly Ala Leu Arg Asn
```

```
                50                  55                  60
Val Pro Val Gly Gly Cys Arg Lys Asn Lys Arg Ala Lys Arg Ala
 65                  70                  75                  80

Val Asp His Pro Val Ser Ala Gln Asn Glu Ala Ser Thr Ser Ala Ala
                 85                  90                  95

Pro Gly Asn Glu Val Pro Asp Arg Ser Pro Phe Glu Pro Pro Ser Ser
                100                 105                 110

Lys Ser Ile Tyr Tyr Gly Gly Glu Asn Met Asn Leu Thr Gly Leu Pro
                115                 120                 125

Phe Ser Arg Ile Gln Gln Asp Arg Ala Ala Leu Ala His Cys Asn Ser
                130                 135                 140

Ser Ser Phe Leu Gly Met Ser Cys Gly Thr Gln Ser Ala Ser Leu Glu
145                 150                 155                 160

Pro His Leu Ser Ala Leu Asn Thr Phe Asn Ser Phe Lys Ser Asn Asn
                165                 170                 175

Pro Gly Leu Asp Phe Pro Ser Leu Ser Thr Asp Gln Asn Ser Leu Phe
                180                 185                 190

Glu Thr Ser Gln Pro Gln Leu Ser Arg Ala Met Ala Ser Ala Leu Phe
                195                 200                 205

Ser Met Pro Met Ala Pro
                210

<210> SEQ ID NO 71
<211> LENGTH: 166
<212> TYPE: PRT
<213> ORGANISM: Pinus radiata

<400> SEQUENCE: 71

Met Ala Ala Leu Ala Thr Thr Glu Val Cys Asp Thr Tyr Pro Arg Leu
 1               5                  10                  15

Val Glu Asn Gly Glu Leu Arg Val Leu Gln Pro Ile Phe Gln Ile Tyr
                20                  25                  30

Gly Arg Arg Arg Ala Phe Ser Gly Pro Ile Val Thr Leu Lys Val Phe
                35                  40                  45

Glu Asp Asn Val Leu Leu Arg Glu Phe Leu Glu Glu Arg Gly Asn Gly
 50                  55                  60

Arg Val Leu Val Val Asp Gly Gly Gly Ser Leu Arg Cys Ala Ile Leu
 65                  70                  75                  80

Gly Gly Asn Val Val Ser Ala Gln Asn Asn Gly Trp Ser Gly Ile
                 85                  90                  95

Ile Val Thr Gly Cys Ile Arg Asp Val Asp Glu Ile Asn Arg Cys Asp
                100                 105                 110

Ile Gly Ile Arg Ala Leu Thr Ser Asn Pro Leu Lys Ala Asn Lys Lys
                115                 120                 125

Gly Val Gly Glu Lys His Ala Pro Ile Tyr Ile Ala Gly Thr Arg Ile
                130                 135                 140

Leu Pro Gly Glu Trp Cys Tyr Ala Asp Ser Asp Gly Ile Leu Val Ser
145                 150                 155                 160

Gln Gln Glu Leu Ser Leu
                165

<210> SEQ ID NO 72
<211> LENGTH: 236
<212> TYPE: PRT
<213> ORGANISM: Pinus radiata
```

<400> SEQUENCE: 72

```
Met Leu Val Leu Ile Ile Phe Gly Cys Cys Phe Ile Gly Val Ile Ala
1               5                   10                  15

Thr Ser Phe Asp Phe Tyr Tyr Phe Val Gln Gln Trp Pro Gly Ser Tyr
            20                  25                  30

Cys Asp Thr Arg Arg Gly Cys Cys Tyr Pro Arg Thr Gly Arg Pro Ala
        35                  40                  45

Ser Glu Phe Ser Ile His Gly Leu Trp Pro Asn Tyr Lys Thr Gly Lys
    50                  55                  60

Trp Pro Gln Phe Cys Gly Ser Ser Glu Glu Phe Asp Tyr Ser Lys Ile
65                  70                  75                  80

Ser Asp Leu Glu Glu Glu Leu Asn Arg Tyr Trp Gly Ser Leu Ser Cys
                85                  90                  95

Pro Ser Ser Asp Gly Gln Glu Phe Trp Gly His Glu Trp Glu Lys His
            100                 105                 110

Gly Thr Cys Ser Leu Asn Leu Asp Glu His Ser Tyr Phe Glu Lys Ala
        115                 120                 125

Leu Ser Leu Arg Gln Asn Ile Asp Ile Leu Gly Ala Leu Lys Thr Ala
    130                 135                 140

Gly Ile Lys Pro Asp Gly Ser Gln Tyr Ser Leu Ser Asp Ile Lys Glu
145                 150                 155                 160

Ala Ile Lys Gln Asn Thr Gly Gln Leu Pro Gly Ile Asp Cys Asn Thr
                165                 170                 175

Ser Ala Glu Gly Glu His Gln Leu Tyr Gln Val Tyr Val Cys Val Asp
            180                 185                 190

Lys Ser Asp Ala Ser Thr Val Ile Glu Cys Pro Ile Tyr Pro His Ser
        195                 200                 205

Asn Cys Pro Ser Met Val Val Phe Pro Pro Phe Gly Glu Asp Gln Glu
    210                 215                 220

Asp Arg Asp Gly Tyr Thr Glu Gly Met Tyr Glu Leu
225                 230                 235
```

<210> SEQ ID NO 73
<211> LENGTH: 92
<212> TYPE: PRT
<213> ORGANISM: Pinus radiata

<400> SEQUENCE: 73

```
Met Ala Ala Pro Arg Ser Ser Ala Lys Leu Gly Ala Leu Leu Ala Ile
1               5                   10                  15

Leu Leu Ile Val Ala Ala Ala Gln Ala Gln Asp Cys Ser Asn Ala Met
            20                  25                  30

Asp Lys Leu Ala Pro Cys Thr Ser Ala Val Gly Leu Ser Ser Asn Gly
        35                  40                  45

Val Lys Pro Ser Ser Glu Cys Cys Asp Ala Leu Lys Gly Thr Ser Thr
    50                  55                  60

Gly Cys Val Cys Lys Ser Val Arg Ala Val Ile Ser Leu Pro Ala Lys
65                  70                  75                  80

Cys Asn Leu Pro Ala Ile Thr Cys Ser Gly Ser Arg
                85                  90
```

<210> SEQ ID NO 74
<211> LENGTH: 92
<212> TYPE: PRT
<213> ORGANISM: Pinus radiata

```
<400> SEQUENCE: 74

Met Ala Ala Pro Arg Ser Ser Ala Lys Ser Ala Leu Phe Ala Ile
1               5                   10                  15

Leu Leu Ile Val Ala Ala Val Gln Ala Glu Asp Cys Ser Asn Ala Met
            20                  25                  30

Asp Lys Leu Ala Pro Cys Thr Ser Ala Val Gly Leu Ser Ser Asn Gly
        35                  40                  45

Val Lys Pro Ser Ser Glu Cys Cys Asp Ala Leu Lys Gly Thr Ser Thr
    50                  55                  60

Gly Cys Val Cys Lys Ser Val Arg Ala Val Ile Ser Leu Pro Ala Lys
65                  70                  75                  80

Cys Asn Leu Pro Ala Leu Thr Cys Ser Gly Ser Arg
                85                  90

<210> SEQ ID NO 75
<211> LENGTH: 92
<212> TYPE: PRT
<213> ORGANISM: Pinus radiata

<400> SEQUENCE: 75

Met Ala Ala Pro Arg Ser Ser Ala Lys Leu Gly Ala Leu Leu Ala Ile
1               5                   10                  15

Leu Leu Ile Val Ala Ala Ala Gln Ala Gln Asp Cys Ser Asn Ala Met
            20                  25                  30

Asp Lys Leu Ala Pro Cys Thr Ser Ala Val Gly Leu Ser Ser Asn Gly
        35                  40                  45

Val Lys Pro Ser Ser Glu Cys Cys Asp Ala Leu Lys Gly Thr Ser Thr
    50                  55                  60

Gly Cys Val Cys Lys Ser Val Arg Ala Val Ile Ser Leu Pro Ala Lys
65                  70                  75                  80

Cys Asn Leu Pro Ala Ile Thr Cys Ser Gly Ser Arg
                85                  90

<210> SEQ ID NO 76
<211> LENGTH: 125
<212> TYPE: PRT
<213> ORGANISM: Eucalyptus grandis

<400> SEQUENCE: 76

Met Ala Asp Arg Met Leu Thr Arg Ser His Ser Leu Arg Glu Arg Leu
1               5                   10                  15

Asp Glu Thr Leu Ser Ala His Arg Asn Asp Ile Val Ala Phe Leu Ser
            20                  25                  30

Arg Val Glu Ala Lys Gly Lys Gly Ile Leu Gln Arg His Gln Ile Phe
        35                  40                  45

Ala Glu Phe Glu Ala Ile Ser Glu Ser Arg Ala Lys Leu Leu Asp
    50                  55                  60

Gly Ala Phe Gly Glu Val Leu Lys Ser Thr Gln Glu Ala Ile Val Ser
65                  70                  75                  80

Pro Pro Trp Val Ala Leu Ala Val Arg Pro Arg Pro Gly Val Trp Glu
                85                  90                  95

His Ile Arg Val Asn Val His Ala Leu Val Leu Glu Gln Leu Glu Val
                100                 105                 110

Ala Glu Tyr Leu His Phe Lys Glu Glu Leu Ala Asp Gly
            115                 120                 125
```

-continued

<210> SEQ ID NO 77
<211> LENGTH: 805
<212> TYPE: PRT
<213> ORGANISM: Eucalyptus grandis

<400> SEQUENCE: 77

```
Met Ala Asp Arg Met Leu Thr Arg Ser His Ser Leu Arg Glu Arg Leu
 1               5                  10                  15

Asp Glu Thr Leu Ser Ala His Arg Asn Asp Ile Val Ala Phe Leu Ser
             20                  25                  30

Arg Val Glu Ala Lys Gly Lys Gly Ile Leu Gln Arg His Gln Ile Phe
         35                  40                  45

Ala Glu Phe Glu Ala Ile Ser Glu Glu Ser Arg Ala Lys Leu Leu Asp
     50                  55                  60

Gly Ala Phe Gly Glu Val Leu Lys Ser Thr Gln Glu Ala Ile Val Ser
 65                  70                  75                  80

Pro Pro Trp Val Ala Leu Ala Val Arg Pro Arg Pro Gly Val Trp Glu
                 85                  90                  95

His Ile Arg Val Asn Val His Ala Leu Val Leu Glu Gln Leu Glu Val
            100                 105                 110

Ala Glu Tyr Leu His Phe Lys Glu Glu Leu Ala Asp Gly Ser Leu Asn
        115                 120                 125

Gly Asn Phe Val Leu Glu Leu Asp Phe Glu Pro Phe Thr Ala Ser Phe
    130                 135                 140

Pro Arg Pro Thr Leu Ser Lys Ser Ile Gly Asn Gly Val Glu Phe Leu
145                 150                 155                 160

Asn Arg His Leu Ser Ala Lys Leu Phe His Asp Lys Glu Ser Leu His
                165                 170                 175

Pro Leu Leu Glu Phe Leu Gln Val His Cys Tyr Lys Gly Lys Asn Met
            180                 185                 190

Met Val Asn Ala Arg Ile Gln Asn Val Phe Ser Leu Gln His Val Leu
        195                 200                 205

Arg Lys Ala Glu Glu Tyr Leu Thr Ser Leu Lys Pro Glu Thr Pro Tyr
    210                 215                 220

Ser Gln Phe Glu His Lys Phe Gln Glu Ile Gly Leu Glu Arg Gly Trp
225                 230                 235                 240

Gly Asp Thr Ala Glu Arg Val Leu Glu Met Ile Gln Leu Leu Leu Asp
                245                 250                 255

Leu Leu Glu Ala Pro Asp Pro Cys Thr Leu Glu Lys Phe Leu Asp Arg
            260                 265                 270

Val Pro Met Val Phe Asn Val Ile Met Ser Pro His Gly Tyr Phe
        275                 280                 285

Ala Gln Asp Asp Val Leu Gly Tyr Pro Asp Thr Gly Gly Gln Val Val
    290                 295                 300

Tyr Ile Leu Asp Gln Val Arg Ala Leu Glu Glu Glu Met Leu His Arg
305                 310                 315                 320

Ile Lys Gln Gln Gly Leu Asp Ile Thr Pro Arg Ile Leu Ile Ile Thr
                325                 330                 335

Arg Leu Leu Pro Asp Ala Val Gly Thr Thr Cys Gly Gln Arg Leu Glu
            340                 345                 350

Lys Val Phe Gly Thr Glu Tyr Ser His Ile Leu Arg Val Pro Phe Arg
        355                 360                 365

Asn Glu Lys Gly Val Val Arg Lys Trp Ile Ser Arg Phe Glu Val Trp
    370                 375                 380
```

```
Pro Tyr Leu Glu Arg Tyr Thr Glu Asp Val Ala Ser Glu Leu Ala Gly
385                 390                 395                 400

Glu Leu Gln Gly Lys Pro Asp Leu Ile Ile Gly Asn Tyr Ser Asp Gly
            405                 410                 415

Asn Ile Val Ala Ser Leu Leu Ala His Lys Leu Gly Val Thr Gln Cys
                420                 425                 430

Thr Ile Ala His Ala Leu Glu Lys Thr Lys Tyr Pro Glu Ser Asp Ile
            435                 440                 445

Tyr Trp Lys Lys Phe Glu Lys Tyr His Phe Ser Cys Gln Phe Thr
        450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Asn Phe Thr Leu Pro Gly Leu Tyr Arg Val Val His Gly Ile
            500                 505                 510

Asp Val Phe Asp Pro Lys Phe Asn Ile Val Ser Pro Gly Ala Asp Met
        515                 520                 525

Ser Ile Tyr Phe Ala Tyr Thr Glu Gln Glu Arg Arg Leu Lys Ser Phe
530                 535                 540

His Pro Glu Ile Glu Glu Leu Leu Phe Ser Asp Val Glu Asn Lys Glu
545                 550                 555                 560

His Leu Cys Val Leu Lys Asp Lys Lys Pro Ile Ile Phe Thr Met
                565                 570                 575

Ala Arg Leu Asp Arg Val Lys Asn Leu Thr Gly Leu Val Glu Trp Tyr
            580                 585                 590

Gly Lys Asn Ser Lys Leu Arg Glu Leu Ala Asn Leu Val Val Gly
        595                 600                 605

Gly Asp Arg Arg Lys Asp Ser Lys Asp Leu Glu Glu Gln Ser Glu Met
610                 615                 620

Lys Lys Met Tyr Asp Leu Ile Glu Lys Tyr Lys Leu Asn Gly Gln Phe
625                 630                 635                 640

Arg Trp Ile Ser Ser Gln Met Asn Arg Val Arg Asn Gly Glu Leu Tyr
            645                 650                 655

Arg Tyr Ile Cys Asp Thr Lys Gly Val Phe Val Gln Pro Ala Ile Tyr
        660                 665                 670

Glu Ala Phe Gly Leu Thr Val Val Glu Ala Met Thr Cys Gly Leu Pro
            675                 680                 685

Thr Phe Ala Thr Cys Asn Gly Gly Pro Ala Glu Ile Ile Val His Gly
690                 695                 700

Lys Ser Gly Tyr His Ile Asp Pro Tyr His Gly Asp Gln Ala Ala Glu
705                 710                 715                 720

Leu Leu Val Asp Phe Phe Asn Lys Cys Lys Ile Asp Gln Ser His Trp
            725                 730                 735

Asp Glu Ile Ser Lys Gly Ala Met Gln Arg Ile Glu Glu Lys Tyr Thr
        740                 745                 750

Trp Lys Ile Tyr Ser Glu Arg Leu Leu Asn Leu Thr Ala Val Tyr Gly
    755                 760                 765

Phe Trp Lys His Val Thr Asn Leu Asp Arg Arg Glu Ser Arg Tyr
770                 775                 780

Leu Glu Met Phe Tyr Ala Leu Lys Tyr Arg Pro Leu Ala Gln Ser Val
785                 790                 795                 800

Pro Pro Ala Val Glu
```

-continued

805

<210> SEQ ID NO 78
<211> LENGTH: 264
<212> TYPE: PRT
<213> ORGANISM: Eucalyptus grandis

<400> SEQUENCE: 78

Met Gly Ser Thr Gly Ser Glu Thr Gln Met Thr Pro Thr Gln Val Ser
1               5                   10                  15

Asp Glu Glu Ala Asn Leu Phe Ala Met Gln Leu Ala Ser Ala Ser Val
            20                  25                  30

Leu Pro Met Val Leu Lys Ala Ala Ile Glu Leu Asp Leu Leu Glu Ile
        35                  40                  45

Met Ala Lys Ala Gly Pro Gly Ala Phe Leu Ser Pro Gly Glu Val Ala
    50                  55                  60

Ala Gln Leu Pro Thr Gln Asn Pro Glu Ala Pro Val Met Leu Asp Arg
65                  70                  75                  80

Ile Phe Arg Leu Leu Ala Ser Tyr Ser Val Leu Thr Cys Thr Leu Arg
                85                  90                  95

Asp Leu Pro Asp Gly Lys Val Glu Arg Leu Tyr Gly Leu Ala Pro Val
            100                 105                 110

Cys Lys Phe Leu Val Lys Asn Glu Asp Gly Val Ser Ile Ala Ala Leu
        115                 120                 125

Asn Leu Met Asn Gln Asp Lys Ile Leu Met Glu Ser Trp Tyr Tyr Leu
    130                 135                 140

Lys Asp Ala Val Leu Glu Gly Gly Ile Pro Phe Asn Lys Ala Tyr Gly
145                 150                 155                 160

Met Thr Ala Phe Glu Tyr His Gly Thr Asp Pro Arg Phe Asn Lys Ile
                165                 170                 175

Phe Asn Arg Gly Met Ser Asp His Ser Thr Ile Thr Met Lys Lys Ile
            180                 185                 190

Leu Glu Thr Tyr Lys Gly Phe Glu Gly Leu Glu Thr Val Val Asp Val
        195                 200                 205

Gly Gly Gly Thr Gly Ala Val Leu Ser Met Ile Val Ala Lys Tyr Pro
    210                 215                 220

Ser Met Lys Gly Ile Asn Phe Asp Arg Pro Asn Gly Leu Lys Thr Pro
225                 230                 235                 240

His Pro Phe Leu Val Ser Ser Thr Ser Glu Ala Thr Cys Ser Ser Ala
                245                 250                 255

Phe Gln Arg Glu Met Pro Phe Ser
            260

<210> SEQ ID NO 79
<211> LENGTH: 136
<212> TYPE: PRT
<213> ORGANISM: Eucalyptus grandis

<400> SEQUENCE: 79

Met Gly Lys Glu Lys Ile His Ile Ser Ile Val Val Ile Gly His Val
1               5                   10                  15

Asp Ser Gly Lys Ser Thr Thr Thr Gly His Leu Ile Tyr Lys Leu Gly
            20                  25                  30

Gly Ile Asp Lys Arg Val Ile Glu Arg Phe Glu Lys Glu Ala Ala Glu
        35                  40                  45

Met Asn Lys Arg Ser Phe Lys Tyr Ala Trp Val Leu Asp Lys Leu Lys

```
                    50                  55                  60
Ala Glu Arg Glu Arg Gly Ile Thr Ile Asp Ile Ala Leu Trp Lys Phe
 65                  70                  75                  80

Glu Thr Thr Lys Tyr Tyr Cys Thr Val Ile Asp Ala Pro Gly His Arg
                 85                  90                  95

Asp Phe Ile Lys Asn Met Ile Thr Gly Thr Ser Gln Ala Asp Cys Ala
            100                 105                 110

Val Leu Ile Ile Asp Ser Thr Thr Gly Gly Phe Glu Ala Gly Ile Ser
        115                 120                 125

Lys Asp Gly Gln Thr Arg Glu His
    130                 135
```

<210> SEQ ID NO 80
<211> LENGTH: 229
<212> TYPE: PRT
<213> ORGANISM: Eucalyptus grandis

<400> SEQUENCE: 80

```
Met Gln Ile Phe Val Lys Thr Leu Thr Gly Lys Thr Ile Thr Leu Glu
 1               5                  10                  15

Val Glu Ser Ser Asp Thr Ile Asp Asn Val Lys Ala Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ala Asp Tyr Asn Ile Gln Lys Glu
     50                  55                  60

Ser Thr Leu His Leu Val Leu Arg Leu Arg Gly Gly Met Gln Ile Phe
 65                  70                  75                  80

Val Lys Thr Leu Thr Gly Lys Thr Ile Thr Leu Glu Val Glu Ser Ser
                 85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Phe
225
```

<210> SEQ ID NO 81
<211> LENGTH: 345
<212> TYPE: DNA
<213> ORGANISM: Eucalyptus grandis

<400> SEQUENCE: 81
taataaatga tgaatttatt ataaacgtat ccgtttgaga ttttttgtggg tcataggtgt     60

-continued

```
atcaatttga aatctttgat agtaacaaaa ataattttag gtagtttatg ttttttcatga      120 tataaacctt gaaagttaat gctactaaat tgttatatat atattaggca aattacaacc      180
ttaatgcaac agttaatgac gtgatactgt tcagattata gatacaatgg ttatccttga      240
atgaataaga agaagtccta agggcaagtg ctatgagctt gcacgactgc ttttgcgcca      300
tttttgttta ccagcccggg ccgtcgacca cgcgtgccct atagt                       345
```

<210> SEQ ID NO 82
<211> LENGTH: 72
<212> TYPE: DNA
<213> ORGANISM: Eucalyptus grandis

<400> SEQUENCE: 82

```
cagtagggga cttgttcccc caagggcacg tgtcgttggt gaagctctgg cggtggatga       60
accgcgtggg cc                                                            72
```

<210> SEQ ID NO 83
<211> LENGTH: 544
<212> TYPE: DNA
<213> ORGANISM: Eucalyptus grandis

<400> SEQUENCE: 83

```
actagtgatt tcgtcgtctt cgtcttcttc gtcttctgga acttcgttgc tccgagcttt       60
atcagaaccg gcgatggaaa tgaaaccctc gttctctctc cctcgctcct ctctttcttc      120
tatccaggag cgtttgtaca ctgggagtac agagcttctt gcgataccga aactacccct     180
ggacgactgg cctttttgcc tcgcgccccc tctctgagcc ggggcgcaat ttgtcccttt     240
cccagagcga agtgtcgatt tgtccttcc acgaggcttt acctactccc atcgcccgag       300
ccccaagccc aggcccaaat gcctgttcct tgtggccctg ccaacattcc ctttgaaatt     360
aaaaaattaa aaaaaactc tctgccaggc aaaagtaaag attaacacca ccaaaattta     420
taacaaattt atcattcatt aattttcgtt aaattttatt ttcaaattac tgagtcgaat     480
tacatgtata aattcacgga tgtatcggtt cgagatttta tcctctaatt atcattagtg     540
tatg                                                                   544
```

<210> SEQ ID NO 84
<211> LENGTH: 515
<212> TYPE: DNA
<213> ORGANISM: Eucalyptus grandis

<400> SEQUENCE: 84

```
gattactata gggcacgcgt ggtcgacggc ccgggctggt ctgccttcct ttaactcccc       60
ttttttgtaa cttttaaaa tgtagtttta aatttaattt aattactttt tatattaatt     120
atttaccaca tcagagacaa aacaatgtct tttttgtatt ttctagtcac gtcaacatgc     180
aaaacaacgc cattttgcac tcaccttgcc ggaaaattgc cacgtcaaca atttggctag     240
agtggcgctt aagtgatcta ttttgctcca attttggcac ttaagtgtca tttttcctaaa     300 ttttagcact taagtattc ctctatgtca gttttgaca cttggggtgt actttgtcca      360
atcataaacc gtataagttc actttaaaca aaaatggcgc aaaagcagtc gtgcaagctc     420
atagcacttg cccttaggac ttcttcttat tcattcaagg ataaccattg tatctataat     480
ctgaacagta tcacgtcatt aactgttgca ttaag                                 515
```

<210> SEQ ID NO 85

```
<211> LENGTH: 515
<212> TYPE: DNA
<213> ORGANISM: Eucalyptus grandis

<400> SEQUENCE: 85
actagtgatt tcgtcgtctt cgtcttcttc gtcttctgga acttcgttgc tccgagcttt      60
atcagaaccg gcgatggaaa tgaaaccctc gttctctctc cctcgctcct ctctttcttc     120
tatccaggag cgtttgtaca ctgggagtac agagcttctt gcgataccga aactacccct     180
ggacgactgg cctttttgcc tcgtgccccc tctctgagcc ggggcgcaat ttgtcccttt     240
cccgagagcga agtgtcgatt tgtccttcc acgaggcttt acctactccc atcgcccgag     300
ccccaagccc aggcccaaat gcctgttcct tgtggccctg ccaacattcc ctttgaaatt     360
aaaaaattaa aaaaaaactc tctgccaggc aaaagtaaag attaacacca ccaaaattta     420
taacaaattt atcattcatt aattttcgtt aaattttatt ttcaaattac tgagtcgaat     480
tacatgtata aattcacgga tgtatcggtt cgaga                                515

<210> SEQ ID NO 86
<211> LENGTH: 782
<212> TYPE: DNA
<213> ORGANISM: Eucalyptus grandis

<400> SEQUENCE: 86
gagggtttca tttccatcgc cggttctgat aaagctcgga gcaacgaagt tccagaagac      60
gaagaagacg aagacgacga cggcgacatg ccttgcttga acatctccac caacgtcagc     120
ctcgacggcc tcgacaccct cgccattctc tccgagacca cctccggcgt cgccaagctc     180
atcggcaagc ccgaggccta tgtgatgatt gtgttgaagg ggtcagtccc catggctttt     240
ggtgggactg agcaacctgc tgcctatggc gagttggtgt caatcggcgg tttgaacccc     300
gatgtgaaca agaagctgag tgctgcaatt gcttcaatcc tcgaaaccaa gctgtccatc     360
cccaagtcgc ggttcttcct gaaatttttat gataccaagg gttccttctt tggatggaat     420
ggatccacct tctgagctgt tggtcgcatt ctcctcagtg tttaccatgt atttcggccc     480
taaactctac ttctaggcct gttaaaagtg tcttttttaa ggtaattctg ctattacccc     540
tcttaagtgc atcttatcag taaacatgga atatcctgaa ctttgattat atgccggctc     600
gtggctgtgg aagcacttct ttatgttacc accagcttct caggtgaata taagctttgc     660
ccagtctgtt ctctggggga tttgcttggt gggtagtggc aatcagatgg ttttgtcact     720
tttgtgcata tttaagtagt aaatgtccac gacagcccaa agagtagcaa tccgggtgca     780
ct                                                                    782

<210> SEQ ID NO 87
<211> LENGTH: 115
<212> TYPE: PRT
<213> ORGANISM: Eucalyptus grandis

<400> SEQUENCE: 87

Met Pro Cys Leu Asn Ile Ser Thr Asn Val Ser Leu Asp Gly Leu Asp
  1               5                  10                  15

Thr Ser Ala Ile Leu Ser Glu Thr Thr Ser Gly Val Ala Lys Leu Ile
             20                  25                  30

Gly Lys Pro Glu Ala Tyr Val Met Ile Val Leu Lys Gly Ser Val Pro
         35                  40                  45

Met Ala Phe Gly Gly Thr Glu Gln Pro Ala Ala Tyr Gly Glu Leu Val
     50                  55                  60
```

```
Ser Ile Gly Gly Leu Asn Pro Asp Val Asn Lys Lys Leu Ser Ala Ala
 65                  70                  75                  80

Ile Ala Ser Ile Leu Glu Thr Lys Leu Ser Ile Pro Lys Ser Arg Phe
                 85                  90                  95

Phe Leu Lys Phe Tyr Asp Thr Lys Gly Ser Phe Phe Gly Trp Asn Gly
            100                 105                 110

Ser Thr Phe
        115

<210> SEQ ID NO 88
<211> LENGTH: 1521
<212> TYPE: DNA
<213> ORGANISM: Pinus radiata

<400> SEQUENCE: 88
ccttcaaaga caacagagaa agttatgcaa tatgctggca gctagctctt gggataatct      60
atttagcgat gggtttgtcg agaagttggg agcattatt gtgaagcttc acagaaaaaa     120
tgtcgaatac atcaagcaca tgaagaagca atttgtgcca taggctatct ttagcctcat     180
ggatgttaaa ataatttctt tctttccttc cttcttcttt cttacccacc aaaacacaaa     240
ataatagttt caaattttga attttcaccc aattttatga gaggacaaaa ttacttagag     300
tctttcactc tttaatttat attctacata agtacctaaa gaggctctcc gacaatcata     360
tgataccata aaagtaacct cgattagaga gcgcctctcc atacaatcat ttgattttcg     420
agttaaatca aaattatagg ctatttccaa atcaatctat cgtccaactg aaaatttcaa     480
atgaatggaa ccagcacgga gtttcgtagg aaatagaagt aataggtgaa agaagcatt      540
gtcgaatttg aaagaatacc ctacgttttc atttcaaaaa ccatggtttt ttgtaagagg     600
gattaagttg actcaaggtt gtagaaggtt gacataacaa tagcatgcag gcacaggatg     660
catgtagtgc ccgtaatttg gaccaaccta gtaagattgt cacccgtttc aaatgactgc     720
ctacaagtgc atgcaaaggc catggaagtt gatggttagt gaaagatcc ggagagacga      780
ttattccatc atgcaatgca catcgcacgc ttgctttatt actcacacga ccaacgttcc     840
cttcatccac ggaattaatt tctctaatcg atccaataaa ccgccttcga tgtcgattc      900
caaatgaatt aaatcgttac atgcccaccc gacttcacac atgctccctg cacgtgcaac     960
caaatccatt acgcccaccg ggcccggccc tgctcacaca tcttgcatcg cccaactact    1020
ctgattttac atgaatatca atactattcc ctccacttat aaaatggcca aacgccctgc    1080
ttagttctca aagcagatca gagcctttca agagcttccg caaagatttt ctttgcgagt    1140
aatttgatcg agaaggatgt ctgcatcgaa cggaactaat ggtgttgtcg cagtcaagtc    1200
tcgccgacag cacagacctg ggaaaacgac agccatggcg ttcgggaggg cgtttccaga    1260
tcagctggtg atgcaggagt tcctcgtcga tggatatttc cgcaacacga attgccagga    1320
ccccgtcctc cgccagaagc tcgaaaggct ttgcaagacg acgacggtga agacgcgata    1380
cgtggtgatg tcggatgaaa tattggcgca gcatcctgag ctggcagtgg aaggttcggc    1440
caccgtccga cagcgactcg agatctcgaa cgtggccgtg accgacatgg cggtggacgc    1500
gtgccgtgac tgcctcaaag a                                              1521

<210> SEQ ID NO 89
<211> LENGTH: 2590
<212> TYPE: DNA
<213> ORGANISM: Eucalyptus grandis
```

<400> SEQUENCE: 89

```
ctgaaactgt cgctcggcga tgcataccaa aggctgaagg tatcagaatc taatgcagct      60
tatgtaaaag cgcgatcaat ttattgaccc cgacgacctt gactccatac ttcacgcctc     120
agctttgtgt tggatggtct tgacctctct caccctaaaa ggtagctcaa aagaatgaga     180
ctttccgtca tacttataaa ccgaccacca gcctctttca caaccgacat gggacaacct     240
caaatagaat ttttaacaac acccttgcac gctctttcta tccactttat tatgccatca     300
catgagcgtt ttccacgcgt aaatcggcta ccacccactt tcacacggcg gcgaaacgag     360
aaaaaggtcc taccttgac tcccccccgcg tcccaaattc tcactcccga ccggtaaccg     420
agctcacaag tttcagcctt tcatcatcat cactcgaagg cagagagaag gacatacact     480
aaagacaacg aaacagtctc tccatcccgc catccgacac gatccacatt acggtacgga     540
acacatcccg cggagcaacc cgacgtccca aactcttcgc tgatcaaaac cagtccggtc     600
gactccgttt cgcgcggacg caacgtgaga gagggagaga gagagagaga gtaccggcga     660
ggggatgatg ctgtgcggaa gcgtcgtcgg gcgctctccc ggcgaacgcg tctctacatt     720
ccggcgacgg cgacgcgac gaaggcgggg aggggaatgc cgcggggttt ctgcaacgac     780
ggaagctcac ggcatttttc agagagagag agagagatgg cacgtcagag cgccattccc     840
ccacgcgacg ttccgccttc cggtattcct tccgggagaa aaagtgggca aattgcaata     900
gacaaaaaaa aaaagaaaaa aaagacggtc acccaaatta tttcttataa cacaaaaaat     960
cgtacctata taatatatct atcactaact tgtgcagtat gacaaattta cacatttacc    1020
tgaaactgtt tttataacat aaaaaattta acattttttc tgtgacaata aatgttcaca    1080
caaatataaa actgggattt ttatttcaat tacaaattta gaataaatgc gcaacataaa    1140
tacaaattta tgattttttcg tgttggcaag aaagtttgag ataaatgtat cattgtaggt    1200
aaagttttaga gtttttttttt atggctttta accaaaatgc acattttagt tccgagttct    1260
aaaagaaaaa ttactatttt cctttacatt tacttatgta ggtgtgtaat tataaatatt    1320
aattctcttt aggatttgta acaattcttt gagcttttgt tttgccttta ggccattaga    1380
attactaaaa agttaataat ataaacattt tttcgaccac ggtcaccatt catacctaac    1440
ttctaattat tgaaagattc tcgcatttga tcgaaatcca tttactctca taaatttgag    1500
gttttgaacg gtatctacca taagatcatg gtttattaca aaacacttat ggcgggtggc    1560
gcggacctgg cgagaatgtg gctactttaa tgatgaggat ttgagatatt ataccacgat    1620
ccataataat aaaggagcgc ggcaatcata tcttttttca tataaaggac gatttatttt    1680
ctatgctgtg agtatttgct cttggaatta taagatatta gagatcaaac ctatcaccaa    1740
cggtgatttg aaattaaaga agtccttgta tcacttacaa aaataaatat ataaaaaaag    1800
ctttcattgt gcacttgaat atttaaacat aaattattag tagtagataa tttttttaatt    1860
taactaataa tgagcactca tttttagaaa aatagttttc aaatcattca ttttctactt    1920
aaaaaaacca attgaccaac taaattagta tctctcattc agttggtgaa tgaatgactc    1980
gcactctaac ccttcacttg gcgagtcatt ctgtgtagac cagtctctgc aaatctagcc    2040
atgctcatct agcaactacc ttcaagcgca agtactttgt catgtagacc aaacgttgag    2100
caacacggaa tgaatcctaa cgcacttgga aaacaatcaa tccacgctac gcaagctaat    2160
gctcacacaa gcatcatgat acccgaagcc gaaaatacat gagtcgaaag acatcgaact    2220
ccgccgtcct cgcgaatcat ccgaatcgca tgtcacgccg ctcgacttgg tagcttaacg    2280
agccttccag tacctgctgt ttaaatgctt tgtcaatgtg attcgaatcc tttcaaagat    2340
```

-continued

```
cctgaaagtg cagcttcaaa aatggcgtcg accaaatggg cttgcgttgc tgcaatctcg    2400
ctcctactga gcctaggatc gagcgctgct cagaggtctc tccttatgag cagcgccaac    2460
tggcaagagg ccggtgagcc gacggatctg gacttacgtg gaggaattgc cggaaccctg    2520
gggtcatcaa gtgagggcgg caccatggcc agctccgaca tgggcggttt tggccaggac    2580
atgcctggtg                                                           2590
```

<210> SEQ ID NO 90
<211> LENGTH: 1172
<212> TYPE: DNA
<213> ORGANISM: Eucalyptus grandis

<400> SEQUENCE: 90

```
actctcacta attctttagt tttccaattt agccccttct gtaattgctc atcttcttta      60
ccaaattctc taatttggcc ggcgaagggc tgacaaggga ttggtcatgt caccctcacc     120
aaaggttgcc gaaggtccgg tgacctcagc tgacggccac ctacaccaaa tctagctcac     180
tagcagccta agcccttcat caactctagt gaaaggtttt gagtattttt aataaaaaa      240 tatttaaaaa atatatagcg agagctcatt acaaaaaaat tttaaaaaaa aatctaaaca     300
ttacttgaac tcaaagtgac tttataaaga gttttttacca aaggatcttg gtttcatcat    360
ttgcactaca cccaaaaccc aatttctaag ttaaatcaaa cccactgtct aatagagata    420
aggtaaatgt tataaaccaa attccaaaat tccgaagcac taaatatatt tgctgatctt    480
ataatcgcca attgagaggg tctcattctc caagggattg tgacatatta gtaattgata    540
gggtctcatc cgtaggactc cgactcagcc gcgccacgtg actggatcgc tgaacggcgc    600
ggaaccagag gagcgtgatt acctaatatt ttctcctacc ttggccttga gattgaattt    660 cagaaaaga aaagaaaaa ggaacaactt cgccgactgt tctataaaat gcatgcgcca    720
ccccgacccc cacccacgca tcacatccat ccagcctcca cgacagacgc ataaacacaa    780
cacacgtcgg ttagagagag agagagagag agagagagag agagagagat gcttggacag    840
ttgtcgcacg agacggaaat gaaggtggga gcaggcaaag catgggagct gtatggcacg    900
ctcaagctgg tcctgctggc caagcaggaa ttctctaata ccatctgcga cgtcttggaa    960
ggtgatggcg gcgttggcac cgtcatcaag ctcaattttg gaagtttatc ctatacagag   1020
aagtacacaa aggtggacca cgagcgccgc gtgaagaaaa cggaggcgat cgaaggtggg   1080
ttcctggaca tggggtctcg ctgtatcgat tgcgattcga agtgataggc aaggacgagg   1140
aggagtcgtt ccgttattaa agccccccccc cc                                1172
```

<210> SEQ ID NO 91
<211> LENGTH: 446
<212> TYPE: DNA
<213> ORGANISM: Eucalyptus grandis

<400> SEQUENCE: 91

```
gggtgaaaac aattaatgag atcatttgaa ttaaggaaag tggaaaggcg gttttctgat      60
tggtacactg aaacaacagg aaggtggtgg aggccgcaat gatggaattt atccacttta    120
atcattttat gaaatcgata cactaacctt tgtttctcct aaacccaaag gcattaatcc    180
ctgtcctcct cactcgatct cgaaggccag aaggggggagg ccgagcctct tgcttttttt    240
cgtgtataaa agggcctccc ccattcctca tttttcacca tcctccgttc gttcgttccc    300
ttccctttcc attgttgcgt ttaagccctc caatttttctt ttggcgtccc gttttgggg     360
```

| | |
|---|---|
| ctcccttgaa gatctcctct tcatttcggg atttcctgcc ttcgccgcgc catttgaagt | 420 |
| tcttttctg agagaagaat ttagac | 446 |

<210> SEQ ID NO 92
<211> LENGTH: 2119
<212> TYPE: DNA
<213> ORGANISM: Pinus radiata

<400> SEQUENCE: 92

| | |
|---|---|
| atcttattcc cacctcacat caataaattt tatacgattt taacatcttt aaaattaaaa | 60 |
| gaatcaagaa ggcatccagg tgataaagcc acgtccaata taaaatctcc tcggtggatc | 120 |
| ctttcaatcc agctacccaa tgcggcgaaa ataacgctga ttggactggg ctacactgta | 180 |
| atcacaaatt cccttccgtt tagatttcaa ctcgttgacc tacgagtatt ttatcgattt | 240 |
| aaaattatac aaaaaattgt ggaatgtttt acataagcaa aacttaaata atgtaaatag | 300 |
| cgatgatgct ttacttgtac ctaaaaattt cttccaaatt aaaccaaata tcaaatccta | 360 |
| gattgatgag ttccagtgga gtctgccatt ttatttcttt ctctctttca ttctttgcaa | 420 |
| cgaaaggaga aaatccttaa cacaattcga aaacgataat gattctggca aaagagaaaa | 480 |
| aaaacgtgaa gattagacac ttgttttgtt ttaaatgagc aatcacatgt gaatagagag | 540 |
| ggttttatgg gcctggtttt gtgtgcataa tttcttatga aagcgatgtg cctggagcgt | 600 |
| tgaagctcat agaacattgc aacaagagat cgagagtgtg ggttagaaaa ccgcaacaat | 660 |
| agtttgtgtc gtgttttct atattcgagg tgttgtgtg gtaaatatct ctggatttat | 720 |
| ctcgaatgcg tcacttttac agacacagaa gctcagcgga aaccctcaac gctttaaggg | 780 |
| ccataaattt gctcagtttt aaaaattgtt tgatttccca ggtttgaata ttttcttttt | 840 |
| gttatcggaa gtggctctgc cttatgagta tcatgttctt ggttttgtgt tgggcgctta | 900 |
| ttgattcagg tatgtattat ttctagtcct tttatcagc ataggtggaa tgttctgtat | 960 |
| tttatatttt ggggccatac acatggaacc gttgtcatta ccatgcttta tagataatgt | 1020 |
| ctctctgaat ttgtttttat aggcttttgc ctcctacgca gattttaaa ggaaaataca | 1080 |
| aagatattta gccaattttt gttgttgtga ccttgaattt ctaaaaaatt taatggattc | 1140 |
| gttttctaaa ttcctgattc gtcaaaggct gaagggcgcg atagtaatag aaaatggacg | 1200 |
| agagtttatc ttttcatggc tggacacaca gaatttgtgg aggggattct ccattctggt | 1260 |
| ttatccaccg ttagttctct ctgtactcca cccttagttc tctttgtact cgagacccttt | 1320 |
| aatgattaac cctgcttatg ctgtcagtac tgaactcact tccagagccc caaaaatctc | 1380 |
| tcccaagttt gccttatttc ttaaaataat tcacaagtag aaaatgagat ttttgcaatt | 1440 |
| ttgtaactaa catttcccgg tctcctctgt atgttttcac cccttaatgt aattgaaatt | 1500 |
| tgcacccggg ttagattcaa agcggagaat aacatcgggg ccttgttcta gacagagatt | 1560 |
| tttcacaaat aacaggttcg aaggtatgtg tagacatctg ggtagttgta gaataaagac | 1620 |
| ggagcccatt aggtggatcc aatcgaagaa ctcagatggg aaaacagata aaattatcg | 1680 |
| ggtggacctt cctccacatg ttaattatat atcaagtgtc gccaatcctt atgtgaaaca | 1740 |
| tttagtaaag cttcgccaga gcacttctta taggcattct gtgggctctg ttgttgtggt | 1800 |
| tggaagtact cctttaaggg aggtatctga atatttgcaa cagaagtcag taaaacaagt | 1860 |
| ggttgactgt ctgtttgtac aagatgttac tggcatacct gtgggcttga tagagacttc | 1920 |
| caggcgcatt gtgcatgtaa atcatttggt gatgcagaag ctagccggag tagagtctat | 1980 |
| agagcccact gaagcaattg gtgtaatcaa gcttcctagc agcttctaca acttggaatc | 2040 |

-continued

```
tcttgaaatc actctagttc ccagatatgg tgctcgtcgc cacatcgtct gcttgtactt    2100
gatggcattc aggatcctg                                                 2119

<210> SEQ ID NO 93
<211> LENGTH: 2571
<212> TYPE: DNA
<213> ORGANISM: Eucalyptus grandis

<400> SEQUENCE: 93
aaggtaactg gttcagcaga gcgcagatac caaatacttg ttcttctagt gtagccgtag      60
ttaggccacc acttcaagaa ctctgtagca ccgcctacat acctcgctct gctaatcctg     120
ttaccagtgg ctgctgccag tggcgataag tcgtgtctta ccgggttgga ctcaagacga     180
tagttaccgg ataaggcgca gcggtcgggc tgaacggggg gttcgtgcac acagcccagc     240
ttggagcgaa cgacctacac cgaactgaga tacctacagc gtgagctatg agaaagcgcc     300
acgcttcccg aagggagaaa ggcggacagg tatccggtaa gcggcagggt cggaacagga     360
gagcgcacga gggagcttcc aggggggaaac gcctggtatc tttatagtcc tgtcgggttt     420
cgccacctct gacttgagcg tcgattttg tgatgctcgt caggggggcg gagcctatgg      480
aaaaacgcca gcaacgcggc ctttttacgg ttcctggcct tttgctggcc ttttgctcac     540
atgttctttc ctgcgttatc ccctgattct gtggataacc gtattaccgc ctttgagtga     600
gctgataccg ctcgccgcag ccgaacgacc gagcgcagcg agtcagtgag cgaggaagcg     660
gaagagcgcc caatacgcaa accgcctctc cccgcgcgtt ggccgattca ttaatgcagc     720
tggcacgaca ggtttcccga ctggaaagcg ggcagtgagc gcaacgcaat taatgtgagt     780
tagctcactc attaggcacc ccaggcttta cactttatgc ttccggctcg tatgttgtgt     840
ggaattgtga gcggataaca atttcacaca ggaaacagct atgaccatga ttacgccaag     900
ctatttaggt gacactatag aatactcaag ctatgcatcc aacgcgttgg gagctctccc     960
atatggtcga cctgcaggcg gccgcgaatt cactagtgat tggcccgggc tggtctggag    1020
tggccaccat cggcataatg actaggaacc cggaacatca actgatggaa gaaaagccga    1080
cattcctcat caagagctcc tctcactcct tccccactac tactataggg cacgcgtggt    1140
cgacggcccg ggctggtctg ctgtcatatt tgtatatgag gtcctatgta tgcttgctat    1200
gtgacctcct tcatgtatgc tgtgaagaga gtgtagcagt aacatggcca tctgcgaaat    1260
atggattcac cttaaaatct gatgattttc agaaaacgag gaaggtgctt gccgagaaga    1320
ttgcacagct caattcagct atagatgatg tatcctctga gctccgaact gaagaatcat    1380
cagatgagat tgctgttgcc cctgatgaaa ttgaagctgc tgtttgatgg cccaaacctc    1440
ccaggcctac gatcatggtc atcttctgtt ttggtgcaat tggctctacc ttttttggtgg    1500 cctccatata acagaataat ggttcatatt gtaaaatctt ctgtttattt ctaaagacca    1560
atgcactcag tttcttttga tatgattgtc tcgattgagg aagtgcatca ttcgtggtat    1620
gattatgcag aataccattt aactcagcag actttgtacc gtatcatcgc agcttttccc    1680
ttcttgtgta tgcataaatc tagtccttca ttgaaggtga tcgccgttac agtctggata    1740
gtgtgtgcca tcagatggca ctacgattag tgtggttgac atggtgtcaa cttgaaagcc    1800
aattggtgac gatggtactt aatgtaagat tggcagatgg tgagaacgag attttgctcc    1860
agaatggcaa agcaaggcta agttgtagcg aatcaaatga tctacgaacc atcctagctg    1920
gctgtgtgac cacacactga agttctattg aactaagcca gttatggatg atatgggagg    1980
```

```
agaaaattga gaaatccatc agatggagtg ttggccgtgt tgggcttttg tcgcaggccg    2040
atacttcgaa ttcaggcgta ttttttattcc tgactgccgc ctctcccgga aagggaaggc   2100
ggatattatt ctctgaacga tttccaccat caactccaca tcgatctcca agccagaaat    2160
atacacaccc caatttctt ttaaatatat gggacatata tggtgtaggc tctcgcgcat     2220
gttaacacat aagctctctc aacaaaaatc tggctcgtgc ttttaaccga aagttcacg     2280 agtcattgaa ggagtggcct ttaggggagg gagagagatg gattggtggt taaaatcagt    2340
ctgtggctca catttatacc gtggagatcc cccaacagca accttatccc attatatatc    2400
cccacaacac catattcacc actcgttcct tctaattggc ttccaaccat aattcacaga    2460
cacacatgta gtgaccaatg agaaaggaag aaaaatacag gctttcgaaa gctagtgcgg    2520
tataaataac ctgggaaaag caagccgctt gagctttagt ttcagtcagc c             2571
```

<210> SEQ ID NO 94
<211> LENGTH: 1406
<212> TYPE: DNA
<213> ORGANISM: Pinus radiata

<400> SEQUENCE: 94

```
aaagaggcgg aggaattgtc tagatggtca aaagtgaccg gaatctaagc aaaaaatttc    60
aaaaaatgtt gtaaaggtag cgtttgaatt gtgttttttga tggtggaaat ggattcaacg   120
ccatcaaaaa cgtctaagac acctaaaatt ttgaatttta acaactatat cttggattta    180
caaaaatcct tgccggattt tctctaaact ccttcaccttt acgcaaaaga tatatatttt    240
tttgtgtgat gttgtgcatt ataagtttga tagtgaagta atgatatata tcctttatgt    300
gatggatgat tgaataatga atatattaaa tgaaataaat aatgatggga taatgaatat    360
attatatgaa ataaatataa agtaaaatgc tattttttaa tggtgttaat gatgaattag    420 tatcatccttt aaataatttg ttagtgaatt attaaaatga tgagttagca tggtcgttaa   480
ataaattgtt agtgaattat tatatttata tatttcctta ttagaaagtt ttttttttgt    540
aaaagttttc cttgaacttc acccatattt aattatcaat aatttatatt taataaatga   600
tatatataac ttctagcaga atgacacgcg acttgtatat cttttcattt tttaacccat   660
gaaaaccgat tagggtattg caaattaggg cattgccatt caaataattc tcagatgaaa   720
gattctctct aacaattaca aatgattatt ttttttccatg agtgttgcat gttcgaacgg    780
tctgcccagt ctgtgagaga gcatagagaa ccctccctgc ccaatttgtt agagcataga    840
gaaccctact gcatgagtag taagaaaaat attcggtctc aattcggcaa agaccacctc    900
gaatggatga cttcaacgac aatctcatga tagtgttctg atcagcacca gttcacctat    960
atattttatc tagggtttag tttgcatgta tcaatcctct ggtgcactag gtaattcttt    1020
cctagtatca tatatcctta atactgtttt gtcttttaat ccatggctac catcagaaca    1080
agctcaaagc agaaatcggg agcatcagcc atcctcttgc ttatcgcgct tgcagggtta    1140
gtaaatgcgt gcaacgctgt gggtattgag ccaatgtgcg cactgtggt gtcgagtctt     1200 ctgaggcttc tgccatgcag gacggctgtt gatccctcaa ttgccgccat tccacttcca    1260
agctgctgca acgcggttga gtcagctggg cttcaatgcc tctgtctcgt cgttaacggc    1320
cctccttttc cagggtcga ccgcggcctc gcaatgcagc tgcctgccaa atgccatctc     1380
acccttcctc cctgtaacag ttagtt                                         1406
```

<210> SEQ ID NO 95
<211> LENGTH: 2546

<212> TYPE: DNA
<213> ORGANISM: Pinus radiata

<400> SEQUENCE: 95

```
ctggtagaac aagcagctca aggagcacca aggcacgagc ccactttgca tgttgtagac      60
taacgaattt tacattagaa taaaatatgt cgacaatatc gaggagatct tctccaaaat     120
ccaactcatt aatctctatt atgcacaaac gagtgatgtg tcgagactca tctgccaaca     180
agccatcaac atcaagaagg gaacggaata gagccaaagg gaaccctaga gaccctcatc     240
cacataataa tgaaatattc cacgtgtgtt tttcaaaatt tgaaaatttc atgtattttt     300
tggttgattg gttgtggtct ggttttttcc aaattcaatc tagttcaagt ttttggagtc     360
gaccagttgg gtaaccagtc taattctggt aacattgcat tgtacttgat ctcaataaaa     420
gcatatagga tagaattatc ttctgtcttg atggtttcca tgagaaccaa ctgctatact     480
atgaaaaata tcaatgttcc acaatatttt tgggacaagg gaacacaaga ttgagtcaac     540
agttcaggac cccagaaaaa ttattcctga gttcgcagat tattttccta aaagtgaaca     600
attcaagacc ctagccaaat cattcccaag tccaagttat gtgacactgc gactaacaag     660
gcaagttgga agaaaccatc aatcaatctc ctagttaatg acagtccttg taagaagttc     720
aagaagatta acaccagaag aggtcatgct gactgctttt atccaattct ctctgctctt     780
caccaacaga aatagccaag atggttgtac ccattcccta atctaattta ttatatgaat     840
ttctctttat ttttctacat ataaaaaaca aaaacttttc ttgatggtca aacagaaaag     900
gcagttcgat tggatttaaa catccaaata cctcccacag attgagaagg ccaagcccca     960
atccaacagt ccatgatata atatttattc aatcacactc aagataatgc aatgaaggtg    1020
caccacgcta ttagattctg cacagaactc agatgactgt aattatcaac tttaaccagg    1080
agtaatttaa aaactcaatt gtgcttcagc tatgtggaaa actttggca ctggaaatgg    1140
tataaatgtt gttgaataag caaacatttt tcaagcactg aattcaaagt caagtcaaag    1200
gaacatctta cttgggctgt acaggaaatc tgaagtacaa aattagcgaa aaaacaggag    1260
aaagagagta gtcattacat gttataacat taccatatag gattttgtaa tacttcttga    1320
tatttcaact tcccgactga tgaaatgtat gccactacag aacaggtcag tcatgtatgt    1380
gagcaattag ccaaactagg tcctaaggtt caaccagtgc agacaacgct gtaactgaaa    1440
caaatttgtg ggacaattaa aaattctcta ccaggatagt tgtaccagta ggtgcccttt    1500
tcaaaccatg atttaaaaca aagggtggc ttaccacttg accaaatcat ttaataacca    1560
accctcgaa catatcaaga aagaaaacat ctgcatataa gtaaattgaa agatgatatt    1620
taagaggcac tgccttaaat tttccatttg gacaaatcca cattgcttga taagcataaa    1680
accttggtta agagcaagtt tagggaacca tcaaatattt ctacatactt tacaatagtg    1740
tgtttataaa gctaatcaaa tgcttctatt taaatatata gcaacctaca caagaaattc    1800
actaggacag caatcacttg gccaatgtga ttaccaatat aaccatactt gaagagcata    1860
cataaatcac aaataatgat tcaattagaa atatcttaaa gataaactat tattcaatgt    1920
acatgttaca aagaacctca cctgtccgcc tttgaggagc aagtagacaa ctaaaagcgg    1980
aggttacatc ctgaactgaa cttgttctcc tctgttccaa gaacttgcat tgtattttga    2040
gtaacttcac tcgtgccgaa ttcggcacga gaaaacactt tgattgcttc cgcgggtggg    2100
ttttacttc tctggaatag ttagttccgc cgttttgga agatttatca gaatggccaa    2160
aattcaggtg tcaaacggga gcgtcgtggt ggtggcggcg atgatattta tggtggcggt    2220
```

```
ggccatgcaa aaccatcacg tcgccgccca aagtgctgac tgcgcaccac cgcggagttg   2280
ctgagcccct gcgcctcggc ggtgggaaac aacccgcaga ccccactccc gaatgctgtg   2340
ctgttctcca gaccgccgat gtcgactgca tctgcgccct cgtcgaatca accataaaat   2400
tgccttccga atgtggtctt gacacccccc agtgcccaag cgactagatt ctcaagaccg   2460
tgactgagtg ttggtttcag agccagtaaa cattcattct gctaataaat gagtgtatgg   2520
agctttaata ttggaaaatg cttcat                                        2546
```

<210> SEQ ID NO 96
<211> LENGTH: 4726
<212> TYPE: DNA
<213> ORGANISM: Pinus radiata

<400> SEQUENCE: 96

```
gattactata gggcacgcgt ggtcgacggc cctggctggt cctaggacac cgtaatatat     60
aacctcgaca tggcttacaa agctttgact tgcattctca ttgggcttac aatggtgctg    120
ccaaaaatga aaagtacat atgtacccct gttgaaatga gcagtaatag gcttgaacaa     180
tagtgaattg ctacaaaatt atgaatgcct ttctttgctt gaatgtgggc taaggagaag    240
tgggatttac atttgacttg caaatcctaa gacttgtcta gagctaagcc tccagaggag    300
gaaccatctt acatagtctt gagtctagag cggagaagat agccaaattt gaaggaaac     360 tttatttat ggggagaagg caaacaactt gagggggaag gatgatcaat aagtagggta     420
agggaatcca caacagaggg cactaaggaa atggggtgt tagaattggc aactagggcc     480
aaattccacc ttgggatagc tctctggatg gagatgatga ttgcattaga ttcctctttt    540
cgagaggacc aagattgata taaagatcat ctcatttgga caagcatagg tatgattttg    600
aatttatacc cactcatgca caatttttt aggtccgcca catcatcatg taggctcatg     660
aagcccaacg gacatgactc ttcgcccta tcgtcttgta taaatacaag tgtcctccca    720
cctcatttgg catcttcatc tcttacagat tctctcttct tccctcattg gttcttgcat    780
cattgggcat tctctctctc ccacgtgtgg cacaaggagg atgaaattac aagaccgaaa    840
ataatagaaa ttttgcaatt tgaccagcat tgaccatgac cttccaagca tcattcgact    900 tcaattttt tgggttattt ttgtctcaac aagccgcata ttttggcaaa aaatcgagg      960 cattctgggc acttcgacta caaaccaaaa ttgtaggttg actgcaaatt tcaaatagtt   1020
tgactattga cattgtcact gttttcgatt gactttgacc tcctaattag gccgagtttg   1080 actagggag gctgatttgt tttaaggaca tttgattgat gctttgacta gcattgactt   1140
ttatagttaa ggttgaagtt tgactacagt tgactgcata aatttgcaga gatgttttga   1200
ctttgaattg ggcaagtcaa tttgaatttt gtactatctc tctattttga acatttgata   1260
taataataag aagattcgat caaagggttt tccccgcatt gggtttttc cctggcatcc    1320 gccaaatctg gtgttctctt gtcttgtctt gtcttatgca ttttgtttca ttttctatct   1380
acttttactg tcaatgtgat tattgtcagt gttattggaa attggaaatt gtgattgggc   1440
tgctaaggaa cattgaagta aattgtgcta acaaagaac ataccattgt taacgaaaat    1500
taacaagggg gaaacacaga ggaatggttg caattgcaag attgtcattg attttgactt   1560
caagtgagga aggtcgcgtg gaggtcgcaa ggggagagga ataggagaga aggccctatc   1620
aacttgttca aggagagggg caatacaagg aatggaggaa ccctcaccaa tgaataatcc   1680
atgcacaaaa gtaatagaat gaacaaactt accacacgga agagcttcct tgttgccaaa   1740
agccttgcct ccgagacctg aatcctccaa tgcatcaaaa ttattgatca ttgaatcaac   1800
```

```
cacgattagg gccacttcct tggctaataa agcaattagt gtagcaaatt ctaaagctaa     1860
cttcaaagaa accttagctt tccaaaaaac aattgaaggg aggcaatgaa gatggcttat     1920
cacactaagc ctaaacatgc cccaccctat ggcatctaaa acatctaaaa gggattcact     1980
agtaatcgat cttttgtact tatgaaaaat tcccatgaac caattcgatc tcttccaaaa     2040
agccatctat gaggtcaacc tcaacctggc tctaatgttg attgagcttg taatcctagc     2100
cctactccaa tcttaagaac caaccaattt tatttccaat tgattcaagg acccctacac     2160
tccaaaagaa gcaagggaag gccaaggaga atggcccaaa cttgagcaga gaataaggat     2220
tctctgtgag ggtcgaaact aacatcccat tcacgtaaaa tcaaaccaga gagacctcaa     2280
ctccaactct tcttaatgat gaagcacaaa tattattttg agtgaaattt gaaaccaaga     2340
aaacctctca ctaatatatg aagaggggc aatattcaac cattggtacc caaatcgcct     2400
caagacactt accaagggag ccaaccaaac aatcttacca caaaaccaac caacagtgtt     2460
tttacccaca agctcttgga tggaatccag gataatgtct tcaccaacaa ccatcttatg     2520
tctatccttg caagcacaaa tgcattgagc tttagatttg gagtgcataa atacaggggg     2580
gtatccaggg gggggagggg gtttgctaga accccagact caccaaggca tgaagacaaa     2640
atgaggagag agggatctag attgggggat gcaagttgat gaagcatgaa aaggcaatcc     2700
atcaccctgc atggcatatt tacgaaggtt gttcagagga atgagaacta atggatgaac     2760
aacagctggt agaacaagca gctcaaggag cgccaaggca cgagcccact ttgcatgttg     2820
tagactaacg aattttacat tagaataaaa tatgtcgaca atatcgagga gatcttctcc     2880
aaaatccaac tcattaatct ctattatgca caaacgagtg atgtgtcgag actcatctgc     2940
caacaagcca tcaacatcaa gaagggaacg gaatagagcc aaagggaacc ctagagaccc     3000
tcatccacat aataatgaaa tattccacgt gtgttttttca aaatttggaa atttcatgta     3060 tttttttggtt gattgttgtg gtctggtttt ttccaaattc aatctagttc aagtttttgg     3120
agtcgaccag ttgggtaacc agtctaattc tggtaacatt gcattgtact tgatctcaat     3180
aaaagcatat aggatagaat tatcttctgt cttgatggtt gccatgagaa ccaactgcta     3240
tactatgaaa aatatcaatg ttccacaata ttttttgggac aagggaacac aagattgagt     3300
caacagttca ggaccccaga aaaattattc ctgagtttgc agattatttt cctaaaagtg     3360
aacaattcaa gaccctagcc aaatcattcc caagtccaag ttatgtgaca ctgcgactaa     3420
caaggcaagt tggaagaaac catcaatcaa tctcctagtt aatgacagtc cttgtaagaa     3480
gttcaagaag attaacacca gaagaggtca tgctgactgc ttttatccaa ttctctctgc     3540
tcttcaccaa cagaaatagc caagatggtt gtacccattc cctaatctaa tttattatat     3600
gaatttctct ttatttttct acatataaaa acaaaaact tttcttgatg gtgaaacaga     3660
aaaggcagtt cgattggatt taaacatcca aatacctccc acagattgag aaggccaagc     3720
cccaatccaa cagtccatga tataatattt attcaatcac actcaagata atgcaatgaa     3780
ggtgcaccac gctattagat tctgcacaga actcagatga ctgtaattat caactttaac     3840
caggagtaat ttaaaaactc aattgtgctt cagctatgtg gaaaaacttt ggcactggaa     3900
atggtataaa tgttgttgaa taagcaaaca ttttagaaca tttttcaagc actgaattca     3960
aagtcaagtc aaaggaacat cttacttggg ctgtacagga aatctgaagt acaaaattag     4020
tgaaaaaaca gggagaaagag agtagtcatt acatgttata acattaccat ataggatttt     4080
gtaatacttc ttgatatttc aacttcccga ctgatgaaat gtataccact acagaacagg     4140
```

```
tcagtcatgt atgtgagcaa ttagccaaac taggtcctaa ggttcaacca gtgcagacaa      4200
cgctgtaact gaaacaaatt tgtgggacaa ttaaaaattc tctaccagga tagttgtgcc      4260
agtaggtgcc cttttcaaac catgatttaa aacacaaggg tggcttacca cttgaccaaa      4320
tcatttaata accaccccct cgaacatatc aagaaagaaa acatctgcat ataagtaaat      4380
tgaaagatga tatttaagag gcactgcctt aaattttcca tttggcaaat ccacattgct      4440
tgataagcat aaaaccttgg ttaagagcaa gtttagggaa ccatcaaata tttctacata      4500
ctttacaata gtgtgtttat aaagctaatc aaatgcttct atttaaatat atagcaacct      4560
acacaagaaa ttcactagga cagcaatcac ttggccaatg tgattaccaa tataaccata      4620
cttgaagagc atacataaat cacaaataat gattcaatta gaaatatctt aagataaac      4680 tattattcaa tgtacatgtt acaaagaacc tcacctgtcc gccttt                    4726

<210> SEQ ID NO 97
<211> LENGTH: 635
<212> TYPE: DNA
<213> ORGANISM: Pinus radiata

<400> SEQUENCE: 97
aaattctatg aaaaaaatcc aatcatatta aaagtccaat tgattagcaa ttttatgaga        60
aaaatccaat tatgttaaaa gtcactgagt gtggccgaaa ttgtgaccga aattgaatgc       120
aataaccgag ggttttttcaa accaaggtta agcctctcat cattggggtg tgtatgaaaa      180
tgtaatgggc atcgataacc ttttattaca acttcacgaa aattgcctct attcaatggg      240
tgtggatgaa aatgtaagtg cgcatcgata atggaaagcg atatgcagca aaatcaataa      300
acctgacttc ccatgtgagt gatgatttga tcgtacaact gatggtgtga agttactttc      360
agcttcacct tcgggcataa tcagggaagt agggccaagt ttgcttagta tcactctaat      420
ccccaacacc gtgattacta tcttcatcaa caatggccac cttcgtcatt actttaactg      480
gtgggataca gctactttac aactgtaaat ttgttgaggc agcctatcct cagcctatac      540
atactaatta ttgcagctcg attaggtatc tgctgtgaga atagctgtgt atctctgcgc      600
tggttgcagg atccaagttc ctctcagagc cctcc                                 635

<210> SEQ ID NO 98
<211> LENGTH: 468
<212> TYPE: DNA
<213> ORGANISM: Pinus radiata

<400> SEQUENCE: 98
ctggtaaatt gagattccaa attattgatg cgaagcttcc tcgtggctgg tcggtgctgc        60
tggcatccaa accctaaatg aaaaagaaaa aggtgtccgg acggatttt ttagtatttt      120 tttcttattt ttttttatgaa ccgtcggatt cgagatcgga cggcgatccg aaactgcaag     180
cgtcggccgt cggatgcagc atcggacgg aaagaaggaa ccctaaaacg cattgcaacg      240
tgcttggtgg gtggagggtc tatggccagt atatgttgat aacaagggag aggaagtagt      300
cctcttcatc tagtgcgagt ctctctgctt ttctacgccg ctgcgaagct gttctgtggt      360
gtttctgatt ctccagactc aggcagtcgt ttttgtaaga gaatttagtt catcatggga      420
aaggagaaaa cccatatcaa cattgtggtt attggccatg tcgactcc                   468

<210> SEQ ID NO 99
<211> LENGTH: 222
<212> TYPE: DNA
<213> ORGANISM: Pinus radiata
```

```
<400> SEQUENCE: 99
atccaaaccc taaatgaaaa agaaaaaggt gtccggacgg attttttttag tattttttt    60 tcttattttt ttttatgaa ccgtcggatt cgagatcgga cggcgatccg aaactgcaag   120
cgtcggccgt cggatgcagc atcggacggc aaagaaggaa ccctaaaacg cattgcaacg   180
tgcttggtgg gtggagggtc tatggccaga tatgttgtaa tc                      222

<210> SEQ ID NO 100
<211> LENGTH: 597
<212> TYPE: DNA
<213> ORGANISM: Pinus radiata

<400> SEQUENCE: 100
aaatgaggca gctaactatt tatttggttt tggcttcact gacttgttcc ttagtgtatt    60
aatgaacaat ctctttagac tcagagatgg tgagaaagat tctatgagaa atattcttgt   120
tattgcttcg actcatatcc cccaaagagt ggatccagct ctaatagctc caaatcgatt   180
agatagatcg atcaatattc gaatgcttgt tatcccacaa cgacaaaggg aatttcctat   240
tcttttatgt agcaaaggat tatactcggg aaaatgtccc gatgaatttg gatctataac   300
catagattat gatgcacgag ctctattagc tcaggcctct ctgctgctcc ttggattgca   360
atctcattct ctgatttgcc gtgctgtttg ctctgctcac ttcagcccag atggagacct   420
tcttgttcac atcggagtct gtaaatgagg gacacccaga caaactctgt gaccagattt   480
ctgatgcagt gttggatgca tgcctcaccc aggaccccga cagcaaggta gcatgcgaga   540
cttgcactaa aacgaacatg gtcatggttt ttggtgaaat caccaccaag gccgatg      597

<210> SEQ ID NO 101
<211> LENGTH: 669
<212> TYPE: DNA
<213> ORGANISM: Pinus radiata

<400> SEQUENCE: 101
cctggaaatg ctatattaac tcaacaaagg attttcagcc aatcacaatt tgacaggttt    60
gaaatgaaag attacaggca tttccaatgg aacagaatat aattacttta ttccctcaaa   120
gtatcgtata aaataaatct tttgctccac acactttgga aaatacattt tcaacaatgc   180
accgacaaac ttttctacc acgttatgga accatacaag ttaaatttaa acacgaatta    240
cgcgtatatt tctaataaat cgatggttga gattgaatgc cgtgggcgat tctcacgcgt   300
ccgattggga tcactagtcc atcactcatg gtctgcattg cctttaaatt ggcggggcga   360
ggaaagacca atgcgtcatt ggtgtagacg agctctatta gctcaggcct ctctgctgct   420
ccttggattg caatctcatt ctctgatttg ccgtgctgtt tgctctgctc acttcagccc   480
agatggagac cttcttgttc acatcggagt ctgtaaatga gggacacccca gacaaactct   540 gtgaccagat ttctgatgca gtgttggatg catgcctcac ccaggacccc gacagcaagg   600
tagcatgcga gacttgcact aaaacgaaca tggtcatggt ttttggtgaa atcaccacca   660
aggccgatg                                                           669

<210> SEQ ID NO 102
<211> LENGTH: 230
<212> TYPE: DNA
<213> ORGANISM: Pinus radiata

<400> SEQUENCE: 102
```

```
atccacctcg gaatgaaatc actatgcaca ctccaccttt tttttggctt cttttctcgt    60
tgcctttacc atcagaatca agcacgaaga gtaaatatca cccatgcttt acaagtgggt   120
tggtagcatt agcgattccc ttcaccaaat gaaccctttg ctggtgatga gtggacaacc   180
taaagttgtt tgctggtgat gagtggacaa ccagagtggg ggttggggaa              230
```

<210> SEQ ID NO 103
<211> LENGTH: 596
<212> TYPE: DNA
<213> ORGANISM: Eucalyptus grandis
<400> SEQUENCE: 103

```
actttgaaag ggtctcgagt caaagtgctc aaattgagag ggagaatttt agaacaaaat    60
cagatttgga gaatacatgc cattttaggg ggattttggg gatttcgcat atggcgtcgc   120
gtcgtcggcg ccttcttctt tacagattgt atcctcccat taaccgcgtg gacctgcact   180
gtaaccccga aacggtgggg gccaatttcg tctttccgcc tcctccactc agcttcgtgg   240
aagattaaaa tcctcaccgt ccgtgcaaac gccacgtggc gcgttagttt gcgcgtggaa   300
aggtcctcac gaaccgtaaa gggcaaaaaa aagggaaaat aaaaaaggag gaggaggagg   360
gaggaggaag aattgtccga ttgaaaataa gagtgcggtg gtgtggtgtg ggtagatctt   420
gaattgaacg agctcaatcc gcgtatttaa acccgccccg cttcctcatt cttccttgtc   480
catttcaact ctccctctct ccctctcttc tgccccctcga tcgatccagc gatcttccta   540
tttccggacg cggggagcag ctcctcttgt cgaaggttct aaattagtgt ggagag       596
```

<210> SEQ ID NO 104
<211> LENGTH: 653
<212> TYPE: DNA
<213> ORGANISM: Eucalyptus grandis
<400> SEQUENCE: 104

```
aaaatttttcc tttattttct tttcattaaa aagataaata aataaaaaaa aaaagaagg    60 aaaacacatc gaggtgaggc ttaaaggtgc taggcaagga ccaccaagcc tacacaaggg   120
tcggcgaccc tcaccaatgc tggggcgagg gtgagcaacc ctcatccaaa tctggagagg   180
gttgtcactc gagaaagggt cactggcccct cccctaaccg ctactaacat cgttggcctt   240
cgtcaccacc gcactaacaa tgggccacta attttatatt tttcgtgata ttaatcctat   300
taaaaatgaa aatatctcct taattaatta agcttgtcag gaccgatgta aacaaaatta   360
atgtaaatgg acgcgccttt gacttgccaa caaactcgaa acgacgtttc ctccgtctga   420
taactatctc gcgacctccg acgacatccg acggtgcaga tcgggtcccg gtcaaccatc   480
cagatccacc cgatttttctc ccggcccctcg acaactccca ccaccaactc tttcctcct   540 ctttccttcc ttcctttctc accagatttt cccgagaaaa tcacagagag agaaagaaaa   600
acctcaccgc ctagagagag aaagagagaa agggaaga gagagagaga gag           653
```

<210> SEQ ID NO 105
<211> LENGTH: 342
<212> TYPE: DNA
<213> ORGANISM: Eucalyptus grandis
<400> SEQUENCE: 105

```
agttgggtaa ccagtctaat tctggtaaca ttgcattgta cttgatctca ataaaagcat    60
ataggataga attatcttct gtcttgatgg tttccatgag aaccaactgc tatactatga   120
aaaatatcaa tgttccacaa tatttttggg acaagggaac acaagattga gtcaacagtt   180
```

```
caggacccca gaaaaattat tcctgagttc gcagattatt ttcctaaaag tgaacaattc    240
aagaccctag ccaaatcatt cccaagtcca agttatgtga cactgcgact aacaaggcaa    300
gttggaagaa accatcaatc aatctcctag ttaatgacag tc                      342
```

<210> SEQ ID NO 106
<211> LENGTH: 342
<212> TYPE: DNA
<213> ORGANISM: Eucalyptus grandis

<400> SEQUENCE: 106

```
ggtctggaag ctcatctctc caatttggtg aagattacag ctataagagg tagctatgat    60
gtgctggcca aatgcaagtg atgaaatacg tggaccacca agtgcgaagg cattcgaaga   120
acgagggtcg aatttatagt gggcgaagga tgattaggtg gaatatgaca agaaaatagg   180
tttgaaagag aaataaatat tatgatagtg aagggtcttc acatggttag tttgatctgt   240
ccgagggtgt ccaccttgt ctgatccgca attgctcttg gtcgtgctga attttagagt    300
gtagccaaag taagaatttt cctttcactg tccggacatt tc                      342
```

<210> SEQ ID NO 107
<211> LENGTH: 948
<212> TYPE: DNA
<213> ORGANISM: Eucalyptus grandis

<400> SEQUENCE: 107

```
ctgacaaatg caaatatcta aaaccattgg ttgtttggtg cttgcaagtc tggattaccc    60
cactttatgt ttcacctttc aataatgaat aacaaggtac tcgggaaaaa aaggaaaggg   120
aaattcgcac aaccaaagtt gctatgcaga agtcaactca atcctaatca agttgatgag   180
agtgttgggc cctatttct gcagcaaaca tgaatctcga ttcatctccc tcgcaaaaga    240
taaggaagct gcaaaagctt tcctcctaag tttgttggca agcaaattga ttttgtacca   300
gaaataaata caaagtgaaa cccaagcaat cacgcatggc ctgatttgtg ccatgtccat   360
ttgatctccc tctactattt ttcctgcttt ctcaagcaaa ctagttgctg taacagtgaa   420 tgatccccg gctctctctc tctctctctc tctctctctc catttattcc atccatgttt    480
ttgcttttcg cacaacactt atcattgagg tgctaactac tgaattcccc taactaaaaa   540
ttggaacctc tcacctaatt tcattttctc ccactttgat gagcaccact ctctttccca   600
gatttcaaat aaattgccac tctctccctc tctttcctc acacaaccaa agccttctt    660 caagtaccac ttcttcactg tcctctcttc acaatccccc tcttaccaag agcaaagcaa   720
aaaacatgat gaagagactg tcatttctgc tcctactggt cctgctcttc caatgctcta   780
ccaccttggc tcagcctgcg gccgccccag ctccgcctgt gatagccccg gctgcacctg   840
ctacgcctgc cttaggcccg gctcctcctg tcttaggccc agctcctgca ggcccaaccg   900
acatcacgaa ggtcctcaag aaggtgagcc aatttacggt gctgctca                948
```

<210> SEQ ID NO 108
<211> LENGTH: 362
<212> TYPE: DNA
<213> ORGANISM: Eucalyptus grandis

<400> SEQUENCE: 108

```
ccatcactca taatcaacaa ggatatctca tcatgtcttc caaccaaatt aaaccccaga    60
catctctaaa gcagtatgga aaagaaaaca gtccggaagt ctctagctca aaaactgtaa   120
```

| | |
|---|---:|
| ccccgaccta attccggttg tctctgatta catcaattct tatgtcttaa cactccattc | 180 |
| gcacctccac aataaataga tcggcccttc atctccctt accatcgaat ccaatcccaa | 240 |
| aaacacttgc tcagacacca tcaaatcctt cgcaaagtct ttttcttaca aaaacaaac | 300 |
| gaaagcaacc atgaagcacc agttcattgt tctggctctc ttattcctca tcaacacagc | 360 |
| cc | 362 |

<210> SEQ ID NO 109
<211> LENGTH: 326
<212> TYPE: DNA
<213> ORGANISM: Eucalyptus grandis

<400> SEQUENCE: 109

| | |
|---|---:|
| aaaaattaca atcaatggtt atcaatggat gttacaaagg gaggttacat atagaggtta | 60 |
| taaagagggg ttacaaatag atgtctcaaa caattaccaa gcggttagat tgactccact | 120 |
| attttgacgg ttctccttgac tttactatct caacgattac tttatttcat catgttgacg | 180 |
| gttgcatcca tgattgttga cttcactttt tgtcgattcc ttcaagctgc tgattcttca | 240 |
| agttgccaat aatttattc ataaatgacg aaactctagc ctcatccatt aagtttgtta | 300 |
| cttgtccaca ataattaaat tcggta | 326 |

<210> SEQ ID NO 110
<211> LENGTH: 296
<212> TYPE: DNA
<213> ORGANISM: Pinus radiata

<400> SEQUENCE: 110

| | |
|---|---:|
| tgctcccggt catgacaccg ccattctcgc tcttcatttc caattcaaat cacttggttg | 60 |
| ttgttcacac acacgggtct ttatatgacg agtgctgctg cgattataaa tagacggggc | 120 |
| aattacaaca aaaactcaca gcatttgaag gaagttggag tggtagagtg agaaatacac | 180 |
| agcctaatct gaaggaagtt cgagtaatag agtgagaaat ggatcttctt ctcctcatga | 240 |
| tgatgcttgt gatgatgggt gtagcaatgc ctactcattc tcaacaaatc actagt | 296 |

<210> SEQ ID NO 111
<211> LENGTH: 723
<212> TYPE: DNA
<213> ORGANISM: Pinus radiata

<400> SEQUENCE: 111

| | |
|---|---:|
| cgttttacgc gggaacaatg aaaacagtac aatcgaaaga gtcaagtcgt gaggttcatt | 60 |
| tcgatgaagt tcccagagat tgtctcgttc aacgtttcct cttttttcgg gtcaagtcgg | 120 |
| gtacagaaga ccactttctt tacgcggtca agacaccgcc attctcgggt caagtcggga | 180 |
| ggtccctcct gctcttcctt tttccaaatc cgtaaaattt acagattttt ttaatgtatg | 240 |
| aagcccactt tctttatgcg gttgctccca gtcaagacac cgccattgtt gttcacacgc | 300 |
| acgggtcttt atatgacgag tgctgctgcg attataaata cggggcaa ttacaacaaa | 360 |
| aactcacagc atttgaagga agttggagtg gtagagtgag aaatcatttg aagggagttg | 420 |
| gagtggtaga gtgagaaatc atttgaaggg agttgagaaa tatattggga atctctcttt | 480 |
| tttgcagcaa ttagatcttt cctttaatgc tttgagtggg agaattccga cagagtttgg | 540 |
| gaacctctct cttttgcggc aataagttgg agtggtagtt ggagtggtag agtgagaaat | 600 |
| acacagccta atctgaagga agttggagtg atagagtgag aaatggatcg tcttcttctc | 660 |
| ttcatgttga tgcttgtgat gatgggtgta gcaatgccta ctcattctca acaaatcact | 720 |

-continued

| | |
|---|---|
| agt | 723 |

<210> SEQ ID NO 112
<211> LENGTH: 1301
<212> TYPE: DNA
<213> ORGANISM: Pinus radiata

<400> SEQUENCE: 112

| | |
|---|---|
| actatagggc acgcgtggtc gacggccctg gctggtagcg acagagctgg ttcagtgacc | 60 |
| gttcgtgatt agccgcagta aaacaaaacc ctaaccgtaa cccttccgcg cagattccat | 120 |
| ccttccccgt cctaccaaaa cccaaacttc ttgcccgaac tcaccttcta tgtattaatt | 180 |
| cttattatta tttaataata ataaatagtt aaacataaat ttataaatta attaattttt | 240 |
| atgattttta ttttagttta aaaatgtgac attgttatag attaatgctt atgaacgttt | 300 |
| attggccata attccctaa ttaattataa ttaaaatata tagttataat taaaaaattg | 360 |
| tatattttat aaattgaatt aagaatttct gatgatattt catcattcaa ttccatctta | 420 |
| tcaaagttag agggaatagt taaccatgta ctagatctat tcatagctaa catttgccaa | 480 |
| gttcgtacta ggagacttgg atttttttta aaacataatt ttggcagtaa aaagtgaatt | 540 |
| ctattgtttt gaaaacaaaa caaaatacag gaagcgtgat tgtgggggttg ttgttgaact | 600 |
| tgcccgggca aagaagaat gattagcggt agaggagtta gtagttacgt tcaactaaat | 660 |
| gcgtgactaa attatttatc ctccgccatg gaagcaggtg attcacacac aacttgctgc | 720 |
| acacattgct ctcaaacctt tcctataaat atccgtagca ggggctgcga tgatacacaa | 780 |
| cgcatttaat caaactactt tgattacttt ctgtgggttc tactttcttt gaatagtcag | 840 |
| ttctgctgtt tttagaagat ttataagaat ggccaaaatt caggtatcaa acgggaacgt | 900 |
| cgtggtggtg gctgcgatgt tatttatggt ggtggtggcc atgcaaaacc atcacgtcgc | 960 |
| cgcccaaagt gctgactgcg ccgccaccgc ggagtccctg agcccctgcg cctcggcggt | 1020 |
| gggaaacaac ccacaggatc ccactcccga atgctgtgct gttcttcaga ccgctaatgt | 1080 |
| cgactgcatc tgcgccctcg tccaatcaac catgcaattg ccttccgaat gcggtcttga | 1140 |
| gactcctcag tgcccaagcg actagggtct caagaccgtg actgagtgct ggtttcagag | 1200 |
| acagtagaca ttctgcctaa taatgattg tatgagagct tttatatatg gaattgctca | 1260 |
| tatgctttcc tagatatgaa attattaaat tccatatgct t | 1301 |

<210> SEQ ID NO 113
<211> LENGTH: 3070
<212> TYPE: DNA
<213> ORGANISM: Eucalyptus grandis

<400> SEQUENCE: 113

| | |
|---|---|
| agcaccatca gcaaaaaata gatgggatag agtgggacac cacctgttca gtttgattcc | 60 |
| cttgagatga cctacagtga tagcttgatg aataagatgg gataatagat tcaccagagg | 120 |
| gataaaaagg tagggagata ggggatctcc ccgtctgatg cctcgggtag gttgaaaata | 180 |
| aggcaaaagt tcgccgttga atttgacagc aaaagacacc gtcgttatgc attgcatgat | 240 |
| ccattgtacc catgtagggt gaaatcctag agtgaggaga tagtccttta gaaagtccca | 300 |
| ttccacccta tcataggctt tctgcatatc cattttaaga acagcccgga attgacgtct | 360 |
| acattttctg actttaaatt gatgtagaac ctcttagact attaaaatat tgtcctgaat | 420 |
| ttgacgtcca ctgacaaaag cgctttgctc ctggaaaata agtacaggca ggtagggctt | 480 |

```
aaggcgattg gcaatcacct tagaaatgat cttatatgcg taattacaaa gactgatggg      540
gcggtattgg tctaattgtt caggatgtgg taccttgggt attagggcta tgatggttcg      600
attgagattc ggtggtatga tgccagaatt aaaaaagtgc tgcactgatg agaatagttc      660
atcctggagt atatcccaat gatgctggta gaagagtcca ttcaagccat ctggaccggg      720
ggccttggta agtcccagtt ggaaagtagc ctctctaact tccttcttgg taacaggagc      780
tattagggac atattcatct cattagtaac aacctaagga cactggttca gaataggcaa      840
gtagtctcga tgtcccactg tctgaaatag atgtgaaaag taacctatcg tcatcatctt      900
caaaatttca ggatcgcgca cccaagcttg attgtcatcc tgcaacatac taatcttgtt      960
tcgttgttgt ctttgtatag ttgttgcatg aaaaaattta gtattttttgt cccccccagct    1020 gagccattta attcgagagc acatcgccca aaattattct tcttgctgcc ataactgtcg     1080
aattttctct tttaggtaag taaccaatga tgcgccatgt tgacaaaaag gctgattagt     1140
atgatcttgg agttgttggt gcaaatttgc aagctgacga tggcccctca gggaaattaa     1200
ggcgccaacc cagattgcaa agagcacaaa gagcacgacc caacctttcc ttaacaagat     1260
catcaccaga tcggccagta agggtaatat taatttaaca aatagctctt gtaccgggaa     1320 ctccgtatttt ctctcacttc cataaacccc tgattaattt ggtgggaaag cgacagccaa    1380
cccacaaaag gtcagatgtc atcccacgag agagagagag agagagagag agagagagtt     1440
ttctctctat attctggttc accggttgga gtcaatggca tgcgtgacga atgtacatat     1500
tggtgtaggg tccaatatttt tgcgggaggg ttggtgaacc gcaaagttcc tatatatcga    1560
acctccacca ccatacctca cttcaatccc caccatttat ccgttttatt tcctctgctt     1620
tcctttgctc gagtctcgcg gaagagagag aagagaggag aggagagaat gggttcgacc     1680
ggctccgaga cccagatgac cccgacccaa gtctcggacg acgaggcgaa cctcttcgcc     1740
atgcagctgg cgagcgcctc cgtgctcccc atggtcctaa aggccgccat cgagatcgac     1800
ctcctcgaga tcatggccaa ggacgggccg ggcgcgttcc tctccacggg ggaaatcgcg     1860
gcacagctcc cgacccagaa ccccgaggca cccgtcatgc tcgaccggat cttccggctg     1920
ctggccagct actccgtgct cacgtgcacc ctccgcgacc tccccgatgg caaggtcgag     1980
cggctctacg gcttagcgcc ggtgtgcaag ttcttggtca gaacgagga cggggtctcc      2040 atcgccgcac tcaacttgat gaaccaggac aaaatcctca tggaaagctg gtattacctg     2100
aaagatgcgg tccttgaagg cggaatccca ttcaacaagg cgtacgggat gaccgcgttc     2160
gagtatcatg gcaccgaccc gcgattcaac aagatctttta accggggaat gtctgatcac     2220
tccaccatta ctatgaagaa gatactggaa acatacaagg gcttcgaggg cctcgagacc     2280
gtggtcgatg tcggaggcgg cactgggccc gtgctcagca tgatcgttgc caaataccca     2340
tcaatgaaag ggatcaactt cgaccgcccc aacggattga agacgcccca ccccttcctg     2400
gtgtcaagca cgtcggaggc gacatgttcg tcagcgttcc aaagggagat gccattttca     2460
tgaagtggat atgccatgac tggagtgacg accattgcgc gaagttcctc aagaactgct     2520
acgatgcgct tccaacaat ggaaaggtga tcgttcaga gtgcgtactc cctgtgtacc       2580
cagacacgag cctagcgacc aagaatgtga tccacatcga ctgcatcatg ttggcccaca     2640
acccaggcgg gaaagagagg acacagaagg agttcgaggc attggccaaa ggggccggat     2700
ttcagggctt ccaagtcatg tgctgcgctt tcggcactca cgtcatggag ttcctgaaga     2760
ccgcttgatc tgctcctctg tggtgatgtt catggttctt ggatttgaaa ggtcgtgaag     2820
gagccctttt ctcacagttg gcttcggcat accaagttct tctcataaaa ggaaacaata     2880
```

-continued

```
agaagcgact gtatgatggc gcaagtggaa gttacaagat ttgttgtttt atgtctataa    2940
agttttgagt cttctgcata ctgatttcac agaatgtgta acgaaacggc gtatatggat    3000
gtgcctgaat gatggaaatt gtgatattct gtcttctttt tcagtaaatc acttcgaaca    3060
aaaaaaaaaa                                                           3070

<210> SEQ ID NO 114
<211> LENGTH: 1227
<212> TYPE: DNA
<213> ORGANISM: Pinus radiata

<400> SEQUENCE: 114
aaatttcaag aggaagagat taattctttt aatttataaa attatataat aaaatattta      60
tatttaattt agatgataag tttatgaggt gtagaataga tagtgatggg tgtattattg     120
agttattccc ctaatgtgga gacaattgat tagaagttct atgagaaaaa tccaatcatg     180
ttaaagtgac ccctaatgtg aagacaattg attagaaatt ctatgaaaaa aatccaatca     240
tattaaaagt ccaattgatt agcaatttta tgagaaaaat ccaattatgt taaaagtcac     300
tgagtgtggc cgaaattgtg accgaaattg aatgcaataa ccgagggttt ttcaaaccaa     360
ggttaagcct ctcatcattg gggtgtgtat gaaaatgtaa tgggcatcga taacctttta     420
ttacaacttc acgaaaattg cctctattca atgggtgtgg atgaaaatgt aagtgcgcat     480
cgataatgga aagcgatatg cagcaaaatc aataaacctg acttcccatg tgagtgatga     540
tttgatcgta caactgatgg tgtgaagtta ctttcagctt caccttcggg cataatcagg     600
gaagtagggc caagtttgct tagtatcact ctaatcccca acaccgtgat tactatcttc     660
atcaacaatg gccaccttcg tcattacttt aactggtggg atacagctac tttacaactg     720
taaatttgtt gaggcagcct atcctcagcc tatacatact aattattgca gctcgattag     780
gtatctgctg tgagaatagc tgtgtatctc tgcgctggtt gcaggatcca agttcctctc     840
agagccctcc atggaagcgc agtcagtttc agttgttgag cagcgccccc atgccctact     900
attttcattt ccgttacagg gccacatcaa gcctttcatg aacttggcca agattttgtc     960
cagccggggc ttctatgtca cttttgccag taccgaattt gttgtaaagc gcctcgcaga    1020
atgtggtgaa agtatcgccc atcgtgattc gatggtgtgc agcgagaacg atgatgtatg    1080
taacataaaa tttgaaacag tgcccgacgg actgcctccc caccacgatc gcagtactca    1140
gaatcttgcg gagctcttcc aatccatgga agagaacgct catattcact tccacaagtt    1200
gatggagaag ctccagaatc ttcggga                                        1227

<210> SEQ ID NO 115
<211> LENGTH: 1169
<212> TYPE: DNA
<213> ORGANISM: Eucalyptus grandis

<400> SEQUENCE: 115
ttcattatat gattattacg tcataatgat cgatttctag aaatttggag acatatgtaa      60
attcaggagg aatttcaaga aacgcgcgtt actttgaaag ggtctcgagt caaagtgctc     120
aaattgagag ggagaatttt agaacaaaat cagatttgga gaatacatgc catttttaggg    180 ggattttggg gatttcgcat atggcgtcgc gtcgtcggcg ccttcttctt tacagattgt     240
atcctcccat taaccgcgtg gacctgcata gggcacgcgt ggtcgacggc ccgggctggt     300
ttcattatat gattattacg tcataatgat cgatttctag aaatttggag acatatgtaa     360
```

| | |
|---|---|
| attcaggagg aatttcaaga aacgcgcgtt actttgaaag ggtctcgagt caaagtgctc | 420 |
| aaattgagag ggagaatttt agaacaaaat cagatttgga gaatacatgc cattttaggg | 480 |
| ggattttggg gatttcgcat atggcgtcgc gtcgtcggcg ccttcttctt tacagattgt | 540 |
| atcctcccat taaccgcgtg gacctgcact gtaaccccga acggtgggg gccaatttcg | 600 |
| tctttccgcc tcctccactc agcttcgtgg aagattaaaa tcctcaccgt ccgtgcaaac | 660 |
| gccacgtggc gcgttagttt gcgcgtggaa aggtcctcac gaaccgtaaa gggcaaaaaa | 720 |
| aagggaaaat aaaaaggag gaggaggagg gaggaggaag aattgtccga ttgaaaataa | 780 |
| gagtgcggtg gtgtggtgtg ggtagatctt gaattgaacg agctcaattc gcgtatttaa | 840 |
| acccgccccg cttcctcatt cttccttgtc catttcaact ctccctctct ccctctcttc | 900 |
| tgcccctcga tcgatccagc gatcttccta tttccggacg cggggagcag ctcctcttgt | 960 |
| cgaaggttct aaattagtgt ggagagatgg tgaagatctg ctgcattggt gctggctatg | 1020 |
| tcggcgggcc tactatggcc gtgattgctc tcaagtgccc gtcagtagaa gttgcggtcg | 1080 |
| ttgatatttc tgtctctcgc atacaagcct ggaacagcga acagctccct atctatgaac | 1140 |
| caggccttga tgcggtggtg aagcaatgc | 1169 |

<210> SEQ ID NO 116
<211> LENGTH: 947
<212> TYPE: DNA
<213> ORGANISM: Eucalyptus grandis

<400> SEQUENCE: 116

| | |
|---|---|
| ggtctggaag ctcatctctc caatttggtg aagattacag ctataagagg tagctatgat | 60 |
| gtgctggcca aatgcaagtg atgaaatacg tggaccacca agtgcgaagg cattcgaaga | 120 |
| acgagggtcg aatttatagt gggcgaagga tgattaggtg gaatatgaca agaaaatagg | 180 |
| tttgaaagag aaataaatat tatgatagtg aagggtcttc acatggttag tttgatctgt | 240 |
| ccgagggtgt ccacccttgt ctgatccgca attgctcttg gtcgtgctga attttagagt | 300 |
| gtagccaaag taagaatttt cctttcactg tccggacatt tcgattgcta catgaccat | 360 |
| cccgtgtcta cccattcttg agaaccttcg agtggaaagc atgaataacc caccttgtac | 420 |
| tatataggtt gccgaatatg cctagggcgc gaccatcatt gagacggagt tgggtgctc | 480 |
| cgctcggttc accaccacca ccaccaccac caccaccac accaccattg ggcactgata | 540 |
| tagcgactcc accactaccc caaccgaggt tggcaaactc tagattgtac atgggatata | 600 |
| tcggagtagt tgaacatgat cagatcaatg gtagtggtta agactctaga aattattgaa | 660 |
| gcaatatgtt aaatcagata cgtgtgagaa agtgacttac taattgctat ggctttcatg | 720 |
| atacttaaac ttcaatgaat tggtaatgtg aagagcaatg tgatctccac aaatactact | 780 |
| agaaggccaa gtccttttct ttatgccgaa gtcctaaagt ttaatatttc aactctacct | 840 |
| atatcaaatt tgtatgcaaa ttgcataatc gcactgattt ctatggtttt attaatctag | 900 |
| ataagaactc tctccaagac attaactaat taagattgac cccattt | 947 |

<210> SEQ ID NO 117
<211> LENGTH: 1766
<212> TYPE: DNA
<213> ORGANISM: Eucalyptus grandis

<400> SEQUENCE: 117

| | |
|---|---|
| atccagatcc ctacgaactg gattcacaca gtcactgctg taagctctgg tttttttag | 60 |
| cttaggaagc aggttatgat caaacatgat taaaccatcg cgtgttcgcc agccatcaga | 120 |

```
aatggaaagg caaatgttgt tatagtgatg acagatcat gctgagatga ttgattatga      180
atcttactga tgactgtcat ttatgttatc gcactctgtg tgtgtgggtg tgtgtaatga      240
gtaatatcaa attaaccaga cgataggtgt tgaagattag ctgttgggcc accgtggcga      300
aaggtgtctt atacaagcca tcggcagtga cgcagaactg tagagaaccg ctgtaacaag      360
tcttcgaatg cattctttta atgtacagca cgacatgaag ggggttcgag tgtagcgaac      420
agttcgtgcg agaaagatca ttttcaatag cataaaagag tctgctttct gctgcaaaca      480
tggaaagaac ttacatttca atcattgagg agaaagattat aacaaatcct aaatggttga      540
gattttagtt agtccattcg aactaaagtg gcgaagatgt cagtttttca agtggatgat      600
atttctcatg tatgttccgc agaggcaatc accttgtttg taactagaca tctagagaac      660
ctaacaagga ttgatggggg tgaggtgaaa tgtctgtttc ctctttaata tggatccagc      720
gatgccttac agagcggatg gatggcactg gcaagtctta atccttagct cgaatgtttg      780
attggtaaca gatgcctttt ctttcttttc aatcacagct gacaaatgca aatatctaaa      840
accattggtt gtttggtgct tgcaagtctg gattacccca ctttatgttt caccttttcaa     900 taatgaataa caaggtactc gggaaaaaaa ggaaagggaa attcgcacaa ccaaagttgc      960
tatgcagaag tcaactcaat cctaatcaag ctgatgagag tgttgggccc tattttctgc     1020
agcaaacatg aatctcgatt catctccctc gcaaaagata aggaagctgc aaaagctttc     1080
ctcctaagtt tgttggcaag caaattgatt ttgtaccaga ataaataca aagtgaaacc      1140 caagcaatca cgcatggcct gatttgtgcc atgtccattt gatctccctc tactattttt     1200
cctgctttct caagcaaact agttgctgta acagtgaatg atccccggc tctcccctc       1260 tctctctctc tctctctcca tttattccat ccatgttttt gcttttcgca caacacttat     1320
cattgaggtg ctaactactg aattccccta actaaaaatt ggaacctctc gcctaatttc     1380
attttctccc actttgatga gcaccactct ctttcccaga tttcaaataa attgccactc     1440
tctccctcct ctttcctcac acaaccaaaa gccttcttca agtaccactt cttcactgtc     1500
ctctcttcac aatcccctc ttaccaagag caaagcaaaa aacatgatga agagactgtc      1560
atttctgctc ctactggtcc tgctcttcca atgctctacc accttggctc agcctgcggc     1620 cgcccccagct ccgcctgtga tagccccggc tgcacctgct acgcctgcct taggcccggc    1680
tcctcctgtc ttaggcccag ctcctgcagg cccaaccgac atcacgaagg tcctcaagaa    1740
ggtgagccaa tttacggtgc tgctca                                           1766

<210> SEQ ID NO 118
<211> LENGTH: 1928
<212> TYPE: DNA
<213> ORGANISM: Eucalyptus grandis

<400> SEQUENCE: 118
ctggttccac gtcaagcacc tcctggagtg acaaggaaat gccaccggaa atcaagatt        60 gctgttttag gctcactttt ttcctgagct aagtgggtcg catttcaaga aacagtagaa      120
gttacgttct ccatggaaac tcgaaaggat aaaaattaag aaacggaagc tccatgagaa      180
cgatgggggt cagcatcact cctattgtat tgtgctctca ttatctctgg cctacttgag      240
aagtgatctg ggattcgcta ttagtgaaaa caatcgcagg ctaactaaga tcttttatgc      300
taatcatatg gagaaatatc cctcttaagg gaagcatatg agttttttct taggatgact      360
acgcttattc aaaacctatc atacacgtca tgccaataat acccacttgt tgttcccttta    420
```

-continued

| | |
|---|---|
| ctcaggatcc tcgatagcca atactaattg gcaagaacct tgagtaacaa gctgaggtat | 480 |
| acataggcct atcattcatt tactagactc gattgcaagc acacatgatg cacatttata | 540 |
| tcagcaatca gcaatcatat ttccgaaaat tgtctctcag agaaaaagag agagagagag | 600 |
| agtccatagt atgtcatagc caaaagaaaa attagcaaca agatctcgag gtattgttga | 660 |
| aaggtagggc aatatcaaga attccattgt aattaatgtg tctagacaac atctaagaaa | 720 |
| aaaaagtgaa agaaaagagc tatatagtta ataatattta tacatgttgg agataaactt | 780 |
| gagttagagg tttatgacct cctagattga ttaaacagac caaatagtag taatcagggc | 840 |
| acttcttaaa tctactaata tattgttcaa acatgacttt taacctatct tgattagaaa | 900 |
| tgagtgttca agaaaacta atcatgcata tattttgtcg cccaatcacc ctagggtgga | 960 |
| aaaaaggcta tctactcaac aaatgctaaa attttacggc tacacgtggc cacagttgca | 1020 |
| gtacaattca tctcaaggaa ggactaaaac tgcaaagaga agaagactac ataggaaaaa | 1080 |
| ggaaaacaaa gaagccttga agtaaagagg agcataactc actcaactga gtgtgttcgc | 1140 |
| caatgtggca agaaaaagc ctctaagatc ctcacaaatg ccacgtgga ctcacacggc | 1200 |
| accctataca agtactacta ctactacagg actatgccag aaggagaagt gttagcgtga | 1260 |
| gtaccacgtg cgcacgcaga atctaagcct agcaaaaact atgctgagtc aagcagctcc | 1320 |
| cccacccatg aagatagtac tgtaatgtga ctcttgacag cgaaaccaaa cagtactcca | 1380 |
| agagaaaagc caaagcagca aaaatggggc ccgcagcaag aacctctgac tcgacctgga | 1440 |
| cccaccaaga caacagcca gccacaaaat aacgtaaaga cttttttgcgg ccactaactc | 1500 |
| ctcgacaagt ggcactgctt ggattccctt catcttgcct tcacttaacc cccacccctc | 1560 |
| ctcacactgc attcacttca aacactcccc agtttcagag tttcattgag aaatatgttg | 1620 |
| aaggaagaca cgagtggcag cggcggcagc agcggcagcg gcagcggtgg taatagctgg | 1680 |
| gcacgtgtgt gtgacacttg ccgctcggca gcatgcaccg tgtactgccg tgccgacttg | 1740 |
| gcttacctat gctccagctg tgacgctcgt attcacgcag ccaccgtgtg gcctcgcgcc | 1800 |
| atgagcgcgt gtgggtgtgc gaagcgtgcg agcgcgcccc ggctgccttc ctctgcaagg | 1860 |
| ctgatgcagc atcactgtgc accgcctgcg atgcagacat acactcagcc aacccgcttg | 1920 |
| cgcgccgc | 1928 |

<210> SEQ ID NO 119
<211> LENGTH: 602
<212> TYPE: DNA
<213> ORGANISM: Eucalyptus grandis

<400> SEQUENCE: 119

| | |
|---|---|
| attgggagga agtagagtgt gctgtgtgag attggtcgat gagctggctc ttgtggagat | 60 |
| ggcaagtgat tgtggcttct gtgatgcata tatataggca agggacgtga tgcggaggaa | 120 |
| gtatgtatca tcagcttata ataatgattg gtcagtttgt aagtgaatat taagggcctc | 180 |
| atgggtgttg gttcacggcc caaggcgggg cccactcacc ggggattta tcgtgtaagg | 240 |
| atacatccag ggtcagggtg tttggggaca cactttgcca tcttatgtgg gcatgatcag | 300 |
| attgagaaga atccgatcct tcttttttcct aaaccattga acccaccatg agaatctttg | 360 |
| tttggaggga aaaataaaaa aatagattga gacgtattct aggagaggat agcaaaagaa | 420 |
| tgtgactttg tttgtttgtg tatcggattg atctaaggaa aaaagacact aaccgttcta | 480 |
| caattttcat acaactcttt catttaagca ccgtgacttc caaaaatcga tcatccttat | 540 |
| acggttggaa atcacacgtg gcattgctgt aaaagaaata gttgatgggt ctcattgaag | 600 |

```
at                                                             602

<210> SEQ ID NO 120
<211> LENGTH: 1326
<212> TYPE: DNA
<213> ORGANISM: Pinus radiata

<400> SEQUENCE: 120
aaaaaaggga acattatac  caaattttat gatatctttc aacaacatac tcttctatat    60
atggtgcctc ctctgatgga cccttgtcaa ctttctcttt ttatgtgtaa tgcctcaaga   120
gcccccactc acaagataat atcttttcca taatataata tatattccta ttgaagcagt   180
cttttgatgt accgagtaca ctactcatgg tgaaggccgt gtcttgcagc ttttcccatg   240
gtttattttg aaagtaatag tactggacct catttgcaac gacacataat attcttactg   300
acgacacttt gtttgatttc ttatagaaaa atgcaaggtg gcacaaaaag atggaaagcc   360
cgacctatca agcatacgaa gggtcatgtt cacaccctct gaaatcttca gagtctcacc   420
ctatgttgga cgctaatcaa tgggatcacg ctgaaacata tcgtaaatga cgaatcaatc   480
aatcaatcat tgaaaaatat accagataac tcctacgatg gaggggatta tttgcgtacc   540
ctccgcgtgg gtgggcacat tgggcaggtc ctttggtaag tcttggagac agagtcacgt   600
ttccataatt gaagtggaca tttatgaatc tttcgaaagt tgtagaactc ttaattttcg   660
acggaatagt ttgacacgtt ttgtacgatc tggttttttcc ggggaacgcc aattttggtt   720
tctgaaggac agcatttaca atattgtctg tcgttgacca ggacagctgg ctcggaactc   780
gggtttccga tgcgcaggaa gcgcattgaa atgagaatat aatctagttc tacctgtgga   840
gctatcacaa aatactaaaa ctggtggaca tacctcttgt ctgttctcga aatcggccaa   900
aatgggaaag aagagggtag agctgaaacg cattcaaaac cctagcagtc gacatgctac   960
tttctctaaa cgcaagaatg gattgctaaa aaaggcgttc gagctttctg tcctctgtga  1020
tgctgaagtc gctctcatca ttttctctga aactggcaag atttacgaat ttgcgagcaa  1080
taacgatatg gcagcaattc tgggaaaata ccgagtacac gaagaaggca ctgaaacgtc  1140
cagtccaaca tcgcttcaaa acgtaaagta tcatgaatca gggcttgaga aattgcaaga  1200
gaagttgacc gctttgcaaa agaaggaaaa gaacttgatt ggtgaagact ggaggtatt   1260 aacaatgaaa gaactgcaac ggcttgaaaa acagttacaa attggcataa aaaggttagt  1320
gataga                                                             1326

<210> SEQ ID NO 121
<211> LENGTH: 1504
<212> TYPE: DNA
<213> ORGANISM: Eucalyptus grandis

<400> SEQUENCE: 121
atccactagt tatataaaaa taataataat atcaaatata tctcgtgatt tatgtatcta    60
tgaattatat atcataattt ggtaattaga catgtgggcc acttcaatgc atggacattt   120
agttcatctt gactcaatac tcaacctcaa cttaaataca tcctgattat tgatggcaac   180
cgaccaattt gacgtagagg ggacaaggat tgcaacttgg gtttgtgtgt tgggcaaagt   240
gagctcaaat aactcatgag ttcctcaact tgtttgtgtt gcccttgctc aacaatcata   300
acaaagctag ctaaacacaa atgaacaatc aagtatatcc acaaaaaaac aaaaacaaaa   360
aaacaagaaa acccaagcac tgataagaaa atctaaattt ccaccaaaaa tgacaaatag   420
```

-continued

| | |
|---|---|
| acattgccta tactttcatt tgccgattat cgaaggaatt tacgcataga atgacccatt | 480 |
| tttttgacaa atgagatttg cataattatt caacggcatt tcgtggtata ttccatctgc | 540 |
| atgggtgttc caaaatagg catcgaatat tcttctggtg aaaaaaagg ggcggggcgt | 600 |
| gaaaaatgaa agaaagaagc atcaagtggg actgaatcgc cgagtaaatc gtgccgagcc | 660 |
| gtacgtcaga agatacacac ttggctcaag tgggcgtcaa agcgatggcg cttgattggg | 720 |
| acctttgacc tttcgtcacc tccccatcct ccgtcctcct ccctgtcgcc cgttcattcc | 780 |
| ctccctccaa taaaaacaaa aaaacaaaaa aacaaaaaaa ctgtgctctc ttttactcgg | 840 |
| tcaaaacctt aaagaagcc ccccgcccac gcaaatccac ttgccacgtc accaaatcca | 900 |
| aatcccacac gtggcgcaca ctgaatcgca ttcaacttgg aacagctggc ggggttttac | 960 |
| ttggagtccc agtcacttag attctttgca gccatgacga tgacagtgac gctggctttt | 1020 |
| ctgcgtcctc tccgtaggaa ggaactccca gtacagactg gatcctccta atcccgtgtc | 1080 |
| ctcttcctga caatccccgt tcatataaag gaacccgaac tcactccctc cgctcccaat | 1140 |
| tcaagcacat gttctactcc accttcatct cacaataaaa accagcagtc cagcacgagc | 1200 |
| acattatcca cttccactcc agaactcaag cgcagacgta ctccaatgaa ccacttcttc | 1260 |
| tcttcttact ccgatcccag ctcctgcagc ctcgactttg ctgaagcgtc gtcctcctcg | 1320 |
| tcgccgctgt ccgatggcag gagtgctatg gtgcccggga acttttctga tgaggaggtg | 1380 |
| ctcctggcgt cgcaccagcc gaagaagcgc gccgggcgga agaagttcca ggagacgcgc | 1440 |
| caccccgtgt accgcggggt gcggcggcga agctcgggca agtgggtctg cgaggtccgc | 1500 |
| gagc | 1504 |

<210> SEQ ID NO 122
<211> LENGTH: 1202
<212> TYPE: DNA
<213> ORGANISM: Pinus radiata

<400> SEQUENCE: 122

| | |
|---|---|
| caataattat ctcaattaat atagtctaac acaatttgaa tttcaaaata aacttaccta | 60 |
| tcaaatttga aaattttcac acttgtccat tcgccatcct atctttacag ctgccaagaa | 120 |
| aaaaattgac aaatttgcaa actaatatct tttatctata ttggatgagg gcaaatcatc | 180 |
| caataaaaag aaaacacaac aaaataaagg aatatccttt gaaaatactg ccagctgaat | 240 |
| ttccaattca actaaaactt tgaaccgtcc ggaatgagaa actcaattct cctctccgcg | 300 |
| tctttaggag taaactatgc tgtacaatcc gttaatttct gacacacaat tcctcacgat | 360 |
| aaagaaaaa tctgtcagtc tatcgggtag ctggcggcac accgtttaac ggacgaccgg | 420 |
| tagctttgcc ctttagatcc accatccagt aactggcaat aggcggtggc ttactggccc | 480 |
| accttgagct tgccaattca ccgacatgaa cgcgtgtcag acggaagaag caacacaatt | 540 |
| ggacacagaa atacgactcg tttgcaacca caaaggaacc atccgttgtc gtgtattaat | 600 |
| taaaaaatga gatgttaaaa attcaaaaaa tgatttataa tagaaaaatt atatatatat | 660 |
| ggatctgaat atgcttctcg ttgcttgttt cgtaggataa ttcagaggga gaagtcgctt | 720 |
| atattctata ctgacaccca ttccttgaag gaagcgctcc agtgttagag gccctggggt | 780 |
| ttgaaagctg attggtagca gggtcttcta tcagtgtacc tcctggttta attttaattt | 840 |
| ctatgaatga catgcatcct tattaggaca agggggtttga tatatcaatt gcaaagggtt | 900 |
| tgagagaagc cagggtttgg tctttgtgtc aggcgagaat ttgttaatct ccagacgcca | 960 |
| tggacgctga attatgggcg gctcgtgtca cggcagcaaa gcgccatcac gcagttcatc | 1020 |

```
attatcatca tcatacagat cggcagttta actttgatga attggagggc gatgatgaca    1080
tacgggcgga tttcacttgc ccattttgtt ttgaggattt tgatatcgca ttgctctgct    1140
gccatcttga ggatgaacat tgcatcgaca caaaaaatgc gctatgtcct gtgtgcgcag    1200
ct                                                                  1202

<210> SEQ ID NO 123
<211> LENGTH: 1397
<212> TYPE: DNA
<213> ORGANISM: Eucalyptus grandis

<400> SEQUENCE: 123
ccttcctaaa gagctaccat ttctcctcat catccccgcc gccagaagaa gaagaagata     60
tttgcgatca tgaccatcag gatgatcatg atcgggtcag tggatttaag tggaagctca    120
agaggtcgat gaagggtttt aatgagtcgg cagcgggaat cgtaatggag gtccgtcgag    180
gactaacgtc ccagaggagg ctcaaaatca gggttttcag ggccaagctc aatcttcact    240
cttctttggt tgccttaacc acgagatgtt tcattccttg gtttagcaaa gttgagcatg    300
cgcagtgacc cacagttcaa ttagctttca ctccagaagt tctctatgtg aatatagttt    360
gaggttaaaa aaggttgcaa ccactctcct tctaagcacc atatgctcct gtcaatatcg    420
attgacctct tgtgagtttg gcaggaagta ctcatgtcca cagaatttct tgaaaataat    480
taacactttt gtcgtaaaga acgtagggta aaggagaaaa ttctacttct cgacatccta    540
cttttacctc ttcaaaatta tgcgattaat accatacgat acgtcttgac gatcctatct    600
cgcatggcac gtgttattgt caaaggtatg atttttgattt ttcgacaatc aaagcaacgt    660
caatccccat tcaagattga tgtactatgt cgaggaacca taaggatct gttctctctg    720 aggacggctc acccacatgg ggggtctgac cccaccaaag acttggtgga tgttgtggat    780
ttcatgcttt tgattcgggc caaaactcat atctcccttat cttctctcgc cccttgactg    840
tccaccaaac actctcgggt atcttgccct caccaatcat ccacgcgcac aaacagacga    900
acgcaacaat atctctctga ccctcctctt tctttcattc tccctccacc tcttgatact    960
ctatttctct tgttctctta attgcgaaaa ttactcttga acttgtctgt tgtcctctc    1020 agcgtggcct gagatgggca ttttttcaaaa ttaaacattg ctgcttggtt tagagacttc    1080
acttgatgag gttgataggt gaagaagaag aagaagaaga agaagaagaa gaagaagaag    1140
atgaagatac agtgtgatgt gtgcgagaga gcgccggcga cagtgatatg ttgcgcggat    1200
gaagctgcgc tgtgtgagaa atgtgatgtg gagattcacg cagcgaacaa actcgcgagc    1260
aagcaccaga ggcttctcct caactgcctc tccaacaaac tccctctctg tgacatttgc    1320
cgggagaagg ccgcgttcat cttctgtgtc gaagaccgag ctctcttctg tcaggactgt    1380
gatgaaccaa tccattc                                                  1397

<210> SEQ ID NO 124
<211> LENGTH: 1142
<212> TYPE: DNA
<213> ORGANISM: Pinus radiata

<400> SEQUENCE: 124
atctgataca attgtgaagg tgttattaat aatattttca tttctctgaa atctaggttt     60
agtcaattac atatttgata atttttcttca tttccttacg caaatgattc catgaacgaa    120
attttgtttt tgatttttt tgtttcgttt atttctacca cgtgttgcat ttatatttga    180
```

| | |
|---|---|
| aagcataagg agcacagtta gttttgatac ctgcaatgcc acgttttttc tgcaattcca | 240 |
| tcttccacca cacattcaaa gataatgtcg gtcatcacat tcttcagaac gcaatttgtc | 300 |
| atcaatgggt cacatgctgc catcagtatt ctgaattttc aaagcagaca aacccaaata | 360 |
| cacctggatt gcagtgggta cattatagtg acatgataaa tatcccacat cacattcttc | 420 |
| agaacgcaat ttgtcatcaa tgggtcacat actgccatca gtattccgaa ttttcaaagt | 480 |
| agacaaaccc aaaatacaac tggagtgcag tgggtacatt atagtgacat gataaatatc | 540 |
| ccacatcaca ttcttccgaa tgcaatttgt catcaatagg tcacatactg ccatcagtat | 600 |
| tcttaattt cacagtagac aaacccaaaa tacaactgga ttgcagtggg tacattatag | 660 |
| tgacatgata aatatcctac cgttttgata gtaaacttga gctgcaagta aactacatgt | 720 |
| gcactcatgg tggggcttgt gctgccaatt gccctttaaa atggagtcca tcaacatctt | 780 |
| tttaacataa gaattcttta gactgggagt tgatttgagc tttatttgg tgtatcatct | 840 |
| tgtagtctga aaagaagat tcacagtacc agcttaatta tttcatcatg gccactgcaa | 900 |
| ccttcataga tatcttgttg gccatacttc tgccaccttt gggagtcttt ctcaaatatg | 960 |
| agtgccattc tgaattctgg atatgtgtgc tgctgactct tttggggtgg ctaccaggga | 1020 |
| ttatatatgc cgtctatatt ctcaccaagt gaaaatgaat attctttgtt tggagcttgg | 1080 |
| tgccacttaa ttgtcatgag taaacataat tgaatttgtt tattcacttg ttttttatgc | 1140 |
| at | 1142 |

<210> SEQ ID NO 125
<211> LENGTH: 1489
<212> TYPE: DNA
<213> ORGANISM: Eucalyptus grandis

<400> SEQUENCE: 125

| | |
|---|---|
| atcattgcac agatgctggc ctatcaagcg tccatcgatt aatgtcatga tgattcgtgt | 60 |
| catcaatttt cccatagcga gtcagcgacc accgcatgca cgatgccgat gtcgccgtgc | 120 |
| gaaaaacatc gagcagacgg catgctaaag acatgcattt cggtcctctc tgatggtgaa | 180 |
| ttgcaatgca gaagagactc ggatggattt gatttcaaag tgacgacact gacttctgcg | 240 |
| cattcgttta tacatgcata ttcttcaaaa ggatgcttct gccacttctc tttttcagtg | 300 |
| gctttcagtt caagaaaccc cattaatttc aaaagagaaa gcaggtggct atctgcacgg | 360 |
| aagaatggtc tcattgttct atttaagcat ttccttttt cattgcacgt gtggtctaga | 420 |
| agagttttc ctttcctcat atgaagccaa ataccatgt ccgagtttca cataatacaa | 480 |
| aacatttccc aggaagaaaa tgttcccaga gaccacatga gttctcttga aatctttgaa | 540 |
| atttataacc ctgacccatg aaatcgggca agaaaaactg taatggcatc agcaggatgt | 600 |
| gaagagaatg gaggcggcgt acacctaatg cggttttacc gagtcggata tggttgtcgt | 660 |
| atggacaaca ggctgttgat ttggtaagtg tcggattttt tagggagaca aaagtccaac | 720 |
| ctatccccaa gcaaatccgg ggaattcgat ggtctcttga atatgtaaat gcttttgaac | 780 |
| ttcagtgact gagtccaaat gatcttcttc ttctgcaagc taactaaccct tcggtccttc | 840 |
| tcttggctgc ttttgcaac tactactata ttattgcttt tagtaatggt ggtagttgca | 900 |
| atagaagtaa gcatagtgaa aaagtgttga tcggcaacaa acaaagaagc ttaattatta | 960 |
| ccgatccagc acaccttaat catctccaac tgttctctat tcttgcatct tcaaccgtaa | 1020 |
| tcagcagata atcctcgtca ttaatcatta ttctgaaaca acctgttgcc ccaccaaaga | 1080 |
| aaactcatag gtgactctgc tttgttctct tgcaatgcca tatatacacc tgaaattctg | 1140 |

-continued

```
atcgctctca ctcatctgtc gcattcaaag cctcaaagcc gcttgtttct tgaactttgc    1200
cttggcttca agaagaaag tcctcaaata gaagatcgac catatgggac tgaagatatt    1260
ctcagtcggc tttgctcttc tttgttgctt ctgttcactt ggcttctgtg atcaagacgg    1320
ttttctgagt ttagcttgtg gtggaactac caattacacg gattcatcca acatctggtg    1380
gattaccgac agtgatttca taagcacagg aaagactacc tatgttgaca atatcgaggg    1440
caattcatct ggtgtttcgc ttcggttctt cccagattcc aaagtccat              1489

<210> SEQ ID NO 126
<211> LENGTH: 1273
<212> TYPE: DNA
<213> ORGANISM: Eucalyptus grandis

<400> SEQUENCE: 126
ttgtaaatta tgtgtgctta ataggggtctt gttaatcaat gatcagtgta ttttttacgc    60
atgtgatgaa aaagtaattg cttttgagaa tatagttaca tcgaaaggac aatcaattcg   120
tttgacattg taatttttta tttgatagtt aacaagtgc ctcggaacac tcttcaacat    180
atcctttcac tttattttgc atatttatgc ttgtacaaca acattttcaa ttgggtgatc    240
ataattcgta atatttataa ttttttgtta acaatgagta actctatact cctggattga    300
gcaaacatat ttgtaaagta gttatgagag tattacttat acttagacgt tgtgagatac    360
tcatgatcgt atcatatgtc cactagagga tatagattta cctagatgaa gccccttct    420 tagaagtagg aaaaaaaaa ctattatatt gacttgaacc catatcataa aaagtacgag    480
actcaaaatc caatcttaca tgtatatgtg tatatatata tgttcgcaaa tgataacaat    540
cttttcaaga atcaagacac cagaaaacca tattttcaat atccgtcaat gtcaatgtcc    600
tactcacatc gaacaggact gccgcgtaca caacaagttc cccagctaca gatttaccta    660
caattaggaa atgcaacccg aaaagacagg tctccatttc ttccttcact ttcccactca    720
tgaaaatgaa atatataatc acaaaatgcc tgagcgacac taaaggaacc aaagaacaac    780
gattccaact cagagagaga gagagagaga gagagaggca ctaattttg gctgctcaac    840 aaaggaagca actttattca aatccatttt gctttagcgt gcccgtaatt ccaaccaaac    900
atatcctcaa agccctaata tatactccca caagcgcacc tcgtttccta cacacaagta    960
caaagcgtca acttcttctt cgctaaactg gtctcacaga cactcgcttg ccctcagtc    1020 cacactttgg cttagctcac agcaactatg gctgagacag cggaaccca gaagctggtc    1080 gagctcgaga aggtgcccga ccccgaggcc ggcgtgcccc cgaaaggaga ggaggcgccc    1140
ccagaacccc cacttccgcc cccagtgccg gcgccgccgg tggaaacttg cgtcttggtt    1200
gacgtggcac ttagggtttt gctcttcgca gcgacactga ccgctgtggt ggtgatggtc    1260
acggcgaacc aaa                                                       1273

<210> SEQ ID NO 127
<211> LENGTH: 3720
<212> TYPE: DNA
<213> ORGANISM: Eucalyptus grandis

<400> SEQUENCE: 127
cgaagttcag ctcccgcttc cctgatgttt tcaaatcttc tttcaagtta gaagtacata     60
tacagcaaac aagatccaac ccttttctta tcatgagccc ttacttccac aagtgacatt   120
tggcactagt cccacaattt aatcattcta tttccattct ctgtaaatgt accctattca   180
```

```
aagttgggac ataatgaccc ttttgaagcg ttaggatcac actttattaa aagggaacaa      240
caacattgac agcaaatgca cgcactttcg ataaagttca gacagtataa taagttctca      300
ttccaaaagg ccccaatgtg gaaggtacga cttctctaac cctgttttga tttgattttt      360
tcgcagagga aaaatcatca ccaaagactt ataaaaattg aagtagcaaa gaaaagaaaa      420
gcaagattag caaacagaga ggagaaagag aggggaagga gtgatgggcc aacagccatt      480
ctcccagaaa ccacataaaa aacaaacaca gaatgatcac ttgtgaagaa cacgcggagt      540
tccaagcaaa gcatctcgag aatcaatgtc gctctttctt cacaagcatt ggacagaaaa      600
aaagagcaag ctctaagttt tccagcgaaa gcccgaaaat taggacgaag ggcgacgaga      660
aaacgaaaaa ctagaaggaa acaaaaatca aaataaaaag gaaagagagg cctgtgcgag      720
taataacgat tgtaaggcaa gacgatgaac cggcaaagct tgattcctgg ttgcaaattg      780
gggacgaaga tggctcaaaa taggagtgac gggcggtgat tttaccgcga agcgaaacct      840
agaatgcaag gagcaaagaa gagggtggtg gcagaatcga cgccgacagt ggcagcagag      900
tcgacgccag cagcagcggc ggagtgtatg agcggagaag gcgtagtagc tgatggtggt      960
ggagtcgaca agaggagaag gcaagaagga agagtcgtcc ggaaccaatg tgtttggctt     1020
tgggtgtgga tgttttgtat tttggtgaga tgagagaacg tgtttgtttc attgtttaag     1080
attaataatg tgttcacgag ccgaacaatg tttcgacctt aacccgactc aaaacatggt     1140
tgtttgcttg ttttgtaatt gttacctaaa taatattaag acctaaaaca tcgtgttcgg     1200
gttgagtttt tggacactcc tacctgtgat agccaccgcg agcgtagact actggatttg     1260
atatttggaa gcacgaccac cttttattgc caattggaaa gataaaaacg aggcacgaat     1320
gggaccaaaa tgagcaagaa atacggtatc tttggatgcc atgtttgcca tttgtcacct     1380
tacgcagagt gctagtgtaa attctcaatc aaagagcacg ggatacgttt tgttcagaac     1440
ttcacaccat gagcaggctt ggaaaaggag gaccgtaaag gaaatcacca tattgtagat     1500
gttcaaaata agttaacgaa tcagaaaaag aatacccatt tagccgaatt taattaacgt     1560
aatctttacg tgggacaact aaagtggaaa tttttttaac ttgtgctgat gttttagctt     1620
taaaatgcaa tcaccagcct aaaatatatc ttgattcatt atttgaaatc tcgaatgtaa     1680 atttagtag tatatcataa atatctccgt ttggcctact ttctaatgca gcatccgttt      1740
gatagggtgt cgacgactca actctacgta cgtaaaaaaa aaaattaaa aaatgccata      1800 ttgactttat agtgtagcac gtcatcaaat tgggcgagca gtcgtcggat ggaattaaaa      1860
ttacatcaaa tggaaattgt ttgttggttg cactttgggt caatttttt tggactttga      1920 tgtaagtaat taagttaagt aatgatttcc attcactagg aagtcgaagc ccacacaacc      1980
ttgaaaaaaa aaaaaaaaa agacatcagt ccatgcaaac aacgaattaa ctgaatttaa      2040
tgaagaatac gagaaacgta aaaacttgat aagtttatta acgatagga atgcactta       2100 gattaatgta agtacaagta tctatagaga gttatacaaa tatatatata tatatatata     2160
tatatataat atttcagata gttttatgaa aatacttaaa attaaataga agaaaaaata     2220
tcaaactgat attgctctaa atgggattct acttttacta tcatagagat aataagctaa     2280
ggtataatta agtagaacta tcgtaatata tataatatca ataagataaa aaagtaaata     2340
gaaagatagc cactttttt gttattgagg aaatggattg aaatgaaata atattacgaa      2400
atcaacaata gtgatagaag gaatgatttg acctagttat ggaatatcga gtgactaaat     2460
caggcaaatc gaaagtttaa gaatttaggt tgcacattta gctatgttta aagaccatat     2520
tgtatctgtc atgatagttt agagacttgc gactctctct cttgcgcatt caaacaaaag     2580
```

-continued

```
aagaacaaaa aatttaagaa tgacgttgtg cactcggtca gagttaaaga actattagtg    2640
tgattttttc attttttaagt aaacaaaaca cgatgtggga gatgtgggag attggaaaag   2700
tgatggctaa aatttggaag aaaaatagaa atatgatcat gattgaagat ttataaaata    2760
aataatcatg gtacggactg aaactttaaa aaaatagtaa atgtactatg gtagacaaaa    2820
acaaattgag agtgtatatg gtaagggcaa cgctctttcc attccttata taactaaatt    2880
cacctaactc ttccaaaaat acaaagttgc atctatttta cattagtagt cccaaattta    2940
tttacttttt ttttttttag tttttatatc tacataagat ttacttacca tagttaagaa    3000
tttatatgtt taatttttagt taatttttata ttttctatgt atattagagg cactatcttt   3060
cttttatccg ataatgcaat tttctttgat acgctaacaa acaaaacatg tgaaaagctt    3120
aattatggca attatcataa atagaaaaaa attagaaaaa aagagaggaa atgggccatt    3180
atttaaattg caatcgaaag attgagggca attctgtttc tctagtgtaa ataagggtgt    3240
atttaataat tgagggatgg aaatagcatg gtcactcggt aattatcaag gaaagcaaga    3300
ataaaaatgg aaaaaaaaaa aaaaaaagct tgaagaggcc aatgtcgaaa ttatgagcgc    3360
gagatgagga cactcctggg aaacgaaaaa tggcattcgc gggggggtgct atataaagcc   3420 tcgtgtaagg gtgcgttcct cactctcaaa ccctaatcct gcccttccct tctgctgctg    3480
ctgctcgtca cctctctcct ccctctcgcg gccagctgcg agatctgccg agtttaagcc    3540
tcgtacatca aaatgggtaa ggagaagatt cacatcagca ttgtggtcat tggccatgtc    3600
gattctggga agtcaaccac aactggccac ttgatataca agctcggagg aatcgacaag    3660
cgtgtgattg agagattcga gaaggaagct gctgagatga acaagagatc gttcaagtat    3720
```

<210> SEQ ID NO 128
<211> LENGTH: 25
<212> TYPE: DNA
<213> ORGANISM: Eucalyptus grandis

<400> SEQUENCE: 128
tgagcggata acaatttcac acagg        25

<210> SEQ ID NO 129
<211> LENGTH: 25
<212> TYPE: DNA
<213> ORGANISM: Eucalyptus grandis

<400> SEQUENCE: 129
tcgagttttt tgatttcacg ggttg        25

<210> SEQ ID NO 130
<211> LENGTH: 54
<212> TYPE: PRT
<213> ORGANISM: Pinus radiata

<400> SEQUENCE: 130

Met Ala Thr Ala Thr Phe Ile Asp Ile Leu Leu Ala Ile Leu Leu Pro
 1               5                   10                  15

Pro Leu Gly Val Phe Leu Lys Tyr Glu Cys His Ser Glu Phe Trp Ile
            20                  25                  30

Cys Val Leu Leu Thr Leu Leu Gly Trp Leu Pro Gly Ile Ile Tyr Ala
        35                  40                  45

Val Tyr Ile Leu Thr Lys
    50

<210> SEQ ID NO 131
<211> LENGTH: 285
<212> TYPE: DNA
<213> ORGANISM: Pinus radiata

<400> SEQUENCE: 131

| | | | | | |
|---|---|---|---|---|---|
| catacgtctc | gagaagcgtg | acggatgtgc | gaccggatga | ccctgtataa | cccaccgaca | 60 |
| cagccagcgc | acagtataca | cgtgtcattt | ctctattgga | aaatgtcgtt | gttatccccg | 120 |
| ctggtacgca | accaccgatg | gtgacaggtc | gtctgttgtc | gtgtcgcgta | gcgggagaag | 180 |
| ggtctcatcc | aacgctatta | aatactcgcc | ttcaccgcgt | tacttctcat | cttttctctt | 240 |
| gcgttgtata | atcagtgcga | tattctcaga | gagcttttca | ttcaa | | 285 |

<210> SEQ ID NO 132
<211> LENGTH: 458
<212> TYPE: DNA
<213> ORGANISM: Pinus radiata

<400> SEQUENCE: 132

| | | | | | |
|---|---|---|---|---|---|
| aatttatttc | ttttatttac | ttaaaaaaac | aaaaagttta | tttattttac | ttaaatggca | 60 |
| taatgacata | tcggagatcc | ctcgaacgag | aatcttttat | ctccctggtt | ttgtattaaa | 120 |
| aagtaattta | ttgtggggtc | cacgcggagt | tggaatccta | cagacgcgct | ttacatacgt | 180 |
| ctcgagaagc | gtgacggatg | tgcgaccgga | tgaccctgta | taacccaccg | acacagccag | 240 |
| cgcacagtat | acacgtgtca | tttctctatt | ggaaaatgtc | gttgttatcc | ccgctggtac | 300 |
| gcaaccaccg | atggtgacag | gtcgtctgtt | gtcgtgtcgc | gtagcgggag | aagggtctca | 360 |
| tccaacgcta | ttaaatactc | gccttcaccg | cgttacttct | catctttcct | cttgcgttgt | 420 |
| ataatcagtg | cgatattctc | agagagcttt | tcattcaa | | | 458 |

<210> SEQ ID NO 133
<211> LENGTH: 536
<212> TYPE: DNA
<213> ORGANISM: Pinus radiata

<400> SEQUENCE: 133

| | | | | | |
|---|---|---|---|---|---|
| ttttcctact | tcaccgttaa | ttacattcct | taagagtaga | taaagaaata | aagtaaataa | 60 |
| aagtattcac | aaaccaacaa | tttatttctt | ttatttactt | aaaaaaacaa | aaagtttatt | 120 |
| tattttactt | aaatggcata | atgacatatc | ggagatccct | cgaacgagaa | tcttttatct | 180 |
| ccctggtttt | gtattaaaaa | gtaatttatt | gtggggtcca | cgcggagttg | gaatcctaca | 240 |
| gacgcgcttt | acatacgtct | cgagaagcgt | gacggatgtg | cgaccggatg | accctgtata | 300 |
| acccaccgac | acagccagcg | cacagtatac | acgtgtcatt | tctctattgg | aaaatgtcgt | 360 |
| tgttatcccc | gctggtacgc | aaccaccgat | ggtgacaggt | cgtctgttgt | cgtgtcgcgt | 420 |
| agcgggagaa | gggtctcatc | caacgctatt | aaatactcgc | cttcaccgcg | ttacttctca | 480 |
| tctttctct | tgcgttgtat | aatcagtgcg | atattctcag | agcttttc | attcaa | 536 |

<210> SEQ ID NO 134
<211> LENGTH: 663
<212> TYPE: DNA
<213> ORGANISM: Pinus radiata

<400> SEQUENCE: 134

| | | | | | |
|---|---|---|---|---|---|
| caggacacct | aaaattttga | agtttaacaa | aaataacttg | gatctacaaa | aatccgtatc | 60 |
| ggattttctc | taaatataac | tagaattttc | ataactttca | aagcaactcc | tccctaacc | 120 |

```
gtaaaactttt tcctacttca ccgttaatta cattccttaa gagtagataa agaaataaag      180
taaataaaag tattcacaaa ccaacaattt atttctttta tttacttaaa aaaacaaaaa      240
gtttatttat tttacttaaa tggcataatg acatatcgga gatccctcga acgagaatct      300
tttatctccc tggttttgta ttaaaaagta atttattgtg gggtccacgc ggagttggaa      360
tcctacagac gcgctttaca tacgtctcga aagcgtgac ggatgtgcga ccggatgacc       420
ctgtataacc caccgacaca gccagcgcac agtatacacg tgtcatttct ctattggaaa     480
atgtcgttgt tatccccgct ggtacgcaac caccgatggt gacaggtcgt ctgttgtcgt     540
gtcgcgtagc gggagaaggg tctcatccaa cgctattaaa tactcgcctt caccgcgtta     600
cttctcatct tttctcttgc gttgtataat cagtgcgata ttctcagaga gcttttcatt     660
caa                                                                   663

<210> SEQ ID NO 135
<211> LENGTH: 843
<212> TYPE: DNA
<213> ORGANISM: Pinus radiata

<400> SEQUENCE: 135
attgatgtac aagtttgaga ggataagaca ttggaatcgt ctaaccagga ggcggaggaa       60
ttccctagac agttaaaagt ggccggaatc ccggtaaaaa agattaaaat tttttttgtag     120 agggagtgct tgaatcatgt tttttatgat ggaaatagat tcagcaccat caaaaacatt     180
caggacacct aaaattttga agtttaacaa aaataacttg gatctacaaa aatccgtatc     240
ggattttctc taaatataac tagaattttc ataactttca aagcaactcc tcccctaacc     300
gtaaaacttt tcctacttca ccgttaatta cattccttaa gagtagataa agaaataaag     360
taaataaaag tattcacaaa ccaacaattt atttctttta tttacttaaa aaaacaaaaa     420
gtttatttat tttacttaaa tggcataatg acatatcgga gatccctcga acgagaatct     480
tttatctccc tggttttgta ttaaaaagta atttattgtg gggtccacgc ggagttggaa     540
tcctacagac gcgctttaca tacgtctcga aagcgtgac ggatgtgcga ccggatgacc      600
ctgtataacc caccgacaca gccagcgcac agtatacacg tgtcatttct ctattggaaa     660
atgtcgttgt tatccccgct ggtacgcaac caccgatggt gacaggtcgt ctgttgtcgt     720
gtcgcgtagc gggagaaggg tctcatccaa cgctattaaa tactcgcctt caccgcgtta     780
cttctcatct tttctcttgc gttgtataat cagtgcgata ttctcagaga gcttttcatt     840
caa                                                                   843

<210> SEQ ID NO 136
<211> LENGTH: 1164
<212> TYPE: DNA
<213> ORGANISM: Pinus radiata

<400> SEQUENCE: 136
catacgtctc gagaagcgtg acggatgtgc gaccggatga ccctgtataa cccaccgaca       60
cagccagcgc acagtataca cgtgtcattt ctctattgga aaatgtcgtt gttatccccg      120
ctggtacgca accaccgatg gtgacaggtc gtctgttgtc gtgtcgcgta gcgggagaag      180
ggtctcatcc aacgctatta aatactcgcc ttcaccgcgt tacttctcat cttttctctt      240
gcgttgtata atcagtgcga tattctcaga gagcttttca ttcaaaggta tggagttttg      300
aagggcttta ctcttaacat tgttttttct ttgtaaattg ttaatggtgg tttctgtggg      360
```

```
ggaagaatct tttgccaggt ccttttgggt ttcgcatgtt tatttgggtt attttttctcg      420 actatggctg acattactag ggctttcgtg ctttcatctg tgttttcttc ccttaatagg      480
tctgtctctc tggaatattt aattttcgta tgtaagttat gagtagtcgc tgtttgtaat      540
aggctcttgt ctgtaaaggt ttcagcaggt gtttgcgttt tattgcgtca tgtgtttcag      600
aaggcctttg cagattattg cgttgtactt aatattttg tctccaacct tgttatagtt       660
tccctccttt gatctcacag gaacccttc ttctttgagc attttcttgt ggcgttctgt       720
agtaatattt aattttggg cccgggttct gagggtaggt gattattcac agtgatgtgc       780
tttccctata aggtcctcta tgtgtaagct gttagggttt gtgcgttact attgacatgt      840
cacatgtcac atattttctt cctcttatcc ttcgaactga tggttctttt tctaattcgt      900
ggattgctgg tgccatattt tatttctatt gcaactgtat tttagggtgt ctctttcttt      960
ttgatttctt gttaatattt gtgttcaggt gtaactatg ggttgctagg gtgtctgccc      1020
tcttcttttg tgcttcttc gcagaatctg tccgttggtc tgtatttggg tgatgaatta      1080
tttattcctt gaagtatctg tctaattagc ttgtgatgat gtgcaggtat attcgttagt      1140
catatttcaa tttcaagatg caga                                             1164

<210> SEQ ID NO 137
<211> LENGTH: 1337
<212> TYPE: DNA
<213> ORGANISM: Pinus radiata

<400> SEQUENCE: 137
aatttatttc ttttatttac ttaaaaaaac aaaaagttta tttattttac ttaaatggca       60
taatgacata tcggagatcc ctcgaacgag aatctttat ctccctggtt ttgtattaaa       120
aagtaattta ttgtggggtc cacgcggagt tggaatccta cagacgcgct ttacatacgt      180
ctcgagaagc gtgacggatg tgcgaccgga tgaccctgta taaccaccg acacagccag      240 cgcacagtat acacgtgtca tttctctatt ggaaaatgtc gttgttatcc ccgctggtac      300
gcaaccaccg atggtgacag tcgtctgtt gtcgtgtcgc gtagcgggag aagggtctca      360
tccaacgcta ttaaatactc gccttcaccg cgttacttct catcttttct cttgcgttgt      420
ataatcagtg cgatattctc agagagcttt tcattcaaag gtatggagtt ttgaagggct      480
ttactcttaa catttgtttt tctttgtaaa ttgttaatgg tggtttctgt gggggaagaa      540
tcttttgcca ggtccttttg ggtttcgcat gtttatttgg gttatttttc tcgactatgg      600
ctgacattac tagggctttc gtgctttcat ctgtgttttc ttcccttaat aggtctgtct      660
ctctggaata tttaattttc gtatgtaagt tatgagtagt cgctgtttgt aataggctct      720
tgtctgtaaa ggtttcagca ggtgtttgcg ttttattgcg tcatgtgttt cagaaggcct      780
ttgcagatta ttgcgttgta ctttaatatt ttgtctccaa ccttgttata gtttccctcc      840
tttgatctca caggaaccct ttcttctttg agcattttct tgtggcgttc tgtagtaata      900
tttaattttt gggcccgggt tctgagggta ggtgattatt cacagtgatg tgctttccct      960
ataaggtcct ctatgtgtaa gctgttaggg tttgtgcgtt actattgaca tgtcacatgt     1020
cacatatttt cttcctctta tccttcgaac tgatggttct ttttctaatt cgtggattgc     1080
tggtgccata ttttatttct attgcaactg tattttaggg tgtctctttc ttttgattt      1140 cttgttaata tttgtgttca ggtgtaact atgggttgct agggtgtctg ccctcttctt      1200
ttgtgcttct ttcgcagaat ctgtccgttg gtctgtattt gggtgatgaa ttatttattc     1260
cttgaagtat ctgtctaatt agcttgtgat gatgtgcagg tatattcgtt agtcatattt     1320
```

-continued

| caatttcaag atgcaga | 1337 |

<210> SEQ ID NO 138
<211> LENGTH: 1415
<212> TYPE: DNA
<213> ORGANISM: Pinus radiata

<400> SEQUENCE: 138

| ttttcctact tcaccgttaa ttacattcct taagagtaga taaagaaata agtaaataa | 60 |
| aagtattcac aaaccaacaa tttatttctt ttatttactt aaaaaaacaa aaagtttatt | 120 |
| tattttactt aaatggcata atgacatatc ggagatccct cgaacgagaa tcttttatct | 180 |
| ccctggtttt gtattaaaaa gtaatttatt gtggggtcca cgcggagttg aatcctaca | 240 |
| gacgcgcttt acatacgtct cgagaagcgt gacggatgtg cgaccggatg accctgtata | 300 |
| acccaccgac acagccagcg cacagtatac acgtgtcatt tctctattgg aaaatgtcgt | 360 |
| tgttatcccc gctggtacgc aaccaccgat ggtgacaggt cgtctgttgt cgtgtcgcgt | 420 |
| agcgggagaa gggtctcatc caacgctatt aaatactcgc cttcaccgcg ttacttctca | 480 |
| tcttttctct tgcgttgtat aatcagtgcg atattctcag agagcttttc attcaaaggt | 540 |
| atggagtttt gaaggctttt actcttaaca tttgttttc tttgtaaatt gttaatggtg | 600 |
| gtttctgtgg gggaagaatc ttttgccagg tcctttttggg tttcgcatgt ttatttgggt | 660 |
| tattttctc gactatggct gacattacta gggctttcgt gctttcatct gtgttttctt | 720 |
| cccttaatag gtctgtctct ctggaatatt taattttcgt atgtaagtta tgagtagtcg | 780 |
| ctgtttgtaa taggctcttg tctgtaaagg tttcagcagg tgtttgcgtt ttattgcgtc | 840 |
| atgtgtttca gaaggccttt gcagattatt gcgttgtact ttaatatttt gtctccaacc | 900 |
| ttgttatagt ttccctcctt tgatctcaca ggaaccctt cttctttgag catttcttg | 960 |
| tggcgttctg tagtaatatt ttaattttgg gcccgggttc tgagggtagg tgattattca | 1020 |
| cagtgatgtg ctttccctat aaggtcctct atgtgtaagc tgttagggtt tgtgcgttac | 1080 |
| tattgacatg tcacatgtca catatttct tcctcttatc cttcgaactg atggttcttt | 1140 |
| ttctaattcg tggattgctg gtgccatatt ttatttctat tgcaactgta ttttagggtg | 1200 |
| tctctttctt tttgatttct tgttaatatt tgtgttcagg ttgtaactat ggttgctag | 1260 |
| ggtgtctgcc ctcttctttt gtgcttcttt cgcagaatct gtccgttggt ctgtatttgg | 1320 |
| gtgatgaatt atttattcct tgaagtatct gtctaattag cttgtgatga tgtgcaggta | 1380 |
| tattcgttag tcatatttca atttcaagat gcaga | 1415 |

<210> SEQ ID NO 139
<211> LENGTH: 1542
<212> TYPE: DNA
<213> ORGANISM: Pinus radiata

<400> SEQUENCE: 139

| caggacacct aaaattttga agtttaacaa aaataacttg gatctacaaa aatccgtatc | 60 |
| ggatttctc taaatataac tagaattttc ataactttca aagcaactcc tcccctaacc | 120 |
| gtaaactttt tcctacttca ccgttaatta cattccttaa gagtagataa agaaataaag | 180 |
| taaataaaag tattcacaaa ccaacaattt atttctttta tttacttaaa aaacaaaaa | 240 |
| gtttatttat tttacttaaa tggcataatg acatatcgga gatccctcga acgagaatct | 300 |
| tttatctccc tggttttgta ttaaaaagta atttattgtg gggtccacgc ggagttggaa | 360 |

```
tcctacagac gcgctttaca tacgtctcga gaagcgtgac ggatgtgcga ccggatgacc    420
ctgtataacc caccgacaca gccagcgcac agtatacacg tgtcatttct ctattggaaa    480
atgtcgttgt tatccccgct ggtacgcaac caccgatggt gacaggtcgt ctgttgtcgt    540
gtcgcgtagc gggagaaggg tctcatccaa cgctattaaa tactcgcctt caccgcgtta    600
cttctcatct tttctcttgc gttgtataat cagtgcgata ttctcagaga gcttttcatt    660
caaaggtatg gagttttgaa gggctttact cttaacattt gtttttcttt gtaaattgtt    720
aatggtggtt tctgtggggg aagaatcttt tgccaggtcc ttttgggttt cgcatgttta    780 tttggttat ttttctcgac tatggctgac attactaggg cttttcgtgct ttcatctgtg    840 ttttcttccc ttaataggtc tgtctctctg gaatatttaa ttttcgtatg taagttatga    900
gtagtcgctg tttgtaatag gctcttgtct gtaaaggttt cagcaggtgt ttgcgtttta    960
ttgcgtcatg tgtttcagaa ggcctttgca gattattgcg ttgtacttta atattttgtc   1020
tccaaccttg ttatagtttc cctcctttga tctcacagga acctttctt ctttgagcat   1080 tttcttgtgg cgttctgtag taatatttta attttgggcc cgggttctga gggtaggtga   1140
ttattcacag tgatgtgctt tccctataag gtcctctatg tgtaagctgt tagggtttgt   1200
gcgttactat tgacatgtca catgtcacat attttcttcc tcttatcctt cgaactgatg   1260 gttcttttc taattcgtgg attgctggtg ccatatttta tttctattgc aactgtattt   1320
tagggtgtct ctttctttt gatttcttgt taatatttgt gttcaggttg taactatggg   1380
ttgctagggt gtctgccctc ttcttttgtg cttctttcgc agaatctgtc cgttggtctg   1440
tatttgggtg atgaattatt tattccttga agtatctgtc taattagctt gtgatgatgt   1500
gcaggtatat tcgttagtca tatttcaatt tcaagatgca ga                     1542

<210> SEQ ID NO 140
<211> LENGTH: 1722
<212> TYPE: DNA
<213> ORGANISM: Pinus radiata

<400> SEQUENCE: 140
attgatgtac aagtttgaga ggataagaca ttggaatcgt ctaaccagga ggcggaggaa     60
ttccctagac agttaaaagt ggccggaatc ccggtaaaaa agattaaaat ttttttgtag    120
agggagtgct tgaatcatgt tttttatgat ggaaatagat tcagcaccat caaaaacatt    180
caggacacct aaaattttga agtttaacaa aaataacttg gatctacaaa aatccgtatc    240
ggattttctc taaatataac tagaattttc ataactttca aagcaactcc tcccctaacc    300
gtaaaacttt tcctacttca ccgttaatta cattccttaa gagtagataa agaaataaag    360
taaataaaag tattcacaaa ccaacaattt atttctttta tttacttaaa aaaacaaaaa    420
gtttatttat tttacttaaa tggcataatg acatatcgga gatccctcga acgagaatct    480
tttatctccc tggttttgta ttaaaaagta atttattgtg gggtccacgc ggagttggaa    540
tcctacagac gcgctttaca tacgtctcga gaagcgtgac ggatgtgcga ccggatgacc    600
ctgtataacc caccgacaca gccagcgcac agtatacacg tgtcatttct ctattggaaa    660
atgtcgttgt tatccccgct ggtacgcaac caccgatggt gacaggtcgt ctgttgtcgt    720
gtcgcgtagc gggagaaggg tctcatccaa cgctattaaa tactcgcctt caccgcgtta    780
cttctcatct tttctcttgc gttgtataat cagtgcgata ttctcagaga gcttttcatt    840
caaaggtatg gagttttgaa gggctttact cttaacattt gtttttcttt gtaaattgtt    900
aatggtggtt tctgtggggg aagaatcttt tgccaggtcc ttttgggttt cgcatgttta    960
```

-continued

```
tttgggttat ttttctcgac tatggctgac attactaggg ctttcgtgct ttcatctgtg     1020
ttttcttccc ttaataggtc tgtctctctg gaatatttaa ttttcgtatg taagttatga     1080
gtagtcgctg tttgtaatag gctcttgtct gtaaaggttt cagcaggtgt ttgcgtttta     1140
ttgcgtcatg tgtttcagaa ggcctttgca gattattgcg ttgtacttta atattttgtc     1200
tccaaccttg ttatagtttc cctcctttga tctcacagga acctttctt ctttgagcat      1260 tttcttgtgg cgttctgtag taatatttta attttgggcc cgggttctga gggtaggtga     1320
ttattcacag tgatgtgctt tccctataag gtcctctatg tgtaagctgt tagggtttgt     1380
gcgttactat tgacatgtca catgtcacat attttcttcc tcttatcctt cgaactgatg     1440 gttcttttc taattcgtgg attgctggtg ccatatttta tttctattgc aactgtattt      1500
tagggtgtct ctttcttttt gatttcttgt taatatttgt gttcaggttg taactatggg     1560
ttgctagggt gtctgccctc ttcttttgtg cttctttcgc agaatctgtc cgttggtctg     1620
tatttgggtg atgaattatt tattccttga agtatctgtc taattagctt gtgatgatgt     1680
gcaggtatat tcgttagtca tatttcaatt tcaagatgca ga                        1722

<210> SEQ ID NO 141
<211> LENGTH: 1193
<212> TYPE: DNA
<213> ORGANISM: Pinus radiata

<400> SEQUENCE: 141 aaaaccctc acaaatacat aaaaaaaatt ctttatttaa ttatcaaact ctccactacc      60
tttcccacca accgttacaa tcctgaatgt tggaaaaaac taactacatt gatataaaaa     120
aactacatta cttcctaaat catatcaaaa ttgtataaat atatccactc aaaggagtct    180
agaagatcca cttggacaaa ttgcccatag ttggaaagat gttcaccaag tcaacaagat    240
ttatcaatgg aaaaatccat ctaccaaact tactttcaag aaaatccaag gattatagag    300
taaaaaatct atgtattatt aagtcaaaaa gaaaaccaaa gtgaacaaat attgatgtac    360
aagtttgaga ggataagaca ttggaatcgt ctaaccagga ggcggaggaa ttccctagac    420
agttaaaagt ggccggaatc ccggtaaaaa agattaaaat ttttttgtag agggagtgct    480
tgaatcatgt ttttttatgat ggaaatagat tcagcaccat caaaaacatt caggacacct    540
aaaattttga agtttaacaa aaataacttg gatctacaaa aatccgtatc ggattttctc    600
taaatataac tagaattttc ataactttca aagcaactcc tcccctaacc gtaaaacttt    660
tcctacttca ccgttaatta cattccttaa gagtagataa agaaataaag taaataaaag    720
tattcacaaa ccaacaattt attctttta tttacttaaa aaacaaaaa gtttattttat     780 tttacttaaa tggcataatg acatatcgga gatccctcga acgagaatct tttatctccc    840
tggttttgta ttaaaagta atttattgtg gggtccacgc ggagttggaa tcctacagac     900
gcgctttaca tacgtctcga gaagcgtgac ggatgtgcga ccggatgacc ctgtataacc    960
caccgacaca gccagcgcac agtatacacg tgtcatttct ctattggaaa atgtcgttgt   1020
tatccccgct ggtacgcaac caccgatggt gacaggtcgt ctgttgtcgt gtcgcgtagc   1080
gggagaaggg tctcatccaa cgctattaaa tactcgcctt caccgcgtta cttctcatct   1140
tttctcttgc gttgtataat cagtgcgata ttctcagaga gcttttcatt caa          1193

<210> SEQ ID NO 142
<211> LENGTH: 2077
<212> TYPE: DNA
```

<213> ORGANISM: Pinus radiata

<400> SEQUENCE: 142

| | | | | | |
|---|---|---|---|---|---|
| aaaaccctc | acaaatacat | aaaaaaaatt | ctttatttaa | ttatcaaact | ctccactacc | 60 |
| tttcccacca | accgttacaa | tcctgaatgt | tggaaaaaac | taactacatt | gatataaaaa | 120 |
| aactacatta | cttcctaaat | catatcaaaa | ttgtataaat | atatccactc | aaaggagtct | 180 |
| agaagatcca | cttggacaaa | ttgcccatag | ttggaaagat | gttcaccaag | tcaacaagat | 240 |
| ttatcaatgg | aaaaatccat | ctaccaaact | tactttcaag | aaaatccaag | gattatagag | 300 |
| taaaaaatct | atgtattatt | aagtcaaaaa | gaaaaccaaa | gtgaacaaat | attgatgtac | 360 |
| aagtttgaga | ggataagaca | ttggaatcgt | ctaaccagga | ggcggaggaa | ttccctagac | 420 |
| agttaaaagt | ggccggaatc | ccggtaaaaa | agattaaaat | ttttttgtag | agggagtgct | 480 |
| tgaatcatgt | ttttatgat | ggaaatagat | tcagcaccat | caaaaacatt | caggacacct | 540 |
| aaaattttga | agtttaacaa | aaataacttg | gatctcaaaa | aatccgtatc | ggattttctc | 600 |
| taaatataac | tagaattttc | ataactttca | aagcaactcc | tcccctaacc | gtaaaacttt | 660 |
| tcctacttca | ccgttaatta | cattccttaa | gagtagataa | agaaataaag | taaataaaag | 720 |
| tattcacaaa | ccaacaattt | attctcttta | tttacttaaa | aaaacaaaaa | gtttatttat | 780 |
| tttacttaaa | tggcataatg | acatatcgga | gatccctcga | acgagaatct | tttatctccc | 840 |
| tggttttgta | ttaaaaagta | atttattgtg | gggtccacgc | ggagttggaa | tcctacagac | 900 |
| gcgctttaca | tacgtctcga | gaagcgtgac | ggatgtgcga | ccggatgacc | ctgtataacc | 960 |
| caccgacaca | gccagcgcac | agtatacacg | tgtcatttct | ctattggaaa | atgtcgttgt | 1020 |
| tatccccgct | ggtacgcaac | caccgatggt | gacaggtcgc | tgttgtcgt | gtcgcgtagc | 1080 |
| gggagaaggg | tctcatccaa | cgctattaaa | tactcgcctt | caccgcgtta | cttctcatct | 1140 |
| tttctcttgc | gttgtataat | cagtgcgata | ttctcagaga | gctttcatt | caaaggtatg | 1200 |
| gagttttgaa | gggctttact | cttaacattt | gtttttcttt | gtaaattgtt | aatggtggtt | 1260 |
| tctgtggggg | aagaatcttt | tgccaggtcc | ttttgggttt | cgcatgttta | tttgggttat | 1320 |
| ttttctcgac | tatggctgac | attactaggg | ctttcgtgct | ttcatctgtg | ttttcttccc | 1380 |
| ttaataggtc | tgtctctctg | gaatatttaa | ttttcgtatg | taagttatga | gtagtcgctg | 1440 |
| tttgtaatag | gctcttgtct | gtaaaggttt | cagcaggtgt | ttgcgttta | ttgcgtcatg | 1500 |
| tgtttcagaa | ggcctttgca | gattattgcg | ttgtacttta | atattttgtc | tccaaccttg | 1560 |
| ttatagtttc | cctcctttga | tctcacagga | acccttctt | ctttgagcat | tttcttgtgg | 1620 |
| cgttctgtag | taatatttta | atttgggcc | cgggttctga | gggtaggtga | ttattcacag | 1680 |
| tgatgtgctt | tccctataag | gtcctctatg | tgtaagctgt | tagggtttgt | gcgttactat | 1740 |
| tgacatgtca | catgtcacat | attttcttcc | tcttatcctt | cgaactgatg | gttctttttc | 1800 |
| taattcgtgg | attgctggtg | ccatatttta | tttctattgc | aactgtattt | tagggtgtct | 1860 |
| ctttctttt | gatttcttgt | taatatttgt | gttcaggttg | taactatggg | ttgctagggt | 1920 |
| gtctgccctc | ttcttttgtg | cttctttcgc | agaatctgtc | cgttggtctg | tatttgggtg | 1980 |
| atgaattatt | tattccttga | agtatctgtc | taattagctt | gtgatgatgt | gcaggtatat | 2040 |
| tcgttagtca | tatttcaatt | tcaagatgca | gaaatca | | | 2077 |

<210> SEQ ID NO 143
<211> LENGTH: 3084
<212> TYPE: DNA
<213> ORGANISM: Pinus radiata

```
<400> SEQUENCE: 143 aaaaccccctc acaaatacat aaaaaaaatt ctttatttaa ttatcaaact ctccactacc      60
tttcccacca accgttacaa tcctgaatgt tggaaaaaac taactacatt gatataaaaa     120
aactacatta cttcctaaat catatcaaaa ttgtataaat atatccactc aaaggagtct     180
agaagatcca cttggacaaa ttgcccatag ttggaaagat gttcaccaag tcaacaagat     240
ttatcaatgg aaaaatccat ctaccaaact tactttcaag aaaatccaag gattatagag     300
taaaaaatct atgtattatt aagtcaaaaa gaaaaccaaa gtgaacaaat attgatgtac     360
aagtttgaga ggataagaca ttggaatcgt ctaaccagga ggcggaggaa ttccctagac     420
agttaaaagt ggccggaatc ccggtaaaaa agattaaaat ttttttgtag agggagtgct     480
tgaatcatgt tttttatgat ggaaatagat tcagcaccat caaaaacatt caggacacct     540
aaaattttga agtttaacaa aaataacttg gatctacaaa aatccgtatc ggattttctc     600
taaatataac tagaattttc ataactttca aagcaactcc tcccctaacc gtaaaacttt     660
tcctacttca ccgttaatta cattccttaa gagtagataa agaaataaag taaataaaag     720
tattcacaaa ccaacaattt atttctttta tttacttaaa aaaacaaaaa gtttatttat     780
tttacttaaa tggcataatg acatatcgga gatccctcga acgagaatct tttatctccc     840
tggttttgta ttaaaaagta atttattgtg gggtccacgc ggagttggaa tcctacagac     900
gcgctttaca tacgtctcga gaagcgtgac ggatgtgcga ccggatgacc ctgtataacc     960
caccgacaca gccagcgcac agtatacacg tgtcatttct ctattggaaa atgtcgttgt    1020
tatccccgct ggtacgcaac caccgatggt gacaggtcgt ctgttgtcgt gtcgcgtagc    1080
gggagaaggg tctcatccaa cgctattaaa tactcgcctt caccgcgtta cttctcatct    1140
tttctcttgc gttgtataat cagtgcgata ttctcagaga ctttttcatt caaaggtatg    1200
gagttttgaa gggctttact cttaacattt gttttttcttt gtaaattgtt aatggtggtt    1260
tctgtggggg aagaatcttt tgccaggtcc ttttgggttt cgcatgttta tttgggttat    1320
ttttctcgac tatggctgac attactaggg ctttcgtgct ttcatctgtg ttttcttccc    1380
ttaataggtc tgtctctctg gaatatttaa ttttcgtatg taagttatga gtagtcgctg    1440
tttgtaatag gctcttgtct gtaaaggttt cagcaggtgt ttgcgttttta ttgcgtcatg    1500
tgtttcagaa ggcctttgca gattattgcg ttgtacttta atattttgtc tccaaccttg    1560
ttatagtttc cctcctttga tctcacagga acctttctt ctttgagcat tttcttgtgg     1620
cgttctgtag taatatttta attttgggcc cgggtctga gggtaggtga ttattcacag      1680
tgatgtgctt tccctataag gtcctctatg tgtaagctgt tagggtttgt gcgttactat    1740
tgacatgtca catgtcacat atttcttcc tcttatcctt cgaactgatg gttctttttc    1800
taattcgtgg attgctggtg ccatattttta tttctattgc aactgtattt tagggtgtct    1860
ctttctttt gatttcttgt taatatttgt gttcaggttg taactatggg ttgctagggt    1920
gtctgccctc ttcttttgtg cttctttcgc agaatctgtc cgttggtctg tatttgggtg    1980
atgaattatt tattccttga agtatctgtc taattagctt gtgatgatgt gcaggtatat    2040
tcgttagtca tatttcaatt tcaagatgca gatctttgtc aagactctca ccggtaagac    2100
catcactctc gaggtcgaga gctctgacac cattgacaat gttaaagcta agatccagga    2160
caaggaaggg attcccccg accagcagcg tctgatcttc gcaggaaagc agcttgagga     2220
cggccgaacc cttgccgatt acaacatcca gaaagaatct accctccacc ttgttctccg    2280
```

```
tttgaggggt ggcatgcaaa tctttgtaaa aacactaact ggaaagacaa ttacattgga  2340
agttgagagc tcggacacca ttgacaacgt caaggccaag atccaggaca aggaaggaat  2400
tccccctgac cagcagaggc ttatcttcgc tggtaagcag ctggaggatg gcaggacctt  2460
ggctgattac aatattcaaa aggaatcgac cctgcatttg gtgcttcgtc taagaggagg  2520
catgcaaatc tttgtgaaaa cccttacagg taaaaccatt actctggaag tggaaagctc  2580
ggacaccatt gacaatgtga aggctaagat ccaggacaag gagggaattc cacctgacca  2640
gcagaggttg atctttgccg gtaagcagct ggaagatggt cgtactctcg ccgattacaa  2700
tattcagaag gaatcgaccc ttcacctggt gctccgtctc cgcggtggct tttaggtttg  2760
ggtgttattt gtggataata aattcgggtg atgttcagtg tttgtcgtat ttctcacgaa  2820
taaattgtgt ttatgtatgt gttagtgttg tttgtctgtt tcagaccctc ttatgttata  2880
tttttctttt cgtcggtcag ttgaagccaa tactggtgtc ctggccggca ctgcaatacc  2940
atttcgttta atataaagac tctgttatcc gttatgtaat tccatgttat gtggtgaaat  3000
gtggatgaaa ttcttagaaa ttattattgt aatttgaaac ttccttcgtc aataatctgc  3060
acaacacatt taccaaaaaa aaaa                                          3084
```

COMPOSITIONS AND METHODS FOR THE MODIFICATION OF GENE EXPRESSION

CROSS-REFERENCE TO RELATED APPLICATIONS

This application claims priority to International Patent Application No. PCT/NZ01/00115, filed Jun. 20, 2001; and is a continuation-in-part of U.S. application Ser. No. 09/724,624 filed Nov. 28, 2000, now abandoned; which is a continuation-in-part of U.S. patent application Ser. No. 09/598,401 filed Jun. 20, 2000, now U.S. Pat. No. 6,596,925; which claims priority to U.S. Provisional Patent Application No. 60/146,591, filed Jul. 30, 1999; and continuation-in-part of U.S. patent application Ser. No. 09/276,599, filed Mar. 25, 1999, now U.S. Pat. No. 6,380,459.

TECHNICAL FIELD OF THE INVENTION

This invention relates to the regulation of polynucleotide transcription and/or expression. More specifically, this invention relates to polynucleotide regulatory sequences isolated from plants that are capable of initiating and driving the transcription of polynucleotides, and the use of such regulatory sequences in the modification of transcription of endogenous and/or heterologous polynucleotides and production of polypeptides. Polypeptide sequences are also disclosed.

BACKGROUND OF THE INVENTION

Gene expression is regulated, in part, by the cellular processes involved in transcription. During transcription, a single-stranded RNA complementary to the DNA sequence to be transcribed is formed by the action of RNA polymerases. Initiation of transcription in eukaryotic cells is regulated by complex interactions between cis-acting DNA motifs, located within the gene to be transcribed, and trans-acting protein factors. Among the cis-acting regulatory regions are sequences of DNA, termed promoters, to which RNA polymerase is first bound, either directly or indirectly. As used herein, the term "promoter" refers to the 5' untranslated region of a gene that is associated with transcription and which generally includes a transcription start site. Other cis-acting DNA motifs, such as enhancers, may be situated further up- and/or down-stream from the initiation site.

Both promoters and enhancers are generally composed of several discrete, often redundant elements, each of which may be recognized by one or more trans-acting regulatory proteins, known as transcription factors. Promoters generally comprise both proximal and more distant elements. For example, the so-called TATA box, which is important for the binding of regulatory proteins, is generally found about 25 basepairs upstream from the initiation site. The so-called CAAT box is generally found about 75 basepairs upstream of the initiation site. Promoters generally contain between about 100 and 1000 nucleotides, although longer promoter sequences are possible.

For the development of transgenic plants, constitutive promoters that drive strong transgene expression are preferred. Currently, the only available constitutive plant promoter that is widely used is derived from Cauliflower Mosaic Virus. Furthermore, there exists a need for plant-derived promoters for use in transgenic food plants due to public conceptions regarding the use of viral promoters. Few gymnosperm promoters have been cloned and those derived from angiosperms have been found to function poorly in gymnosperms. There thus remains a need in the art for polynucleotide promoter regions isolated from plants for use in modulating transcription and expression of polynucleotides in transgenic plants.

SUMMARY OF THE INVENTION

Briefly, isolated polynucleotide regulatory sequences from eucalyptus and pine that are involved in the regulation of gene expression are disclosed, together with methods for the use of such polynucleotide regulatory regions in the modification of expression of endogenous and/or heterologous polynucleotides in transgenic plants. The present invention provides polynucleotide promoter sequences from 5' untranslated, or non-coding, regions of plant genes that initiate and regulate transcription of polynucleotides placed under their control, together with isolated polynucleotides comprising such promoter sequences.

In a first aspect, the present invention provides isolated polynucleotide sequences comprising a polynucleotide selected from the group consisting of: (a) sequences recited in SEQ ID NO: 1–14, 20, 22–62, 81–86 and 88–127; (b) complements of the sequences recited in SEQ ID NO: 1–14, 20, 22–62, 81–86 and 88–127; (c) reverse complements of the sequences recited in SEQ ID NO: 1–14, 20, 22–62, 81–86 and 88–127; (d) reverse sequences of the sequences recited in SEQ ID NO: 1–14, 20, 22–62, 81–86 and 88–127; (e) sequences having either 40%, 60%, 75% or 90% identical nucleotides, as defined herein, to a sequence of (a)–(d); probes and primers corresponding to the sequences set out in SEQ ID NO: 1–14, 20, 22–62, 81–86 and 88–127; polynucleotides comprising at least a specified number of contiguous residues of any of the polynucleotides identified as SEQ ID NO: 1–14, 20, 22–62, 81–86 and 88–127; and extended sequences comprising portions of the sequences set out in SEQ ID NO: 1–14, 20, 22–62, 81–86 and 88–127; all of which are referred to herein as "polynucleotides of the present invention." The present invention also provides isolated polypeptide sequences identified in the attached Sequence Listing as SEQ ID NO: 63–80, 87 and 130; polypeptide variants of those sequences; and polypeptides comprising the isolated polypeptide sequences and variants of those sequences.

In another aspect, the present invention provides genetic constructs comprising a polynucleotide of the present invention, either alone, or in combination with one or more additional polynucleotides of the present invention, or in combination with one or more known polynucleotides, together with cells and target organisms comprising such constructs.

In a related aspect, the present invention provides genetic constructs comprising, in the 5'-3' direction, a polynucleotide promoter sequence of the present invention, a polynucleotide to be transcribed, and a gene termination sequence. The polynucleotide to be transcribed may comprise an open reading frame of a polynucleotide that encodes a polypeptide of interest, or it may be a non-coding, or untranslated, region of a polynucleotide of interest. The open reading frame may be orientated in either a sense or antisense direction. Preferably, the gene termination sequence is functional in a host plant. Most preferably, the gene termination sequence is that of the gene of interest, but others generally used in the art, such as the *Agrobacterium tumefaciens* nopalin synthase terminator may be usefully employed in the present invention. The genetic construct may further include a marker for the identification of transformed cells.

In a further aspect, transgenic plant cells comprising the genetic constructs of the present invention are provided, together with organisms, such as plants, comprising such transgenic cells, and fruits, seeds and other products, derivatives, or progeny of such plants. Propagules of the inventive transgenic plants are included in the present invention. As used herein, the word "propagule" means any part of a plant that may be used in reproduction or propagation, sexual or asexual, including cuttings.

Plant varieties, particularly registerable plant varieties according to Plant Breeders' Rights, may be excluded from the present invention. A plant need not be considered a "plant variety" simply because it contains stably within its genome a transgene, introduced into a cell of the plant or an ancestor thereof.

In yet another aspect, methods for modifying gene expression in a target organism, such as a plant, are provided, such methods including stably incorporating into the genome of the organism a genetic construct of the present invention. In a preferred embodiment, the target organism is a plant, more preferably a woody plant, most preferably selected from the group consisting of eucalyptus and pine species, most preferably from the group consisting of *Eucalyptus grandis* and *Pinus radiata*.

In another aspect, methods for producing a target organism, such as a plant, having modified polypeptide expression are provided, such methods comprising transforming a plant cell with a genetic construct of the present invention to provide a transgenic cell, and cultivating the transgenic cell under conditions conducive to regeneration and mature plant growth.

In other aspects, methods for identifying a gene responsible for a desired function or phenotype are provided, the methods comprising transforming a plant cell with a genetic construct comprising a polynucleotide promoter sequence of the present invention operably linked to a polynucleotide to be tested, cultivating the plant cell under conditions conducive to regeneration and mature plant growth to provide a transgenic plant; and comparing the phenotype of the transgenic plant with the phenotype of non-transformed, or wild-type, plants.

In yet a further aspect, the present invention provides isolated polynucleotides that encode ubiquitin. In specific embodiments, the isolated polynucleotides comprise a polynucleotide selected from the group consisting of: (a) sequences recited in SEQ ID NO: 1 and 34; (b) complements of the sequences recited in SEQ ID NO: 1 and 34; (c) reverse complements of the sequences recited in SEQ ID NO: 1 and 34; (d) reverse sequences of the sequence recited in SEQ ID NO: 1 and 34; and (e) sequences having either 40%, 60%, 75% or 90% identical nucleotides, as defined herein, to a sequence of (a)–(d). Polypeptides encoded by such polynucleotides are also provided, together with genetic constructs comprising such polynucleotides, and host cells and transgenic organisms, for example plants, transformed with such genetic constructs. In specific embodiments, such polypeptides comprise a sequence provided in SEQ ID NO: 80 or 67.

In yet further aspects, the present invention provides isolated polynucleotides comprising the DNA sequence of SEQ ID NO: 21, or a complement, reverse complement or variant of SEQ ID NO: 21, together with genetic constructs comprising such polynucleotides and cells transformed with such sequences. As discussed below, removal of the sequence of SEQ ID NO: 21 from a polynucleotide that comprises the sequence of SEQ ID NO: 21 may enhance expression of the polynucleotide. Conversely, the inclusion of the sequence of SEQ ID NO: 21 in a genetic construct comprising a polynucleotide of interest may decrease expression of the polynucleotide.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

BRIEF DESCRIPTION OF THE DRAWINGS

FIGS. 6A and 6B show an annotated version of the full-length superubiquitin promoter, including the intron and the coding sequence (SEQ ID NO: 143). The intron is underlined and the coding sequence is in bold. Motifs are identified in boxes and described in the specification.

FIG. 7 shows an annotated superubiquitin construct without the intron identified and described as a 195 bp deletion (SEQ ID NO: 131).

FIG. 8 shows an annotated superubiquitin construct without the intron identified and described as a 368 bp deletion (SEQ ID NO: 132).

FIG. 9 shows an annotated superubiquitin construct without the intron identified and described as a 446 bp deletion (SEQ ID NO: 133).

FIG. 10 shows an annotated superubiquitin construct without the intron identified and described as a 573 bp deletion (SEQ ID NO: 134).

FIG. 11 shows an annotated superubiquitin construct without the intron identified and described as a 753 bp deletion (SEQ ID NO: 135).

FIG. 12 shows an annotated superubiquitin construct with the intron identified and described as a 195 bp deletion (SEQ ID NO: 136).

FIG. 13 shows an annotated superubiquitin construct with the intron identified and described as a 368 bp deletion (SEQ ID NO: 137).

FIG. 14 shows an annotated superubiquitin construct with the intron identified and described as a 446 bp deletion (SEQ ID NO: 138).

FIG. 15 shows an annotated superubiquitin construct with the intron identified and described as a 573 bp deletion (SEQ ID NO: 139).

FIGS. 16A and 16B show an annotated sup erubiquitin construct with the intron identified and described as a 753 bp deletion (SEQ ID NO: 140).

DETAILED DESCRIPTION OF THE INVENTION

Figure 1:
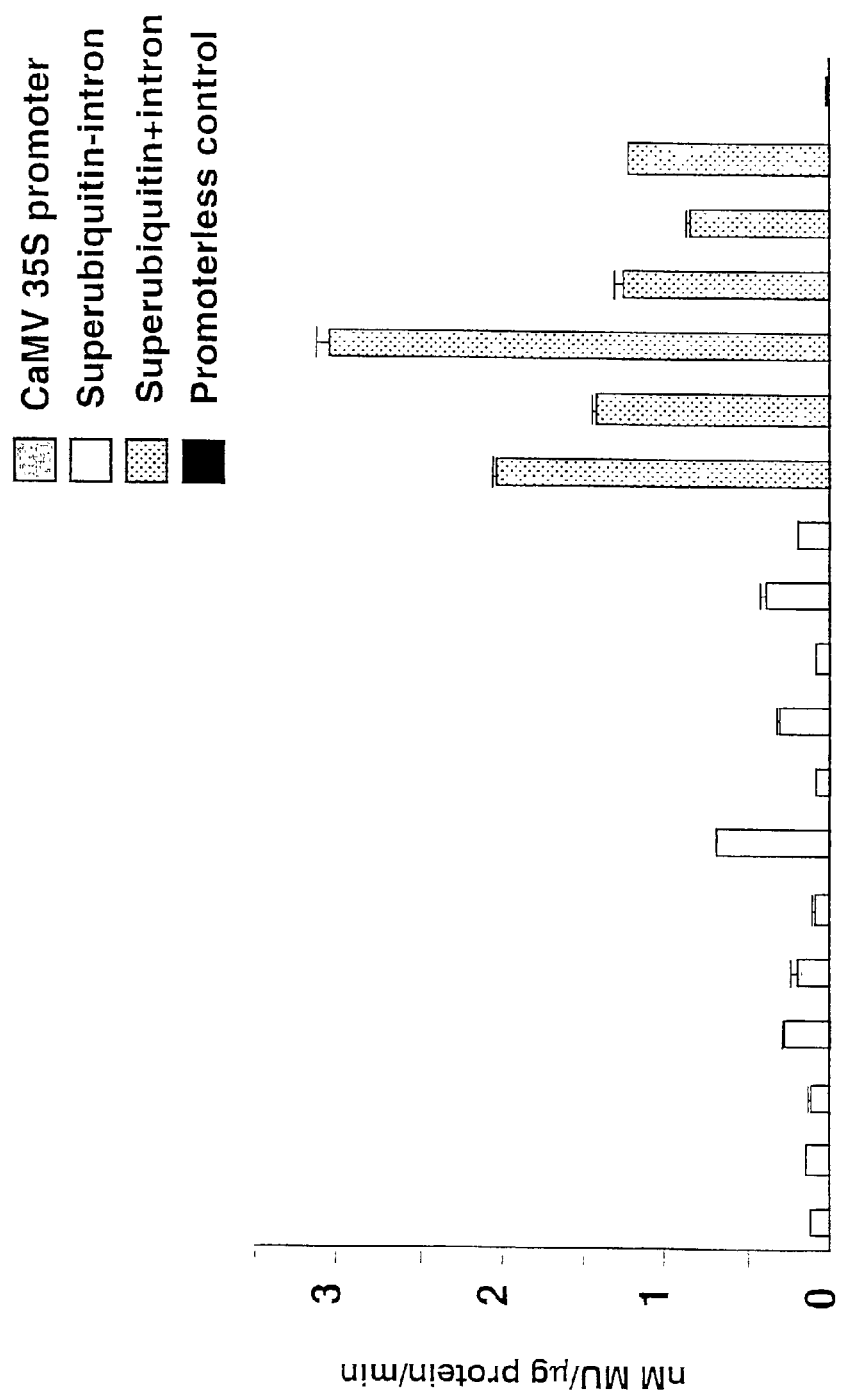
FIG. 1 shows the expression in *A. thaliana* of the GUS gene in promoter reporter constructs containing either the superubiquitin promoter with introns, the superubiquitin promoter without introns, or the CaMV 35S promoter. The GUS expression was measured by fluorimetric determination of 4-methyl-umbelliferone (MU) in protein extracts from these plants.

The present invention provides isolated polynucleotide regulatory regions that may be employed in the manipulation of plant phenotypes, together with isolated polynucleotides comprising such regulatory regions. More specifically, polynucleotide promoter sequences isolated from pine and eucalyptus are disclosed. As discussed above, promoters are components of the cellular "transcription apparatus" and are involved in the regulation of gene expression. Both tissue- and temporal-specific gene expression patterns have been shown to be initiated and controlled by promoters during the natural development of a plant. The isolated polynucleotide promoter sequences of the present invention may thus be employed in the modification of growth and development of plants, and of cellular responses to external stimuli, such as environmental factors and disease pathogens.

Using the methods and materials of the present invention, the amount of a specific polypeptide of interest may be increased or reduced by incorporating additional copies of genes, or coding sequences, encoding the polypeptide, operably linked to an inventive promoter sequence, into the genome of a target organism, such as a plant. Similarly, an increase or decrease in the amount of the polypeptide may be obtained by transforming the target plant with antisense copies of such genes.

The polynucleotides of the present invention were isolated from forestry plant sources, namely from *Eucalyptus grandis* and *Pinus radiata,* but they may alternatively be synthesized using conventional synthesis techniques. Specifically, isolated polynucleotides of the present invention include polynucleotides comprising a sequence selected from the group consisting of sequences identified as SEQ ID NO: 1–14, 20, 22–62, 81–86, 88–127 and 131–143; complements of the sequences identified as SEQ ID NO: 1–14, 20, 22–62, 81–86, 88–127 and 131–143; reverse complements of the sequences identified as SEQ ID NO: 1–14, 20, 22–62, 81–86, 88–127 and 131–143; at least a specified number of contiguous residues (x-mers) of any of the above-mentioned polynucleotides; extended sequences corresponding to any of the above polynucleotides; antisense sequences corresponding to any of the above polynucleotides; and variants of any of the above polynucleotides, as that term is described in this specification.

In another embodiment, the present invention provides isolated polypeptides encoded by the polynucleotides of SEQ ID NO: 63–80, 87 and 130.

The polynucleotides and polypeptides of the present invention were identified by DNA and polypeptide similarity searches. In the attached Sequence Listing, SEQ ID NOS. 1–14, 20, 22–62, 81–86, 88–127 and 131–143 are polynucleotide sequences, and SEQ ID NOS. 63–80, 87 and 130 are polypeptide sequences. The polynucleotides and polypeptides of the present invention are involved in regulation of transcription and/or expression in plants. The identity of each of the inventive polynucleotides is shown below in Table 1, together with the 5' untranslated region (5' UTR) or promoter region (identified by residue number).

TABLE 1

| Polynucleotide SEQ ID NO: | Polypeptide SEQ ID NO: | 5' UTR | IDENTITY |
|---|---|---|---|
| 1 | 80 | 1-2064 | Super Ubiquitin coding region and UTRs |
| 2 | — | 1-2064 | Super Ubiquitin promoter with intron |
| 3 | — | 1-1226 | Super Ubiquitin promoter without intron |
| 4 | — | 1-431 | Cell division control |
| 5 | — | 1-167 | Xylogenesis - specific |
| 6 | — | 1-600 | 4-Coumarate-CoA Ligase (4CL) |
| 7 | — | 1-591 | Cellulose synthase |
| 8 | — | 1-480 | 3' end, Cellulose synthase |
| 20 | — | 1-363 | 5' end, Cellulose synthase |
| 9 | — | 1-259 | Leaf specific |
| 10 | — | 1-251 | Leaf specific |
| 11 | — | 1-248 | Leaf specific |
| 12 | — | 1-654 | O-methyl transferase |
| 13 | — | 1-396 | Root specific |
| 14 | — | 1-763 | Root specific |
| 22 | 63 | 1-406 | Pollen coat protein |
| 23 | — | 1-350 | Pollen allergen |
| 24 | — | 1-49 | Pollen allergen |
| 25 | 64 | 1-284 | Pollen allergen |
| 26 | 65 | 1-77 | Auxin-induced protein |
| 27 | — | 1-74 | Auxin-induced protein |
| 28 | 66 | 1-99 | Auxin-induced protein |
| 29 | — | 1-927 | Flower specific |
| 30 | — | 1-411 | Flower specific |
| 31 | — | 1-178 | Flower specific |
| 32 | — | 1-178 | Flower specific |

TABLE 1-continued

| Polynucleotide SEQ ID NO: | Polypeptide SEQ ID NO: | 5' UTR | IDENTITY |
|---|---|---|---|
| 33 | — | 1-178 | Flower specific |
| 34 | 67 | 1-805 | Ubiquitin |
| 35 | 68 | 1-81 | Glyceraldehyde-3-phosphate dehydrogenase |
| 36 | 69 | 1-694 | Carbonic anhydrase |
| 37 | — | 1-648 | Isoflavone reductase |
| 38 | — | 1-288 | Isoflavone reductase |
| 39 | — | 1-382 | Glyceraldehyde-3-phosphate dehydrogenase |
| 40 | 70 | 1-343 | Bud specific |
| 41 | — | 1-313 | Xylem-specific |
| 42 | — | 1-713 | Xylem-specific |
| 43 | — | 1-28 | Xylem-specific |
| 44 | — | 1-35 | Xylem-specific |
| 45 | 71 | 1-180 | Meristem-specific |
| 46 | 72 | 1-238 | Senescence-like protein |
| 47 | — | 1-91 | Senescence-like protein |
| 48 | — | 1-91 | Senescence-like protein |
| 49 | — | 1-809 | Pollen-specific |
| 50 | — | 1-428 | Pollen-specific |
| 51 | 73 | 1-55 | Pollen-specific |
| 52 | 74 | 1-575 | Pollen-specific |
| 53 | 75 | 1-35 | Pollen-specific |
| 54 | — | 1-335 | Nodulin homolog pollen specific |
| 55 | — | 1-336 | Nodulin homolog pollen specific |
| 56 | 76 | 1-157 | Sucrose synthase |
| 57 | 77 | 1-446 | Sucrose synthase |
| 58 | — | 1-326 | Sucrose synthase |
| 59 | — | 1-311 | Flower specific |
| 60 | 78 | 1-694 | O-methyl transferase |
| 61 | 79 | 1-112 | Elongation factor A |
| 62 | — | 1-420 | Elongation factor A |
| 81 | — | — | MIF homologue |
| 82 | — | — | MIF homologue |
| 83 | — | — | MIF homologue |
| 84 | — | — | MIF homologue |
| 85 | — | — | MIF homologue |
| 86 | 87 | 1-87 | MIF homologue |
| 88 | — | 1-1156 | Chalcone synthase |
| 89 | — | 1-2590 | Unknown flower specific |
| 90 | — | 1-1172 | Unknown flower specific |
| 91 | — | 1-446 | Sucrose synthase |
| 92 | — | 1-2119 | Unknown xylem specific |
| 93 | — | 1-2571 | Glyceraldehyde-3-Phosphate dehydrogenase |
| 94 | — | 1-1406 | Unknown pollen specific |
| 95 | — | 1-2546 | *Pinus radiata* male-specific protein (PrMALE1) |
| 96 | — | 1-4726 | *Pinus radiata* male-specific protein (PrMALE1) |
| 97 | — | 1-635 | UDP glucose glycosyltransferase |
| 98 | — | 1-468 | Elongation Factor A1 |
| 99 | — | 1-222 | Elongation Factor A1 |
| 100 | — | 1-410 | S-adenosylmethionine synthetase |
| 101 | — | 1-482 | S-adenosylmethionine synthetase |
| 102 | — | 1-230 | S-adenosylmethionine synthetase |
| 103 | — | 1-596 | UDP glucose 6 dehydrogenase |
| 104 | — | 1-653 | Hypothetical protein |
| 105 | — | 1-342 | Laccase 1 |
| 106 | — | 1-342 | Laccase 1 |
| 106 | — | 1-948 | Arabinogalactan-like 1 |
| 108 | — | 1-362 | Arabinogalactan-like 2 |
| 109 | — | 1-326 | Arabinogalactan like-2 |
| 110 | — | 1-296 | Root Receptor-like kinase |
| 111 | — | 1-723 | Root Receptor-like kinase |
| 112 | — | 1-1301 | *Pinus radiata* Lipid Transfer Protein 2 (PrLTP2) |
| 113 | — | 1-1668 | Caffeic acid O-methyltransferase |
| 114 | — | 1-850 | UDP glucose glycosyltransferase |
| 115 | — | 1-986 | UDP glucose 6 dehydrogenase |
| 116 | — | 1-947 | Laccase 1 |
| 117 | — | 1-1766 | Arabinogalactan like-1 |
| 118 | — | 1-1614 | Constans |
| 119 | — | 1-602 | Flowering Promoting Factor 1 (FPF1) |
| 120 | — | 1-901 | Agamous |
| 121 | — | 1-1,245 | Dreb 1A Transcription factor |
| 122 | — | 1-959 | Drought Induced Protein 19 |
| 123 | — | 1-1,140 | Salt Tolerance protein |
| 124 | 130 | 1-887 | Low Temperature Induced LTI-16 |
| 125 | — | 1-1,243 | Xylem specific receptor-like kinase |
| 126 | — | 1-1,047 | Root specific |
| 127 | — | 1-3,552 | Elongation Factor 1-alpha |

TABLE 1-continued

| Polynucleotide SEQ ID NO: | Polypeptide SEQ ID NO: | 5' UTR | IDENTITY |
|---|---|---|---|
| 131 | 1 | - | Superubiquitin deletion sequence without intron including 195 bp upstream of TATA box |
| 132 | 1 | - | Superubiquitin deletion sequence without intron including 368 bp upstream of TATA box |
| 133 | 1 | - | Superubiquitin deletion sequence without intron including 446 bp upstream of TATA box |
| 134 | 1 | - | Superubiquitin deletion sequence without intron including 573 bp upstream of TATA box |
| 135 | 1 | - | Superubiquitin deletion sequence without intron including 753 bp upstream of TATA box |
| 136 | 1 | 1-1156 | Superubiquitin deletion sequence with intron including 195 bp upstream of TATA box |
| 137 | 1 | 1-1329 | Superubiquitin deletion sequence with intron including 368 bp upstream of TATA box |
| 138 | 1 | 1-1407 | Superubiquitin deletion sequence with intron including 446 bp upstream of TATA box |
| 139 | 1 | 1-1534 | Superubiquitin deletion sequence with intron including 573 bp upstream of TATA box |
| 140 | 1 | 1-1714 | Superubiquitin deletion sequence with intron including 753 bp upstream of TATA box |
| 141 | 1 | 1-1193 | Full length superubiquitin promoter |
| 142 | 1 | - | Full length superubiquitin promoter with intron |
| 143 | 1 | - | Full length superubiquitin promoter with intron and coding sequence and 3' UTR |

In one embodiment, the present invention provides polynucleotide sequences isolated from *Pinus radiata* and *Eucalyptus grandis* that have promoter activity and, in *Pinus radiata* and *Eucalyptus grandis* are associated with the coding region for a ubiquitin polypeptide. The ubiquitin promoter isolated from *Pinus radiata* and disclosed herein is referred to herein as "superubiquitin" as a consequence of its high level of promoter activity. Full-length sequences for the ubiquitin polynucleotide isolated from *Pinus radiata*, including the full-length superubiquitin promoter, an intron, the ubiquitin coding sequence and the 3' UTR are provided in SEQ ID NOS: 1 and 143, with sequences for the promoter region including an intron being provided in SEQ ID NOS: 2 and 142, and sequences for the promoter region excluding the intron being provided in SEQ ID NOS: 3 and 141. The sequences vary slightly in length and composition as a consequence of using different sequencing techniques and criteria.

An annotated version of the full-length ubiquitin polynucleotide of SEQ ID NO: 143, including the full-length superubiquitin promoter, an intron, the ubiquitin coding sequence and the 3' UTR, is shown in FIGS. 6A and 6B. In the figures, an intron is shown, underlined, at residues 1196–2035; the coding region for the ubiquitin protein is shown, in bold, at residues 2066–2755; the 3' UTR is shown at residues 2756–3084; and the full-length promoter is shown at residues 1–1193.

Polynucleotide motifs identified in the full-length ubiquitin polynucleotide of SEQ ID NO: 143 are shown in the annotations of FIGS. 6A and 6B.

Numerous forms and variations of the superubiquitin promoter have demonstrated promoter activity in experimental studies. Preliminary studies, performed by introducing constructs containing the GFP reporter gene operably linked to either the superubituitin promoter of SEQ ID NO: 2 (promoter with intron) or SEQ ID NO: 3 (promoter without intron) into *Arabidopsis*, are described below in Example 1. These preliminary studies showed that the superubiquitin promoter, both with and without the intron, demonstrated promoter activity, with the intron-less sequence showing higher levels of expression than the promoter sequence with the intron.

Subsequent studies are described in Examples 16, 17, 20 and 21. Experimental studies described in Example 16, done in *Arabidopsis* plants and quantitating GUS activity, demonstrated that a construct containing the superubiquitin promoter without the intron showed seven (7) times more GUS activity than the commercial CaMV 35S promoter, and the construct containing the superubiquitin promoter with the intron showed sixty-two (62) times more GUS activity than the CaMV 35S promoter. These follow-up studies thus confirmed that both the superubiquitin promoter sequence, with and without the intron, show high levels of promoter activity, with the superubiquitin sequence including the intron showing exceptionally high levels of promoter activity. Studies described in Example 17, done in tobacco protoplasts, demonstrated promoter activity of deletion constructs of the superubiquitin promoter, both with and without the intron. These studies confirmed that both the superubiquitin promoter sequence, with and without the intron, show high levels of promoter activity, with the superubiquitin sequence including the intron showing exceptionally high levels of promoter activity. Some of the deletion constructs demonstrated promoter activity, with greater activity in the longer constructs and no activity in the shortest constructs.

Experimental studies using superubiquitin deletion constructs, both with and without the intron, were repeated in *Arabidopsis* and tobacco plants, as described in Example 21. These experiments demonstrated that the partial superubiquitin promoter sequences of SEQ ID NOS: 132, 133, 134, 135, 137, 138, 139 and 140 showed constitutive promoter activity by GUS staining, in both *Arabidopsis* and tobacco plants. Only the shortest deletion constructs, SEQ ID NOS: 131 and 136, did not show constitutive promoter activity by GUS staining in the experimental studies described in Example 21.

Example 20 describes experimental work done to determine the effect of the 3' UTR superubiquitin sequences on gene expression in *Arabidopsis*. These studies showed that a construct containing the superubiquitin 3' UTR in the sense orientation and the intron-less superubiquitin promoter demonstrated high GUS expression levels, and enhanced the expression of the superubiquitin intron-less promoter to nearly the level of the superubiquitin promoter with the intron. This demonstrates that the combination of the superubiquitin promoter without the intron and the ubiquitin 3' UTR shows high levels of promoter activity.

The present invention thus contemplates a polynucleotide having promoter activity comprising a sequence of one of SEQ ID NOS: 2, 3, 132–135 and 137–142, as well as fragments and variants of such sequences having promoter activity. The present invention furthermore contemplates a polynucleotide having promoter activity comprising a sequence of one of SEQ ID NOS: 2, 3, 132–135 and 137–142, as well as fragments and variants of such sequences having promoter activity, in combination with a fragment of the 3' UTR ubiquitin sequence in the sense orientation. The 3' UTR ubiquitin sequence includes residues 2,755–3,073 of SEQ ID NO: 1 and is shown, in FIGS. 6A and 6B, as residues 2756–3084. A 250 bp fragment of the 3' UTR ubiquitin sequence, including residues 2,755–3,073 of SEQ ID NO: 1 is suitable and one of skill in the art would anticipate that smaller fragments and fragments from elsewhere within the ubiquitin 3' UTR would, in combination with a sequence of one of SEQ ID NOS: 2, 3, 132–135 and 137–142, as well as fragments and variants of such sequences, provide a sequence having promoter activity.

Numerous motifs have been identified in superubiquitin sequences, and in deletion constructs used to test the promoter activity of fragments of the superubiquitin promoter. Various of the motifs are described below in Table 2, and are identified in the sequences shown in FIGS. 6–16.

TABLE 2

| REFERENCE NUMBER | POLYNUCLEOTIDE MOTIF | DESCRIPTION |
|---|---|---|
| 1 | TATAAT | −10 Mustard plastid box, also a Pribnow box, first TA and last T highly conserved |
| 2 | TATAAAA | (TATTAAA in SU promoter); a −35 Mustard plastid gene TATA box |
| 3 | TATTTWAT | (TATTTAAT in SU promoter); Nodule specific nuclear factor (NAT2, soybean). This sequence is important for protein recognition (Forde et al., Plant Cell 2:925–939, 1990) |
| 4 | CACGTG | G-box-binding factor (GBF) commonly found in many plant promoters which binds a subclass of bZIP DNA binding proteins. These elements are targets for nuclear DNA-binding factors, e.g. chlorophyll a/b binding proteins and chalcone synthase. ACGT is the core sequence and is also known as R-motif. Found in light-responsive genes, e.g., rbcS and chalcone synthase (chs), but also in other unrelated genes such as adh, Bz-2, Em, and chs. Binds with GBF (G box of rbcS), with GT-1 or with cG-1 (chs); ABA; UV; visible light; Factors groups 1, 2 and 3 have affinity for C-box; G-box is not essential for the elicitor responsiveness of the Str1 gene. GBF4 has similarities to Fos oncoprotein (Menkens and Cashmore, Proc. Natl. Acad. Sci. USA 91:2522–2526, 1994). The G-box is a cis-acting DNA sequence present in several plant promoters that are regulated by diverse signals such as UV irradiation, anaerobiosis, abscissic acid and light. Several basic/leucine zipper (bZIP) proteins from different plant species have been identified as high affinity G-box binding proteins. Although their capability to enhance transcription has been demonstrated, their precise function in transcriptional activation is still unknown (Meier and Gruissem, Nucleic Acids Res. 22:470–478, 1994). |
| 5 | TCTTTTC (C/T CTTTT C/T) | Pyrimidine box sequence, amylase gene, is implied but not required for GA3 inducibility. |
| 6 | ACCTTTCC | If G is substituted for T, this motif is an 8 bp motif adjacent to wound inducible nuclear protein binding site. |
| 7 | TCTCCAC | Origin of genes and nuclear extract - Parsley PAL and 4CL genes |
| 8 | GATAAG | Origin of genes and nuclear extract- *Lemna* and *Arabidopsis* rbcS gene, tobacco cabE gene I-box, binding factor LRF-1 |
| 9 | AACCCA | Soybean embryo factor 3 (SEF3) binding site. Soybean B-conglycinin gene alpha subunit (embryo-specific) SEF-3, SEF-1 binding factors. Soybean (*Glycine max*) consensus sequence found in the 5' upstream region of beta-conglycinin (7S globulin) gene; AACCCA(-27bp-)AACCCA. |
| 10 | TGACG | ASF-1 binding site in CaMV 35S promoter. ASF-1 binds to two TGACG motifs. The same |

TABLE 2-continued

| REFERENCE NUMBER | POLYNUCLEOTIDE MOTIF | DESCRIPTION |
|---|---|---|
| | | motif is also found in HBP-1 binding site of wheat histone H3 gene. TGACG motifs are found in many promoters and are involved in transcriptional activation of several genes by auxin and/or salicylic acid and play a role in light regulation. It is also the binding site of tobacco TGA1a (TGA1a-sequence specific binding protein). Activating sequence factor 1 (ASF-1) is a nuclear DNA-binding activity that is found in monocots and dicots. It interacts with several TGACG-containing elements that have been characterized from viral and T-DNA genes, the prototypes of which are the as-1 element of the CaMV 35S promoter and the ocs element from the octopine synthase promoter. This class of cis-acting elements can respond to auxin and salicylic acid treatments (Lam and Lam, Nucleic Acids Res. 23:3778–3785, 1005). |
| 11 | GATA | Binding site, designated as-2 (activating sequence-2) at the −100 region of the cauliflower mosaic virus 35S promoter. These motifs are related to the I-boxes which bind nuclear factors. Similar to the GATA motif in CaMV 35S promoter. Binding with ASF-2; three GATA box repeats were found in the promoter of Petunia (P.h.) chlorophyll a/b binding protein, Cab22 gene; required for high level, light regulated, and tissue specific expression; Conserved in the promoter of all LHCII type I Cab genes. |
| 12 | GTGG | Maize Adh1 B1 G-box cis-acting DNA sequence elements are present in the promoter region of a number of signal-inducible plant genes and are essential for gene expression. |
| 13 | CCCC | *Arabidopsis* AdH interacts with GBF |
| 14 | CCAGCGG | The AT-1 binding site in cabE gene, tobacco, if C were a T. |
| 15 | GAGAAG | I-box binding GA-1 for tobacco cabE gene >IBOX "I box"; "I-box"; Conserved sequence upstream of light-regulated genes; Sequence found in the promoter region of rbcS of tomato and *Arabidopsis*; I box (Giuliano et al. 1988); Binding site of LeMYB1, which is a member of a novel class of myb-like proteins; LeMYBI act as a transcriptional activator GAGAA = >IBOXCORE "I box"; "I-box"; Conserved sequence upstream of light-regulated genes; Conserved sequence upstream of light-regulated genes of both monocots and dicots; See IBOX (S000124) |
| 16 | GGATA | MYBST1 core motif >MYBST1 Core motif of MybSt1 (a potato MYB homolog) binding site; core motif of MybSt1 (a potato MYB homolog) binding site; MybSt1 cDNA clone was isolated by using CaMV 35S promoter domain A as a probe (Baranowskij et al. 1994); The Myb motif of the MybSt1 protein is distinct from the plant Myb DNA binding domain described thus far. |
| 17 | TGTAAAG | Prolamin box or P Box is a highly conserved 7-bp sequence element found in the promoters of many cereal seed storage protein genes. Nuclear factors from maize endosperm specifically interact with the P-box present in maize prolamin genes (zeins). A prolamin-box binding factor (PBF) has been identified that encodes a member of the recently described Dof class of plant Cys2—Cys2 zinc-finger DNA binding proteins. PBF interacts in vitro with the basic leucine zipper protein Opaque2, a known transcriptional activator of zein gene expression. (Vicente-Carbajosa et al., Proc. Natl. Acad. Sci. USA 94: 7685–7690, 1997). |
| 18 | TGTCTC | Occurs 3 times in intron: auxin response factor (ARF) binding site found in the promoters of primary/early auxin response genes of *Arabidopsis thaliana*. More than 10 ARFs have |

TABLE 2-continued

| REFERENCE NUMBER | POLYNUCLEOTIDE MOTIF | DESCRIPTION |
|---|---|---|
| | | been identified in *A. thaliana*. This conserved sequence is the binding site of *Arabidopsis* ARF1 (Auxin response factor 1) in auxin response elements (Ulmasov et al., Science 276:1865–1868, 1997). The sequence is also found in the NDE element in soybean (Li et al., Plant Physiol. 106:37–43, 1994) 15A gene promoter. The NDE element is involved in auxin responsiveness in SAUR (Small Auxin-Up RNA) by conferring auxin inducibility to the SAUR promoters. |
| 19 | AGCGGG | BS1 (binding site 1) found in *Eucalyptus gunnii* Cinnamoyl-CoA reductase (CCR) gene promoter. Cinnamoyl-CoA reductase (CCR) catalyzes the first specific step in the biosynthesis of monolignols, the monomeric units of lignins. BS1 is a nuclear protein binding site that is required for vascular expression. |
| 20 | CAAT | CAAT promoter consensus sequence is found in legA gene of pea |
| 21 | TGCAGG | This motif is commonly found at the 3' of intron-exon splice junctions of plant introns and exons. |
| 22 | ACCGACA | Low temperature responsive element (LTRE) found in *Arabidopsis thaliana* low-temperature-induced (lti) genes. This element is repeated four times in lti78 or cor78 and rd29A (Baker et al., Plant Mol. Biol. 24:701, 1994). The element is also found in the barley low temperature responsive genes blt4.2, blt4.6, blt4.9 (lipid transfer genes) and is cold inducible (Nordin et al., Plant Mol. Biol. 21:641–653, 1993). The core motif is CCGAC and is a portion of repeat-C (C-repeat), TGGCCGAC, which is repeated twice in cor15a promoter. This element plays a role in cold-regulated gene expression of the cor15a gene and is also involved in drought and abscisic acid (ABA) responsiveness (Baker et al., Plant Mol. Biol. 24:701–713 1994). |
| 23 | CTAACCA | Binding site for MYB (ATMYB2) in the dehydration-responsive gene rd22, that is induced by ABA-induction (Iwasaki et al., Mol. Gen. Genet. 247:391–398, 1995). |
| 24 | TAACAAA | Central element of gibberellin (GA) response complex (GARC) in high-pI alpha-amylase gene in barley and similar to c-myb and v-myb consensus binding site. GAmyb binds specifically to the TAACAAA box in vitro and is the sole GA-regulated transcriptional factor required for transcriptional activation of the high-pI alpha-amylase (Rogers and Rogers, Plant Cell 4:1443–1451, 1992). |
| 25 | CCWACC | Core of consensus maize P (myb homolog) binding site where W could be A or T. Maize P gene specifies red pigmentation of kernel pericarp, cob, and other floral organs. (Grotewold et al., Cell 76:543–553 1994). |
| 26 | CACATG | Identified in SU intron. Binding site for MYC (rd22BP1) in *Arabidopsis* dehydration-resposive gene, rd22 rd22, that is induced by ABA-induction (Iwasaki et al., Mol. Gen. Genet. 247:391–398, 1995). |
| 27 | CATCCAACG | Nonamer motif found in promoter of wheat histone genes H3 and H4 (Shen and Gigot, Plant Mol. Biol. 33:367–379, 1997). |
| 28 | ACTTTA | Identified in SU intron - BBF1 (Dof protein from tobacco) binding site in *Agrobacterium rhizogenes* rolB oncogene and is required for tissue-specific expression and auxin induction of rolB (Baumann et al., Plant Cell 11:323–334, 1999). |
| 29 | AGAAA | AGAAA and TCCACCATA (S000246) are required for pollen specific expression in SU; TCCACCATA: one of two co-dependent regulatory elements responsible for pollen |

TABLE 2-continued

| REFERENCE NUMBER | POLYNUCLEOTIDE MOTIF | DESCRIPTION |
| --- | --- | --- |
| | | specific activation of tomato (L.e.) lat52 gene; Found at −72 to −68 region; See S000246 (POLLEN2LELAT52). |
| 30 | CCTTTT | In intron; pyrimidine box found in rice (O.s.) alpha-amylase (RAmy1A) gene; Gibberellin-response cis-element of GARE and pyrimidine box are partially involved in sugar repression. |
| 31 | CAACA | Binding consensus sequence of *Arabidopsis* (A.t.) transcription factor, RAV1; RAV1 specifically binds to DNA with bipartite sequence motifs of RAV1-A (CAACA) and RAV1-B (CACCTG); RAV1 protein contain AP2-like and B3-like domains; The AP2-like and B3-like domains recognize the CAACA and CACCTG motifs, respectively; The expression level of RAV1 were relatively high in rosette leaves and roots; See S000315(CACCTG). |
| 32 | AATCCAA | "rbcS general consensus sequence"; AATCCAA or AATCCAAC |
| 33 | AACCAA | 2 motifs present; "REalpha" found in *Lemna gibba* Lhcb21 gene promoter; Located at −134 to −129; Binding site of proteins of whole-cell extracts; The DNA bindnig activity is high in etiolated plants but much lower in green plants; Required for phytochrome regulation; See S000363 |
| 34 | TACTATT | In intron; one of SPBF binding site (SP8b); Found at −330, −220, and −200 of gSPO-B1 (sporamin) gene, and also at −80 of gB-Amy (beta-amylase) gene; SP8BF recognizes both SP8a and SP8b sequences; See also SP8BFIBSP8AIB (S000183); SP8BF activity is also found in tobacco; "SP8b" found in the 5' upstream region of three different genes coding for sporamin and beta-amylase; Binding site of SPF1; SPF1 also binds to the SP8b; See S000184. |
| 35 | TATCCAY | (TATCCAC in SU promoter); "TATCCAY motif" found in rice (O.s) RAmy3D alpha-amylase gene promoter; Y = T/C; a GATA motif as its antisense sequence; TATCCAY motif and G motif (see S000130) are responsible for sugar repression (Toyofuku et al. 1998). |
| 36 | ATAAAAAAAATT | The AT-1 binding site in cabE gene, tobacco, if A were a T. |

SEQ ID NO: 132 is the shortest fragment of the superubiquitin promoter for which promoter activity has been demonstrated experimentally. SEQ ID NO: 32 includes motifs 12, 14, 4, 15, 10, 9, 22, 4, 13, 19, 15, 27, 2, 5, 1 and 11, as described above in Table 2. It is expected that a sequence comprising at least ten (10), more preferably twelve (12), and most preferably fifteen (15) of the sixteen (16) motifs, selected from the group consisting of: motifs 12, 14, 4, 15, 10, 9, 22, 4, 13, 19, 15, 27, 2, 5, 1 and 11, as described above in Table 2, would exhibit promoter activity, and such sequences are contemplated by the present invention. Such sequences may also be combined with a 3' UTR fragment of the ubiquitin sequence comprising at least 50 consecutive bp, more preferably at least 100 or 150 consecutive bp, and most preferably at least 250 consecutive bp from the ubiquitin 3' UTR sequence identified as residues 2,755–3,073 of SEQ ID NO: 1. Additionally or alternatively, such sequences may also be combined with an intron, such as the intron identified as residues 1196–2034 of SEQ ID NO: 143 or 142. Fragments of the 3' UTR and intron sequences may also be combined with the sequences of SEQ ID NOS: 132–135 and 137–140 to provide promoters of the present invention. All of these sequences have features in common, in that they share ten or more common motifs, as described above, and more likely share sequence similarities over a substantial portion of the sequence.

The sequence for the ubiquitin polynucleotide isolated from *Eucalyptus grandis* is provided in SEQ ID NO: 34. In a related embodiment, the present invention provides isolated polypeptides encoded by the isolated polynucleotides of SEQ ID NO: 1 and 34, including polypeptides comprising the sequences of SEQ ID NO: 80 and 67.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide"

therefore includes all such operable anti-sense fragments. Anti-sense polynucleotides and techniques involving anti-sense polynucleotides are well known in the art and are described, for example, in Robinson-Benion et al. "Anti-sense techniques," *Methods in Enzymol.* 254(23):363–375, 1995; and Kawasaki et al., in *Artific. Organs* 20(8):836–848, 1996.

All of the polynucleotides and polypeptides described herein are isolated and purified, as those terms are commonly used in the art. Preferably, the polypeptides and polynucleotides are at least about 80% pure, more preferably at least about 90% pure, and most preferably at least about 99% pure.

The definition of the terms "complement", "reverse complement" and "reverse sequence", as used herein, is best illustrated by the following example. For the sequence 5' AGGACC 3', the complement, reverse complement and reverse sequence are as follows:

| | |
|---|---|
| Complement | 3' TCCTGG 5' |
| Reverse complement | 3' GGTCCT 5' |
| Reverse sequence | 5' CCAGGA 3' |

Some of the polynucleotides of the present invention are "partial" sequences, in that they do not represent a full-length gene encoding a full-length polypeptide. Such partial sequences may be extended by analyzing and sequencing various DNA libraries using primers and/or probes and well known hybridization and/or PCR techniques. Partial sequences may be extended until an open reading frame encoding a polypeptide, a full-length polynucleotide and/or gene capable of expressing a polypeptide, or another useful portion of the genome is identified. Such extended sequences, including full-length polynucleotides and genes, are described as "corresponding to" a sequence identified as one of the sequences of SEQ ID NO: 1–14, 20, 22–62, 81–86 and 88–127, or a variant thereof, or a portion of one of the sequences of SEQ ID NO: 1–14, 20, 22–62, 81–86 and 88–127, or a variant thereof, when the extended polynucleotide comprises an identified sequence or its variant, or an identified contiguous portion (x-mer) of one of the sequences of SEQ ID NO: 1–14, 20, 22–62, 81–86 and 88–127, or a variant thereof. Such extended polynucleotides may have a length of from about 50 to about 4,000 nucleic acids or base pairs, and preferably have a length of less than about 4,000 nucleic acids or base pairs, more preferably yet a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Similarly, RNA sequences, reverse sequences, complementary sequences, antisense sequences, and the like, corresponding to the polynucleotides of the present invention, may be routinely ascertained and obtained using the cDNA sequences identified as SEQ ID NO: 1–14, 20, 22–62, 81–86 and 88–127.

The polynucleotides identified as SEQ ID NO: 1–14, 20, 22–62, 81–86 and 88–127, and their extensions, may contain open reading frames ("ORFs") or partial open reading frames encoding polypeptides. Additionally, open reading frames encoding polypeptides may be identified in extended or full length sequences corresponding to the sequences set out as SEQ ID NO: 1–14, 20, 22–62, 81–86 and 88–127. Open reading frames may be identified using techniques that are well known in the art. These techniques include, for example, analysis for the location of known start and stop codons, most likely reading frame identification based on codon frequencies, etc. Suitable tools and software for ORF analysis include, for example, "GeneWise", available from The Sanger Center, Wellcome Trust Genome Campus, Hinxton, Cambridge, CB10 1SA, United Kingdom; "Diogenes", available from Computational Biology Centers, University of Minnesota, Academic Health Center, UMHG Box 43, Minneapolis Minn. 55455 and "GRAIL", available from the Informatics Group, Oak Ridge National Laboratories, Oak Ridge, Tennessee Tenn. Open reading frames and portions of open reading frames may be identified in the polynucleotides of the present invention. Once a partial open reading frame is identified, the polynucleotide may be extended in the area of the partial open reading frame using techniques that are well known in the art until the polynucleotide for the full open reading frame is identified. Thus, open reading frames encoding polypeptides may be identified using the polynucleotides of the present invention.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, bacterial cells, algae and the like.

Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

The term "polypeptide", as used herein, encompasses amino acid chains of any length including full length proteins, wherein amino acid residues are linked by covalent peptide bonds. Polypeptides of the present invention may be isolated and purified natural products, or may be produced partially or wholly using recombinant techniques. The term "polypeptide encoded by a polynucleotide" as used herein, includes polypeptides encoded by a nucleotide sequence which includes the partial isolated DNA sequences of the present invention.

In a related aspect, polypeptides are provided that comprise at least a functional portion of a polypeptide having a sequence selected from the group consisting of sequences provided in SEQ ID NO: 63–80, 87 and 130, and variants thereof. As used herein, the "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity.

Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using, for example, the representative assays provided below. A functional portion comprising an active site may be made up of separate portions present on one or more polypeptide chains and generally exhibits high substrate specificity.

Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, wherein amino acids are sequentially added to a growing amino acid chain. (Merrifield, *J. Am. Chem. Soc.* 85: 2149–2154, 1963). Equipment for automated synthesis of polypeptides is commercially available from suppliers such as Perkin Elmer/Applied Biosystems, Inc. (Foster City, Calif.), and may be operated according to the manufacturer's instructions. Variants of a native polypeptide may be prepared using standard mutagenesis techniques, such as oligonucleotide-directed site-specific mutagenesis (Kunkel, *Proc. Natl. Acad. Sci. USA* 82: 488–492, 1985). Sections of DNA sequences may also be removed using standard techniques to permit preparation of truncated polypeptides.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 50%, more preferably at least 75%, and most preferably at least 90% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotide and polypeptide sequences may be aligned, and percentage of identical residues in a specified region may be determined against other polynucleotide and polypeptide sequences, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The similarity of polypeptide sequences may be examined using the BLASTP algorithm. The BLASTN algorithm Version 2.0.4 [Feb. 24, 1998], Version 2.0.6 [Sep. 16, 1998] and Version 2.0.11 [Jan. 20, 2000], set to the default parameters described in the documentation and distributed with the algorithm, are preferred for use in the determination of polynucleotide variants according to the present invention. The BLASTP algorithm, is preferred for use in the determination of polypeptide variants according to the present invention. The use of the BLAST family of algorithms, including BLASTN, BLASTP, and BLASTX, is described in the publication of Altschul, et al., "Gapped BLAST and PSI-BLAST: a new generation of protein database search programs," *Nucleic Acids Res.* 25: 3389–3402, 1997. The BLASTN software is available on the NCBI anonymous FTP server and from the National Center for Biotechnology Information (NCBI), National Library of Medicine, Building 38A, Room 8N805, Bethesda, Md. 20894 USA.

The FASTA software package is available from the University of Virginia (University of Virginia, PO Box 9025, Charlottesville, Va. 22906-9025). Version 2.0u4, February 1996, set to the default parameters described in the documentation and distributed with the algorithm, may be used in the determination of variants according to the present invention. The use of the FASTA algorithm is described in Pearson and Lipman, "Improved Tools for Biological Sequence Analysis," *Proc. Natl Acad. Sci. (JSA* 85: 2444–2448, 1988; and Pearson, "Rapid and Sensitive Sequence Comparison with FASTP and FASTA," *Methods in Enzymol.* 183: 63–98, 1990.

The following running parameters are preferred for determination of alignments and similarities using BLASTN that contribute to the E values and percentage identity for polynucleotide sequences: Unix running command: blastall -p blastn -d embldb -e 10 -G0 -E0 -r 1 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (BLASTN only) [Integer]; -v Number of one-line descriptions (V) [Integer]; -b Number of alignments to show (B) [Integer]; -i Query File [File In]; and -o BLAST report Output File [File Out] Optional.

The following running parameters are preferred for determination of alignments and similarities using BLASTP that contribute to the E values and percentage identity of polypeptide sequences: blastall -p blastp -d swissprotdb e 10 -G 0 -E 0 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA and BLASTP algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides and polypeptides. with reference to each of the polynucleotides and polypeptides of the present invention, preferably comprise sequences having the same number or fewer nucleic or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being the same as the polynucleotide or polypeptide of the present invention, measured as having an E value of 0.01 or less using the BLASTN, FASTA, or BLASTP algorithms set at parameters described above. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at parameters described above. Similarly, according to a preferred embodiment, a variant polypeptide is a sequence having the same number or fewer amino acids than a polypeptide of the present invention that has at least a 99% probability of being the same as a polypeptide of the present invention, measured as having an E value of 0.01 or less using the BLASTP algorithm set at the parameters described above.

Alternatively, variant polynucleotides of the present invention hybridize to the polynucleotide sequences recited in SEQ ID NO: 1–14, 20, 22–62, 81–86 and 88–127, or complements, reverse sequences, or reverse complements of those sequences under stringent conditions. As used herein, "stringent conditions" refers to prewashing in a solution of 6×SSC, 0.2% SDS; hybridizing at 65° C., 6×SSC, 0.2% SDS overnight: followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar activity to a polypeptide encoded by a polynucleotide of the present invention. Thus, polynucleotides comprising sequences that differ from the polynucleotide sequences recited in SEQ ID NO: 1–14, 20, 22–62, 81–86 and 88–127, or complements, reverse sequences, or reverse complements thereof, as a result of conservative substitutions are contemplated by and encompassed within the present invention. Additionally, polynucleotides comprising sequences that differ from the polynucleotide sequences recited in SEQ ID NO: 1–14, 20, 22–62, 81–86 and 88–127, or complements, reverse complements or reverse sequences thereof, as a result of deletions and/or insertions totaling less than 10% of the total sequence length are also contemplated by and encompassed within the present invention. Similarly, polypeptides comprising sequences that differ from the polypeptide sequences recited in SEQ ID NO: 63–80, 87 and 130, as a result of amino acid substitutions, insertions, and/or deletions totaling less than 10% of the total sequence length are contemplated by an encompassed within the present invention. In certain embodiments, variants of the inventive polypeptides and polynucleotides possess biological activities that are the same or similar to those of the inventive polypeptides or polynucleotides. Such variant polynucleotides function as promoter sequences and are thus capable of modifying gene expression in a plant.

The polynucleotides of the present invention may be isolated from various libraries, or may be synthesized using techniques that are well known in the art. The polynucleotides may be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having for example, 80 nucleic acids, and hybridizing that segment to a synthesized complementary 85 nucleic acid segment to produce a 5-nucleotide overhang. The next segment may then be synthesized in a similar fashion, with a 5-nucleotide overhang on the opposite strand. The "sticky" ends ensure proper ligation when the two portions are hybridized. In this way, a complete polynucleotide of the present invention may be synthesized entirely in vitro.

Polynucleotides of the present invention also comprehend polynucleotides comprising at least a specified number of contiguous residues (x-mers) of any of the polynucleotides identified as SEQ ID NO: 1–14, 20, 22–62, 81–86 and 88–127, complements, reverse sequences, and reverse complements of such sequences, and their variants. Similarly, polypeptides of the present invention comprehend polypeptides comprising at least a specified number of contiguous residues (x-mers) of any of the polypeptides identified as SEQ ID NO: 63–80, 87 and 130, and their variants. As used herein, the term "x-mer," with reference to a specific value of "x," refers to a sequence comprising at least a specified number ("x") of contiguous residues of any of the polynucleotides identified as SEQ ID NO: 1–14, 20, 22–62, 81–86 and 88–127, or the polypeptides identified as SEQ ID NO: 63–80, 87 and 130. According to preferred embodiments, the value of x is preferably at least 20, more preferably at least 40, more preferably yet at least 60, and most preferably at least 80. Thus, polynucleotides and polypeptides of the present invention comprise a 20-mer, a 40-mer, a 60-mer, an 80-mer, a 100-mer, a 120-mer, a 150-mer, a 180-mer, a 220-mer, a 250-mer, a 300-mer, 400-mer, 500-mer or 600-mer of a polynucleotide or polypeptide identified as SEQ ID NO: 1–14, 20, 22–62, 81–86 and 88–127, and variants thereof.

As noted above, the inventive polynucleotide promoter sequences may be employed in genetic constructs to drive transcription and/or expression of a polynucleotide of interest. The polynucleotide of interest may be either endogenous or heterologous to an organism, for example a plant, to be transformed. The inventive genetic constructs may thus be employed to modulate levels of transcription and/or expression of a polynucleotide, for example gene, that is present in the wild-type plant, or may be employed to provide transcription and/or expression of a DNA sequence that is not found in the wild-type plant.

In certain embodiments, the polynucleotide of interest comprises an open reading frame that encodes a target polypeptide. The open reading frame is inserted in the genetic construct in either a sense or antisense orientation, such that transformation of a target plant with the genetic construct will lead to a change in the amount of polypeptide compared to the wild-type plant. Transformation with a genetic construct comprising an open reading frame in a sense orientation will generally result in over-expression of the selected polypeptide, while transformation with a genetic construct comprising an open reading frame in an antisense orientation will generally result in reduced expression of the selected polypeptide. A population of plants transformed with a genetic construct comprising an open reading frame in either a sense or antisense orientation may be screened for increased or reduced expression of the polypeptide in question using techniques well known to those of skill in the art, and plants having the desired phenotypes may thus be isolated.

Alternatively, expression of a target polypeptide may be inhibited by inserting a portion of the open reading frame, in either sense or antisense orientation, in the genetic construct. Such portions need not be full-length but preferably comprise at least 25 and more preferably at least 50 residues of the open reading frame. A much longer portion or even the full length DNA corresponding to the complete open reading frame may be employed. The portion of the open reading frame does not need to be precisely the same as the endogenous sequence, provided that there is sufficient sequence similarity to achieve inhibition of the target gene. Thus a sequence derived from one species may be used to inhibit expression of a gene in a different species.

In further embodiments, the inventive genetic constructs comprise a polynucleotide including an untranslated, or non-coding, region of a gene coding for a target polypeptide, or a polynucleotide complementary to such an untranslated region. Examples of untranslated regions which may be usefully employed in such constructs include introns and 5'-untranslated leader sequences. Transformation of a target plant with such a genetic construct may lead to a reduction in the amount of the polypeptide expressed in the plant by the process of cosuppression, in a manner similar to that discussed, for example, by Napoli et al., *Plant Cell* 2:279–290, 1990 and de Carvalho Niebel et al., *Plant Cell* 7:347–358, 1995.

Alternatively, regulation of polypeptide expression can be achieved by inserting appropriate sequences or subsequences (e.g. DNA or RNA) in ribozyme constructs (McIntyre and Manners, *Transgenic Res.* 5(4):257–262, 1996). Ribozymes are synthetic RNA molecules that comprise a hybridizing region complementary to two regions, each of which comprises at least 5 contiguous nucleotides in a mRNA molecule encoded by one of the inventive polynucleotides. Ribozymes possess highly specific endonuclease activity, which autocatalytically cleaves the mRNA.

The polynucleotide of interest, such as a coding sequence, is operably linked to a polynucleotide promoter sequence of the present invention such that a host cell is able to transcribe an RNA from the promoter sequence linked to the polynucleotide of interest. The polynucleotide promoter sequence is generally positioned at the 5' end of the polynucleotide to be transcribed. Use of a constitutive promoter, such as the *Pinus radiata* ubiquitin polynucleotide promoter sequence of SEQ ID NO: 2 and 3 or the *Eucalyptus grandis* ubiquitin polynucleotide promoter sequence contained within SEQ ID NO: 34, will affect transcription of the polynucleotide of interest in all parts of the transformed plant. Use of a tissue specific promoter, such as the leaf-specific promoters of SEQ ID NO: 9–11, the root-specific promoters of SEQ ID NO: 13 and 14, the flower-specific promoters of SEQ ID NO: 29–33, 59 and 89–90, the pollen-specific promoters of SEQ ID NO: 49–55 and 94, the bud-specific promoter of SEQ ID NO: 40 or the meristem-specific promoter of SEQ ID NO: 45, will result in production of the desired sense or antisense RNA only in the tissue of interest. Temporally regulated promoters, such as the xylogenesis-specific promoters of SEQ ID NO: 5, 41–44 and 92, can be employed to effect modulation of the rate of DNA transcription at a specific time during development of a transformed plant. With genetic constructs employing inducible gene promoter sequences, the rate of DNA transcription can be modulated by external stimuli, such as light, heat, anaerobic stress, alteration in nutrient conditions and the like.

The inventive genetic constructs further comprise a gene termination sequence which is located 3' to the polynucleotide of interest. A variety of gene termination sequences which may be usefully employed in the genetic constructs of the present invention are well known in the art. One example of such a gene termination sequence is the 3' end of the *Agrobacterium tumefaciens* nopaline synthase gene. The gene termination sequence may be endogenous to the target plant or may be exogenous, provided the promoter is functional in the target plant. For example, the termination sequence may be from other plant species, plant viruses, bacterial plasmids and the like.

The genetic constructs of the present invention may also contain a selection marker that is effective in cells of the target organism, such as a plant, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in Weissbach A and H, eds. *Methods for Plant Molecular Biology*, Academic Press Inc.: San Diego, Calif., 1988). Transformed cells can thus be identified by their ability to grow in media containing the antibiotic in question. Alternatively, the presence of the desired construct in transformed cells can be determined by means of other techniques well known in the art, such as Southern and Western blots.

Techniques for operatively linking the components of the inventive genetic constructs are well known in the art and include the use of synthetic linkers containing one or more restriction endonuclease sites as described, for example, by Sambrook et al., (*Molecular cloning: a laboratory manual*, CSHL Press: Cold Spring Harbor, N.Y., 1989). The genetic construct of the present invention may be linked to a vector having at least one replication system, for example *E. coli*, whereby after each manipulation, the resulting construct can be cloned and sequenced and the correctness of the manipulation determined.

The genetic constructs of the present invention may be used to transform a variety of target organisms including, but not limited to, plants. Plants which may be transformed using the inventive constructs include both monocotyledonous angiosperms (e.g., grasses, corn, grains, oat, wheat and barley) and dicotyledonous angiosperms (e.g., *Arabidopsis*, tobacco, legumes, alfalfa, oaks, eucalyptus, maple), and Gymnosperms (e.g., Scots pine; see Aronen, *Finnish Forest Res. Papers*, Vol. 595, 1996), white spruce (Ellis et al., *Biotechnology* 11:84–89, 1993), and larch (Huang et al., *In Vitro Cell* 27:201–207, 1991). In a preferred embodiment, the inventive genetic constructs are employed to transform woody plants, herein defined as a tree or shrub whose stem lives for a number of years and increases in diameter each year by the addition of woody tissue. Preferably the target plant is selected from the group consisting of eucalyptus and pine species, most preferably from the group consisting of *Eucalyptus grandis* and *Pinus radiata*. Other species which may be usefully transformed with the genetic constructs of the present invention include, but are not limited to: pines such as *Pinus banksiana, Pinus brutia, Pinus caribaea, Pinus clausa, Pinus contorta, Pinus coulteri, Pinus echinata, Pinus eldarica, Pinus ellioti, Pinus jeffreyi, Pinus lambertiana, Pinus monticola, Pinus nigra, Pinus palustrus, Pinus pinaster, Pinus ponderosa, Pinus resinosa, Pinus rigidca, Pinus serotina, Pinus strobus, Pinus sylvestris, Pinus taeda, Pinus virginiana;* other gymnosperms, such as *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Huniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata;* and Eucalypts, such as *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-anglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo* and *Eucalyptus youmanni;* and hybrids of any of these species.

Techniques for stably incorporating genetic constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by *Agrobacterium* Ti plasmid technology, as described, for example by Bevan, *Nucleic Acids Res.* 12:8711–8721, 1984. Targets for the introduction of the genetic constructs of the present invention include tissues, such as leaf tissue, dissociated cells, protoplasts, seeds, embryos, meristematic regions; cotyledons, hypocotyls, and the like. The preferred method for transforming eucalyptus and pine is a biolistic method using pollen (see, for example, Aronen, *Finnish Forest Res. Papers,* Vol. 595, 53pp, 1996) or easily regenerable embryonic tissues.

Once the cells are transformed, cells having the inventive genetic construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al., "Somatic embryogenesis in woody plants," in Thorpe T A, ed., *In Vitro Embryogenesis of Plants* (*Current Plant Science and Biotechnology in Agriculture* Vol. 20), Chapter 12, pp. 471–540, 1995. Specific protocols for the regeneration of spruce are discussed by Roberts et al., "Somatic embryogenesis of spruce," in Redenbaugh K, ed., *Synseed: applications of synthetic seed to crop improvement,* CRC Press: Chapter 23, pp. 427–449, 1993). Transformed plants having the desired phenotype may be selected using techniques well known in the art. The resulting transformed plants may be reproduced sexually or asexually, using methods well known in the art, to give successive generations of transgenic plants.

As discussed above, the production of RNA in target cells can be controlled by choice of the promoter sequence, or by selecting the number of functional copies or the site of integration of the polynucleotides incorporated into the genome of the target host. A target organism may be transformed with more than one genetic construct of the present invention, thereby modulating the activity of more than gene. Similarly, a genetic construct may be assembled containing more than one open reading frame coding for a polypeptide of interest or more than one untranslated region of a gene coding for such a polypeptide.

The isolated polynucleotides of the present invention also have utility in genome mapping, in physical mapping, and in positional cloning of genes. As detailed below, the polynucleotide sequences identified as SEQ ID NO: 1–14, 20, 22–62, 81–86 and 88–127, and their variants, may be used to design oligonucleotide probes and primers. Oligonucleotide probes designed using the polynucleotides of the present invention may be used to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology of Affymetrix (Santa Clara, Calif.).

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

An oligonucleotide probe or primer is described as "corresponding to" a polynucleotide of the present invention, including one of the sequences set out as SEQ ID NO: 1–14, 20, 22–62, 81–86 and 88–127, or a variant, if the oligonucleotide probe or primer, or its complement, is contained within one of the sequences set out as SEQ ID NO: 1–14, 20, 22–62, 81–86 and 88–127, or a variant of one of the specified sequences. Oligonucleotide probes and primers of the present invention are substantially complementary to a polynucleotide disclosed herein.

Two single stranded sequences are said to be substantially complementary when the nucleotides of one strand, optimally aligned and compared, with the appropriate nucleotide insertions and/or deletions, pair with at least 80%, preferably at least 90% to 95% and more preferably at least 98% to 100% of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The probes can be easily selected using procedures well known in the art, taking into account DNA-DNA hybridization stringencies, annealing and melting temperatures, and potential for formation of loops and other factors, which are well known in the art. Preferred techniques for designing PCR primers are disclosed in Dieffenbach, C W and Dyksler, G S. *PCR Primer: a laboratory manual*, CSHL Press: Cold Spring Harbor, N.Y., 1995. A software program suitable for designing probes, and especially for designing PCR primers, is available from Premier Biosoft International, 3786 Corina Way, Palo Alto, Calif. 94303-4504.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NO: 1–14, 20, 22–62, 81–86 and 88–120.

In one embodiment useful for high-throughput assays, the oligonucleotide probe kits of the present invention comprise multiple probes in an array format, wherein each probe is immobilized at a predefined, spatially addressable location on the surface of a solid substrate. Array formats which may be usefully employed in the present invention are disclosed, for example, in U.S. Pat. Nos. 5,412,087 and 5,545,451; and PCT Publication No. WO 95/00450, the disclosures of which are hereby incorporated by reference.

The polynucleotides of the present invention may also be used to tag or identify an organism or reproductive material therefrom. Such tagging may be accomplished, for example, by stably introducing a non-disruptive non-functional heterologous polynucleotide identifier into an organism, the polynucleotide comprising one of the polynucleotides of the present invention.

The following examples are offered by way of illustration and not by way of limitation.

EXAMPLE 1

Isolation and Characterization of a Ubiquitin Gene Promoter from *Pinus radiata*

*Pinus radiata* cDNA expression libraries were constructed and screened as follows. mRNA was extracted from plant tissue using the protocol of Chang et al., *Plant Molecular Biology Reporter* 11:113–116, 1993 with minor modifications. Specifically, samples were dissolved in CPC-RNAXB (100 mM Tris-Cl, pH 8,0; 25 mM EDTA; 2.0 M NaCl; 2% CTAB; 2% PVP and 0.05% Spermidine*3HCl) and extracted with chloroform:isoamyl alcohol, 24:1. mRNA was precipitated with ethanol and the total RNA preparate was purified using a POLY(A) QUIK™ mRNA Isolation Kit (Stratagene, La Jolla, Calif.). A cDNA expression library was constructed from the purified mRNA by reverse transcriptase synthesis followed by insertion of the resulting cDNA clones in LAMBDA ZAP™ using a ZAP Express cDNA Synthesis Kit (Stratagene), according to the manufacturer's protocol. The resulting cDNAs were packaged using a GIGAPACK II™ Packaging Extract (Stratagene) employing 1 μl of sample DNA from the 5 μl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems Division, Foster City, Calif.) according to the manufacturer's protocol.

DNA sequence for positive clones was obtained using a Perkin Elmer/Applied Biosystems Division Prism 377 sequencer. cDNA clones were sequenced first from the 5' end and, in some cases, also from the 3' end. For some clones, internal sequence was obtained using subcloned fragments. Subcloning was performed, using standard procedures of restriction mapping and subcloning to pBLUE-SCRIPT II™ SK+ vector.

As described below, one of the most abundant sequences identified was a ubiquitin gene, hereinafter referred to as the "Super-Ubiquitin or SU" gene.

Isolation of cDNA Clones Containing the Ubiquitin Gene

Sequences of cDNA clones with homology to the ubiquitin gene were obtained from high-throughput cDNA sequencing as described above. Sequences from several independent clones were assembled in a contig and a consensus sequence was generated from overlapping clones. The determined nucleotide sequence of the isolated Super Ubiquitin clone, comprising the promoter region (including an intron), coding region and 3' untranslated region (UTR) is provided in SEQ ID NO: 1. The 5' UTR is represented by residues 1 to 2,064, the intron by residues 1,196 to 2,033, and the coding region of the gene, which contains three direct repeats, by residues 2,065 to 2,751. The 3' UTR is 328 residues long (residues 2,755 to 3,083). The nucleotide sequence of the Super Ubiquitin promoter region only, including the intron, is given in SEQ ID NO: 2. The nucleotide sequence of the Super Ubiquitin promoter region only, excluding the intron, is given in SEQ ID NO: 3. The predicted amino acid sequence for the Pinus radiata Super Ubiquitin is provided in SEQ ID NO: 80.

Ubiquitin proteins function as part of a protein degradation pathway, in which they covalently attach to proteins, thereby targeting them for degradation (for a review, see Belknap and Garbarino, *Trends in Plant Sciences* 1:331–335, 1996). The protein is produced from a precursor polypeptide, encoded by a single mRNA. The Super Ubiquitin mRNA contains three copies of the ubiquitin monomer.

Cloning of the Super Ubiquitin Promoter

Fragments of the Super Ubiquitin promoter were cloned by two different PCR-based approaches.

Method 1: Long Distance Gene Walking PCR

Using "Long Distance Gene-Walking" PCR (Min and Powell, *Biotechniques* 24:398–400, 1998), a 2 kb fragment was obtained that contained the entire coding region of the ubiquitin gene, a 900 bp intron in the 5' UTR and approximately 100 bp of the promoter.

To generate this fragment, 2 nested primers were designed from the 3' UTR of the Super Ubiquitin cDNA sequence isolated from pine. Generally, the 5' UTR is used for primer design to amplify upstream sequence. However, the available 5' UTR of Super Ubiquitin was very short, and two initial primers derived from this region failed to amplify any fragments. Therefore, the primers of SEQ ID NO: 15 and 16 were designed from the 3' UTR.

The method involved an initial, linear PCR step with pine genomic DNA as template using the primer of SEQ ID NO: 15, and subsequent C-tailing of the single stranded DNA product using terminal transferase. The second PCR-step used these fragments as template for amplification with the primer of SEQ ID NO: 16 and primer AP of SEQ ID NO: 17. The AP primer was designed to bind to the polyC tail generated by the terminal transferase. Both primers (SEQ ID NO: 16 and 17) contained a 5'-NotI restriction site for the cloning of products into the NotI site of a suitable vector. The final PCR product contained fragments of different sizes. These fragments were separated by electrophoresis and the largest were purified from the gel, digested with restriction endonuclease NotI and cloned in the NotI site of expression vector pBK-CMV (Stratagene, La Jolla, Calif.). The largest of these clones contained the complete coding region of the gene (no introns were found in the coding sequence) and a 5' UTR which contained a 900 bp intron.

Method 2: "Genome Walker" Kit

The Super Ubiquitin gene promoter was cloned using a "Genome Walker" kit (Clontech, Palo Alto, Calif.). This is also a PCR-based method, which requires two PCR primers to be constructed, one of which must be gene-specific. Although the ubiquitin coding region is highly conserved, the 5' UTR from different ubiquitin genes is not conserved and could therefore be used to design a gene-specific primer. A 2.2 kb fragment was amplified and subcloned in pGEM-T-easy (Promega, Madison, Wis.). Analysis by PCR and DNA sequencing showed that the clone contained 5' UTR sequence of the Super Ubiquitin gene, including the 900 bp intron and approximately 1 kb of putative promoter region. An intron in the 5' UTR is a common feature of plant polyubiquitin genes and may be involved in determining gene expression levels.

The gene specific primers used for these PCR reactions are provided in SEQ ID NO: 18 and 19.

Expression of Super Ubiquitin

Using primers derived from the gene-specific 5' and 3' UTR sequences, expression levels of Super Ubiquitin in different plant tissues was examined by means of RT-PCR. Super Ubiquitin was found to be expressed in all plant tissues examined, including branch phloem and xylem, feeder roots, fertilized cones, needles, one year old cones, pollen sacs, pollinated cones, root xylem, shoot buds, structural roots, trunk phloem and trunk. Expression of Super Ubiquitin in plant tissues was also demonstrated in a Northern blot assay using a PCR probe prepared from the 5' UTR.

Functional Analysis of the Super Ubiquitin Promoter

To test the function of the Super Ubiquitin promoter in plants, *Arabidopsis thaliana* was transformed with constructs containing the reporter gene for Green Fluorescent Protein (GFP) operably linked to either the Super Ubiquitin promoter of SEQ ID NO: 2 or SEQ ID NO: 3 (i.e., either with or without the intron). Constructs lacking a promoter were used as a negative control, with a plant T-DNA vector carrying a CaMV 35S promoter cloned in front of GFP being used as a positive control. The constructs were introduced into *Arabidopsis* via *Agrobacterium*-mediated transformation.

All the plant culture media were according to the protocol of Valvekens and Van Montagu, *Proc. Natl. Acad. Sci. USA* 85:5536–5540, 1988 with minor modifications. For root transformation, sterilized seeds were placed in a line on the surface of germination medium, the plates were placed on their sides to facilitate root harvesting, and the seeds were grown for two weeks at 24° C. with a 16 h photoperiod.

Expression of the constructs was measured by determining expression levels of the reporter gene for Green Fluorescent Protein (GFP). Preliminary GFP expression (transient) was detected in early transgenic roots during T-DNA transfer. Transgenic roots that developed green callus, growing on shoot-inducing medium containing 50 µg/ml Kanamycin and 100 µg/ml Timentin, were further tested for GFP expression. After several weeks of stringent selection on Kanamycin medium, several independent transgenic *Arabidopsis* lines were engineered and tested for GFP expression.

Expression was seen both with the Super Ubiquitin promoter including intron and the Super Ubiquitin promoter without the intron. However, preliminary results indicated that the levels of expression obtained with the Super Ubiquitin intron-less promoter construct were significantly higher than those seen with the promoter including intron, suggesting that the intron may contain a repressor. The sequence of the intron is provided in SEQ ID NO: 21.

EXAMPLE 2

Isolation of a CDC Promoter from *Pinus radiata*

Plant polynucleotide sequences homologous to the Cell Division Control (CDC) protein gene were isolated from a *Pinus radiata* cDNA expression library as described in Example 1. Using the "Genome Walker" protocol described above and gene specific primers designed from these plant polynucleotide sequences, 5' UTR sequence containing the putative promoter of the *P. radiata* CDC gene was isolated from genomic DNA. The determined nucleotide sequence is given in SEQ ID NO: 4.

EXAMPLE 3

Isolation of a Xylogenesis-Specific Promoter from *Pinus radiata*

Plant polynucleotide sequences specific for plant xylogenesis were isolated from *Pinus radiata* cDNA expression libraries prepared from xylem, essentially as described in Example 1. Using the "Genome Walker" protocol described above and gene specific primers designed from these plant polynucleotide sequences, sequences containing putative *Pinus radiata* xylogenesis-specific promoters were isolated from genomic DNA. The determined nucleotide sequences are provided in SEQ ID NO: 5 and 41–44. An extended cDNA sequence for the clone of SEQ ID NO: 41–44 is provided in SEQ ID NO: 92.

EXAMPLE 4

Isolation of a 4-Coumarate-CoA Ligase Promoter from *Pinus radiata*

Plant polynucleotide sequences homologous to the 4-Coumarate-CoA Ligase (4CL) gene were isolated from a *Pinus radiata* cDNA expression library as described in Example 1. Using the "Genome Walker" protocol described above and gene specific primers designed from these plant polynucleotide sequences, sequences containing the putative promoter of the *P. radiata* 4CL gene was isolated from genomic DNA. The determined nucleotide sequence is given in SEQ ID NO: 6.

Genetic constructs comprising the reporter gene for Green Fluorescent Protein (GFP) or GUS reporter genes operably linked to the promoter of SEQ ID NO: 6 were prepared and used to transform *Arabidopsis thaliana* plants.

EXAMPLE 5

Isolation of a Cellulose Synthase Promoter from *Eucalyptus grandis*

Plant polynucleotide sequences homologous to the cellulose synthase gene were isolated from a *Eucalyptus grandis* cDNA expression library essentially as described in Example 1. Using the "Genome Walker" protocol described above and gene specific primers designed from these plant polynucleotide sequences, 5' UTR sequences containing the putative promoter of the *E. grandis* cellulose synthase gene were isolated from genomic DNA. Independent PCR experiments using different DNA bands as templates yielded two sequences which contained a number of base differences. One band was 750 bp in length and the nucleotide sequence of this band is given in SEQ ID NO: 7. The other band was 3 kb in length. The sequence of the 3' end of this band corresponded to the sequence given in SEQ ID NO: 7, with a number of base pair differences. The sequence of this 3' end is given in SEQ ID NO: 8. The sequence of the 5' end of this band is given in SEQ ID NO: 20.

EXAMPLE 6

Isolation of a Leaf-Specific Promoter from *Eucalyptus grandis*

Plant polynucleotide sequences specific for leaf were isolated from *Eucalyptus grandis* cDNA expression libraries prepared from leaf tissue, essentially as described in Example 1. Using the "Genome Walker" protocol described above and gene specific primers designed from these plant polynucleotide sequences, 5' UTR sequence containing a leaf-specific promoter of a novel *E. grandis* gene (of unknown function) was isolated from genomic DNA. Independent PCR experiments using different DNA bands as templates yielded three sequences which contained a number of base differences and deletions. The determined nucleotide sequences of the three PCR fragments are given in SEQ ID NO: 9–11.

EXAMPLE 7

Isolation of an O-Methyl Transferase Promoter from *Eucalyptus grandis*

Plant polynucleotide sequences homologous to an O-methyl transferase (OMT) gene were isolated from a *Eucalyptus grandis* cDNA expression library essentially as described in Example 1. Using the "Genome Walker" protocol described above and gene specific primers designed from these plant polynucleotide sequences, 5' UTR sequences containing the putative promoter of the *E. grandis* OMT gene was isolated from genomic DNA. The determined nucleotide sequence is given in SEQ ID NO: 12. This promoter sequence was extended by further sequencing. The extended cDNA sequences are given in SEQ ID NO: 60 and 113.

Genetic constructs comprising the reporter gene for Green Fluorescent Protein (GFP) operably linked to the promoter of SEQ ID NO: 12 were prepared and used to transform *Arabidopsis thaliana*.

EXAMPLE 8

Isolation of Root-Specific Promoters from *Pinus radiata*

Plant polynucleotide sequences homologous to the root-specific receptor-like kinase gene were isolated from a *Pinus radiata* cDNA expression library as described in Example 1. Using the "Genome Walker" protocol described above and gene specific primers designed from these plant polynucleotide sequences, 5' UTR sequence containing a putative *P. radiata* root-specific promoter was isolated from genomic DNA. Two independent PCR experiments yielded sequences that contained a number of base differences. The determined nucleotide sequences from the two experiments are given in SEQ ID NO: 13, 14, 110 and 111.

EXAMPLE 9

Isolation of an EFI-Alpha Promoter from *Eucalyptus Grandis*

Plant polynucleotide sequences homologous to the *Eucalyptus* Elongation Factor-alpha (EF1-alpha) gene were isolated from a *Eucalyptus grandis* cDNA expression library and used to screen a *Eucalyptus grandis* genomic DNA library as follows.

The *Eucalyptus grandis* genomic DNA library was constructed using genomic DNA extracted from *Eucalyptus nitens x grandis* plant tissue, according to the protocol of Doyle and Doyle, *Focus* 12:13–15, 1990, with minor modifications. Specifically, plant tissue was ground under liquid nitrogen and dissolved in 2×CTAB extraction buffer (2% CTAB, hexadecyltrimethylammonium bromide; 1.4 M NaCl, 20 mM EDTA pH 8.0, 100 mM Tris. HCl pH 8.0, 1% polyvinylpyrollidone). After extraction with chloroform:isoamylalcohol (24:1), 10% CTAB was added to the aqueous layer and the chloroform:isoamylalcohol extraction repeated. Genomic DNA was precipitated with isopropanol.

The resulting DNA was digested with restriction endonuclease Sau3A1 following standard procedures, extracted once with phenol:chloroform:isoamylalcohol (25:24:1) and ethanol precipitated. The digested fragments were separated on a sucrose density gradient using ultracentrifugation. Fractions containing fragments of 9–23 kb were pooled and ethanol precipitated. The resulting fragments were cloned into the lambda DASH II/BamHI vector (Stratagene, La Jolla, Calif.) following the manufacturer's protocol and packaged using a Gigapack II Packaging Extract (Stratagene). The library was amplified once.

The library was screened with radiolabeled EST fragments isolated from a *Eucalyptus grandis* library (as described in Example 1), that showed homology to the *Eucalyptus* EF1-alpha gene. Phage lysates were prepared from positive plaques and genomic DNA was extracted.

From this genomic DNA, the 5' UTR region containing the putative promoter of the *Eucalyptus* EF1-alpha gene was obtained using the ELONGASE Amplification System (Gibco BRL). A 10 kb fragment was amplified and restriction mapped. The putative promoter region of the *Eucalyptus* elongation factor A (EF1-alpha) gene was identified on a 4 kb fragment, which was subcloned into a pUC19 vector (Gibco BRL) containing an engineered NotI-site. The determined genomic DNA sequences of the isolated fragment containing the promoter region are provided in SEQ ID NO: 61 and 62, with the amino acid encoded by SEQ ID NO: 61 being provided in SEQ ID NO: 79. An extended sequence of the clone of SEQ ID NO: 61 is provided in SEQ ID NO: 127.

EXAMPLE 10

Isolation of Flower-Specific Promoters from *Eucalyptus grandis*

Plant polynucleotide sequences specific for flower-derived tissue were isolated from *Eucalyptus grandis* cDNA expression libraries prepared from flower tissue, essentially as described in Example 1. Using the "Genome Walker" protocol described above and gene specific primers designed from these plant polynucleotide sequences, several sequences, each containing a putative *Eucalyptus grandis* flower-specific promoter, were isolated from genomic DNA. The determined nucleotide sequences are given in SEQ ID NO: 29–33 and 59. An extended sequence of the clone of SEQ ID NO: 30–33 is provided in SEQ ID NO: 89. An extended sequence of the clone of SEQ ID NO: 29 is provided in SEQ ID NO: 90.

EXAMPLE 11

Isolation of Pollen-Specific Promoters from *Eucalyptus grandis* and *Pinus radiata*

Plant polynucleotide sequences specific for pollen were isolated from *Eucalyptus grandis* and *Pinus radiata* cDNA expression libraries prepared from pollen, essentially as described in Example 1. Using the "Genome Walker" protocol described above and gene specific primers designed from these plant polynucleotide sequences, several sequences, each containing a putative pollen-specific promoter, were isolated from genomic DNA. The determined nucleotide sequences isolated from *Pinus radiata* are given in SEQ ID NO: 49–53, with the predicted amino acid sequences encoded by SEQ ID NO: 51–53 being provided in SEQ ID NO: 73–75, respectively. An extended sequence for the clone of SEQ ID NO: 49 is provided in SEQ ID NO: 94.

EXAMPLE 12

Isolation of Bud-Specific and Meristem-Specific Promoter from *Pinus radiata*

Plant polynucleotide sequences specific for bud and meristem were isolated from *Pinus radiata* cDNA expression libraries prepared from bud and meristem, essentially as described in Example 1. Using the "Genome Walker" protocol described above and gene specific primers designed from these plant polynucleotide sequences, two sequences, one containing a putative bud-specific promoter and the other containing a putative meristem-specific promoter, were isolated from genomic DNA. The determined nucleotide sequences for these two promoters are given in SEQ ID NO: 40 and 45, respectively. The predicted amino acid sequences encoded by the DNA sequences of SEQ ID NO: 40 and 45 are provided in SEQ ID NO: 70 and 71, respectively.

EXAMPLE 13

Isolation of Promoters from *Eucalyptus grandis*

Plant polynucleotide sequences showing some homology to various known genes were isolated from *Eucalyptus grandis* cDNA expression libraries essentially as described in Example 1. Using the "Genome Walker" protocol described above and gene specific primers designed from these plant polynucleotide sequences, sequences containing the putative promoters for the following *E. grandis* genes were isolated from genomic DNA: auxin induced protein (SEQ ID NO: 26–28); carbonic anhydrase (SEQ ID NO: 36); isoflavone reductase (SEQ ID NO: 37 and 38); pollen allergen (SEQ ID NO: 23–25); pollen coat protein (SEQ ID NO: 22), sucrose synthase (SEQ ID NO: 56–58); ubiquitin (SEQ ID NO: 34); glyceraldehyde-3-phosphate dehydrogenase (SEQ ID NO: 35 and 39); O-methyl transferase (OMT; SEQ ID NO: 60); macrophage migration inhibition factor from mammals (MIF; SEQ ID NO: 81–86); UDP glucose 6-dehydrogenase (SEQ ID NO: 103); laccase 1 (SEQ ID NO: 105, 106 and 116); arabinogalactan-like 1 (SEQ ID NO: 107); arabinogalactan-like 2 (SEQ ID NO: 108, 109); a hypothetical protein (SEQ ID NO: 104); constans (SEQ ID NO: 118); Flowering Promoting Factor 1 (FPF1; SEQ ID NO: 119); transcription factor DREB-1 (SEQ ID NO: 121); salt tolerance protein (SEQ ID NO: 123); xylem-specific histidine kinase-like (SEQ ID NO: 125) and root specific (SEQ ID NO: 126). The amino acid sequences encoded by the DNA sequences of SEQ ID NO: 22, 25, 26, 28, 34, 35, 36, 56, 57, 60, 86 and 124 are provided in SEQ ID NO: 63, 64, 65, 66, 67, 68, 69, 76, 77, 78, 87 and 130, respectively. Extended cDNA sequences for the clones of SEQ ID NO: 58, 35, 60, 103, 106 and 107 are provided in SEQ ID NO: 91, 93, 113 and 115–117, respectively.

EXAMPLE 14

Isolation of Promoters from *Pinus radiata*

Plant polynucleotide sequences showing some homology to various known genes were isolated from *Pinus radiata* cDNA expression libraries essentially as described in Example 1. Using the "Genome Walker" protocol described above and gene specific primers designed from these plant polynucleotide sequences, sequences containing the putative promoters for the following *Pinus radiata* genes were isolated from genomic DNA: senescence-like protein (SEQ ID NO: 46–48); nodulin homolog pollen specific (SEQ ID NO: 54 and 55); chalcone synthase (SEQ ID NO: 88); PrMALE1 (SEQ ID NO: 95, 96); UDP glucose glycosyltransferase (SEQ ID NO: 97); elogation factor 1 alpha (SEQ ID NO: 98, 99); S-adenosylmethionine synthase (SEQ ID NO: 100–102); *Pinus radiata* lipid transfer protein 2 (PrLTP2; SEQ ID NO: 112); *Pinus radiata* agamous protein (SEQ ID NO: 120); Drought Induced DI-19 (SEQ ID NO: 122) and low temperature induced protein LTI (SEQ ID NO 124). The amino acid sequences encoded by the polynucleotide sequences of SEQ ID NOS: 46 and 124 are provided in SEQ ID NOS: 72 and 130. An extended cDNA sequence for the clone of SEQ ID NO: 97 is provided in SEQ ID NO: 114.

EXAMPLE 15

Polynucleotide and Amino Acid Analysis

The determined cDNA sequences described above were compared to and aligned with known sequences in the EMBL database (as updated to October 2000). Specifically, the polynucleotides identified in SEQ ID NOS: 22–62 and 88–120 were compared to polynucleotides in the EMBL database using the BLASTN algorithm Version 2.0.6 [Sep. 16, 1998] and the polynucleotides identified in SEQ ID NOS: 121–127 were compared to polynucleotides in the EMBL database using the BLASTN algorithm Version 2.0.11 [Jan. 20, 2000] set to the following running parameters: Unix running command: blastall -p blastn -d embldb -e 10 -G0 -E0 -r1 -v30 -b30 -i queryseq -o results. Multiple alignments of redundant sequences were used to build up reliable consensus sequences. Based on similarity to known sequences from other plant or non-plant species, the isolated polynucleotides of the present invention identified as SEQ ID NOS: 22–62 and 88–127 were putatively identified as having the functions shown in Table 1, above.

The cDNA sequences of SEQ ID NO: 1–22, 23, 25–42, 45–49, 57–59, 62, 88–99, 101–112 and 114–127 were determined to have less than 40% identity to sequences in the EMBL database using the computer algorithm BLASTN, as described above. The cDNA sequences of SEQ ID NO: 56 and 113 were determined to have less than 60% identity to sequences in the EMBL database using BLASTN, as described above. The cDNA sequences of SEQ ID NO: 43, 52, 60 and 61 were determined to have less than 75% identity to sequences in the EMBL database using BLASTN, as described above. The cDNA sequences of SEQ ID NO: 24, 51 and 100 were determined to have less than 90% identity to sequences in the EMBL database using BLASTN, as described above.

EXAMPLE 16

Modification of a Reporter Gene Under Control of the Superubiquitin Promoter

Six independent *Arabidopsis thaliana* transgenic lines were transformed with *Pinus radiata* superubiquitin promoter constructs to demonstrate the relative expression of a GUS reporter gene under control of different superubiquitin promoter constructs. The reporter constructs in the plasmid pBI-101 contained the GUS (β-D-glucuronidase) reporter gene in frame with the superubiquitin promoter with the intron (SEQ ID NO: 2), the superubiquitin promoter without the intron (SEQ ID NO: 3), and the CaMV 35S promoter. A reporter gene construct without a promoter sequence was used as control.

Groups of six *Arabidopsis thaliana* plants were transformed with the reporter constructs described above, using *Agrobacterium tumefaciens* transformation protocols. *A. tumefaciens* was transformed with 100 ng of the plasmid DNA according to standard techniques, as described, for example, by Bevan (*Nucleic Acids Res*. 12:8711–8721, 1984). Fresh plant material was collected from each plant, protein extracted from the whole plant, and the protein concentration determined (Bradford, *Anal. Biochem.* 72:248–254, 1976). The protein samples were diluted with carrier bovine serum albumin to 100 ng protein to maintain readings on the fluorimeter in the linear part of the standard curve using 4-methyl-umbelliferone (MU). GUS activity was quantified by fluorimetric analysis, using a Victor$^2$ 1420 multi-label counter (Wallac, Turku, Finland) as described by Jefferson (*Plant Mol. Biol. Rep.* 5:387–405, 1987). As shown in FIG. 1, the construct containing the superubiquitin promoter without the intron showed seven times more GUS activity than the CaMV 35S promoter and the construct containing the superubiquitin promoter with the intron showed sixty two times more GUS activity than the CaMV 35S promoter. No activity was detected for the promoter-less control construct.

EXAMPLE 17

Determination of the Activity of Superubiquitin Promoter Constructs in Tobacco Plant Protoplasts Isolation of Protoplasts Protoplasts were isolated from sterile tobacco (*Nicotiana tabacum*) leaf tissue and transformed with superubiquitin promoter constructs. Mesophyll protoplasts were prepared according to the method of Bilang et al., *Plant Molecular Biology Manual* A1:1–16, 1994. A number of fully expanded leaves were removed from sterile wild type tobacco plants, sliced perpendicular to the midrib and submerged in a digestion enzyme solution containing 1.2% cellulase and 0.4% pectinase (Sigma, St. Louis Mo.). The leaves were left to incubate in the dark without agitation at 26° C. for approximately 18 hours. The leaf strips were then gently agitated for 30 min to release the protoplasts. Protoplasts were further purified by filtration through 100 μm nylon mesh. One ml of W5 solution (154 mM $MgCl_2$, 125 mM $CaCl_2$, 5 mM KCl, 5 mM glucose, pH 5.8–6) was carefully layered on top of the filtrate and centrifuged at 80×g for 10 min. The live protoplast layer was removed with a wide bore pipette, washed twice with 10 ml W5 solution using centrifugation at 70×g for 5 min, with final resuspension in 5 ml W5 solution. Protoplasts were counted in a hemocytometer and viability was determined under the microscope after staining with 5 mg/ml fluoroscein diacetate (FDA) in 100% acetone.

Transformation with Promoter Constructs

The isolated protoplasts were transformed with plasmid DNA using a polyethylene glycol protocol. After centrifugation of the purified protoplasts at 70×g for 5 min, they were resuspended in MMM solution (15 mM $MgCl_2$, 0.1% w/v 2[N-morpholino]ethanesulfonic acid (MES), 0.5 M mannitol pH 5.8) to a density of 2×10$^6$ protoplasts/ml.

Aliquots containing 5×10⁵ protoplasts/ml in 250 µl were distributed to 15 ml tubes and mixed with 20 µg plasmid DNA. 250 µl polyethylene glycol-4000 (40%) was gently added and incubated for 5 minutes at room temperature. Ten ml W5 solution was slowly added, the protoplasts centrifuged at 70×g for 5 min and finally resuspended in 2 ml K3 medium (Bilang et al., *Plant Molecular Biology Manual* A1:1–16, 1994). The transformed protoplasts were incubated in the dark at 26° C. for 24 hours before protein was extracted for reporter enzyme assays using 4-methyl-umbelliferyl-glucuronide (MUG).

Protein was extracted from the protoplasts using the following protocol. Transformed protoplast suspensions were centrifuged at 70×g for 10 min, resuspended in 50 µl extraction buffer (Jefferson, *Plant Mol. Biol. Rep.* 5:387–405, 1987) and vigorously mixed using a vortex. The homogenate was cleared by centrifugation at 4,300 rpm for 5 min, the supernatant removed and used for protein assays (Bradford, *Anal. Biochem.* 72:248–254, 1976).

Figure 2:
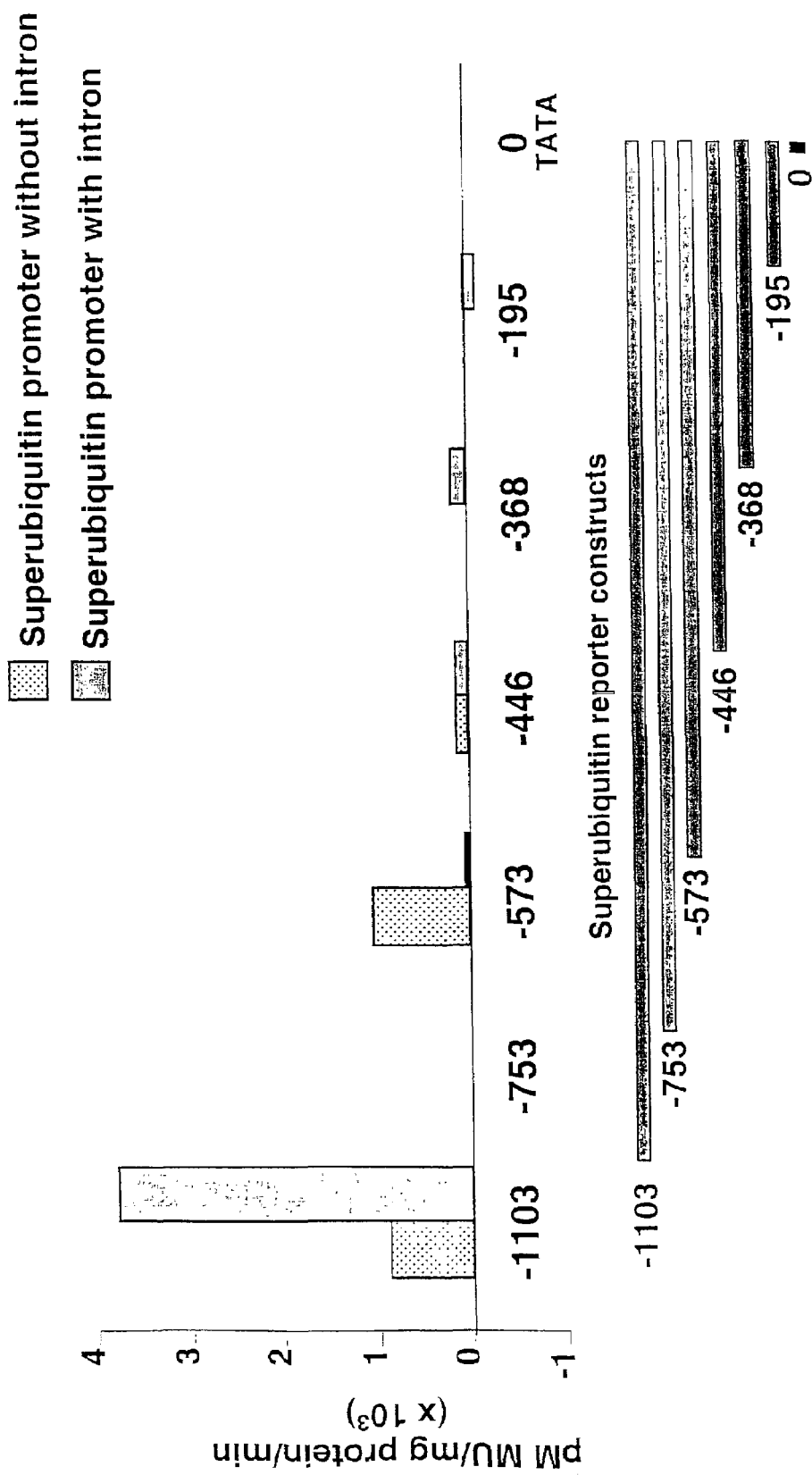
FIG. 2 shows the expression of the GUS gene in tobacco plant protoplasts by deletion constructs containing the superubiquitin promoter with or without the intron. The constructs contained 1,103; 753; 573; 446; 368; and 195 bp upstream of the TATA sequence (bp numbers 1,104–1,110 of SEQ ID NO: 2). The GUS expression was measured by fluorimetric determination of 4-methyl-umbelliferone (MU) in protein extracts from these protoplasts.

The results shown in FIG. 2 demonstrate the promoter activity of deletion constructs of the superubiquitin promoter without the intron (SEQ ID NO: 3) and the superubiquitin promoter with the intron (SEQ ID NO: 2) in tobacco plant protoplasts transformed as described above. The deletion constructs were made in plasmid pBI-101 that contained the GUS reporter gene, using Endonuclease III (Gibco BRL, Gaithersburg, Md.) according to the manufacturer's protocols. The deletion constructs contained 1,103; 753; 573; 446; 368 and 195 bp of superubiquitin promoter sequence, respectively, upstream of the TATA sequence (bp numbers 1,104–1,110 of SEQ ID NO: 2). A control construct containing no sequence upstream of the TATA sequence was also made. These results show that the construct containing the entire superubiquitin promoter with the intron had the highest MU activity in the protoplasts.

Figure 3:
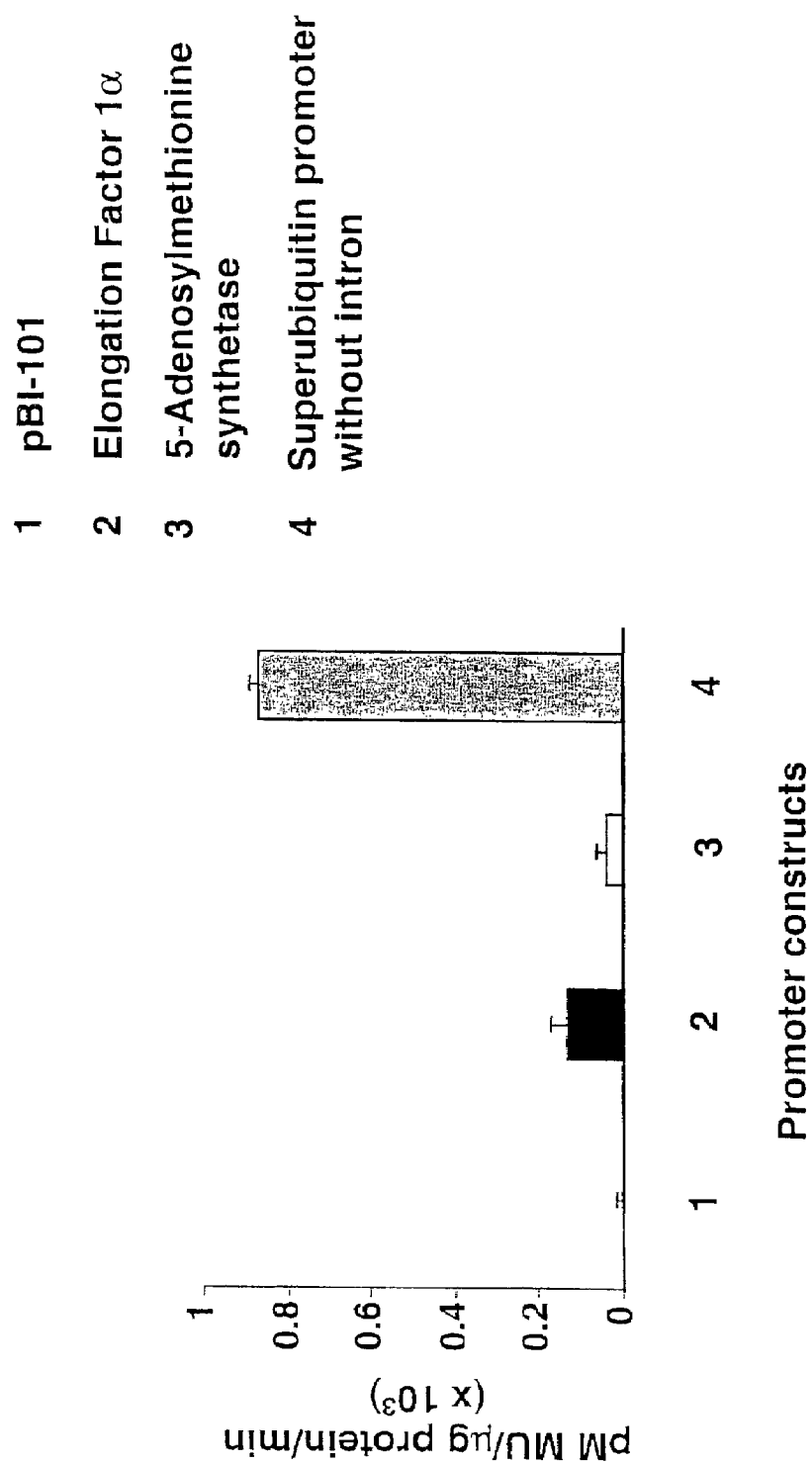
FIG. 3 shows the expression of the GUS gene in tobacco plant protoplasts by constructs containing *P. radiata* either the constitutive promoters Elongation factor-1 alpha, 5-adenosylmethionine synthetase or the superubiquitin promoter without the intron. The GUS expression was measured by fluorimetric determination of 4-methyl-umbelliferone (MU) in protein extracts from these protoplasts.

In FIG. 3, the tobacco protoplasts were transformed with four different promoter constructs in plasmid pBI-101 containing the GUS reporter gene. These included the superubiquitin promoter without the intron (SEQ ID NO: 3), an elongation factor 1α promoter (SEQ ID NO: 99) and a 5-adenosylmethionine synthetase promoter (SEQ ID NO: 100). A promoterless control was included in the experiment, and is referred to in FIG. 3 as pBI-101.

EXAMPLE 18

Determination of the Activity of *P. radiata* Pollen-Specific Promoter and *E. grandis* Pollen Specific Promoter Constructs in Transformed *Arabidopsis thaliana* cv Columbia

*Arabidopsis thaliana* transgenic lines were transformed with *A. tumefaciens* containing constructs of the *P. radiata* pollen specific promoter (SEQ ED NO: 94) and *E. grandis* pollen specific promoter (SEQ ID NO: 22) to demonstrate the relative expression of a GUS reporter gene under control of these promoter constructs. The promoter sequences were cloned into plasmid pBI-101 containing a GUS reporter gene.

*Agrobacterium tumefaciens* Transformation

*Agrobacterium tumefaciens* strain GV3101 was transformed with these constructs using electroporation. Electrocompetent *A. tumefaciens* cells were prepared according to the method of Walkerpeach and Velten, *Plant Mol. Biol. Man.* B1:1–19, 1994. Construct DNA (4 ng) was added to 40 µl competent *A. tumefaciens* GV3101 cells and electroporation was done using a BTX Electro Cell Manipulator 600 at the following settings: Mode: T 2.5 kV Resistance high voltage (HV), Set Capacitance: C (not used in HV mode), Set Resistance: R R5 (129 Ohm), Set charging voltage: S 1.44 kV, Desired field strength: 14.4 kV/cm and Desired pulse strength: t 5.0 msec. 400 µl YEP liquid media (20 g/l yeast, 20 g/l peptone and 10 g/l sodium chloride) was added to the cuvette and left to recover for one hour at room temperature. Transformed bacteria in YEP medium were spread out on solid YEP medium containing 50 mg/l kanamycin and 50 mg/l rifampicin and incubated at 29° C. for two days to allow colony growth.

Confirmation of Transformation of Constructs into *A. tumefaciens*

To confirm that the constructs have been transformed into *A. tumefaciens*, DNA from the *A. tumefaciens* colonies from the YEP plates were isolated using standard protocols and amplified using the polymerase chain reaction (PCR) with primers designed from the pBI-101 vector sequence. The primer sequences are given in SEQ ID NOS: 128 and 129. PCR reactions were set up following standard protocols and 30 PCR cycles were done with extension temperature of 72° C.

Transformation of *A. thaliana* with Transformed *A. tumefaciens*

The optical density of the *A. tumefaciens* bacterial culture was adjusted to 0.7 with infiltration medium (5% sucrose, 0.05% Silwett L-77 surfactant). *A. thaliana* cv. Columbia plants (6 punnets per construct and 10–12 plants per punnet) were pruned by removing secondary bolts. Pruned *A. thaliana* plants in punnets were dipped into infiltration solution and moved back and forth for 5 seconds. Punnets were put on their side to allow excess infiltration medium to drain covered with a top tray and wrapped in plastic wrap to maintain humidity. Plants were placed in a growth room at ambient conditions for 24 hours. After this period, the top tray and plastic wrap were removed and plants were set upright until siliques formed.

Seeds were harvested and sterilized with a 5% sodium hypochlorite solution to destroy any residual *A. tumefaciens* bacteria and fungal contamination.

Under sterile conditions, 100 µl seeds from the transformed *A. thaliana* plants were placed into an Eppendorf tube. One ml sterile water was added and the seeds left to imbibe the water for no longer than an hour. The water was remove by centrifugation, 1 ml 70% ethanol added to the seeds and gently mixed. This step was not allowed to last longer than one minute. The ethanol was removed by centrifugation, 1 ml 5% sodium hypochlorite solution was added to the seeds and gently mixed for up to 5 min. The sodium hypochlorite solution was removed by centrifugation and the seeds washed with sterile water for 1 min. The washing step was repeated three more times with centrifugation. Seeds were finally resuspended in sterile water. 500 µl of seeds in solution were pipetted onto half-strength Murashige and Skoog medium (MS; Gibco BRL) agar plates containing 50 mg/l kanamycin and 250 mg/l timentin and spread evenly with a flamed wire-loop. The Petri dishes were placed in a refrigerator for 3 days to allow the seeds to stratify. Thereafter the plates were placed in growth room and grown under lights at 22° C. with a 14 hour photoperiod until germination. Putative transformant seedlings were selected as those growing on the antibiotic-containing medium, with large, healthy-looking dark green leaves and a strong root system. These transgenic plants were removed and placed into soil culture at 22° C. with a 12 hour photoperiod.

Staining of Plant Tissues

Tissue were taken from the flower, leaf, stem and root of *A. thaliana* transformed with constructs of *P. radiata* unknown pollen specific promoter and *E. grandis* pollen specific promoter and stained histochemically to determine the expression of the GUS gene under control of the pollen specific promoters. The GUS staining protocol is described by Campisi et al., *Plant J.* 17:699–707, 1999.

*A. thaliana* flower, leaf, stem and root tissue were immersed in staining solution (50 mM NaPO$_4$ pH 7.2; 0.5% Triton X-100; 1 mM×Glucuronide sodium salt (Gibco BRL)) for immunochemical staining. Vacuum was applied twice for 5 min to infiltrate the tissue with the staining solution. The tissue was left in the staining solution for 2 days (with agitation) at 37° for color development and then destained in 70% ethanol for 24 hours at 37° C. (with agitation). The tissues were examined for blue GUS staining using a light microscope. GUS expression was observed only in the flower buds of plants transformed with the *P. radiata* pollen specific promoter construct, and not in the leaf, stem or root tissue. With the *E. grandis* pollen specific promoter construct, Gus expression was observed in the floral buds as well as in the hydathodes of the leaves. No expression was observed in the stem or root tissues.

To determine in which cell layers the GUS gene was expressed, flower buds were fixed for thin sectioning. The flower buds were fixed with formaldehyde acetic acid (FAA) in an Eppendorf tube and vacuum was applied twice for 15 min. After incubation for 2 hours at room temperature, vacuum was again applied for 15 min and the tissue left overnight at 4° C. The tissues were then dehydrated using a series of ethanol and then passed into a xylene series. Paraffin wax (Sigma) was added slowly and the tissues left for 72 hours with wax changes every 12 hours. Sections of 8 to 10 μm thickness were prepared using a microtome.

The thin sections illustrated that GUS expression was restricted to the tapetum cell layer in the anther of the floral bud of *A. thaliana* transformed with the *P. radiata* construct (SEQ ID NO: 49). No staining was observed in other tissues from the floral bud. GUS expression was confined to the pollen grains within the flower bud of *A. thaliana* transformed with the *E. grandis* pollen specific promoter construct, with low levels of GUS expression in the fibrous and connective tissue of the anther. No GUS expression was observed in other organs of the floral bud.

EXAMPLE 19

Determination of the Activity of an *E. grandis* EF1 Alpha Promoter Deletion Construct in transformed *Arabidopsis thaliana* cv Columbia Protoplasts from *Nicotiana tabacum* Bright Yellow 2 (BY-2) cell suspension were transformed with a deletion construct of the *E. grandis* EF1-alpha promoter to determine GUS expression. Base pairs 2,174 to 3,720 of SEQ ID NO: 127 were cloned into expression vector pART9, containing the reporter gene GUS and an OCS termination sequence.

Preparation of Protoplasts

Sterile *Nicotiana tabacum* Bright Yellow-2 (BY-2) suspension cultures were prepared as described in Example 17. After incubation for 3 to 5 days, 3 g of the *N. tabacum* BY-2 cell suspension were suspended in an enzyme solution containing 1% cellulase, 0.3% pectinase and 0.5% driselase in 0.4 M mannitol. These were left to digest in the dark, with agitation at 26° C., for 3–4 hours. Protoplasts were purified by filtration through a 63 μm nylon mesh. Protoplasts were centrifuged at 80×g for 5 min, washed twice with 10 ml FMS medium (Fukuda, Murashige and Skoog medium; Hasezawa & Syono, *Plant Cell Physiol.* 24:127–132, 1983) and finally resuspended in 5 ml FMS medium. Protoplasts were counted in a hemocytometer and viability determined by staining with 5 mg/ml FDA (fluorescein deacetate; Sigma St Louis Mich.) in 100% acetone by viewing under the fluorescent microscope.

Transformation of Protoplasts

Protoplasts were transformed according to the protocol described by Morgan and Ow (In: Methods in Plant Molecular Biology: a laboratory course manual, pp. 1–16. P. Maliga, D. Klessig, A. R. Cashmore, W. Gruissem, and J. E. Varner, eds. Cold Spring Harbor Laboratory, CSHP, NY). Briefly, the protocol is as follows. Following the counting step, protoplasts were centrifuged at 80×g for 5 min and resuspended in 1×MaMg solution (0.4 M manniotol, 15 mM MgCl$_2$.6H$_2$O, 0.1% 2-(N-Morpholino)ethane sulfonic acid (MES)) to a density of 5×10$^6$ protoplasts/ml. Aliquots of 100 μl (0.5×10$^5$ protoplasts) were distributed to 15 ml tubes and washed with 5 ml 1×MaMg (200g, 5 min). Pelleted protoplasts were resuspended in 500 ul 1×MaMg solution, and heat shocked by placing at 45° C. for 5 minutes. After incubation at room temperature 5–10 minutes, the transforming DNA was added (10–20 μg DNA+10 μg carrier DNA). To this, 500 μl 40% PEG-3500 was gently added and incubated for 25 minutes at room temperature. 5 ml W5 (154 mM NaCl, 125 mM CaCl$_2$.2H$_2$O, 5 mM KCl, 5 mM Glucose) solution was slowly added stepwise followed by centrifugation at 200×g for 5 min. Pelleted protoplasts were resuspended in 1 ml K3AM medium at approximately 0.5×10$^5$ protoplasts/ml. Samples were transferred to 6-well plates and incubated in the dark at 26° C. for 48 hours.

To extract protein, protoplasts were centrifuged at 200×g for 5 min a microfuge, resuspended in 100 μl GUS extraction buffer (50 mM NaPO$_4$ pH 7.2, 10 mM EDTA pH 8, 0.01% Sarcosyl, 0.1% Triton X-100) containing β-mercaptoethanol (Jefferson et al., *Plant Mol. Biol. Rep.* 5:387–405, 1987) and vortexed for 1 min. The homogenate was cleared by centrifugation at 5,000 rpm for 5 minutes. The supernatant containing the protein was transferred to a fresh tube and stored at −80° C. The protein concentrations were determined by BioRad protein assay kit (BioRad, Hercules, Calif.) following the manufacturer's protocols. Protein extracts were diluted 1/10 with extraction buffer.

Determination of GUS Expression

GUS expression in the protoplast extracts was determined using a MUG (4-methyl umbelliferyl β-D-glucuronide) assay. Protein samples, containing 1 μg protein made up to a total volume of 45 μl with extraction buffer, were aliquoted onto a microtitre plate and incubated at 37° C. To each sample, 5 μl of 10 mM MUG was added so that the final concentration of MUG was 1 mM. The plate was incubated at 37° C. for 30 min and terminated by adding 150 μl stop solution (0.2 M Na$_2$CO$_3$, pH 11.20), still keeping the plates at 37° C. Plates were read in a Victor$^2$ 1420 Multilabel counter with excitation set at 365 nm and emission at 455 nm. The concentration of 4-methyl-umbelliferone (MU) was calculated against a standard curve and the GUS expression calculated.

Figure 5:
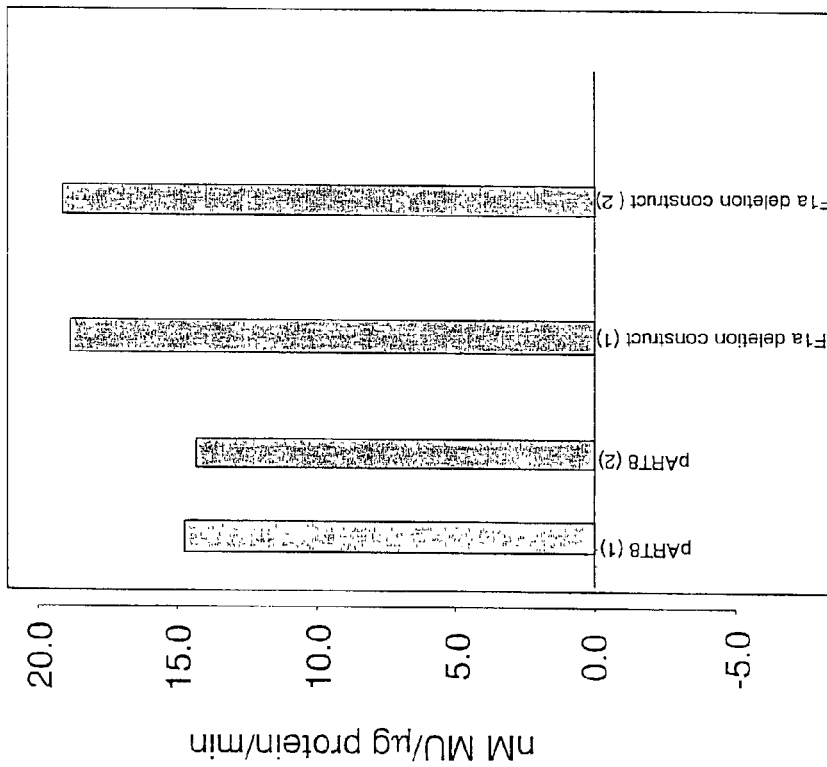
FIG. 5 shows the expression of the GUS gene in tobacco plant protoplasts by a deletion construct containing a fragment of the *E. grandis* constitutive promoter Elongation factor-1 alpha.

In FIG. 5, increased expression of the GUS reporter gene in *N. tabacum* BY-2 protoplasts transformed with an *E.* grandis EF1 alpha deletion construct was seen compared to the control plasmid without an insert.

EXAMPLE 20

Determination of the Effect of the 3' UTR Super-Ubiquitin (SU) Sequences on Gene Expression in *Arabidopsis thaliana* cv Columbia In the polynucleotide sequences given in SEQ ID NO: 1 encoding *P. radiata* superubiquitin (SU) promoter and gene sequences, an 3' untranslated region (UTR) was identified (nucleotides 1,754 to 3,083). To determine the effect of this region on the expression of genes, 250 bp of the 3' UTR (nucleotides 2,755 to 3,073 from SEQ ID NO: 1) was cloned in the sense and antisense orientation into plasmid pBI-121 containing the GUS gene under control of the 35S CaMV promoter and plasmid pBI-101 containing the GUS gene under control of the *P. radiata* SU promoter (including the intron) given in SEQ ID NO: 2. For controls, constructs were made that contained the SU promoter without an intron (SEQ ID NO: 3) and without the SU 3' UTR sequence, the SU promoter with an intron (SEQ ID NO: 2) and without the SU 3' UTR sequence as well as a construct containing the 35S CaMV promoter but not the SU 3' UTR sequence.

*A. thaliana* cv Columbia were transformed with these constructs using the floral dip protocol described in Example 18.

Determining the Level of Gene Expression using a MUG Assay.

Six *A. thaliana* plants were harvested by trimming off the dried tissue and then harvesting the rest of the plant, including the roots. The roots were rinsed in tap water and the samples immersed in liquid nitrogen before storing at −80° C. Six plants from each construct were ground under liquid nitrogen and approximately 100 mg transferred to a microfuge tube. Five samples from each control were included in the assay. Extraction buffer (50 mM $NaPO_4$ pH 7.2, 10 mM EDTA pH 8, 0.01% Sarcosyl, 0.1% Triton X-100) was prepared. To 32 ml of extraction buffer, 8 ml methanol and 28 µl β-mercaptoethanol was added. Of this buffer, 200 µl was added to each sample, vortexed and stored on ice. Samples were spun at 4° C. at 15,000 rpm for 15 min. The supernatant was transferred to a fresh tube and diluted with 800 µl of extraction buffer. Protein concentration was determined using the BioRad Protein Assay Kit.

The expression of GUS by the four constructs was determined using a MUG assay, as follows. To 28 ml extraction buffer (as described in Example 18), 8 ml methanol, 56 µl β-mercaptoethanol and 4 ml of 10 mg/ml bovine serum albumin (BSA) were added. To microtitre plate wells, 100 and 10 ng of protein from each construct was added as well as 25 µl extraction buffer containing BSA and 5 µl 10 mM MUG. The plate was covered in foil and incubated at 37° C. for exactly 20 minutes. The reaction was terminated by adding 150 µl 0.2 M $Na_2CO_3$ pH 11.2. Plates were read with a Victor$^2$ 1420 Multilabel counter with excitation set at 365 nm and emission at 455 nm. GUS expression levels were determined against a MU standard curve.

Figure 4:
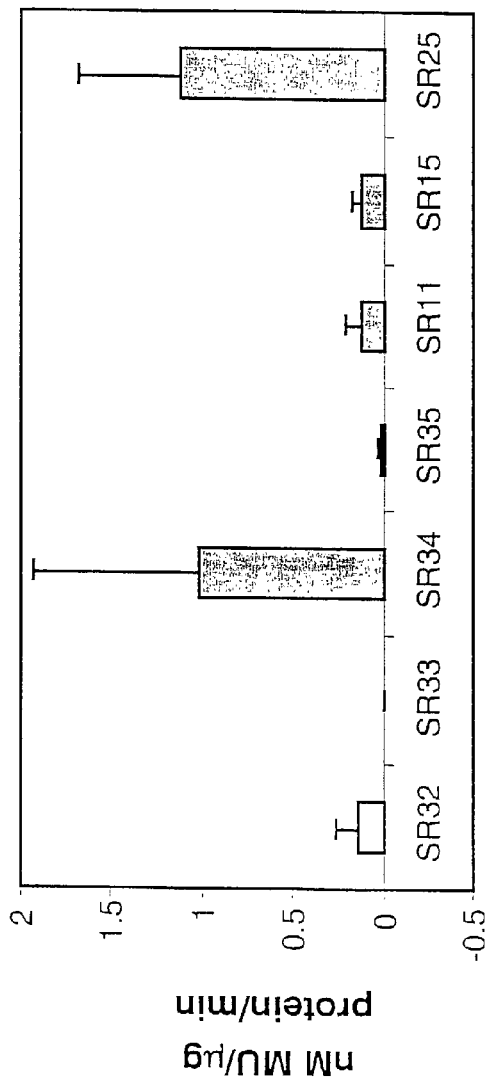
FIG. 4 shows the expression in *A. thaliana* of the GUS gene in promoter reporter constructs containing the 3' UTR of the superubiquitin promoter in sense or antisense orientation together with either the superubiquitin promoter with intron, the superubiquitin promoter without intron, or the CaMV 35S promoter. The GUS expression was measured by fluorimetric determination of 4-methyl-umbelliferone (MU) in protein extracts from these plants.

In FIG. 4, construct SR34 containing the SU 3' UTR in the sense orientation enhanced the expression of the SU without intron promoter almost to the level of the SU promoter with the intron. In constructs SR33 and SR35 containing the 3' UTR in the antisense orientation, promoter activity was reduced to basal levels.

EXAMPLE 21

Determination of the Activity of *P. radiata* Ubiquitin Promoter Constructs in Transformed *Arabidopsis thaliana* cv Columbia and Tobacco Plant Protoplasts A. Tobacco Plant Protoplasts 1. Isolation of Protoplasts Protoplasts were isolated from sterile tobacco (*Nicotiana tabacum*) leaf tissue and transformed with superubiquitin promoter constructs. Mesophyll protoplasts were prepared according to the method of Bilang et al., *Plant Molecular Biology Manual* A1:1–16, 1994. A number of fully expanded leaves were removed from sterile wild type tobacco plants, sliced perpendicular to the midrib and submerged in a digestion enzyme solution containing 1.2% cellulase and 0.4% pectinase (Sigma, St. Louis Mo.). The leaves were left to incubate in the dark without agitation at 26° C. for approximately 18 hours. The leaf strips were then gently agitated for 30 min to release the protoplasts. Protoplasts were further purified by filtration through 100 µm nylon mesh. One ml of W5 solution (154 mM $MgCl_2$, 125 mM $CaCl_2$, 5 mM KCl, 5 mM glucose, pH 5.8–6) was carefully layered on top of the filtrate and centrifuged at 80×g for 10 min. The live protoplast layer was removed with a wide bore pipette, washed twice with 10 ml W5 solution using centrifugation at 70×g for 5 min, with final resuspension in 5 ml W5 solution. Protoplasts were counted in a hemocytometer and viability was determined under the microscope after staining with 5 mg/ml fluoroscein diacetate (FDA) in 100% acetone.

2. Transformation with Promoter Constructs

The isolated protoplasts were transformed with plasmid BI-101 containing the the GUS (β-D-glucuronidase) reporter gene in frame with the specified deletion constructs of the superubiquitin promoter, with and without the intron. The deletion constructs contained 753, 573, 446, 368 and 195 bp of superubiquitin promoter sequence, respectively, upstream of the TATA sequence (bp numbers 1104–1,110 of SEQ ID NO: 2. The constructs tested, and the results, are described in the table, below.

| Construct Ref. | Deletion construct | SEQ ID NO: | Annotated FIG. | GUS staining constitutive? |
| --- | --- | --- | --- | --- |
| S38 | 195 bp | 131 | FIG. 7 | No |
| S39 | 368 bp | 132 | FIG. 8 | Yes |
| S40 | 446 bp | 133 | FIG. 9 | Yes |
| S41 | 573 bp | 134 | FIG. 10 | Yes |
| S48 | 753 bp | 135 | FIG. 11 | yes |
| S52 | 195 bp | 136 | FIG. 12 | No |
| S53 | 446 bp | 138 | FIG. 14 | Yes |
| S54 | 368 bp | 137 | FIG. 13 | Yes |
| S55 | 573 bp | 139 | FIG. 15 | Yes |
| S56 | 753 bp | 140 | FIGS. 16A, B | Yes |

Transformation was carried out using a polyethylene glycol protocol. After centrifugation of the purified protoplasts at 70×g for 5 min, they were resuspended in MMM solution (15 mM $MgCl_2$, 0.1% w/v 2[N-morpholino]ethanesulfonic acid (MES), 0.5 M mannitol pH 5.8) to a density of $2×10^6$ protoplasts/ml. Aliquots containing $5×10^5$ protoplasts/ml in 250 µl were distributed to 15 ml tubes and mixed with 20 µg plasmid DNA. 250 µl polyethylene glycol-4000 (40%) was gently added and incubated for 5 minutes at room temperature. Ten ml W5 solution was slowly added, the protoplasts centrifuged at 70×g for 5 min and finally resuspended in 2 ml K3 medium (Bilang et al., *Plant Molecular Biology Manual* A1:1–16, 1994).

For quantitation of GUS activity, the transformed protoplasts are incubated in the dark at 26° C. for 24 hours before protein is extracted for reporter enzyme assays using 4-methyl-umbelliferyl-glucuronide (MUG). GUS activity is quantified by fluorimetric analysis, as described by Jefferson (*Plant Mol Biol Rep.* 5: 387–405, 1987).

Protein is extracted from the protoplasts using the following protocol. Transformed protoplast suspensions were centrifuged at 70×g for 10 min, resuspended in 50 µl extraction buffer (Jefferson, *Plant Mol. Biol. Rep.* 5:387–405, 1987) and vigorously mixed using a vortex. The homogenate is cleared by centrifugation at 4,300 rpm for 5 mm, the supernatant removed and used for protein assays (Bradford, *Anal. Biochem.* 72:248–254, 1976).

B. *Arabidopsis thaliana* Transgenic Lines

*Arabidopsis thaliana* plants were transformed with *A. tumefaciens* containing deletion constructs of the *P. radiata* ubiquitin promoter described above.

1. *Agrobacterium tumefaciens* Transformation

*Agrobacterium tumefaciens* strain GV3101 was transformed with the above-described deletion constructs using electroporation. The deletion constructs were prepared using restriction digestion and PCR. The deletion constructs were made in plasmid pBI-101 that contained the GUS reporter gene, using Endonuclease III (Gibco BRL, Gaithersburg, Md.) according to the manufacturer's protocols. A control construct containing no sequence upstream of the TATA sequence was also made.

Electrocompetent *A. tumefaciens* cells were prepared according to the method of Walkerpeach and Velten, *Plant Mol. Biol. Man.* B1:1–19, 1994. Construct DNA (4 ng) was added to 40 µl competent *A. tumefactens* GV3101 cells and electroporation was done using a BTX Electro Cell Manipulator 600 at the following settings: Mode: T 2.5 kV Resistance high voltage (HV), Set Capacitance: C (not used in HV mode), Set Resistance: R R5 (129 Ohm), Set charging voltage: S 1.44kV, Desired field strength: 14.4 kV/cm and Desired pulse strength: t 5.0 msec. 400 µl YEP liquid media (20 g/l yeast, 20 g/l peptone and 10 g/l sodium chloride) was added to the cuvette and left to recover for one hour at room temperature. Transformed bacteria in YEP medium were spread out on solid YEP medium containing 50 mg/l kanamycin and 50 mg/l rifampicin and incubated at 29° C. for two days to allow colony growth.

2. Confirmation of Transformation of Constructs Into *A. tumefaciens*

To confirm that the constructs have been transformed into *A. tumefaciens*, DNA from the *A. tumefaciens* colonies from the YEP plates were isolated using standard protocols and amplified using the polymerase chain reaction (PCR) with primers designed from the pBI-101 vector sequence. The primer sequences are given in SEQ ID NOS: 128 and 129. PCR reactions were set up following standard protocols and 30 PCR cycles were done with extension temperature of 72° C.

3. Transformation of *A. thaliana* with Transformed *A. tumefaciens*

The optical density of the *A. tumefaciens* bacterial culture was adjusted to 0.7 with infiltration medium (5% sucrose, 0.05% Silwett L-77 surfactant). *A. thaliana* cv. Columbia plants (6 punnets per construct and 10–12 plants per punnet) were pruned by removing secondary bolts. Pruned *A. thaliana* plants in punnets were dipped into infiltration solution and moved back and forth for 5 seconds. Punnets were put on their side to allow excess infiltration medium to drain covered with a top tray and wrapped in plastic wrap to maintain humidity. Plants were placed in a growth room at ambient conditions for 24 hours. After this period, the top tray and plastic wrap were removed and plants were set upright until siliques formed.

Seeds were harvested and sterilized with a 5% sodium hypochlorite solution to destroy any residual *A. tumefaciens* bacteria and fungal contamination.

Under sterile conditions, 100 µl seeds from the transformed *A. thaliana* plants were placed into an Eppendorf tube. One ml sterile water was added and the seeds left to imbibe the water for no longer than an hour. The water was remove by centrifugation, 1 ml 70% ethanol added to the seeds and gently mixed. This step was not allowed to last longer than one minute. The ethanol was removed by centrifugation, 1 ml 5% sodium hypochlorite solution was added to the seeds and gently mixed for up to 5 min. The sodium hypochlorite solution was removed by centrifugation and the seeds washed with sterile water for 1 min. The washing step was repeated three more times with centrifugation. Seeds were finally resuspended in sterile water. 500 µl of seeds in solution were pipetted onto half-strength Murashige and Skoog medium (MS; Gibco BRL) agar plates containing 50 mg/l kanamycin and 250 mg/l timentin and spread evenly with a flamed wire-loop. The Petri dishes were placed in a refrigerator for 3 days to allow the seeds to stratify. Thereafter the plates were placed in growth room and grown under lights at 22° C. with a 14 hour photoperiod until germination. Putative transformant seedlings were selected as those growing on the antibiotic-containing medium, with large, healthy-looking dark green leaves and a strong root system. These transgenic plants were removed and placed into soil culture at 22° C. with a 12 hour photoperiod.

4. Staining of Plant Tissues

Tissue were taken from the flower, leaf, stem and root of *A. thaliana* transformed with constructs of *P. radiata* ubiquitin promoter and stained histochemically to determine the expression of the GUS gene under control of the pollen specific promoters. The GUS staining protocol is described by Campisi et al., *Plant J.* 17:699–707, 1999.

*A. thaliana* flower, leaf, stem and root tissue were immersed in staining solution (50 mM $NaPO_4$ pH 7.2; 0.5% Triton X-100; 1 mM×Glucuronide sodium salt (Gibco BRL)) for immunochemical staining. Vacuum was applied twice for 5 min to infiltrate the tissue with the staining solution. The tissue was left in the staining solution for 2 days (with agitation) at 37° for color development and then destained in 70% ethanol for 24 hours at 37° C. (with agitation). The tissues were examined for blue GUS staining using a light microscope.

The results showed that constitutive expression was lost in the smallest deletion constructs (SEQ ID NOS: 131 AND 136) but was observed in all the other constructs tested, including both the intronless and intron-containing deletion constructs. These results demonstrate that the sequences described in SEQ ID NOS: 132–135 and 138–140 have constitutive promoter activity in both *Arabidopsis* and tobacco plants.

The invention claimed is:

1. An isolated polynucleotide comprisinng SEQ ID NO: 88.

2. A genetic construct comprising the polynucleotide of claim 1.

3. A genetic construct comprising, in the 5'-3' direction:
(a) a promoter sequence,
(b) a DNA sequence of interest; and
(c) a gene termination sequence,
wherein the promoter sequence comprises the isolated polynucleotide of claim 1.

4. The genetic construct of claim 3, wherein the DNA sequence of interest comprises an open reading frame encoding a polypeptide of interest.

5. A transgenic cell comprising the genetic construct of claim 3.

6. A plant comprising the transgenic cell of claim 1, or a part or propagule or progeny thereof, wherein the part, propagule or progeny comprises the transgenic cell of claim 1.

7. A method for modifying gene expression in a target plant comprising stably incorporating into the genome of the plant the genetic construct according to claim 3, wherein the gene expression in said plant is modified.

8. A method for producing a plant having modified gene expression comprising:
(a) transforming a plant cell with a genetic construct to provide a transgenic cell,
wherein the genetic construct comprises:
(i) a promoter sequence comprising the polynucleotide of claim 1;
(ii) a DNA sequence of interest; and
(iii) a gene termination sequence;
(b) cultivating the transgenic cell under conditions conducive to regeneration and mature plant growth; and
(c) regenerating a plant having modified genetic expression, wherein said plant comprises said genetic construct.

9. A method for modifying a phenotype of a target plant, comprising stably incorporating into the genome of the target plant a genetic construct comprising:
(a) the polynucleotide of claim 1;
(b) a DNA sequence of interest; and
(c) a gene termination sequence, wherein the phenotype of said plant is modified.

* * * * *